(12) United States Patent
Boyden et al.

(10) Patent No.: US 8,936,629 B2
(45) Date of Patent: Jan. 20, 2015

(54) AUTOFLUORESCENT IMAGING AND TARGET ABLATION

(75) Inventors: Edward S. Boyden, Cambridge, MA (US); Roderick A. Hyde, Redmond, WA (US); Muriel Y. Ishikawa, Livermore, CA (US); Eric C. Leuthardt, St. Louis, MO (US); Nathan P. Myhrvold, Medina, WA (US); Dennis J. Rivet, Portsmouth, VA (US); Thomas Allan Weaver, San Mateo, CA (US); Lowell L. Wood, Jr., Bellevue, WA (US)

(73) Assignee: Invention Science Fund I LLC, Bellevue, WA (US)

( * ) Notice: Subject to any disclaimer, the term of this patent is extended or adjusted under 35 U.S.C. 154(b) by 1628 days.

(21) Appl. No.: 11/901,299

(22) Filed: Aug. 24, 2007

(65) Prior Publication Data

US 2008/0103355 A1    May 1, 2008

Related U.S. Application Data

(63) Continuation-in-part of application No. 11/403,230, filed on Apr. 12, 2006, and a continuation-in-part of application No. 11/645,357, filed on Dec. 21, 2006, now Pat. No. 7,857,767.

(51) Int. Cl.
| | | |
|---|---|---|
| *A61N 5/06* | (2006.01) | |
| *A61B 5/00* | (2006.01) | |
| *A61B 5/07* | (2006.01) | |
| *A61B 18/20* | (2006.01) | |
| *A61N 5/10* | (2006.01) | |

(52) U.S. Cl.
CPC ............... *A61B 5/412* (2013.01); *A61B 5/0071* (2013.01); *A61B 5/0084* (2013.01); *A61B 5/07* (2013.01); *A61B 18/20* (2013.01); *A61B 5/0086* (2013.01); *A61B 5/0088* (2013.01); *A61B 5/0091* (2013.01); *A61B 5/4547* (2013.01); *A61N 5/10* (2013.01)
USPC .......................................................... 607/88

(58) Field of Classification Search
USPC ................ 606/10–15; 607/88, 89, 90, 92, 94; 600/302, 10, 593; 128/898
See application file for complete search history.

(56) References Cited

U.S. PATENT DOCUMENTS

| | | | |
|---|---|---|---|
| 3,391,697 | A | 7/1968 | Greatbatch |
| 3,802,417 | A | 4/1974 | Lang |
| 3,821,469 | A | 6/1974 | Whetstone et al. |
| 3,941,127 | A | 3/1976 | Froning |

(Continued)

FOREIGN PATENT DOCUMENTS

| | | |
|---|---|---|
| EP | 1 245 201 A1 | 10/2002 |
| JP | 10-099261 | 4/1998 |

(Continued)

OTHER PUBLICATIONS

Hammer-Wilson et al., Scandinavian J of Gastroenterology, 42: 941-950, Jan. 2007.*

(Continued)

*Primary Examiner* — Cris L Rodriquez
*Assistant Examiner* — Matthew Seward
(74) *Attorney, Agent, or Firm* — Dorsey & Whitney LLP

(57) ABSTRACT

Apparatus, devices, methods, systems, computer programs and computing devices related to autofluorescent imaging and ablation are disclosed.

23 Claims, 40 Drawing Sheets

(56) References Cited

U.S. PATENT DOCUMENTS

| | | |
|---|---|---|
| 3,983,474 A | 9/1976 | Kuipers |
| 4,054,881 A | 10/1977 | Raab |
| 4,119,900 A | 10/1978 | Kremnitz |
| 4,202,349 A | 5/1980 | Jones |
| 4,262,306 A | 4/1981 | Renner |
| 4,314,251 A | 2/1982 | Raab |
| 4,317,078 A | 2/1982 | Weed et al. |
| 4,339,953 A | 7/1982 | Iwasaki |
| 4,396,885 A | 8/1983 | Constant |
| 4,403,321 A | 9/1983 | Krüger |
| 4,418,422 A | 11/1983 | Richter et al. |
| 4,431,005 A | 2/1984 | McCormick |
| 4,638,798 A | 1/1987 | Shelden et al. |
| 4,642,786 A | 2/1987 | Hansen |
| 4,651,732 A | 3/1987 | Frederick |
| 4,658,214 A | 4/1987 | Petersen |
| 4,733,661 A | 3/1988 | Palestrant |
| 4,771,772 A | 9/1988 | DeWitt |
| 4,785,806 A | 11/1988 | Deckelbaum |
| 4,805,615 A | 2/1989 | Carol |
| 4,889,526 A | 12/1989 | Rauscher et al. |
| 4,943,296 A | 7/1990 | Funakubo et al. |
| 4,962,453 A | 10/1990 | Pong et al. |
| 4,981,138 A | 1/1991 | Deckelbaum et al. |
| 4,994,071 A | 2/1991 | MacGregor |
| 5,019,372 A | 5/1991 | Folkman et al. |
| 5,031,109 A | 7/1991 | Gloton |
| 5,042,494 A | 8/1991 | Alfano |
| 5,046,501 A | 9/1991 | Crilly |
| 5,051,906 A | 9/1991 | Evans, Jr. et al. |
| 5,078,140 A | 1/1992 | Kwoh |
| 5,086,401 A | 2/1992 | Glassman et al. |
| 5,115,137 A | 5/1992 | Andersson-Engels et al. |
| 5,165,064 A | 11/1992 | Mattaboni |
| 5,188,111 A | 2/1993 | Yates et al. |
| 5,204,814 A | 4/1993 | Noonan et al. |
| 5,234,457 A | 8/1993 | Andersen |
| 5,269,303 A | 12/1993 | Wernicke et al. |
| 5,275,594 A | 1/1994 | Baker et al. |
| 5,279,607 A | 1/1994 | Schentag et al. |
| 5,289,557 A | 2/1994 | Sheinis et al. |
| 5,293,872 A | 3/1994 | Alfano et al. |
| 5,313,835 A | 5/1994 | Dunn |
| 5,314,451 A | 5/1994 | Mulier |
| 5,321,614 A | 6/1994 | Ashworth |
| 5,335,657 A | 8/1994 | Terry, Jr. et al. |
| 5,337,732 A | 8/1994 | Grundfest et al. |
| 5,338,625 A | 8/1994 | Bates et al. |
| 5,350,375 A | 9/1994 | Deckelbaum et al. |
| 5,381,786 A | 1/1995 | Spears |
| 5,386,741 A | 2/1995 | Rennex |
| 5,395,390 A | 3/1995 | Simon et al. |
| 5,398,670 A | 3/1995 | Ortiz et al. |
| 5,411,551 A | 5/1995 | Winston et al. |
| 5,476,450 A | 12/1995 | Ruggio |
| 5,497,147 A | 3/1996 | Arms et al. |
| 5,502,638 A | 3/1996 | Takenaka |
| 5,507,287 A | 4/1996 | Palcic et al. |
| 5,522,394 A | 6/1996 | Zurbrügg |
| 5,554,914 A | 9/1996 | Miyazawa |
| 5,569,968 A | 10/1996 | Lal et al. |
| 5,574,347 A | 11/1996 | Neubauer |
| 5,589,932 A | 12/1996 | Garcia-Rubio et al. |
| 5,590,660 A | 1/1997 | MacAulay et al. |
| 5,593,434 A | 1/1997 | Williams |
| 5,610,488 A | 3/1997 | Miyazawa |
| 5,623,932 A | 4/1997 | Ramanujam et al. |
| 5,624,398 A | 4/1997 | Smith et al. |
| 5,634,920 A | 6/1997 | Hohla |
| 5,647,368 A | 7/1997 | Zeng et al. |
| 5,662,587 A | 9/1997 | Grundfest et al. |
| 5,674,276 A | 10/1997 | Andersen et al. |
| 5,697,967 A | 12/1997 | Dinh et al. |
| 5,702,432 A | 12/1997 | Chen et al. |
| 5,705,293 A | 1/1998 | Hobson |
| 5,728,089 A | 3/1998 | Lal et al. |
| 5,735,276 A | 4/1998 | Lemelson |
| 5,758,298 A | 5/1998 | Guldner |
| 5,759,767 A | 6/1998 | Lakowicz et al. |
| 5,769,792 A | 6/1998 | Palcic et al. |
| 5,782,798 A | 7/1998 | Rise |
| 5,804,563 A | 9/1998 | Still et al. |
| 5,827,190 A | 10/1998 | Palcic et al. |
| 5,830,179 A | 11/1998 | Mikus et al. |
| 5,830,207 A | 11/1998 | Leeb et al. |
| 5,831,012 A | 11/1998 | Nilsson et al. |
| 5,833,603 A | 11/1998 | Kovacs et al. |
| 5,843,139 A | 12/1998 | Goedeke et al. |
| 5,865,754 A | 2/1999 | Sevick-Muraca et al. |
| 5,865,828 A | 2/1999 | Jeng |
| 5,873,835 A | 2/1999 | Hastings et al. |
| 5,964,773 A | 10/1999 | Greenstein |
| 6,016,449 A | 1/2000 | Fischell et al. |
| 6,022,316 A | 2/2000 | Eppstein et al. |
| 6,030,653 A | 2/2000 | Rosenthal |
| 6,053,873 A | 4/2000 | Govari et al. |
| 6,058,932 A | 5/2000 | Hughes |
| 6,061,591 A | 5/2000 | Freitag et al. |
| 6,108,597 A | 8/2000 | Kirchner et al. |
| 6,111,520 A | 8/2000 | Allen et al. |
| 6,123,719 A | 9/2000 | Masychev |
| 6,128,538 A | 10/2000 | Fischell et al. |
| 6,134,474 A | 10/2000 | Fischell et al. |
| 6,149,603 A | 11/2000 | Parker |
| 6,159,230 A | 12/2000 | Samuels |
| 6,164,284 A | 12/2000 | Schulman et al. |
| 6,170,488 B1 | 1/2001 | Spillman, Jr. et al. |
| 6,175,757 B1 | 1/2001 | Watkins et al. |
| 6,185,452 B1 | 2/2001 | Schulman et al. |
| 6,197,013 B1 | 3/2001 | Reed et al. |
| 6,219,577 B1 | 4/2001 | Brown, III et al. |
| 6,221,099 B1 | 4/2001 | Andersen et al. |
| 6,240,312 B1 * | 5/2001 | Alfano et al. .................. 600/476 |
| 6,249,076 B1 | 6/2001 | Madden et al. |
| 6,255,361 B1 | 7/2001 | Rajagopalan et al. |
| 6,255,793 B1 | 7/2001 | Peless et al. |
| 6,258,576 B1 | 7/2001 | Richards-Kortum et al. |
| 6,263,245 B1 | 7/2001 | Snell |
| 6,269,818 B1 | 8/2001 | Lui et al. |
| 6,278,379 B1 | 8/2001 | Allen et al. |
| 6,280,386 B1 | 8/2001 | Alfano et al. |
| 6,289,270 B1 | 9/2001 | Baumgarten |
| 6,290,668 B1 | 9/2001 | Gregory et al. |
| 6,295,990 B1 | 10/2001 | Lewis et al. |
| 6,322,532 B1 | 11/2001 | D'Sa et al. |
| 6,337,997 B1 | 1/2002 | Rise |
| 6,372,248 B1 | 4/2002 | Qin et al. |
| 6,377,841 B1 | 4/2002 | Lin et al. |
| 6,398,280 B1 | 6/2002 | Parker et al. |
| 6,402,678 B1 | 6/2002 | Fischell et al. |
| 6,409,674 B1 | 6/2002 | Brockway et al. |
| 6,417,641 B2 | 7/2002 | Peless et al. |
| 6,436,120 B1 | 8/2002 | Meglin |
| 6,462,770 B1 | 10/2002 | Cline et al. |
| 6,464,687 B1 | 10/2002 | Ishikawa et al. |
| 6,475,639 B2 | 11/2002 | Shahinpoor et al. |
| 6,491,618 B1 * | 12/2002 | Ganz .................................. 600/3 |
| 6,493,607 B1 | 12/2002 | Bourne et al. |
| 6,512,950 B2 | 1/2003 | Li et al. |
| 6,530,950 B1 | 3/2003 | Alvarado et al. |
| 6,547,723 B1 | 4/2003 | Ouchi |
| 6,547,825 B1 | 4/2003 | Shimizu et al. |
| 6,585,763 B1 | 7/2003 | Keilman et al. |
| 6,591,137 B1 | 7/2003 | Fischell et al. |
| 6,592,567 B1 | 7/2003 | Levin et al. |
| 6,597,954 B1 | 7/2003 | Pless et al. |
| 6,607,553 B1 | 8/2003 | Healy et al. |
| 6,612,982 B1 | 9/2003 | Ouchi |
| 6,616,676 B2 | 9/2003 | Bashiri et al. |
| 6,623,519 B2 | 9/2003 | Edwin et al. |
| 6,632,216 B2 | 10/2003 | Houzego et al. |
| 6,669,683 B2 | 12/2003 | Santini, Jr. et al. |
| 6,673,363 B2 | 1/2004 | Luo et al. |
| 6,679,893 B1 | 1/2004 | Tran |

(56) References Cited

U.S. PATENT DOCUMENTS

| | | | |
|---|---|---|---|
| 6,709,388 B1 | 3/2004 | Mosse et al. |
| 6,711,423 B2 | 3/2004 | Colvin, Jr. |
| 6,712,835 B2 | 3/2004 | Mazzocchi et al. |
| 6,719,684 B2 | 4/2004 | Kim et al. |
| 6,735,475 B1 | 5/2004 | Whitehurst et al. |
| 6,743,211 B1 | 6/2004 | Prausnitz et al. |
| 6,754,536 B2 | 6/2004 | Swoyer et al. |
| 6,755,802 B2 | 6/2004 | Bell |
| 6,764,441 B2 | 7/2004 | Chiel et al. |
| 6,770,071 B2 | 8/2004 | Woloszko et al. |
| 6,773,429 B2 | 8/2004 | Sheppard, Jr. et al. |
| 6,776,165 B2 | 8/2004 | Jin |
| 6,797,522 B1 | 9/2004 | Still et al. |
| 6,802,811 B1 | 10/2004 | Slepian |
| 6,816,632 B1 | 11/2004 | Slice |
| 6,817,998 B2 | 11/2004 | LaHaye |
| 6,824,508 B2 | 11/2004 | Kim et al. |
| 6,824,561 B2 | 11/2004 | Soykan et al. |
| 6,834,118 B2 | 12/2004 | Kim |
| 6,849,183 B2 | 2/2005 | Gorsuch et al. |
| 6,855,115 B2 | 2/2005 | Fonseca et al. |
| 6,861,001 B2 | 3/2005 | Lee et al. |
| 6,866,626 B2 | 3/2005 | Long et al. |
| 6,869,430 B2 | 3/2005 | Balbierz et al. |
| 6,890,303 B2 | 5/2005 | Fitz |
| 6,911,004 B2 | 6/2005 | Kim et al. |
| 6,920,359 B2 | 7/2005 | Meadows et al. |
| 6,921,413 B2 | 7/2005 | Mahadevan-Jansen et al. |
| 6,925,357 B2 | 8/2005 | Wang et al. |
| 6,929,636 B1 | 8/2005 | Von Alten |
| 6,939,290 B2 | 9/2005 | Iddan |
| 6,939,376 B2 | 9/2005 | Shulze et al. |
| 6,950,707 B2 | 9/2005 | Whitehurst |
| 6,953,589 B1 | 10/2005 | Trautman et al. |
| 6,958,034 B2 | 10/2005 | Iddan |
| 6,959,215 B2 | 10/2005 | Gliner et al. |
| 6,960,227 B2 | 11/2005 | Jones et al. |
| 6,984,205 B2 | 1/2006 | Gazdzinski |
| 6,984,952 B2 | 1/2006 | Peless et al. |
| 6,991,617 B2 | 1/2006 | Hektner et al. |
| 7,003,352 B1 | 2/2006 | Whitehurst |
| 7,013,177 B1 | 3/2006 | Whitehurst et al. |
| 7,020,231 B1 | 3/2006 | Frey et al. |
| 7,027,134 B1 | 4/2006 | Garcia-Rubio et al. |
| 7,037,343 B2 | 5/2006 | Imran |
| 7,039,453 B2 | 5/2006 | Mullick et al. |
| 7,042,184 B2 | 5/2006 | Oleynikov et al. |
| RE39,133 E | 6/2006 | Clayton et al. |
| 7,060,793 B2 | 6/2006 | Tsien et al. |
| 7,083,578 B2 | 8/2006 | Lewkowicz et al. |
| 7,118,531 B2 | 10/2006 | Krill |
| 7,125,382 B2 | 10/2006 | Zhou et al. |
| 7,131,979 B2 | 11/2006 | DiCarlo et al. |
| 7,171,285 B2 | 1/2007 | Kim et al. |
| 7,181,261 B2 | 2/2007 | Silver et al. |
| 7,194,063 B2 | 3/2007 | Dilmanian et al. |
| 7,212,110 B1 | 5/2007 | Martin et |
| 7,214,182 B2 | 5/2007 | Shimizu et al. |
| 7,236,821 B2 | 6/2007 | Cates et al. |
| 7,244,232 B2 | 7/2007 | Connelly et al. |
| 7,245,954 B2 | 7/2007 | Glukhovsky |
| 7,359,574 B2 | 4/2008 | Lennon et al. |
| 7,365,614 B2 | 4/2008 | McCorquodale et al. |
| 7,398,734 B1 | 7/2008 | Jean |
| 7,451,537 B2 | 11/2008 | Liu et al. |
| 7,486,967 B2 | 2/2009 | Pan et al. |
| 7,510,699 B2 | 3/2009 | Black et al. |
| 7,572,228 B2 | 8/2009 | Wolinsky et al. |
| 7,596,403 B2 | 9/2009 | Horn |
| 7,625,338 B2 | 12/2009 | Gilad et al. |
| 7,684,840 B2 | 3/2010 | Palti |
| 7,736,300 B2 | 6/2010 | Ziegler et al. |
| 7,744,542 B2 | 6/2010 | Piaget et al. |
| 7,801,626 B2 | 9/2010 | Moser |
| 7,840,271 B2 | 11/2010 | Kieval et al. |
| 7,967,016 B2 | 6/2011 | Anderson et al. |
| 8,036,731 B2 | 10/2011 | Kimchy et al. |
| 8,055,329 B2 | 11/2011 | Kimchy et al. |
| 8,140,141 B2 | 3/2012 | McGreevy et al. |
| 2001/0039385 A1 | 11/2001 | Ellenz |
| 2001/0051766 A1 | 12/2001 | Gazdzinski |
| 2002/0026188 A1* | 2/2002 | Balbierz et al. ............... 606/41 |
| 2002/0077369 A1 | 6/2002 | Noolandi et al. |
| 2002/0090388 A1 | 7/2002 | Humes et al. |
| 2002/0103417 A1 | 8/2002 | Gazdzinski |
| 2002/0147480 A1 | 10/2002 | Mamayek |
| 2002/0165592 A1 | 11/2002 | Glukhovsky et al. |
| 2002/0188323 A1 | 12/2002 | Penner et al. |
| 2002/0193874 A1 | 12/2002 | Crowley |
| 2002/0198470 A1 | 12/2002 | Imran et al. |
| 2002/0198604 A1 | 12/2002 | Schulman et al. |
| 2003/0004403 A1 | 1/2003 | Drinan et al. |
| 2003/0024534 A1 | 2/2003 | Silvestri et al. |
| 2003/0040704 A1 | 2/2003 | Dorros et al. |
| 2003/0065250 A1 | 4/2003 | Chiel et al. |
| 2003/0065358 A1 | 4/2003 | Frecker et al. |
| 2003/0069475 A1 | 4/2003 | Banik et al. |
| 2003/0078485 A1 | 4/2003 | Hartlep |
| 2003/0093031 A1 | 5/2003 | Long et al. |
| 2003/0151524 A1 | 8/2003 | Clark |
| 2003/0152823 A1 | 8/2003 | Heller |
| 2003/0153866 A1 | 8/2003 | Long et al. |
| 2003/0191430 A1 | 10/2003 | D'Andrea et al. |
| 2003/0214580 A1 | 11/2003 | Iddan |
| 2003/0220556 A1 | 11/2003 | Porat et al. |
| 2004/0008853 A1 | 1/2004 | Pelrine et al. |
| 2004/0018508 A1 | 1/2004 | Friedman |
| 2004/0039242 A1 | 2/2004 | Tolkoff et al. |
| 2004/0064093 A1 | 4/2004 | Hektner et al. |
| 2004/0073190 A1 | 4/2004 | Deem et al. |
| 2004/0098030 A1 | 5/2004 | Makower et al. |
| 2004/0111019 A1 | 6/2004 | Long |
| 2004/0133147 A1 | 7/2004 | Woo |
| 2004/0147939 A1 | 7/2004 | Rabkin et al. |
| 2004/0152988 A1 | 8/2004 | Weirich |
| 2004/0162469 A1 | 8/2004 | Imran |
| 2004/0162501 A1 | 8/2004 | Imran |
| 2004/0176664 A1 | 9/2004 | Iddan |
| 2004/0193010 A1 | 9/2004 | Fujimori et al. |
| 2004/0193235 A1 | 9/2004 | Altshuler et al. |
| 2004/0218724 A1 | 11/2004 | Chornenky et al. |
| 2004/0225325 A1 | 11/2004 | Bonutti |
| 2004/0225326 A1 | 11/2004 | Weiner et al. |
| 2004/0260278 A1 | 12/2004 | Anderson et al. |
| 2004/0260391 A1 | 12/2004 | Santini, Jr. et al. |
| 2004/0267240 A1 | 12/2004 | Gross et al. |
| 2005/0004474 A1 | 1/2005 | Iddan |
| 2005/0043583 A1 | 2/2005 | Killmann et al. |
| 2005/0058701 A1 | 3/2005 | Gross et al. |
| 2005/0062562 A1 | 3/2005 | Ries |
| 2005/0079132 A1 | 4/2005 | Wang et al. |
| 2005/0096712 A1* | 5/2005 | Abraham-Fuchs et al. .... 607/89 |
| 2005/0107870 A1 | 5/2005 | Wang et al. |
| 2005/0113460 A1 | 5/2005 | Glick |
| 2005/0121411 A1 | 6/2005 | Cohen |
| 2005/0126916 A1 | 6/2005 | Lockard et al. |
| 2005/0149170 A1 | 7/2005 | Tassel et al. |
| 2005/0171418 A1 | 8/2005 | Lin |
| 2005/0171434 A1 | 8/2005 | Madden et al. |
| 2005/0177223 A1 | 8/2005 | Palmaz |
| 2005/0182482 A1 | 8/2005 | Wang et al. |
| 2005/0203613 A1 | 9/2005 | Arney et al. |
| 2005/0215911 A1 | 9/2005 | Alfano et al. |
| 2005/0216074 A1 | 9/2005 | Sahatjian et al. |
| 2005/0221529 A1 | 10/2005 | Bang et al. |
| 2005/0228259 A1 | 10/2005 | Glukhovsky et al. |
| 2005/0238689 A1 | 10/2005 | Carpenter et al. |
| 2005/0272974 A1 | 12/2005 | Iddan |
| 2005/0277839 A1 | 12/2005 | Alderman et al. |
| 2005/0278020 A1 | 12/2005 | Wang et al. |
| 2006/0004395 A1 | 1/2006 | Chiel et al. |
| 2006/0009810 A1 | 1/2006 | Mann et al. |
| 2006/0015146 A1 | 1/2006 | Girouard et al. |
| 2006/0037617 A1 | 2/2006 | Walke et al. |

(56) References Cited

U.S. PATENT DOCUMENTS

| | | | |
|---|---|---|---|
| 2006/0058647 | A1 | 3/2006 | Strommer et al. |
| 2006/0119304 | A1 | 6/2006 | Farritor et al. |
| 2006/0152309 | A1 | 7/2006 | Mintchev et al. |
| 2006/0167339 | A1 | 7/2006 | Gilad et al. |
| 2006/0169294 | A1 | 8/2006 | Kaler et al. |
| 2006/0195015 | A1 | 8/2006 | Mullick et al. |
| 2006/0235275 | A1 | 10/2006 | Rabinovitz et al. |
| 2006/0241577 | A1 | 10/2006 | Balbierz et al. |
| 2006/0252987 | A1 | 11/2006 | Hasegawa et al. |
| 2007/0066929 | A1 | 3/2007 | Ferren et al. |
| 2007/0083099 | A1 | 4/2007 | Henderson et al. |
| 2007/0156211 | A1 | 7/2007 | Ferren et al. |
| 2007/0213613 | A1 | 9/2007 | Ishida et al. |
| 2007/0213698 | A1 | 9/2007 | Altshuler et al. |
| 2008/0063703 | A1 | 3/2008 | Gross et al. |
| 2008/0121054 | A1 | 5/2008 | Goldenberg et al. |
| 2008/0241847 | A1 | 10/2008 | Hoon et al. |
| 2008/0266106 | A1 | 10/2008 | Lim et al. |
| 2009/0062646 | A1 | 3/2009 | Creighton, IV et al. |
| 2009/0069821 | A1 | 3/2009 | Farritor et al. |
| 2009/0082652 | A1 | 3/2009 | Koh et al. |
| 2009/0182388 | A1 | 7/2009 | Von Arx et al. |
| 2013/0274658 | A1 | 10/2013 | Steinke et al. |
| 2013/0304446 | A1 | 11/2013 | Rabinovitz et al. |

FOREIGN PATENT DOCUMENTS

| | | | |
|---|---|---|---|
| JP | 2002-010990 | | 1/2002 |
| JP | 2005-74229 | | 3/2005 |
| KR | 2002-0010990 | A | 2/2002 |
| WO | WO 98/14243 | | 4/1998 |
| WO | WO 99/20335 | | 4/1999 |
| WO | WO 99/44665 | | 9/1999 |
| WO | WO 03/072157 | A1 | 9/2003 |
| WO | WO 03/106966 | A2 | 12/2003 |

OTHER PUBLICATIONS

Yavari, Nazila; "Optical spectroscopy for tissue diagnostics and treatment control"; Doctoral Thesis; Department of Physics and Technology; University of Bergen; bearing a date of Apr. 2006; 130 pages.

UK Intellectual Property Office Examination Report under Section 18(3); App. No. GB0821521.2; Jan. 12, 2011 (received by our agent on Jan. 13, 2011); pp. 1-4.

Arkin, Ronald C.; "Towards the Unification of Navigational Planning and Reactive Control"; Working Notes of the AAAI Spring Symposium on Robot Navigation; bearing dates of Mar. 20-28, 1989; pp. 1-6.

Arleo et al.; "Spatial Cognition and Neuro-Mimetic Navigation: A Model of Hippocampal Place Cell Activity"; bearing a date of Oct. 28, 1999; pp. 1-13.

Balakrishnan et al.; "Spatial Learning and Localization in Rodents: A Computational Model of the Hippocampus and its Implications for Mobile Robots"; Adaptive Behavior; bearing a date of 1999; pp. 173-216 plus cover page; vol. 7, No. 2; SAGE Publications.

Bellin et al.; "Polymeric triple-shape materials"; PNAS; bearing dates of Nov. 18, 2006 and 2006; pp. 18043-18047; vol. 103, No. 48; The National Academy of Sciences of the USA; located at www.pnas.org/cgi/doi/10.1073/pnas.0608586103.

Berman et al.; "Decentralized Autonomous AGV System for Material Handling"; iFirst; bearing a date of Oct. 2002; pp. 3995-4006 (Only the Abstract is being provided); vol. 40, No. 15; located at: http://www.informaworld.com/smpp/content~content=a713846479~db=ai; printed on Apr. 24, 2007.

Bianco et al.; "Carbon Nanotube-based Vectors for Delivering Immunotherapeutics and Drugs"; Nanotechnologies for the Live Sciences: Nanomaterials for Medical Diagnosis and Therapy; bearing a date of 2007; Chapter 3; pp. 85-142.; vol. 10; WILEY-VCH Verlag GmbH & Co. KGaA; Weinheim.

Breslin et al.; "Autofluorescence and Diffuse Reflectance Properties Malignant and Benign Breast Tissues"; Annals of Surgical Oncology; bearing dates of 2003 and 2004; pp. 65-70; vol. 11, No. 1; Lippincott Williams & Wilkin.

Bright et al.; "Automated Pipe Inspection Robot"; Industrial Robot: An International Journal; bearing a date of Aug. 1997; pp. 285-289 (Only the Abstract is being provided); vol. 24, No. 4; located at: http://www.emeraldinsight.com/10.1108/01439919710176372; printed on Apr. 23, 2007.

Brinn, David; "A incredible journey from an Israeli robotics team"; ISRAEL21c: A Focus Beyond; bearing a date of Nov. 12, 2006; pp. 1-3; ISRAEL21c.org.

Brown et al.; "Performance Test Results of an Integrated GPS/MEMS Inertial Navigation Package"; Proceedings of ION GNSS 2004, bearing a date of Sep. 2004; pp. 1-8.

Budgett et al.; "Novel technology for the provision of power to implantable physiological devices"; Journal of Applied Physiology; bearing dates of Jan. 27, 2006, Jan. 5, 2007, and 2007; pp. 1658-1663; vol. 102; The American Physiological Society.

Bullitt et al.; "Analysis of Time-Varying Images Using 3D Vascular Models"; Proceedings 30th Applied Imagery Pattern Recognition Workshop; bearing a date of Apr. 2001; pp. 9-14; IEEE Computer Society; Piscataway, NJ.

Burke et al.; "Towards a single-chip, implantable RFID system: is a single-cell radio possible?"; Biomed Microdevices; bearing a date of 2009; pp. 1-8; Springer.

Cady et al.; "Optimized linkage and quenching strategies for quantum dot molecular beacons"; Molecular and Cellular Probes; bearing dates of Jul. 5, 2006, Sep. 7, 2006, Sep. 17, 2006, 2006, and 2007; pp. 116-124; vol. 21; Elsevier Ltd.

Cavalcanti et al.; "Autonomous Multi-Robot Sensor-Based Cooperation for Nanomedicine"; Nanotechnology Special Edition; bearing a date of Aug. 2002; pp. 1-4; International Journal of Nonlinear Science and Numerical Stimulation.

Chen et al.; "Review on the Achievements in Simultaneous Localization and Map Building for Mobile Robot" CSA Illumina; bearing a date of Jun. 2005; pp. 455-460 (Only the Abstract is being provided); vol. 22, No. 3; ProQuest-CSA LLC; located at: http://mdl.csa.com/partners/viewrecord.php?requester=gs&collection=TRD&recid=A056354818AH&recid=2005134422784EA&q=Review+on+the+Achievements+in+Simultaneous+Localization+and+Map+Building+for+Mobile+Robot&uid=790366044&setcookie=yes.

Chiyo et al.; "Effective detection of bronchial preinvasive lesions by a new autofluorescence imaging bronchovideoscope system"; Lung Cancer; bearing dates of May 12, 2004, Nov. 17, 2004, Nov. 23, 2004, 2004, and 2005; pp. 307-313; vol. 48; Elsevier Ireland Ltd.

Chung et al.; "Advanced Optical Imaging Requiring No Contrast Agents—A New Armamentarium for Medicine and Surgery"; Current Surgery; bearing dates of May/Jun. 2005 and 2005; pp. 365-370; vol. 62, No. 3; Elsevier Inc.

Dacosta et al.; "Autofluorescence characterisation of isolated whole crypts and primary cultured human epithelial cells from normal, hyperplastic, and adenomatous colonic mucosa"; Journal of Clinical Pathology; bearing dates of 2004 and 2005; pp. 766-774; vol. 58.

Degani et al.; "Minimalistic, Dynamic, Tube Climbing Robot"; 2010 IEEE International Conference on Robotics and Automation; bearing dates of May 3-8, 2010 and 2010; pp. 1100-1101; IEEE.

Desouza et al.; "Vision for Mobile Robot Navigation: A Survey"; IEEE Transactions on Pattern Analysis and Machine Intelligence; bearing a date of Feb. 2002; pp. 237-267 (Only the Abstract is being provided); vol. 24, No. 2; located at: http://csdl2.computer.org/persagen/DLAbsToc.jsp?resourcePath=/dl/trans/tp/&toc=comp/trans/tp/2002/02/i2toc.xml&DOI=10.1109/34.982903; printed on Apr. 23, 2007.

Diard et al.; "A theoretical comparison of probabilistic and biomimetic models of mobile robot navigation"; Proceedings of the 2004 IEEE International Conference on Robotics & Automation; bearing dates of Apr. 2004 and 2004; pp. 933-938; IEEE.

Dweik et al.; "Exhaled breath analysis: the new frontier in medical testing"; Journal of Breath Research; bearing a date of 2008; pp. 1-3; vol. 2; IOP Publishing Ltd; UK.

Edwards, Lin; "Spider pill to seek out disease"; PhysOrg.com; bearing dates of Oct. 16, 2009 and 2009; p. 1.

(56) References Cited

OTHER PUBLICATIONS

Eker et al.; "Clinical spectral characterisation of colonic mucosal lesions using autofluorescence and δ aminolevulinic acid sensitization"; Gut; bearing dates of 1998 and 1999; pp. 511-518; vol. 44.

Eulenstein et al.; "Ultrasound-Based Navigation System Incorporating Preoperative Planning for Liver Surgery"; International Congress Series CARS 2004—Computer Assisted Radiology and Surgery, Proceedings of the 18$^{th}$ International Congress and Exhibition; bearing a date of 2004; pp. 758-763; vol. 1268.

Filliat et al.; "Map Based Navigation in Mobile Robots: I. A Review of Localization Strategies"; Science Direct-Cognitive Systems Research; bearing dates of Feb. 12, 2003 and Dec. 2003; pp. 1-58; vol. 4, No. 4; Elsevier Science.

Foxlin et al.; "Miniature 6-DOF inertial system for tracking HMDs"; Helmet and Head-Mounted Displays III, AeroSense 98; bearing dates of Apr. 13-14, 1998; pp. 1-15; vol. 3362; SPIE.

Gabrecht et al.; "Detection of early bronchial cancer by autofluorescence: results in patients with H&N cancer"; Diagnostic Optical Spectroscopy in Biomedicine IV, Proc. SPIE-OSA Biomedical Optics; bearing a date of 2007; pp. 1-8; vol. 6628; SPIE-OSA.

Gao et al., "A Micro Sensing Probe for Detecting Individual Biological Cells"; Proceedings of the 25$^{th}$ Annual International Conference of the IEEE EMBS; bearing dates of Sep. 17-21, 2003 and 2003; pp. 3348-3351; IEEE.

Gillenwater et al.; "Noninvasive Diagnosis of Oral Neoplasia Based on Fluorescence Spectroscopy and Native Tissue Autofluorescence"; Archives of Otolaryngology—Head & Neck Surgery; bearing a date of Nov. 1998 and 1998; pp. 1251-1258; vol. 124.

Grifantini, Kristina; "Voyage of the Bacteria Bots"; Technology Review; bearing a date of Oct. 31, 2008; pp. 1-4; Technology Review.

Groothuis et al.; "The entry of antiviral and antiretroviral drugs into the central nervous system"; Journal of NeuroVirology; bearing a date of 1997; pp. 387-400; vol. 3; Journal of NeuroVirology, Inc.

"Guessing Robots Predict Their Environments, Navigate Better"; PhysOrg.com; printed on Sep. 16, 2008; pp. 1-2; original story found at www.phyorg.com/news100887209.html.

Gur, Amir; "The Nanobots are Coming"; TFOT; bearing a date of Jul. 9, 2007; pp. 1-2; The Future of Things.

Hattori, Kevin; "Robot Can Crawl Through Human Body"; American Technion Society; bearing a date of Jul. 7, 2009; pp. 1-2; American Technion Society; located at http://www.ats.org/site/News2?page=NewsArticle&id=6063&news_iv_ctrl=1161&printer_friendly=1.

Herth et al.; "Successful Bronchoscopic Placement of Tracheobronchial Stents Without Fluoroscopy"; Chest; bearing a date of Jun. 2001; pp. 1910-1912; vol. 119, No. 6; American College of Chest Physicians.

Hertzberg et al.; "Landmark-Based Autonomous Navigation in Sewerage Pipes"; Proceedings of EUROBOT; bearing a date of 1996; pp. 68-73; IEEE.

Hirsch et al.; "A new device with PZT ultrasonic transducers in MEMS technology"; Journal of Physics: Conference Series 34, International MEMS Conference 2006; bearing a date of 2006; pp. 475-480; IOP Publishing Ltd.

Hollings et al.; "Diagnostic imaging of lung cancer"; European Respiratory Journal; bearing a date of 2002, pp. 722-742; vol. 19; ERS Journals Ltd.

Hornyak, Tim; "RFID Powder"; Scientific American Magazine; bearing dates of Feb. 2008 and 2008; pp. 68-71; Scientific American, Inc.

Hosseini-Khayat, Saied; "A Lightweight Security Protocol for Ultra-low Power ASIC Implementation for Wireless Implantable Medical Devices"; 2011 Symposium on Medical Information and Communication Technology (ISMICT); bearing dates of 2001 and Mar. 27-30, 2011 ; pp. 6-9; IEEE.

Howell et al.; "Practical Mobile Robot Self-Localization"; Proceedings of the IEEE International Conference on Robotics and Automation, 2000; bearing dates of Apr. 24-28, 2000; pp. 3485-3492; vol. 4.

Jaiswal et al.; "Long-term multiple color imaging of live cells using quantum dot bioconjugates"; Nature Biotechnology; bearing dates of Jan. 2003 and 2003; pp. 47-51; vol. 21; Nature Publishing Group.

Jovanov et al.; "A wireless body area network of intelligent motion sensors for computer assisted physical rehabilitation"; Journal of NeuroEngineering and Rehabilitation; bearing dates of Mar. 1, 2005, Jan. 28, 2005, Mar. 1, 2005 and 2005; pp. 1-10; vol. 2, No. 6; BioMed Central Ltd.

Karino et al.; "Flow Patterns in Vessels of Simple and Complex Geometries$^a$"; Annals of the New York Academy of Sciences; bearing a date of 1987; pp. 422-441; vol. 516.

Kawaguchi et al.; "Internal Pipe Inspection Robot"; IEEE Xplore; bearing dates of May 21-27, 1995 and 2005; pp. 857-862 (Only the Abstract is being provided); vol. 1; IEEE; located at: http://ieeexplore.ieee.org/xpls/abs_all.jsp?rnumber=525390; printed on Apr. 23, 2007.

Kharitonov et al.; "Exhaled Markers of Pulmonary Disease"; American Journal of Respiratory and Critical Care Medicine; bearing dates of Sep. 5, 2000, Jan. 24, 2001, and 2001; pp. 1693-1722; vol. 163.

Kim et al.; "Inchworm-Like Microbot for Capsule Endoscope"; Proceedings of the 2004 IEEE International Conference on Robotics and Biomimetics; bearing dates of Aug. 22-26, 2004 and 2004; pp. 458-463; IEEE.

Kim et al.; "Ultrasensitive carbon nanotube-based biosensors using antibody-binding fragments"; Analytical Biochemistry; bearing a date of 2008; pp. 193-198; vol. 381; Elsevier Inc.

Kirchner et al.; "A Prototype Study of an Autonomous Robot Platform for Sewerage System Maintenance"; Autonomous Robots; bearing a date of 1997; pp. 319-331; vol. 4; Kluwer Academic Publishers.

Kitaoka et al.; "A three-dimensional model of the human airway tree"; Journal of Applied Physiology; bearing a date of 1999; pp. 2207-2217; vol. 87; The American Physiological Society.

Kitching, John; "Time for a Better Receiver: Chip-Scale Atomic Frequency References"; GPS World; bearing a date of Nov. 2007; pp. 52-57.

Knappe, Svenja; "Emerging Topics: MEMS Atomic Clocks"; Comprehensive Microsystems; bearing a date of 2007; pp. 571-612; vol. 3; Elsevier B.V.; Netherlands.

Koenig et al.; "Laser-Induced Autofluorescence for Medical Diagnosis"; Journal of Fluorescence; bearing a date of 1994, pp. 17-40; vol. 4, No. 1; Plenum Publishing Corporation.

Kuipers et al.; "A Robot Exploration and Mapping Strategy Based on a Semantic Hierarchy of Spatial Representations"; Robotics and Autonomous Systems; bearing a date of 1981; pp. 47-63; vol. 8; Elsevier Science Publishers B.V.

Kuntze et al.; "Experiences With the Development of a Robot for Smart Multisensoricpipe Inspection"; IEEE Xplore; bearing dates of May 16-20, 1998 and 2005; pp. 1773-1778 (Only the Abstract is being provided); vol. 2; IEEE; located at: http://ieeexplore.ieee.org/xpls/abs_all.jsp?rnumber=677423; printed on Apr. 23, 2007.

Latombe, Jean-Claude; "Chapter 1: Introduction and Overview"; Robot Motion Planning; bearing a date of 1991; 11 pages total, pp. 12-20; Kluwer Academic Publishers.

Laumond et al.; "Robot Motion Planning and Control"; bearing a date of 1998; pp. 1-343 plus cover page, foreword and table of contents (353 total pages); Springer.

Leong et al.; "Tetherless thermobiochemically actuated microgrippers"; PNAS; bearing dates of Jan. 20, 2009 and 2009; pp. 703-708; vol. 106, No. 3; The National Academy of Sciences of the USA; located at www.pnas.org_cgi_doi_10.1073_pnas.0807698106.

Luckevich, Mark, "MEMS microvalves: the new valve world"; Valve-World; bearing a date of May 2007; pp. 79-83.

Lynch et al.; "Design of Piezoresistive MEMS-Based Accelerometer for Integration with Wireless Sensing Unit for Structural Monitoring"; Journal of Aerospace Engineering; bearing a date of Jul. 2003; pp. 108-114; vol. 3; ASCE.

Machado et al., "Detection of Lung Cancer by Sensor Array Analyses of Exhaled Breath"; American Journal of Respiratory and Critical Care Medicine; bearing a date of 2005; pp. 1286-1291; vol. 171.

(56) References Cited

OTHER PUBLICATIONS

Marcu et al.; "In vivo detection of macrophages in a rabbit atherosclerotic model by time-resolved laser-induced fluorescence spectroscopy"; Atherosclerosis; bearing a date of 2005, pp. 295-303; vol. 181; Elsevier Ireland Ltd.

Martel, Sylvain; "Fundamental Principles and Issues of High-speed Piezoactuated Three-legged Motion for Miniature Robots Designed for Nanometer-scale Operations"; The International Journal of Robotics Research; bearing dates of Jul. 2005 and 2005; pp. 575-588; vol. 24, No. 7; Sage Publications.

Mataric, Maja J.; "Integration of Representation into Goal-Driven Behavior-Based Robots"; IEEE Transactions on Robotics and Automation; bearing dates of Jun. 1992 and 1992; pp. 304-312; vol. 8, No. 3; IEEE.

Mattley et al.; "Blood Characterization using uv/vis Spectroscopy"; Advances in Fluorescence Sensing Technology II (Proceedings Volume); bearing a date of 1995; pp. 462-470; vol. 2388; SPIE.

Mehmood et al.; "Autonomous Navigation of Mobile Agents Using RFID-Enabled Space Partitions"; ACMGIS '08; bearing dates of Nov. 5-7, 2008 and 2008; pp. 1-10; ACM.

Menciassi et al.; "Towards Active Capsular Endoscopy: Preliminary Results on a Legged Platform"; Proceedings of the 28th IEEE EMBS Annual International Conference; bearing dates Aug. 30, 2006-Sep. 3, 2006 and 2006; pp. 2215-2218; IEEE.

Meyer et al.; "Map-Based Navigation in Mobile Robots: II. A Review of Map-Learning and Path-Learning Strategies"; Science Direct-Cognitive Systems Research; bearing dates of Feb. 12, 2003 and Dec. 4, 2003; pp. 1-51; vol. 4, No. 4; Elsevier Science.

Mohan et al., "Bokode: Imperceptible Visual tags for Camera Based Interaction from a Distance"; ACM Transactions on Graphics (Proceedings of SIGGRAPH 2009); bearing dates of Aug. 3-7, 2009; pp. 1-8.

Mok et al.; "Recent Progress in Nucleic Acid Aptamer-Based Biosensors and Bioassays"; Sensors; bearing a date of 2008; pp. 7050-7084; vol. 8.

Morrison et al., "Clinical Applications of Micro- and Nanoscale Biosensors"; Biomedical Nanostructures; bearing a date of 2008; Chapter 17; pp. 433-454; John Wiley & Sons, Inc.

Motomiya et al.; "Flow Patterns in the Human Carotid Artery Bifurcation"; Stroke; bearing dates of Jan.-Feb. 1984; pp. 50-56; vol. 15, No. 1.

Nehmzow et al.; "Robot Navigation in the Real World: Experiments with Manchester's *FortyTwo* in Unmodified, Large Environments"; Robotics and Autonomous Systems; bearing a date of 2000; pp. 223-242; vol. 33; Elsevier Science B.V.

Nguyen, Clark T.-C.; "MEMS Technology for Timing and Frequency Control"; IEEE Transactions on Ultrasonics, Ferroelectrics, and Frequency Controls; bearing dates of Feb. 2007 and 2007; pp. 251-270; vol. 54, No. 2; IEEE.

Nordstrom et al.; "Identification of Cervical Intraepithelial Neoplasia (CIN) Using UV-Excited Fluorescence and Diffuse-Reflectance Tissue Spectroscopy"; Lasers in Surgery and Medicine; bearing a date of 2001; pp. 118-127; vol. 29; Wiley-Liss, Inc.

Nowinski et al.; "Three-dimensional Atlas of the Brain Anatomy and Vasculature[1]"; RadioGraphics; bearing dates of Jan.-Feb. 2005 and 2005; pp. 263-271; vol. 25, No. 1; RSNA.

Pan et al.; "A magnetically driven PDMS micropump with ball check-valves"; Journal of Micromechanics and Microengineering; bearing a date of 2005, pp. 1021-1026; vol. 15; IOP Publishing Ltd.

Pavlidis, N.; "The diagnostic and therapeutic management of leptomeningeal carcinomatosis"; Annals of Oncology; bearing a date of 2004; pp. iv285-iv291; vol. 15 (Supp. 4); European Society for Medical Oncology.

Peng et al.; "Ultraviolet light-emitting diodes operating in the 340 nm wavelength range and application to time-resolved fluorescence spectroscopy"; Applied Physics Letters; bearing dates of Aug. 23, 2004 and 2004; pp. 1436-1438; vol. 85, No. 8; American Institute of Physics.

Pfister et al.; "Weighted Line Fitting Algorithms for Mobile Robot Map Building and Efficient Data Representation"; Proceedings of the 2003 IEEE International Conference on Robotics and Automation; bearing a date of Sep. 14-19, 2003; pp. 1-8.

"Philips develops "intelligent pill""; Reuters; bearing a date of Nov. 11, 2008; p. 1; Thomson Reuters.

"Philips' intelligent pill targets drug development and treatment for digestive tract diseases"; PhysOrg.com; bearing a date of Nov. 11, 2008; pp. 1-3; located at http://www.physorg.com/news145640874.html.

Phillips et al.; "Detection of Lung Cancer With Volatile Markers in the Breath"; Chest; bearing dates of Jun. 2003 and 2003; pp. 2115-2123; vol. 123, No. 6; American College of Chest Physicians.

Pisupati et al.; "A Central Axis Algorithm for 3D Bronchial Tree Structures"; Proceedings of the International Symposium on Computer Vision; bearing a date of 1995; pp. 259-264; IEEE.

Psathakis et al.; "8-Isoprostane, a Marker of Oxidative Stress, Is Increased in the Expired Breath Condensate of Patients With Pulmonary Sarcoidosis"; Chest; bearing dates of Mar. 2004 and 2004, pp. 1005-1011; vol. 125, No. 3; American College of Chest Physicians.

Quaglia et al.; "An endoscopic capsule robot: a meso-scale engineering case study"; Journal of Micromechanics and Microengineering; bearing a date of 2009; pp. 1-11; vol. 19; IOP Publishing Ltd.

Quirini et al.; "Design of a Pill-Sized 12-legged Endoscopic Capsule Robot"; 2007 IEEE International Conference on Robotics and Automation; bearing dates of Apr. 10-14, 2007 and 2007; pp. 1856-1862; IEEE.

Raman et al.; "In Vivo Atherosclerotic Plaque Characterization Using Magnetic Susceptibility Distinguishes Symptom-Producing Plaques"; JACC: Cardiovascular Imaging; bearing dates of Jan. 2008 and 2008; pp. 49-57; vol. 1, No. 1; Elsevier.

Rasmussen et al.; "Proximity-based Access Control for Implantable Medical Devices"; CCS '09, Proceedings of the 16th ACM Conference on Computer and Communications Security; bearing dates of Nov. 9-13, 2009 and 2009; pp. 1-10.

"Remote-controlled capsule endoscope safely examines the stomach"; PhysOrg.com; bearing a date of Jan. 18, 2011; pp. 1-2; located at http://www.physorg.com/news-2011-01-remote-controlled-capsule-endoscope-safely-stomach.html.

"Researchers Create Tiny, Self-Propelled Devices"; PhysOrg.com; printed on Feb. 12, 2007; pp. 1-3; located at: http://www.physorg.com/printnews.php?newsid=90521279.

Roh et al.; "Strategy for Navigation Inside Pipelines With Differential-Driveinpipe Robot"; IEEE Xplore; 2002 and 2005; pp. 2575-2580 (Only the Abstract is being provided); vol. 3; IEEE; located at: http://ieeexplore.ieee.org/xpls/abs_all.jsp?arnumber=1013619; printed on Apr. 23, 2007.

Roh et al.; "Actively Steerable In-Pipe Inspection Robots for Underground Urban Gas Pipelines"; IEEE Xplore; bearing dates of 2001 and 2005; pp. 761-766 (Only the Abstract is being provided); vol. 1; IEEE; located at: http://ieeexplore.ieee.org/xpls/abs_all.jsp?arnumber=932642; printed on Apr. 23, 2007.

Rolfe, Brigitte; "Toward Nanometer-Scale Sensing Systems: Natural and Artificial Noses as Models for Ultra-Small, Ultra-Dense Sensing Systems"; Advances in Computers; bearing dates of Nov. 2004, 2004, and 2007; pp. 11-46; vol. 71; Elsevier, B.V.

Schertler et al.; "Effects of ECG Gating and Postprocessing Techniques on 3D MDCT of the Bronchial Tree"; AJR; bearing a date of Jul. 2004; pp. 83-89; vol. 183; American Roentgen Ray Society.

Schnakenberg et al.; "Intravascular pressure monitoring system"; Sensors and Actuators A: Physical; bearing a date of 2004; pp. 61-67; vol. 110; Elsevier B.V.

Schwartz, John; "In the Lab: Robots That Slink and Squirm"; The New York Times: Science; bearing a date of Mar. 27, 2007; pp. 1-4; The New York Times Company; located at: http://www.nytimes.com/2007/03/27/science/27robo.html?ex=1332648000&en=d4541141c174b454&ei=5124&partner=digg&exprod=digg; printed on Mar. 27, 2007.

"Spider pill to seek out diseases"; PhysOrg.com; bearing a date of Oct. 16, 2009 and 2009; p. 1; located at http://www.physorg.com/news174893082.html.

Sun et al.; "A Miniature RF Communication System for Micro Gastrointestinal Robots"; Journal of Medical Engineering & Technology; bearing a date of 2003; pp. 160-163; vol. 27.

(56) References Cited

OTHER PUBLICATIONS

Suzumori et al.; "Micro Inspection Robot for 1-in Pipes"; IEEE/ASME Transactions on Mechatronics; bearing dates of Sep. 1999 and 1999; pp. 286-292; vol. 4, No. 3; IEEE.

Tang et al.; "Cerebral Vascular Tree Matching of 3D-RA Data Based on Tree Edit Distance"; Medical Imaging and Augmented Reality; bearing a date of 2006; pp. 116-123.

The Biomedical Engineering Handbook, Second Edition; bearing a date of 2000; pp. IV-1-43-31; vol. I; CRC Press LLC.

The Biomedical Engineering Handbook, Second Edition; bearing a date of 2000; pp. V-1-51-9; vol. I; CRC Press LLC.

Thrun, Sebastian; "Learning Metric-Topological Maps for Indoor Mobile Robot Navigation"; Artificial Intelligence; bearing a date of 1998; pp. 21-71; vol. 99; Elsevier Science B.V.

Thrun, Sebastian; "Probabilistic Algorithms in Robotics"; AI Magazine; bearing dates of Winter 2000 and 2000; pp. 93-109; vol. 21, No. 4; American Association for Artificial Intelligence.

Thrun, Sebastian; "Robotic Mapping: A Survey"; Exploring Artificial Intelligence in the New Millenium; bearing a date of Feb. 2002; pp. 1-29 (31 total pages); Morgan Kaufmann.

Thrun et al.; "A Real-Time Algorithm for Mobile Robot Mapping With Applications to Multi-Robot and 3D Mapping"; IEEE International Conference on Robotics and Automation; bearing a date of Apr. 2000; pp. 1-8.

Thrun et al.; "Integrating Topological and Metric Maps for Mobile Robot Navigation: A Statistical Approach"; pp. 1-7.

Tomatis et al.; "Simultaneous Localization and Map Building: A Global Topological Model with Local Metric Maps"; Robotics Autonomous Systems; bearing a date of 2003; pp. 1-6; vol. 44.

Tsuruta et al.; "Control Circuit in an In-Pipe Wireless Micro Inspection Robot"; IEEE Xplore; bearing dates of 2000 and 2005; pp. 59-64 (Only the Abstract is being provided); IEEE; located at: http://ieeexplore.ieee.org/xpls/abs_all.jsp?arnumber=903290; printed on Apr. 23, 2007.

Ulrich et al.; "Appearance-Based Place Recognition for Topological Localization"; IEEE International Conference on Robotics and Automation; bearing a date of Apr. 2000; pp. 1023-1029.

Verheye et al.; "Selective Clearance of Macrophages in Atherosclerotic Plaques by Autophagy"; Journal of the American College of Cardiology; bearing dates of Feb. 13, 2007 and 2007; pp. 706-715; vol. 49, No. 6; Elsevier Inc.

Wacharasindhu et al.; "Radioisotope microbattery based on liquid semiconductor"; Applied Physics Letters; bearing dates of Dec. 11, 2008, Jun. 9, 2009, Jul. 6, 2009, Dec. 8, 2009 and 2009; pp. 014103-1-014103-3; vol. 95; American Institute of Physics.

Wakimoto et al.; "A Micro Snake-Like Robot for Small Pipe Inspection"; International Symposium on Micromechatronics and Human Science; bearing a date of 2003; pp. 303-308; IEEE.

Wang et al.; "A MEMS-based Air Flow Sensor with a Free-standing Micro-cantilever Structure"; Sensors; bearing dates of Aug. 27, 2007, Oct. 10, 2007, Oct. 17, 2007, and 2007; pp. 2389-2401; vol. 7; MDPI.

Watson et al.; "Piezoelectric ultrasonic resonant motor with stator diameter less than 250 μm: the *Proteus* motor"; Journal of Micromechanics and Microengineering; bearing dates of Sep. 25, 2008, Nov. 18, 2008, Jan. 20, 2009, and 2009; pp. 1-5; vol. 19; IOP Publishing Ltd.

Weingandt et al.; "Autofluorescence spectroscopy for the diagnosis of cervical intraepithelial neoplasia"; BJOG: an International Journal of Obstetrics and Gynaecology; bearing dates of Aug. 2002 and 2002; pp. 947-951; vol. 109; RCOG.

Xi et al.; "Self-assembled microdevices driven by muscle"; Nature Materials; bearing dates of Feb. 2005 and 2005; pp. 180-184 (10 pages total); vol. 4; Nature Publishing Group.

Yang et al.; "Power generation with laterally packaged piezoelectric fine wires"; Nature Nanotechnology; bearing dates of Nov. 9, 2008, Jan. 2009, and 2009; pp. 34-39; vol. 4; Macmillan Publishers Limited.

Yang et al.; "Converting Biomechanical Energy into Electricity by a Muscle-Movement-Driven Nanogenerator"; Nano Letters; bearing dates of Dec. 25, 2008, Jan. 31, 2009, and 2009; pp. 1201-1205; vol. 9, No. 3; American Chemical Society.

Yu et al.; "System for the analysis and visualization of large 3D anatomical trees"; Computers in Biology and Medicine; bearing dates of Oct. 6, 2006, May 31, 2007, Jun. 4, 2007, and 2007; pp. 1802-1820; vol. 37; Elsevier Ltd.

Zhao et al.; "Physicist Develops Natural Motor Technique"; PhysOrg.com; bearing dates of Apr. 21, 2007 and 2007; 1 page; United Press International; located at: http://www.physorg.com/news96357975.html; printed on Apr. 23, 2007.

Zheng et al.; "Design and Fabrication of a Micro Coulter Counter with Thin Film Electronics"; Proceedings of 2006 International Conference on Microtechnologies in Medicine and Biology; bearing dates of May 9-12, 2006 and 2006; pp. 16-19; IEEE.

Zhu et al.; "Flattening Maps for the Visualization of Multibranched Vessels"; IEEE Transactions on Medical Imaging; bearing dates of Feb. 10, 2004, Sep. 27, 2004, Feb. 2005, and 2005; pp. 191-198; vol. 24, No. 2; IEEE.

Zrimec et al.; "3D Modelling and Visualization of the Human Lung"; Proceedings of the 2nd International Symposium on 3D Data Processing, Visualization, and Transmission (3DPVT'04); bearing a date of 2004; pp. 110-115; IEEE.

Zyga, Lisa; "Microswimmer Propels Itself With Near-Zero Friction"; PhysOrg.com; bearing dates of Jun. 4, 2007 and 2007; pp. 1-2; PhyOrg.com; located at: http://www.physorg.com/news100176842.html; printed on Jun. 6, 2007.

U.S. Appl. No. 11/417,898, Hillis et al.
U.S. Appl. No. 11/454,343, Jung et al.
U.S. Appl. No. 11/455,010, Jung et al.
U.S. Appl. No. 11/478,368, Ferren et al.
U.S. Appl. No. 11/485,619, Hillis et al.
U.S. Appl. No. 11/526,089, Jung et al.
U.S. Appl. No. 11/526,144, Jung et al.
U.S. Appl. No. 11/526,201, Jung et al.
U.S. Appl. No. 11/526,203, Jung et al.
U.S. Appl. No. 11/541,377, Jung et al.
U.S. Appl. No. 11/541,378, Jung et al.

"001_08 Comparison of Capsule Cameras: M2A (Given Imaging) vs. NORIKA3 (RF System lab)" RF System lab; bearing dates of 2001-2004; pp. 1-2; located at http://www.rfnorika.com/eng/system/sys_008.html; printed on May 4, 2006.

U.S. Appl. No. 11/541,448, Jung et al.
U.S. Appl. No. 11/541,452, Jung et al.
U.S. Appl. No. 11/541,492, Jung et al.

Agarwal, Abhishek K.; Atencia, Javier; Beebe, David J.; Jiang, Hongrui; "Magnetically-driven temperature-controlled microfluidic actuators"; pp. 1-5; located at: http://www.unl.im.dendai.ac.jp/INSS2004/INSS2004_papers/OralPresentations/C2.pdf.

"Agile new plastics change shape with heat"; MIT News Office; Nov. 20, 2006; pp. 1-4; Massachusetts Institute of Technology; printed on Nov. 22, 2006; located at http://web.mit.edu/newsoffice/2006/tripleshape.html.

"Agile new plastics change shape with heat"; MIT Tech Talk; Nov. 22, 2006; p. 5 (1 page).

Ammor, Mohammed Salim; "Short Communication: Recent Advances in the Use of Intrinsic Fluorescence for Bacterial Identification and Characterization"; Journal of Fluorescence; bearing a dates of Dec. 20, 2006 and Mar. 12, 2007; pp. 1-5; Springer.

Ananthaswamy, Anil; "First robot moved by muscle power"; bearing a date of Feb. 27, 2004; pp. 1-3; New Scientist; located at http://www.newscientist.com/article.ns?id=dn4714; printed on Sep. 12, 2006.

Anderson, John G.; Rowan, Neil J.; MacGregor, Scott J.; Fouracre, Richard A.; Farish, Owen; "Inactivation of Food-Borne Enteropathogenic Bacteria and Spoilage Fungi Using Pulsed-Light"; IEEE Transactions on Plasma Science; bearing a date of Feb. 2000; pp. 83-88; vol. 28, No. 1; IEEE.

Andrejevic-Blant, Snezana; Major, Attila; Ludicke, Franck; Ballini, Jean-Pierre; Wagnieres, Georges; Van Den Bergh, Hubert; Pelte, Marie-Francoise; "Time-Dependent Hexaminolaevulinate Induced Protoporphyrin IX Distribution After Topical Application in Patients With Cervical Intraepithelial Neoplasia: A Fluoresence Microscopy Study"; Lasers in Surgery and Medicine; bearing a date of 2004; pp. 276-283; vol. 35; Wiley-Liss, Inc.

(56) References Cited

OTHER PUBLICATIONS

"Antimicrobial Resistance—Selected Areas of Scientific Research"; National Institute of Allergy and Infectious Diseases; pp. 52-55.
Asari, Vijayan K.; Kumar, Sanjiv; Kassim, Irwan M.; "A Fully Autonomous Microrobotic Endoscopy System"; Journal of Intelligent and Robotic Systems; bearing a date of 2000; pp. 325-341; vol. 28; Kluwer Academic Publishers.
"BacLight™ Bacterial Stains—Product Information"; Molecular Probes; bearing a date of Mar. 4, 2004; pp. 1-3.
Bartels, Kenneth E.; Morton, Rebecca J.; Dickey, D. Thomas; Stair, E.L.; Payne, Marie E.; Schafer, Steven A.; "Use of Diode Laser Energy (808 nm) for Selective Photothermolysis of Contaminated Wounds"; SPIE; bearing a date of May 1995; pp. 602-606; vol. 2395; SPIE.
Behkam, Bahareh; Sitti, Metin; "Towards Hybrid Swimming Microrobots: Bacteria Assisted Propulsion of Polystyrene Beads"; Proceedings of the 28$^{th}$ IEEE EMBS Annual International Conference; bearing dates of Aug. 30, 2006-Sep. 3, 2006 and 2006; pp. 2421-2424; IEEE.
Bekassy, Zoltan; "Long-Term Follow-Up of Cervical Intraepithelial Neoplasia Treated With Minimal Conization by Carbon Dioxide Laser"; Lasers in Surgery and Medicine; bearing a date of 1997; pp. 461-466; vol. 20; Wiley-Liss, Inc.
Berlinger, Norman T.; "Robotic Surgery—Squeezing into Tight Places"; New England Journal of Medicine; bearing dates of May 17, 2006, May 18, 2006, and 2006; pp. 2099-2101; Massachusetts Medical Society; located at www.nejm.org.
Bezrouk, A.; Hanuš, J.; Záhora, J.; "Temperature Characteristics of Nitinol Spiral Stents"; Scripta Medica (BRNO); bearing a date of Oct. 2005; pp. 219-226; vol. 78, No. 4.
Bialek, Ralf; Binder, Nicole; Dietz, Klaus; Knobloch, Jurgen; Zelck, Ulrike E.; "Comparison of Autofluorescence and Iodine Staining for Detection of Isospora Belli in Feces"; Am J. Trop. Med. Hyg.; bearing a date of 2002; pp. 304-305; vol. 67, No. 3; The American Society of Tropical Medicine and Hygiene.
Bialek, William; Rieke, Fred; De Ruyter Van Steveninck, Rob R.; Warland, David; "Reading a Neural Code"; Science; bearing a date of Jun. 28, 1991; pp. 1854-1857; vol. 252.
Blanca, Carlo Mar; Saloma, Caesar; "Two-Color Excitation Fluorescence Microscopy Through Highly Scattering Media"; Applied Optics; bearing a date of Jun. 1, 2001; pp. 2722-2729; vol. 40, No. 16; Optical Society of America.
Borovicka, J.; Fischer, J.; Neuweiler, J.; Netzer, P.; Gschossmann, J.; Ehmann, T.; Bauerfeind, P.; Dorta, G.; Zurcher, U.; Binek, J.; Meyenberger, C.; "Original Article: Autofluorescence Endoscopy in Surveillance of Barrett's Esophagus: A Multicenter Randomized Trial on Diagnostic Efficacy"; bearing a date of 2006; pp. 867-872; vol. 38, No. 9; Georg Thieme Verlag KG Stuttgart.
Bouchard, Alain; Frechette, Julie; Vernon, Marcia; Cormier, Jean-Francois; Beaulieu, Rene; "Optical Characterization of *Pseudomonas fluorescens* on Meat Surfaces Using Time-Resolved Fluorescence"; Journal of Biomedical Optics; bearing a date of Jan./Feb. 2006; pp. 014011, 1-7; vol. 11, No. 1.
Braichotte, Daniel R.; Wagnieres, Georges A.; Bays, Roland; Monnier, Phillipe; Van Den Bergh, Hubert E.; "Clinical Pharmacokinetic Studies of Photofrin by Fluorescence Spectroscopy in the Oral Cavity, the Esophagus, and the Bronchi"; Cancer; bearing a date of Jun. 1, 1995; pp. 2768-2778; vol. 75, No. 11.
Breslin, Tara M., MD; Xu, Fushen, MD; Palmer, Gregory M., MS; Zhu, Changfang, MS; Gilchrist, Kennedy W., MD.; Ramanujam, Nirmala, PhD; "Autofluorescence and Diffuse Reflectance Properties of Malignant and Benign Breast Tissues"; Annals of Surgical Oncology; bearing a date of 2003; pp. 65-70; vol. 11, No. 1; Society of Surgical Oncology, Inc.
Broer, Nina M.; Liesenhoff, Tim; Horch, Hans-Henning; "Laserinduced Fluorescence Spectroscopy for Real-Time Tissue Differentiation" Medical Laser Application; bearing a date of 2004; pp. 45-53; vol. 19; Elsevier—Urban & Fischer; located at http://www.elsevier.de/lasermed.

Bucher, Volker; Graf, Michael; Stelzle, Martin; Nisch, Wilfried; "Low-Impedance Thin-Film Polycrystalline Silicon Microelectrodes for Extracellular Stimulation and Recording"; Biosensors and Bioelectronics; bearing a date of 1999; pp. 639-649; vol. 14; Elsevier Science S.A.; located at: www.elsevier.com/locate/bios.
Burke, Thomas G.; Malak, Henryk; Gryczynski, Ignacy; MI, Zihou; Lakowicz, Joseph R.; "Fluorescence Detection of the Anticancer Drug Topotecan in Plasma and Whole Blood by Two-Photon Excitation"; Analytical Biochemistry; bearing a date of 1996; pp. 266-270; vol. 242; Academic Press, Inc.
Burr, Jennifer; Hay, David; Ludgate, Susanne; "Interventional Technologies for Tissue Volume Reduction: A Primer"; Review Body for Interventional Procedures; bearing a date of Oct. 2004; pp. 1-10 plus i-ii.
Butson, Christopher R.; McIntyre, Cameron C.; "Role of Electrode Design on the Volume of Tissue Activated During Deep Brain Stimulation"; Journal of Neural Engineering; bearing a date of 2006; vol. 3; pp. 1-8; IOP Publishing Ltd.
Cabredo, Susana; Parra, Alejandro; Anzano, Jesus; "Original Paper: Bacteria Spectra Obtained by Laser Induced Fluorescence"; J. Fluoresc; bearing a date of 2007; pp. 171-180; vol. 17; Springer.
Cambaliza, MA. Obiminda; Saloma, Caesar; "Advantages of Two-Color Excitation Fluorescence Microscopy with Two Confocal Excitation Beams"; Optics Communications; bearing a date of Oct. 1, 2000; pp. 25-35; vol. 184; Elsevier Science B.V.; located at: www.elsevier.com/locate/optcom.
Chan, You; Lai, Chern-Hsiung; "Original Article: Bactericidal Effects of Different Laser Wavelengths on Periodontopathic Germs in Photodynamic Therapy"; Lasers in Medicine and Science; bearing a date of 2003; pp. 51-55; vol. 18; Springer-Verlag.
Chang, Suk Tai; Paunov, Vesselin N.; Petsev, Dimiter N.; Velev, Orlin D.; "Articles: Remotely Powered Self-Propelling Particles and Micropumps Based on Miniature Diodes"; Nature Materials; bearing a date of 2007; pp. 1-6; Nature Publishing Group; located at: www.nature.com/naturematerials.
Chen, Haitao; Ebner, Armin D.; Ritter, James A.; Kaminski, Michael D.; Rosengart, Axel J.; "Sequestration of Blood-Borne Magnetic Drug Carrier Particles Using Magnetizable Intravascular Stents"; Collaborative Investigators for Applied Nanotechnology in Medicine; pp. 1; Chicago, Illinois.
Chen, Ting; Barton, Scott Calabrese, Binyamin, Gary; Gao, Zhiqiang; Zhang, Yongchao, Kim, Hyug-Han; Heller, Adam; "A Miniature Biofuel Cell"; Journal of the American Chemical Society; Aug. 11, 2001; pp. 8630-8631; vol. 123; 2001 American Chemical Society.
Chiyo, Masako; Shibuya, Kiyoshi; Hoshino, Hidehisa; Yasufuku, Kazuhiro; Sekine, Yasuo; Iizasa, Toshihiko; Hiroshima, Kenzo; Fujisawa, Takehiko; "Effective Detection of Bronchial Preinvasive Lesions by a New Autofluorescence Imaging Bronchovideoscope System"; Lung Cancer; bearing a date of 2005; pp. 307-313; vol. 48; Elsevier Ireland Ltd; located at: www. Elsevier.Com/locate/lungcan.
Christensen, Bill; "Musclebot: Microrobot with a Heart"; Technovelgy.com; pp. 1-2; bearing a date of Feb. 27, 2004; located at http://www.technovelgy.com/ct/Science-Fiction-News.asp?NewsNum=46; printed on Sep. 12, 2006.
Christensen, Bill; "Propulsion System for 'Fantastic Voyage' Robot"; Technovelgy.com; pp. 1-4; Technovelgy.com; located http://www.technovelgy.com/ct/Science-Fiction-News.asp?NewsNum=811; printed on Jan. 4, 2007.
Chung, Alice; Karlan, Scott; Lindsley, Erik; Wachsmann-Hogiu, Sebastian; Farkas, Daniel L.; "In Vivo Cytometry: A Spectrum of Possibilities" Cytometry Part A; bearing a date of 2006; pp. 142-146; vol. 69A; International Society for Analytical Cytology.
Chung, Alice, MD; Wachsmann-Hogiu, Sebastian, PhD; Zhao, Tong, PhD; Xiong, Yizhi, PhD; Joseph, Anika; Farkas, Daniel L., PhD; "Technology Focus: Advanced Optical Imaging Requiring No Contrast Agents—A New Armamentarium for Medicine and Surgery"; Current Surgery; bearing a date of May/Jun. 2005; pp. 365-370; vol. 62, No. 3; Association of Program Directors in Surgery; Elsevier, Inc.
Clavero, M. Rocelle S.; Monk, J. David; Beuchat, Larry R.; Doyle, Michael P.; Brackett, Robert E.; "Inactivation of *Escherichia coli* O157:H7, *Salmonellae*, and *Campylobacter jejuni* in Raw Ground Beef by Gamma Irradiation"; Applied and Environmental Microbiol-

(56) References Cited

OTHER PUBLICATIONS ogy; bearing a date of Jun. 1994; pp. 2069-2075; vol. 60, No. 6; American Society for Microbiology.

Coburn, J.T.; Lytle, F.E.; "Identification of Bacterial Pathogens by Laser Excited Fluorescence"; Anal. Chem; bearing a date of 1985; pp. 1669-1673; vol. 57; American Chemical Society.

Collier, Mark; "Recognition and Management of Wound Infections"; World Wide Wounds; bearing a date of Jan. 2004; pp. 1-10; located at: http://www.worldwidewounds.com/2004/january/Collier/Management-of-Wound-infections.html.

Costamagna; Guido M.D.; "PillCam™ SB Capsule Endoscopy"; GivenImaging.com; bearing dates of 2001-2006; pp. 1-4; located at http://www.givenimaging.com/Cultures/en-US/Given/English/Products/CapsuleEndoscopy/; printed on May 4, 2006.

Cui, Xinyan; Hetke, Jamille F.; Wiler, James A.; Anderson, David J.; Martin, David C.; "Electrochemical Deposition and Characterization of Conducting Polymer Polypyrrole/PPS on Multichannel Neural Probes"; Sensors and Actuators A Physical; bearing a date of 2001; pp. 8-18; vol. 93; Elsevier Science B.V.; located at: www.elsevier.com/locate/sna.

Dacosta, R.S.; Andersson, H.; Cirocco, M.; Marcon, N.E.; Wilson, B.C.; "Original Article: Autofluorescence Characterisation of Isolated Whole Crypts and Primary Cultured Human Epithelial Cells from Normal, Hyperplastic, and Adenomatous Colonic Mucosa"; JCP Online; bearing a date of 2005; pp. 766-774; vol. 58; located at: http://www.bmjjournals.com/cgi/reprintform.

Dario, P.; Carrozza, M.C.; Lencioni, L.; Magnani, B.; D'Attanasio, S.; "A Micro Robotic System for Colonoscopy"; Proceedings of the 1997 IEEE International Conference on Robotics and Automation; bearing dates of Apr. 1997 and 1997; pp. 1567-1572; IEEE.

Davies, Mark A.; Hogan, Michael P.; "Body-Site Variation of Skin Autofluorescence"; Applied Spectroscopy; bearing a date of 2001; pp. 1489-1494; vol. 55, No. 11; Society for Applied Spectroscopy.

Dellinger, E. Patchen; Gross, Peter A.; Barrett, Trisha L.; Krause, Peter J.; Martone, William J.; McGowan, John E. Jr.; Sweet, Richard L.; Wenzel, Richard P.; "Quality Standard for Antimicrobial Prophylaxis in Surgical Procedures"; Clinical Infectious Diseases; bearing a date of 1994; pp. 422-427; vol. 18; The University of Chicago.

Demos, Stavros G.; Gandour-Edwards, Regina; Ramsamooj, Rajen; deVere White, Ralph; "Near-Infrared Autofluorescence Imaging for Detection of Cancer"; Journal of Biomedical Optics; bearing a date of May/Jun. 2004; pp. 587-592; vol. 9, No. 3.

Desimone, Noelle A.; Christiansen, Cory; Dore, David; "Research Report: Bactericidal Effect of 0.95-mW Helium—Neon and 5-mW Indium—Gallium—Aluminum-Phosphate Laser Irradiation at Exposure Times of 30, 60, and 120 Seconds on Photosensitized *Staphylococcus aureus* and *Pseudomonas aeruginosa* In Vitro"; Physical Therapy; bearing a date of Sep. 1999; pp. 839-846; vol. 79, No. 9.

De Veld, Diana C.G.; Skurichina, Marina; Witjes, Max J.H.; Duin, Robert P.W.; Sterenborg, Henricus J.C.M.; Roodenburg, Jan L.N.; "Autofluorescence and Diffuse Reflectance Spectroscopy for Oral Oncology"; Lasers in Surgery and Medicine; bearing a date of 2005; pp. 356-364; vol. 36; Wiley-Liss, Inc.

Dillier, Norbert; Lai, Wai Kong; Almqvist, Bengt; Frohne, Carolin; Müller-Deile, Joachim; Stecker, Matthias; Von Wallenberg, Ernst; "Measurement of the Electrically Evoked Compound Action Potential Via a Neural Response Telemetry System"; Annals of Otology Rhinology and Laryngology; bearing a date of May 2002; pp. 407-414; vol. 111, No. 5; Annals Publishing Company.

Dongxiang, Chi; Guozheng, Yan; "An earthworm based miniature robot for intestinal inspection"; Proceedings of SPIE; bearing dates of Nov. 7-9, 2001; pp. 396-400; vol. 4601; SPIE.

Donoghue, John P.; "Review: Connecting Cortex to Machines: Recent Advances in Brain Interfaces"; Nature Neuroscience Supplement; bearing a date on Nov. 2002; pp. 1085-1088; vol. 5; Nature Publishing Group; located at: http://www.nature.com/natureneuroscience.

Drepper, Thomas; Eggert, Thorsten; Circolone, Franco; Heck, Achim; Kraub, Ulrich; Guterl, Jan-Karl; Wendorff, Marion; Losi, Aba; Gartner, Wolfgang; Jaeger, Karl-Erich; "Brief Communications: Reporter Proteins for in Vivo Fluorescence Without Oxygen"; Nature Biotechnology; bearing a date of 2007; pp. 443-445; vol. 25; Nature Publishing Group; located at: http://www.nature.com/naturebiotechnology.

Eker, C.; Montan, S.; Jaramillo, E.; Koizumi, K.; Rubio, C.; Andersson-Engels, S.; Svanberg. K.; Svanberg. S.; Slezak, P.; "Clinical Spectral Characterisation of Colonic Mucosal Lesions Using Autofluorescence and δ Aminolevulinic Acid Sensitisation"; Gut; bearing a date of Apr. 1999; pp. 511-518; vol. 44, No. 4.

Fang, Zi-Ping; Mortimer, J. Thomas; "Selective Activation of Small Motor Axons by Quasitrapezoidal Current Pulses"; IEEE Transactions on Biomedical Engineering; bearing a date of Feb. 1991; pp. 168-174; vol. 38, No. 2; IEEE.

Farkas, Daniel L.; Becker, Dorothea; "Review: Innovative Technology: Applications of Spectral Imaging: Detection and Analysis of Human Melanoma and Its Precursors"; Pigment Cell Res; bearing a date of 2001; pp. 2-8; vol. 14, No. 1; Pigment Cell Res.; located at: http://www.blackwell-synergy.com/doi/abs/10.1034/j.1600-0749.2001.140102.x.

Fiaccabrino, G.C.; Tang, X.-M.; Skinner, N.; De Rooij, N.F.; Koudelka-Hep, M.; "Electrochemical Characterization of Thin-Film Carbon Interdigitated Electrode Arrays"; Analytica Chimica Acta; bearing a date of 1996; pp. 155-160; vol. 326; Elsevier Science B.V.

Finer, Gal; Landau, Daniel; "Urinary Tract Infections: Review: Pathogenesis of Urinary Tract Infections With Normal Female Anatomy"; The Lancet Infectious Diseases; bearing a date of Oct. 2004; pp. 631-635; vol. 4; located at: http://infection.thelancet.com.

Fireman, Zvi; Paz, D.; Kopelman, Y.; "Capsule Endoscopy: Improving Transit Time and Image View"; World Journal of Gastroenterology; bearing a date of 2005; pp. 5863-5866; vol. 11, No. 37; WJG Press and Elsevier Inc.

Freitas Jr., Robert A.; "8.2.1.2 Arteriocenous Microcirculation"; "9.4.3.5 Legged Ambulation"; "9.4.3.6 Tank-Tread Rolling"; "9.4.3.7 Amoeboid Locomotion"; "9.4.3.8 Inchworm Locomotion"; "Nanomedicine vol. I: Basic Capabilities"; bearing a date of 1999; pp. 211-214, pp. 316-318; Landes Bioscience; Georgetown, Texas, USA.

Fujimoto, James G.; "Perspective: Focus on Optical Imaging: Optical Coherence Tomography for Ultrahigh Resolution in Vivo Imaging"; bearing a date of Nov. 2003; pp. 1361-1367; vol. 21, No. 11; Nature Publishing Group; located at: http://www.nature.com/naturebiotechnology.

Fujiya, Mikihiro; Saitoh, Yusuke; Watari, Jiro; Moriichi, Kentaro; Kohgo, Yutaka; "Future Expectations of Autofluorescence Imaging in Colonoscopy: Autofluorescence Imaging is Useful to Assess Activity of Ulerative Colitis"; Digestive Endoscopy; bearing a date of 2007; pp. S145-S149; vol. 19, No. Suppl. 1; Japan Gastroenterological Endoscopy Society.

Gabrecht, Tanja; Radu, Alexandre; Zellweger, Matthieu; Lovisa, Blaise; Goujon, Didier; Grosjean, Pierre; Van Den Bergh, Hubert; Monnier, Philippe; Wagnieres, Georges; "Invited Paper: Detection of Early Bronchial Cancer by Autofluorescence: Results in Patients with H&N Cancer"; Diagnostic Optical Spectroscopy in Biomedicine IV: Procedures of SPIE-OSA; bearing a date of 2007; pp. 66280c-1-66280c-8; vol. 6628; SPIE-OSA.

Ganz, Robert A., MD; Viveiros, Jennifer, BS; Ahmad, Aamir, MD; Ahmadi, Atosa, BS; Khalil, Ayesha, MD; Tolkoff, M. Joshua, MS; Nishioka, Norman S., MD; Hamblin, Michael R., PhD; "*Helicobacter pylori* in Patients Can Be Killed by Visible Light"; Lasers in Surgery and Medicine; bearing a date of 2005; pp. 260-265; vol. 36; Wiley-Liss, Inc.

Gatto, Rodolfo; D'Amico, Enrico; Mantulin, William; Gratton, Enrico; Charbel, Fady; "Optical Microprobe for Blood Clot Detection"; Biomedical Topical Meeting in Fort Lauderdale, Florida; bearing a date of Mar. 19, 2006; pp. 1-3; Optical Society of America.

Giana, Hector Enrique; Silveira Jr.; Zangaro, Renato Amaro; Pacheco, Marcos Tadeu T.; "Rapid Identification of Bacterial Species by Fluorescence Spectroscopy and Classification Through Principal Components Analysis"; Journal of Fluorescence; bearing a date of Nov. 2003; pp. 489-493; vol. 13, No. 6; Plenum Publishing Corporation.

(56) References Cited

OTHER PUBLICATIONS

Gibson, S.C.; Byrne, D.S.; McKay, A.J.; "Original Article: Ten-Year Experience of Carbon Dioxide Laser Ablation as Treatment for Cutaneous Recurrence of Malignant Melanoma"; British Journal of Surgery; bearing a date of 2004; pp. 893-895; vol. 91; John Wiley & Sons Ltd.

Gilbey, A.M.; Burnett, D.; Coleman, R.E.; Holen, I.; "The Detection of Circulating Breast Cancer Cells in Blood"; JCP Online; bearing a date of 2004; pp. 903-911; vol. 57; located at: www.jclinpath.com.

Gillenwater, Ann; Jacob, Rhonda; Ganeshappa, Ravi; Kemp, Bonnie; El-Naggar, Adel K.; Palmer, J. Lynn; Clayman, Gary; Mitchell, Michele Follen; Richards-Kortum, Rebecca; "Original Article: Noninvasive Diagnosis of Oral Neoplasia Based on Fluorescence Spectroscopy and Native Tissue Autofluorescence"; Arch Otolaryngol Head Neck Surg; bearing a date of Nov. 1998; pp. 1251-1258; vol. 124; American Medical Association.

Gitter, Alfred H.; Fromm, Michael; Schulzke, Jörg-Dieter; "Impedance Analysis for the Determination of Epithelial and Subepithelial Resistance in Intestinal Tissues"; Journal of Biochemical and Biophysical Methods, bearing a date of 1998; pp. 35-46; vol. 37; Elsevier Science B.V.

Glazier, Scott A.; Weetall, Howeard H.; "Autofluoresecence Detection of *Escherichia coli* on Silver Membrane Filters"; Journal of Microbiological Methods; bearing a date of 1994; pp. 23-27; vol. 20; Elsevier Science B.V.

Goda, Yukiko; Colicos, Michael A.; "Protocol: Photoconductive Stimulation of Neurons Cultured on Silicon Wafers"; Nature Protocols; bearing a date of 2006; pp. 461-467; vol. 1, No. 1; Nature Publishing Group; located at: http://www.nature.com/natureprotocols.

Gozani, Shai N.; Miller, John P.; "Optimal Discrimination and Classification of Neuronal Action Potential Waveforms from Multiunit, Multichannel Recordings Using Software-Based Linear Filters"; IEEE Transactions on Biomedical Engineering; bearing a date of Apr. 1994; pp. 358-372; vol. 41, No. 4; IEEE.

Graham, Anna R.; "Fungal Autofluorescence with Ultraviolet Illumination"; Brief Scientific Reports: A.J.C.P.; bearing a date of Feb. 1983; pp. 231-234; American Society of Clinical Pathologists.

Gray, Charles M.; Maldonado, Pedro E.; Wilson, Mathew; McNaughton, Bruce; "Tetrodes Markedly Improve the Reliability and Yield of Multiple Single-Unit Isolation from Multi-Unit Recordings in Cat Striate Cortex"; Journal of Neuroscience Methods; bearing a date of 1995; pp. 43-54; vol. 63; Elsevier Science B.V.

Green, Christopher F.; Scarpino, Pasquale V.; Jensen, Paul; Jensen, Nancy J.; Gibbs, Shawn G.; "Note/Note: Disinfection of Selected *Aspergillus* spp. Using Ultraviolet Germicidal Irradiation"; Can. J. Microbiol.; bearing a date of 2004; pp. 221-224; vol. 50; NRC Canada.

Gronqvist, Anders; Wistrom, Johan; Axner, Ove; Monsen, Johan; "Bactericidal Effect of Pulsed 1,064 nm Nd: YAG Laser Light on *Staphylococcus epidermidis* Is of Photothermal Orgin: An In Vitro Study"; Lasers in Surgery and Medicine: bearing a date of 2000; pp. 336-340; vol. 27; Wiley-Liss, Inc.

Gryczynski, Ignacy; Malak, Henryk; Lakowicz, Joseph R.; "Two-Color Two-Photon Excitation of Indole"; Center for Fluorescence Spectroscopy and Medical Biotechnology Center; bearing a date of 1996; pp. 97-101; John Wiley & Sons, Inc.

Guezennec, C.Y.; Lienard, F.; Louisy, F.; Renault, G.; Tusseau, M.H.; Portero, P.; "In Situ NADH Laser Fluorimetry During Muscle Contraction in Humans"; European Journal of Applied Physiology and Occupational Physiology; bearing a date of 1991; pp. 36-42; vol. 63; Sprinter-Verlag.

Guffey, J. Stephen; Wilborn, Jay; "Effects of Combined 405-nm and 880-nm Light on *Staphylococcus aureus* and *Pseudomonas aeruginosa* in Vitro"; Photomedicine and Laser Surgery; bearing a date of 2006; pp. 680-683; vol. 24, No. 6; Mary Ann Liebert, Inc.

Gupta, Pradeep Kumar; Majumder, Shovan Kumar; Uppal, Abha; "Breast Cancer Diagnosis Using $N_2$ Laser Excited Autofluorescence Spectroscopy"; Lasers in Surgery and Medicine; bearing a date of 1997; pp. 417-422; vol. 21; Wiley-Liss, Inc.

Hagleitner, C.; Hierlemann, A.; Lange, D.; Kummer, A.; Kerness, N.; Brand, O.; Baltes, H.; "Smart single-chip gas sensor microsystem"; Nature; Nov. 15, 2001; pp. 293-296; vol. 414; Macmillan Magazines Ltd.; www.nature.com.

Hamblin, Michael R.; O'Donnell, David A.; Murthy, Naveen; Contag, Christopher H.; Hasan, Tayyaba; "Rapid Control of Wound Infections by Targeted Photodynamic Therapy Monitored by In Vivo Bioluminescence Imaging"; Photochemistry and Photobiology; bearing a date of Jan. 2002; pp. 51-57; vol. 75, No. 1; American Society for Photobiology.

Hammer-Wilson, Marie J.; Gray, Rodger M.; Wilder-Smith, Petra; Meister, Friedrich; Osann, Kathy; Wilder-Smith, Clive H.; "Fluorescence Diagnostics of *Helicobacter pylori*-Infected Human Gastric Mucosa: Establishing Technique and Validity"; Scandinavian Journal of Gastroenterology; bearing a date of 2007; pp. 941-950; vol. 42, No. 8; Taylor & Francis; located at: http://hx.doi.org/10.1080/00365520701210797.

Hamblin, Michael R.; Viveiros, Jennifer; Yang, Changming; Ahmadi, Atosa; Ganz, Robert A.; Tolkoff, M. Joshua; "*Helicobacter pylori* Accumulates Photoactive Porphyrins and Is Killed by Visible Light"; Antimicrobial Agents and Chemotherapy; bearing a date of Jul. 2005; pp. 2822-2827; vol. 49, No. 7; American Society for Microbiology.

Hancock, Patrick; Curry, Randy D.; McDonald, Kenneth F.; Altgilbers, Larry; "Megawatt, Pulsed Ultraviolet Photon Sources for Microbial Inactivation"; IEEE Transactions on Plasma Science; bearing a date of Oct. 2004; pp. 2026-2031; vol. 32, No. 5; IEEE.

Hanlon, E.B.; Manoharan, R.; Koo, T-W; Shafer, K.E.; Motz, J.T.; Fitzmaurice, M.; Kramer, J.R.; Itzkan, I.; Dasari, R.R.; Feld, M.S.; "Topical review: Prospects for in vivo Raman Spectroscopy"; Physics in Medicine and Biology; bearing a date of 2000; pp. R1-R59; vol. 45, No. 2; IOP Publishing Ltd.

Hanna, Darrin M.; Oakley, Barbara A.; Stryker, Gabrielle A.; "Using a System-on-Chip Implantable Device to Filter Circulating Infected Cells in Blood or Lymph"; IEEE Transactions on Biomedical Engineering; bearing dates of Jan. 25, 2003, Mar. 2003; pp. 6-13; vol. 2, No. 1; IEEE.

Hansen, Gunnar; Sundset, Arve; "Review Article: Transbronchial Laser Ablation of Benign and Malignant Tumors"; Minimally Invasive Therapy; bearing a date of 2006; pp. 4-8; vol. 15, No. 1; Taylor & Francis.

Hayden, Patrick J.; O'Connell, Niamh M.; O'Brien, David A.; O'Rourke, Paul; Lawlor, Emer; Browne, Paul V.; "Letters to the Editor: Acute Myeloid Leukemia: The Value of Autofluorescence as a Diagnostic Feature of Acute Promyelocytic Leukemia"; The Hematology Journal; bearing a date of 2006; pp. 417-418; vol. 91, No. 3; located at: http://www.haematologica.org/journal/2006/03/417.html.

Helfinstine, Shannon L.; Vargas-Aburto, Carlos; Uribe, Roberto M.; Woolverton, Christopher J.; "Inactivation of *Bacillus* Endospores in Envelopes by Electron Beam Irradiation"; Applied and Environmental Microbiology; bearing a date of Nov. 2005; pp. 7029-7032; vol. 71, No. 11; American Society for Microbiology.

Hilton, Peter J.; "Laser Induced Fluorescence Imaging of Bacteria"; SPIE; bearing a date of Dec. 1998; pp. 1174-1178; vol. 3491; The International Society for Optical Engineering.

Hilton, Peter J.; Plagmann, Manfred; "Discrimination of Bacteria on Food Using Laser Induced Bacterial Autofluorescence"; Applications of Photonic Technology; bearing a date of 2000; pp. 1020-1026; vol. 4087; SPIE.

Hjelm, H.; Hjelm, K.; Sjoquist, J.; "Protein A from *Staphylococcus aureus*. It's Isolation by Affinity Chromatography and Its Use as an Immunosorbent for Isolation of Immunoglobulins"; FEBS Letters; bearing a date of Nov. 1972; pp. 73-76; vol. 28, No. 1; North-Holland Publishing Company—Amsterdam.

Hodgkin, A.L.; Huxley, A.F.; "A Quantitative Description of Membrane Current and its Application to Conduction and Excitation in Nerve"; Journal of Physiology; bearing a date of 1952; pp. 500-544; vol. 117.

Høeg, H.D.; Slatkin, A.B.; Burdick, J.W.; Grundfest, Dr. Warren S.; "Biomechanical Modeling of the Small Intestine as Required for the Design and Operation of a Robotic Endoscope"; Proceedings ICRA '00 IEEE International Conference on Robotics and Automation; Apr. 24-28, 2000; pp. 1-8; vol. 2.

(56) References Cited

OTHER PUBLICATIONS

Hofmann, U.G.; Folkers, A.; Mösch, F.; Höhl, D.; Kindlundh, M.; Norlin, P.; "A 64(128)-Channel Multisite Neuronal Recording System"; bearing a date of 2002; pp. 1-4.

Huang, Zheng; "A Review of Progress in Clinical Photodynamic Therapy"; Technol Cancer Res Treat; bearing a date of Jun. 2005; pp. 283-293; vol. 4, No. 3; National Institutes of Health Public Access: Author Manuscript.

Ikeuchi, K.; Yoshinaka, K.; Hashimoto, S.; Tomita, N.; "Locomotion of Medical Micro Robot with Spiral Ribs Using Mucus"; Seventh International Symposium on Micro Machine and Human Science; bearing a date of 1996; pp. 217-222; IEEE.

Inmann, Andreas; Haugland, Morten; Haase, Jens; Biering-Sørensen, Fin; Sinkjaer, Thomas; "NeuroReport: Signals from Skin Mechanoreceptors used in Control of a Hand Grasp Neuroprosthesis"; Motor Systems; bearing a date of Sep. 17, 2001; pp. 2817-2819; vol. 12, No. 13; Lippincott Williams & Wilkins.

Janders, M.; Egert, U.; Stelze, M.; Nisch, W.; "Novel Thin Film Titanium Nitride Micro-Electrodes with Excellent Charge Transfer Capability for Cell Stimulation and Sensing Applications"; IEEE Engineering in Medicine and Biology Society; bearing a date of 1996; pp. 245-247; IEEE.

"Japanese Researchers Unveil Medical Mini Robot"; Yahoo! News; bearing a date of Mar. 8, 2007; pp. 1-2; Yahoo! Inc.; located at: http://news.yahoo.com/s/afp/20070308/hl_afp/afplifestyleshealthscience; printed on Mar. 8, 2007.

Jawhara, Samir; Mordon, Serge; "Original Article: Monitoring of Bactericidal Action of Laser by in Vivo Imaging of Bioluminescent E. coli in a Cutaneous Wound Infection"; Laser Med Sci; bearing a date of 2006; pp. 153-159; vol. 21; Springer-Verlag London.

Ji, Jin; Najafi, Khalil; Wise, Kensall D.; "A Low-Noise Demultiplexing System for Active Multichannel Microelectrode Arrays"; IEEE Transactions of Biomedical Engineering; bearing a date of Jan. 1991; pp. 77-81; vol. 38, No. 1; IEEE.

Jori, Giulio; Fabris, Clara; Soncin, Marina; Ferro, Stefania; Coppellotti, Olimpia; Dei, Donata; Fantetti, Lia; Chiti, Giacomo; Roncucci, Gabrio; "Photodynamic Therapy in the Treatment of Microbial Infections: Basic Principles and Perspective Applications"; Lasers in Surgery and Medicine; bearing a date of 2006; pp. 468-481; vol. 38; Wiley-Liss, Inc.

Karrer, S.; Szeimies, R.M.; Ernst, S.; Abels, C.; Baumier, W.; Landthaler, M.; "Photodynamic Inactivation of Staphylococci with 5-Aminolaevulinic Acid or Photofrin"; Lasers Med Sci; bearing a date of 1999; pp. 54-61; vol. 14; Springer-Verlag London Limited.

Kassim, Irwan; Phee, Louis; Ng, Wan S.; Gong, Feng; Dario, Paolo; Mosse, Charles A.; "Locomotion Techniques for Robotic Colonoscopy"; IEEE Engineering in Medicine and Biology Magazine; bearing dates of May/Jun. 2006 and 2006; pp. 49-56; IEEE.

Katz, A.; Alimova, Alexandra; Siddique, Masood; Savage, Howard E.; Shah, Mahendra; Rosen, Richard B.; Alfano, R.R.; "Time-Resolved and Steady-State Fluorescence Spectroscopy from Bacteria Subjected to Bactericidal Agents"; Proc. of SPIE; bearing a date of 2004; pp. 217-220; Chemical and Biological Point Sensors for Homeland Defense.

Keefe, Kristin A.; Tadir, Yona; Tromberg, Bruce; Berns, Michael; Osann, Kathryn; Hashad, Rasha; Monk, Bradley J.; "Photodynamic Therapy of High-Grade Cervical Intraepithelial Neoplasia With 5-Aminolevulinic Acid"; Lasers in Surgery and Medicine; bearing a date of 2002; pp. 289-293; vol. 31; Wiley-Liss, Inc.

Kennedy, P.R.; Bakay, R.A.E.; Moore, M.M.; Adams, K.; Goldwaithe, J.; "Direct Control of a Computer from the Human Central Nervous System"; IEEE Transactions on Rehabilitation Engineering; bearing a date of Jun. 2000; pp. 198-202; vol. 8, No. 2; IEEE.

Kim, Hea-Young; Estes, Cory R.; Duncan, Andrew G.; Wade, Brad D.; Cleary, Florine C.; Lloyd, Christopher R.; Ellis, Walther R.; Powers, Linda S.; "Homeland Security: Real-Time Detection of Microbial Contamination"; IEEE Engineering in Medicine and Biology Magazine; bearing a date of Jan./Feb. 2004; pp. 122-129; Artville, LLC.

Kobetic, Rudi; Triolo, Ronald J.; Uhlir, James P.; Bieri, Carole; Wibowo, Michael; Polando, Gordie; Marsolais, E. Byron; Davis Jr., John A.; Ferguson, Kathleen A.; Sharma, Mukut; "Implanted Functional Electrical Stimulation System for Mobility in Paraplegia: A Follow-Up Case Report"; IEEE Transactions on Rehabilitation Engineering; bearing a date of Dec. 1999; pp. 390-398; vol. 7, No. 4; IEEE.

Konig, K.; Ehlers, A.; Stracke, F.; Riemann, I.; "In Vivo Drug Screening in Human Skin Using Femtosecond Laser Multiphoton Tomography"; Skin Pharmacology and Physiology; bearing a date of May 9, 2006; pp. 78-88; vol. 19; S. Karger AG Basel.

Koenig, K.; Schneckenburger, H.; "Laser-Induced Autofluorescence for Medical Diagnosis"; Journal of Fluorescence; bearing a date of 1994; pp. 17-40; vol. 4, No. 1; Plenum Publishing Corporation.

Kosmider, Suzanne; Lipton, Lara; "Adjuvant Therapies for Colorectal Cancer"; World Journal of Gastroenterology; bearing a date of Jul. 28, 2007; pp. 3799-3805; vol. 13, No. 28; located at: www.wjgnet.com.

Krueger, Curtis; "New light on blood testing"; Oct. 20, 2006; pp. 1-2; St. Petersburg Times; printed on Oct. 24, 2006; located at http://www.sptimes.com/2006/10/20news_pf/Tampabay/New_light_on_blood_te.shtml.

Laflamme, Christian; Verreault, Daniel; Ho, Jim; Duchaine, Caroline; "Short Communication: Flow Cytometry Sorting Protocol of Bacillus Spore Using Ultraviolet Laser and Autofluorescence as Main Sorting Criterion"; J. Fluoresc; bearing a date of 2006; pp. 733-737; vol. 16; Springer.

Lakowicz, Joseph R.; Gryczynski, Ignacy; Malak, Henryk; Gryczynski, Zygmunt; "Fluorescence Spectral Properties of 2,5-Diphenyl-1,3,4-Oxadiazole with Two-Color Tow-Photon Excitation"; Journal of Physical Chemistry; bearing a date of 1996; pp. 19406-19411; vol. 100, No. 50; American Chemical Society; located at: http://pubs.acs.org/cgi-bin/abstract.cgi/jpchax/1996/100/i50/abs/jp962114w.html.

Lakowicz, Joseph R.; Gryczynski, Ignacy; Malak, Henryk; Gryczynski, Zygmunt; "Two-Color Two-Photon Excitation of Fluorescence"; Proceedings of SPIE; bearing a date of May 1997; pp. 368-380; vol. 2980; Advances in Fluorescence Sensing Technology III; located at: http://spiedl.aip.org/getabs/servlet/GetabsServlet?prog=normal&id=PSISDG002980 000001000368000001& idtype=cvips&gifs= yes.

"Lasers in Cancer Treatment: Questions and Answers"; National Cancer Institute FactSheet; bearing a date of Aug. 10, 2004; pp. 1-4; vol. 7.8.

Li, Dong; Craik, Stephen A.; Smith, Daniel W.; Belosevic, Miodrag; "Comparison of Levels of Inactivation of Two Isolates of Giardia Lamblia Cysts by UV Light"; Applied and Environmental Microbiology; bearing a date of Apr. 2007; pp. 2218-2223; vol. 73, No. 7; American Society for Microbiology.

Li, Qigui; Gerena, Lucia; Xie, Lisa; Zhang, Jing; Kyle, Dennis; Milhous, Wilbur; "Development and Validation of Flow Cytometric Measurement for Parasitemia in Cultures of P. falciparum Vitally Stained with YOYO-1"; Cytometry Part A; bearing a date of 2007; pp. 297-307; vol. 71A; Wiley-Interscience.

Lichtenstern, C.; Schmidt, J.; Knaebel, H.P. Martin, E.; Buchler, M.W.; Weigand, M.A.; "Postoperative Bacterial/Fungal Infections: A Challenging Problem in Critically Ill Patients after Abdominal Surgery"; Digestive Surgery; bearing a date of Jan. 25, 2007; pp. 1-11; vol. 24; Karger.

Lindsley, Erik; Wachman, Elliot S.; Farkas, Daniel L.; "The Hyperspectral Imaging Endoscope: A New Tool for in Vivo Cancer Detection"; Imaging, Manipulation, and Analysis of Biomolecules, Cells, and Tissues II; bearing a date of Jul. 1, 2004; pp. 75-82; vol. 5322 located at: http://spie.org/x648.xml?product_id=561884&search_text=The%20Hyperspectral%20Imaging%20Endoscope&category=All&go=submit.

Liu, Shimin; Connor, John; Peterson, Steven; Shuttleworth, C. William; Liu, Ke Jian; "Direct Visualization of Trapped Erythrocytes in Rat Brain After Focal Ischemia and Reperfusion"; Journal of Cerebral Blood Flow & Metabolism; bearing a date of 2002; pp. 1222-1230; vol. 22; Lippincott Williams & Wilkins, Inc.

(56) References Cited

OTHER PUBLICATIONS

Loeb, Gerald E.; Peck, Raymond A.; Moore, William H.; Hood, Kevin; "BION System for Distributed Neural Prosthetic Interfaces"; Medical Engineering and Physics; bearing a date of 2001; pp. 9-18; vol. 23; Elsevier Science Ltd.; located at: www.elsevier.com/locate/medengphy.

Loeb, G.E.; Peck, R.A.; Martyniuk, J.; "Toward the Ultimate Metal Microelectrode"; Journal of Neuroscience Methods; bearing a date of 1995; pp. 175-183; vol. 63; Elsevier Science B.V.

Lu, Zhao; Martel, Sylvain; "Preliminary Investigation of Bio-carriers Using Magnetotactic Bacteria"; Proceedings of the 28$^{th}$ IEEE EMBS Annual International Conference; bearing dates of Aug. 30, 2006-Sep. 3, 2006 and 2006; pp. 3415-3418; IEEE.

Maisch, Tim; "Original Article: Anti-Microbial Photodynamic Therapy: Useful in the Future?"; Lasers Med Sci; bearing a date of 2007; pp. 83-91; vol. 22; Springer-Verlag London Limited.

Mangan, Elizabeth V.; Kingsley, Dan A.; Quinn, Roger D.; Chiel, Hillel J.; "Development of a Peristaltic Endoscope"; IEEE International Conference on Robotics & Automation 2002; pp. 1-6; located at http://biorobots.cwru.edu/publications/ICRA02_Mangan_Endoscope.pdf.

Mann, Jordan L.; "Autofluorescence of Fungi: An Aid to Detection in Tissue Sections"; A.J.C.P.; bearing a date of May 1983; pp. 587-590; American Society of Clinical Pathologists.

Marcu, Laura; Fang, Qiyin; Jo, Javier A.; Papaioannou, Thanassis; Dorafshar, Amir; Reil, Todd; Qiao, Jian-Hua; Baker, J. Dennis; Freischlag, Julie A.; Fishbein, Michael C.; "In Vivo Detection of Macrophages in a Rabbit Atherosclerotic Model by Time-Resolved Laser-Induced Fluorescence Spectroscopy"; Atherosclerosis; bearing a date of 2005; pp. 295-303; vol. 181; Elsevier Ireland Ltd; located at: www.elsevier.com/locate/atherosclerosis.

Marcu, Laura; Grundfest, Warren S.; Maarek, Jean-Michel I.; "Photobleaching of Arterial Fluorescent Compounds: Characterization of Elastin, Collage and Cholesterol Time-Resolved Spectra during Prolonged Ultraviolet Irradiation"; Photochemistry and Photobiology; bearing a date of 1999; pp. 713-721; vol. 69, No. 6; American Society for Photobiology.

Marks, William B.; Loeb, Gerald E.; "Action Currents, Internodal Potentials, and Extracellular Records of Myelinated Mammalian Nerve Fibers Derived from Node Potentials"; Biophysical Journal; 1976; pp. 655-668; vol. 16.

Martel, Sylvain; "Fundamentals of high-speed piezo-actuated three-legged motion for miniature robots designed for nanometer-scale operations"; pp. 1-8.

Martel, Sylvain; "Towards MRI-Controlled Ferromagnetic and MC-1 Magnetotactic Bacterial Carriers for Targeted Therapies in Arteriolocapillar Networks Stimulated by Tumoral Angiogenesis"; Proceedings of the 28$^{th}$ IEEE EMBS Annual International Conference; bearing dates of Aug. 30, 2006-Sep. 3, 2006 and 2006; pp. 3399-3402; IEEE.

Martel, Sylvain; Mathieu, Jean-Baptiste; Felfoul, Ouajdi; Chanu, Arnaud; Aboussouan, Eric; Tamaz, Samer; Pouponneau, Pierre; "Automatic Navigation of an Untethered Device in the Artery of a Living Animal Using a Conventional Clinical Magnetic Resonance Imaging System"; Applied Physics Letters; bearing a date of 2007; pp. 114105-1-114105-3; vol. 90; American Institute of Physics.

Mateus, Carolina; Crow, Sidney A.; Ahearn, Donald G.; "Adherence of *Candida albicans* to Silicone Induces Immediate Enhanced Tolerance to Fluconazole"; Antimicrobial Agents and Chemotherapy; bearing a date of Sep. 2004; pp. 3358-3366; vol. 48, No. 9; American Society for Microbiology.

Mathieu, J-B.; Martel, S.; Yahia, L'H.; Soulez, G.; Beaudoin, G.; "MRI Systems as a Mean of Propulsion for a Microdevice in Blood Vessels"; bearing a date of 2003; pp. 3419-3422; IEEE.

Mathieu, J.B.; Soulez, G.; Martel, S.; "Potential Applications of Untethered Microdevices in the Blood Vessels within the Constraints of an MRI System"; Proceedings of the 2005 IEEE: Engineering in Medicine and Biology 27$^{th}$ Annual Conference: Shanghai, China; bearing a date of Sep. 1-4, 2005; pp. 4850-4853; IEEE.

Matsui, Takemi; Matsumura, Kouji; Hagisawa, Kousuke; Ishihara, Masayuki; Ishizuka, Toshiaki; Suzuki, Minoru; Kurita, Akira; Kikuchi, Makoto; "A Novel Ferromagnetic Thermo-Stent for Plaque Stabilization That Self-Regulates the Temperature"; IEEE Transactions on Biomedical Engineering; bearing dates of Jun. 2002 and 2002; pp. 621-623; vol. 49, No. 6; IEEE.

Matsumoto, Takayuki; Kudo, Tetsuji; Yao, Takashi; Iida, Mitsuo; "Future Expectations of Autofluorescence Imaging in Colonoscopy: Autofluorescence Imaging Colonoscopy in Ulcerative Colitis: Comparison with Conventional and Narrow-Band Imaging Colonoscopy"; Digestive Endoscopy; bearing a date of 2007; pp. S139-S144; vol. 19, No. Suppl. 1; Japan Gastroenterological Endoscopy Society.

Mayinger, Brigitte; Horner, Peter; Jordan, Martin; Gerlach, Christof; Horbach, Thomas; Hohenberger, Werner,; Hahn, Eckhart G.; "Endoscopic Fluorescence Spectroscopy in the Upper GI Tract for the Detection of GI Cancer: Initial Experience"; The American Journal of Gastroenterology; bearing a date of 2001; pp. 2616-2621; vol. 96, No. 9; Elsevier Science, Inc.

McNeal, Donald R.; "Analysis of a Model for Excitation of Myelinated Nerve"; IEEE Transactions on Biomedical Engineering; bearing a date of Jul. 1976; pp. 329-337; vol. BME-23, No. 4.

Meier, P.; Oberthür, S.; Lang, M.; "Development of a compliant device for minimally invasive surgery"; Proceedings of the 28$^{th}$ IEEE EMBS Annual International Conference; bearing dates of Aug. 30, 2006-Sep. 3, 2006 and 2006; pp. 331-334; IEEE.

"MEMS at the cutting edge®, Patent Pending"; Verimetra; pp. 1-2; located at http://www.verimetra.com/flow.htm; printed on May 4, 2006.

Menciassi, A.; Park, Jong H.; Lee, S.; Gorini, S.; Dario, P.; Park, Jong-Oh; "Robotic Solutions and Mechanisms for a Semi-Autonomous Endoscope"; Proceedings of the 2002 IEEE/RSJ International Conference on Intelligent Robots and Systems; bearing a date of 2002; pp. 1379-1384; IEEE.

Mohseni, Kamran; "Biomimetic & Bio-Inspired Aerial and Underwater Vehicles"; bearing a date of Sep. 23, 2006; pp. 1-10; printed on Jan. 4, 2007; located at http://enstrophy.colorado.edu/~mohseni/MicroVehicles1.html#UUV1#UUV1.

Molnar, Bela; Ladanyi, Andras; Tanko, Lenke; Sreter, Lydia; Tulassay, Zsolt; "Circulating Tumor Cell Clusters in the Peripheral Blood of Colorectal Cancer Patients"; Clinical Cancer Research; bearing a date of Dec. 2001; pp. 4080-4085; vol. 7.

Morguet, Andreas J., MD; Korber, Beate, MSc; Abel, Bernd, MSc; Hippler, Horst, MSc; Wiegand, Volker, MD; Kreuzer, Heinrich, MD; "Autofluorescence Spectroscopy Using a XeCl Excimer Laser System for Simultaneous Plaque Ablation and Fluorescence Excitation"; Lasers in Surgery and Medicine; bearing a date of 1994; pp. 238-248; vol. 14; Wiley-Liss, Inc.

Mosse, Charles; Mills, Tim; Appleyard, Mark; Swain, Paul; "Electrostimulation to move endoscopes in the small bowel"; Proceedings of SPIE; bearing a date of 2001; pp. 24-28; vol. 4158.

Murthy, S. Narasimha; Hiremath, Shobha Rani R.; "Physical and Chemical Permeation Enhancers in Transdermal Delivery of Terbutaline Sulphate"; AAPS PharmSciTech; bearing a date of 2001; pp. 1-5; vol. 2001, 2(1); Technical Note 1; located at http://www.pharmscitech.com/.

Mycek, Mary-Ann, PhD; Schomacker, Kevin T., PhD; Nishioka, Norman S., MD; "New Methods and Materials: Colonic Polyp Differentiation Using Time-Resolved Autofluorescence Spectroscopy"; Gastrointestinal Endoscopy; bearing a date of 1998; pp. 390-394; vol. 48, No. 4; American Society for Gastrointestinal Endoscopy.

Nakayama, Yasuhide; Ji-Youn, Kim; Nishi, Shogo; Ueno, Hikaru; Matsuda, Takehisa; "Development of high-performance stent: gelatinous photogel-coated stent that permits drug delivery and gene transfer"; J Biomed Mater Res; bearing dates of Nov. 13, 2000, Apr. 23, 2001, May 10, 2001 and 2001; pp. 559-566; vol. 57; John Wiley & Sons, Inc.

Naqvi, Nasir H.; Rudrauf, David; Damasio, Hanna; Bechara, Antoine; "Damage to the Insula Disrupts Addiction to Cigarette Smoking"; Science; bearing a date of Jan. 26, 2007; pp. 531-534; vol. 315, No. 531; located at: www.sciencemag.org; printed on Jan. 25, 2007.

(56) References Cited

OTHER PUBLICATIONS

Neto, A.M. Figueiredo; Godinho, M.H.; Toth-Katona, T.; Palffy-Muhoray, P.; "Optical, Magnetic and Dielectric Properties of Non-Liquid Crystalline Elastomers Doped with Magnetic Colloids"; Brazilian Journal of Physics; Bearing a date of Mar. 2005; pp. 184-189; vol. 35, No. 1.
"New Medical Device Combines Wireless and MEMS Technology"; Georgia Institute of Technology; pp. 1-4; PhysOrg.com; located at: http://www.physorg.com/printnews.php?newsid=10533; printed on Feb. 20, 2006.
Nieuwenhuizen-Berkovits, P.; "lubrelastic medical appliances"; Lubrelastic Medical Appliances; pp. 1-4; located at: http://www.xs4all.nl/~plien070/caeng.html; printed on Feb. 20, 2006.
Nitzan Y.; Kauffman, M.; "Endogenous Porphyrin Production in Bacteria by δ-Aminolaevulinic Acid and Subsequent Bacterial Photoeradication"; Lasers Med Sci; bearing a date of 1999; pp. 269-277; vol. 14; Springer-Verlag London Limited.
Nokubo, Munetaka; ZS.-Nagy, Imre; Kitani, Kenichi; Ohta, Minoru; Characterization of the Autofluorescence of Rat Liver Plasma Membranes; Biochimica et Biophysica Acta; bearing a date of 1988; pp. 441-448; vol. 939; Elsevier Science Publishers B.V.
Norberto, L.; Polese, L.; Angriman, I.; Erroi, F.; Cecchetto, A.; D'Amico, D.F.; "Laser Photoablation of Colorectal Adenomas"; Surgery Endoscopy; bearing a date of 2005; pp. 1045-1048; vol. 19; Springer Science + Business Media, Inc.
Nordstrom, Robert J.; Burke, Louis; Niloff, Jonathan M.; Myrtle, James F.; "Identification of Cervical Intraepithelial Neoplasia (CIN) Using UV-Excited Fluorescence and Diffuse-Reflectance Tissue Spectroscopy"; Lasers in Surgery and Medicine; bearing a date of 2001; pp. 118-127; vol. 29; Wiley-Liss, Inc.
Nussbaum, Ethne L.; Lilge, Lothar; Mazzulli, Tony; "Effects of 630-, 660-, 810-, and 905-nm Laser Irradiation Delivering Radiant Exposure of 1-50 J/cm$^2$ on Three Species of Bacteria In Vitro"; Journal of Clinical Laser Medicine & Surgery; bearing a date of 2002; pp. 325-333; vol. 20, No. 6; Mary Ann Liebert, Inc.
Nyitrai, Zsolt; Illyefalvi-Vitéz, Zsolt; Pinkola, János; "Preparing Stents with Masking & Etching Technology"; 26$^{th}$ International Spring Seminar on Electronics Technology; bearing dates of May 8-11, 2003 and 2003; pp. 321-324; IEEE.
Oliver, James D.; Roberts, Diane M.; White, Virginia K.; Dry, Malinda A.; Simpson, Linda M.; "Bioluminescence in a Strain of the Human Pathogenic Bacterium Vibrio Vulnificus"; Applied and Environmental Microbiology; bearing a date of Nov. 1986; pp. 1209-1211; vol. 52, No. 5; American Society for Microbiology.
Olsson III, R.H.; Gulari, M.N.; Wise, K.D.; "Poster 114: Silicon Neural Recording Arrays with On-Chip Electronics for In-Vivo Data Acquisition"; Microtechnologies in Medicine and Biology; bearing dates of May 2-4, 2002; pp. 237-240; IEEE.
Oweiss, Karim G.; Anderson, David J.; "A New Technique for Blind Source Separation Using Subband Subspace Analysis in Correlated Multichannel Signal Environments"; bearing a date of 2001; pp. 2813-2816; IEEE.
Palero, Jonathan; Garcia, Wilson; Saloma, Caesar; "Two-Color (Two-Photon) Excitation Fluorescence with Two Confocal Beams and a Raman Shifter"; Optics Communications; bearing a date of Oct. 1, 2002; pp. 65-71; vol. 211; Elsevier Science B.V.; located at: www.elsevier.com/locate/optcom.
Pande, Ashvin N.; Kohler, Rainer H.; Aikawa, Elena; Weissleder, Ralph; Jaffer, Farouc A.; "Detection of Macrophage Activity in Atherosclerosis in vivo Using Multichannel, High-Resolution Laser Scanning Fluorescence Microscopy"; Journal of Biomedical Optics; bearing a date of Mar./Apr. 2006; vol. 11, No. 2; Society of Photo-Optical Instrumentation Engineers.
Panjehpour, Masoud; Julius, Clark E.; Phan, Mary N.; Vo-Dinh, Tuan; Overholt, Suzanne; "Laser-Induced Fluorescence Spectroscopy for In Vivo Diagnosis of Non-Melanoma Skin Cancers"; Lasers in Surgery and Medicine; bearing a date of 2002; pp. 367-373; vol. 31; Wiley-Liss, Inc.
Park, Sarah Y.; Kelminson, Karen L.; Lee, Anthea K.; Zhang, Peng; Warner, Rachel E.; Rehkopf, David H.; Calderwood, Stephen B.; Koehler, Jane E.; "Identification, Characterization, and Functional Analysis of a Gene Encoding the Ferric Uptake Regulation Protein in Bartonella Species"; Journal of Bacteriology; bearing a date of Oct. 2001; pp. 5751-5755; vol. 183, No. 19; American Society for Microbiology.
Patronik, N.A.; Ota, T.; Zenati, M.A.; Riviere, C.N.; "Improved Traction for a Mobile Robot Traveling on the Heart"; Proceedings of the 28$^{th}$ IEEE EMBS Annual International Conference; bearing dates of Aug. 30, 2006-Sep. 3, 2006 and 2006; pp. 339-342; IEEE.
Peckham, P. Hunter; Knutson, Jayme S.; "Functional Electrical Stimulation for Neuromuscular Applications"; Annual Review Biomedical Engineering; bearing a date of 2005; pp. 327-360; vol. 7; Annual Reviews.
Pfefer, T. Joshua; Paithankar, Dilip Y.; Poneros, John M.; Schomacker, Kevin T.; Nishioka, Norman S.; "Temporally and Spectrally Resolved Fluorescence Spectroscopy for the Detection of High Grade Dysplasia in Barrett's Esophagus"; Lasers in Surgery and Medicine; bearing a date of 2003; pp. 10-16; vol. 32; Wiley-Liss, Inc.
Podgorsak, E.B.; "Treatment Machines for External Beam Radiotherapy"; pp. 123-160; Chapter 5; located at: http://www-naweb.iaea.org/nahu/dmrp/pdf_files/Chapter5.pdf.
Punglia, Rinaa S.; Morrow, Monica; Winer, Eric P.; Harris, Jay R.; "Review Article: Current Concepts: Local Therapy and Survival in Breast Cancer"; The New England Journal of Medicine; bearing a date of Jun. 7, 2007; pp. 2399-2405; vol. 356; Massachusetts Medical Society.
"Radiation Therapy for Cancer: Questions and Answers"; National Cancer Institute FactSheet; bearing a date of Aug. 25, 2004; pp. 1-11; vol. 7.1.
Rattay, F.; "The Basic Mechanism for the Electrical Stimulation of the Nervous System"; Neuroscience; 1999; pp. 335-346; vol. 98. No. 2; Elsevier Science Ltd; printed on Mar. 15, 2007.
Rattay, Frank; "Analysis of Models for Extracellular Fiber Stimulation"; IEEE Transactions on Biomedical Engineering; bearing a date of Jul. 1989; pp. 676-682; vol. 36, No. 7; IEEE.
Rattay, Frank, Aberham, Matthias; "Modeling Axon Membranes from Functional Electrical Stimulation"; IEEE Transactions on Biomedical Engineering; bearing a date of Dec. 1993; pp. 1201-1209; vol. 40, No. 12; IEEE.
"Remote-Control Electrostimulation Capsule"; Popular Science; bearing dates of 2002 and 2003; pp. 1-2; located at http://www.popsci.com/popsci/brown/2003/article/0,18881,537028,00.html; printed on May 4, 2006.
Rentschler, Mark E.; Dumpert, Jason; Platt, Stephen R.; Farritor, Shane M.; Oleynikov, Dmitry; "Natural Orifice Surgery with an Endoluminal Mobile Robot"; Surgical Endoscopy; bearing a date of Jul. 2007; pp. 1212-1215; vol. 21, No. 7 Springer Science+Business Media, LLC.
"Researchers: Squid-Inspired Vortex Generators Could Mean Better Propulsion for Unmanned Underwater Vehicles"; UnderwaterTimes.com; Dec. 12, 2006; pp. 1-2; UnderwaterTimes.com; printed on Jan. 4, 2007; located at http://www.underwatertimes.com/print.php?article_id=51030782641.
Rice, Mike; "Implantable Neurostimulation Device Market Poised for Explosive Growth"; Future Fab International; Jan. 7, 2006; pp. 1-4; printed on Oct. 6, 2006; located at http://www.future-fab.com/documents.asp?d_ID=3725.
Rice, Mike; "New Products, Emphasis on Miniaturization Driving Medical Device Innovation"; bearing a date Aug. 23, 2006; pp. 1-3; Advantage Business Media; located at http://www.mdtmag.com/scripts/ShowPR.asp?PUBCODE=046&ACCT=0006109&ISSUE=0603&RELTYPE=PR&PRODCODE=0790&PRODLETT=A; printed on Aug. 23, 2006.
Riedmüller, J.; Bolz, A.; Rebling, H.; Schaldach, M.; "Improvement of Stimulation and Sensing Performance of Bipolar Pacemaker Leads"; IEEE Eng. Med. Biol. Soc.; 1992; pp. 2364-2365; IEEE.
Robinson, David A.; "The Electrical Properties of Metal Microelectrodes"; Proceedings of the IEEE; bearing a date of Jun. 1968; pp. 1065-1071; vol. 56, No. 6.
Ross, Gillian; "Commentary: Accelerated Partial Breast Irradiation: Technically Feasible But Who Will Benefit?"; Breast Cancer Research; bearing a date of May 2005; pp. 110-112; vol. 7, No. 3; BioMed Central Ltd.

(56) References Cited

OTHER PUBLICATIONS

Rossow, Molly, J.; Gatto, Rodolfo; D'Amico, Enrico; Mantulin, William W.; Gratton, Enrico; "Blood Flow Measurements and Clot Detection with Near-Infrared Spectroscopy"; Biomedical Topical Meeting: Optics InfoBase; bearing a date of Mar. 19, 2006; pp. 1-3; paper ME72; Optical Society of America; located at: http://www.opticsinfobase.org/abstract.cfm?URI=BIO-2006-ME72.

Rousche, Patrick J.; Pellinen, David S.; Pivin, David P.; Williams, Justin C.; Vetter, Rio J.; Kipke, Daryl R.; "Flexible Polyimide-Based Intracortical Electrode Arrays with Bioactive Capability"; IEEE Transactions on Biomedical Engineering; bearing a date Mar. 2001; pp. 361-371; vol. 48, No. 3; IEEE.

Rutten, Wim; Mouveroux, Jean-Marie; Buitenweg, Jan; Heida, Ciska; Ruardij, Teun; Marani, Enrico; Lakke, Egbert; "Neuroelectronic Interfacing with Cultured Multielectrode Arrays Toward a Cultured Probe"; Proceedings of the IEEE; bearing a date of Jul. 2001; pp. 1013-1029; vol. 89, No. 7; IEEE.

Sage, Andrew; Schwedock, Julie; London, Roanna; Valley, Heather; Meadows, Jamie; Jones, David; Straus, Don; "A Rapid and Nondestructive Method for Microbiological Testing in Pharmaceutical Manufacturing"; American Biotechnology Laboratory; bearing a date of Nov./Dec. 2006; pp. 1-5.

Saltzman, John R.; "Endoscopic Advances—A View Toward the Future"; bearing dates of May 4, 2006, May 17, 2005, and 2005; pp. 1-4; Medscape; located at http://www.medscape.com/viewarticle/505100; printed on May 4, 2006.

Sargeant, K.C.; Williams, S.K.; Hinton, A. Jr.; "The Effect of Electron Beam Irradiation on the Survivial of *Salmonella enterica* Serovar Typhimurium and Psychrotophic Bacteria on Raw Chicken Breasts Stored at Four Degrees Celsius for Fourteen Days"; Poultry Science; bearing a date of 2005; pp. 955-958; vol. 84, No. 6; Poultry Science Association.

Schmidt, W.; Behrens, P.; Behrend, D.; Schmitz, K.-P.; Andresen, R.; "Experimental Study of Peripheral, Balloon-expandable Stent Systems"; Progress in Biomedical Research; bearing a date of May 2001; pp. 246-255.

Schoonhoven, R.; Stegeman, D.F.; "Models and Analysis of Compound Nerve Action Potentials"; Critical Reviews in Biomedical Engineering; bearing a date of 1991; pp. 47-111; vol. 19, No. 1; CRC Press, Inc.

Senel, Sevda; Hincal, A. Atilla; "Drug permeation enhancement via buccal route: possibilities and limitations"; Journal of Controlled Release; bearing a date of 2001; pp. 133-144; vol. 72 (2001); Elsevier; located at www.elsevier.com/locate/jconrel.

Serruya, Mijail D.; Hatsopoulos, Nicholas G.; Paninski, Liam; Fellows, Matthew R.; Donoghue, John P.; "Brief Communications: Instant Neural Control of a Movement Signal"; Nature; bearing a date of Mar. 14, 2002; pp. 141-142; vol. 416; Macmillan Magazines Ltd; located at: www.nature.com.

Serruys, Patrick W.; Kutryk, Michael J.B.; Ong, Andrew T.L.; "Coronary-Artery Stents"; The New England Journal of Medicine; bearing dates of Feb. 2, 2006 and Feb. 15, 2006; pp. 483-495; vol. 354;5; Massachusetts Medical Society.

Shabalovskaya, Svetlana, A.; "Surface, corrosion and biocompatibility aspects of Nitinol as an implant material"; Bio-Medical Materials and Engineering; bearing dates of Apr. 4, 2001, and 2002; pp. 69-109; vol. 12; IOS Press.

Shalita, Alan R.; Harth, Yoram; Elman, Monica; Slatkine, Michael; Talpalariu, Gerry; Rosenberg, Yitzhak; Korman, Avner; Klein, Arie; "Acne Phototherapy Using U.V Free High Intensity Narrow Band Blue Light—3 Center Clinical Study"; Proc. Of SPIE; bearing a date of 2001; pp. 61-73; vol. 4244; Lasers in Surgery: Advanced Characterization, Therapeutics and Systems.

Shahinpoor, Mohsen; Kim, Kwang J.; Ionic polymer-metal composites: IV. Industrial and medical applications; Smart Materials and Structures; 2005; pp. 197-214; vol. 14; Institute of Physics Publishing.

Shor, Yuh-Pyng; Shih, Jin-Yuan; Yang, Pan-Chyr; Roffler, Steve R.; Chu, Yi-Wen; Wu, Cheng-Wen; Yu, Chia-Li; Peck, Konan; "Prognosis of Non-Small Cell Lung Cancer Patients by Detecting Circulating Cancer Cells in the Peripheral Blood with Multiple Marker Genes"; Clinical Cancer Research; bearing a date of Jan. 1, 2005; pp. 173-179; vol. 11; American Association for Cancer Research.

"Short Technical Reports: Photobleaching of Arterial Autofluorescence for Immunofluorescence Applications"; Bio Techniques; bearing a date of Apr. 2001; pp. 794-797; vol. 30, No. 4; Eaton Publishing Company.

Slifkin, Malcolm; Cumbie, Richard; "Congo Red as a Fluorochrome for the Rapid Detection of Fungi"; Journal of Clinical Microbiology; bearing a date of May 1988; pp. 827-830; vol. 26, No. 5; American Society for Microbiology.

Snoek, GJ; Ijzerman, MJ; In 'T Groen, Facg; Stoffers, TS; Zilvold, G; "Use of the NESS Handmaster to Restore Handfunction in Tetraplegia: Clinical Experiences in Ten Patients"; Spinal Cord; bearing a date of 2000; pp. 244-249; vol. 38; International Medical Society of Paraplegia.

Snow, E.S.; Perkins, F.K.; Houser, E.J.; Badescu, S.C.; Reinecke, T. L.; "Chemical Detection with a Single-Walled Carbon Nanotube Capacitor"; Science; Mar. 25, 2005; pp. 1942-1945; vol. 307; www.sciencemag.org.

Sorrell, Matthew J.; Tribble, Jerri; Reinisch, Lou; Werkhaven, Jay A.; Ossoff, Robert H.; "Bacteria Identification of Otitis Media With Fluorescence Spectroscopy"; Lasers in Surgery and Medicine; bearing a date of 1994; pp. 155-163; vol. 14; Wiley-Liss, Inc.

Stael Von Holstein, C.; Nilsson, A.M.K.; Andersson-Engels, S.; Willen, R.; Walther, B.; Svanberg K.; "Detection of Adenocarcinoma in Barrett's Oesophagus by Means of Laser Induced Fluorescence"; Gut; bearing a date of 1996; pp. 711-716; vol. 39.

Stoeckel, Dieter; Pelton, Alan; Duerig, Tom; "Self-expanding Nitinol Stents: material and design considerations"; European Radiology; bearing dates of Jan. 28, 2003, May 22, 2003, Jul. 1, 2003, Sep. 3, 2003, Feb. 2004 and 2004; pp. 292-301(1-2); vol. 14, No. 2; Springer-Verlag GmbH-SpringerLink—Article; located at: http://www.springerlink.com/(1begg455gtgjfseqqptyb43m)/app/home/contribution.asp?referrer=parent&backto=issue,17,26;journal,27,147;browsepublicationsresults,444,1551; printed on Feb. 22, 2006.

Strauss, Bradley H., M.D., Ph.D.; Li, Chris, M.D.; Whittingham, Heather A., M.Sc; Tio, Fermin O., M.D.; Kutryk, Michael J.B., M.D., Ph.D.; Janicki, Christian, Ph.D.; Sparkes, John, D., M.Sc.; Turnlund, Todd, B.Sc.; Sweet, William L., M.D.; "Late Effects of Low-Energy Gamma-Emitting Stents in a Rabbit Iliac Artery Model"; Int. J. Radiation Oncology Biol. Phys.; bearing dates of Oct. 23, 2001, May 13, 2002 and May 15, 2002 and 2002; pp. 551-561; vol. 54, No. 2; Elsevier Science Inc.

Struijk, Johannes Jan; "The Extracellular Potential of a Myelinated Nerve Fiber in an Unbounded Medium and in Nerve Cuff Models"; Biophysical Journal; bearing a date of Jun. 1997; pp. 2457-2469; vol. 72; Biophysical Society.

"Surgery for Brain Tumors"; University of Florida Shands Cancer Center; pp. 1-5; located at: http://www.ufscc.ufl.edu/patient/content.aspx?section=ufscc&id=37451.

Taylor, Dawn M.; Helms Tillery, Stephen I.; Schwartz, Andrew B.; "Research Article: Direct Cortical Control of 3D Neuroprosthetic Devices"; Science; bearing a date of Jun. 7, 2002; pp. 1829-1832; vol. 296; located at: www.sciencemag.org.

Thacker, W. Lanier; Benson, Robert F.; Hawes, Lesley; Mayberry, William R.; Brenner, Don J.; "Notes: Characterization of a Legionella Anisa Strain Isolated from a Patient with Pneumonia"; Journal of Clinical Microbiology; bearing a date of Jan. 1990; pp. 122-123; vol. 28, No. 1; American Society for Microbiology.

Thai, Thao P.; Keast, David H.; Campbell, Karen E.; Woodbury, M. Gail; Houghton, Pamela E.; "Feature: Effect of Ultraviolet Light C on Bacterial Colonization in Chronic Wounds"; Ostomy Wound Management; printed on Jul. 27, 1007; pp. 1-20; HMP Communications.

"Tiny Robot Reduces Need for Surgery"; Pink Tentacle; bearing a date of Feb. 26, 2007; p. 1; located at: http://www.pinktentacle.com/2007/02/tiny-robot-reduces-need-for-surgery; printed on Mar. 8, 2007.

"Trying to control pain can be a double-edged sword, say scientists"; PhysOrg.com; printed on Nov. 2, 2006; pp. 1-2; located at http://www.physorg.com/printnews.php?newsid=81599312.

(56) References Cited

OTHER PUBLICATIONS

Tsai, Tsuimin, PhD; Chen, Hsin-Ming, BDS, MS; Wang, Chih-Yu, PhD; Tsai, Jui-Chang, MD, PhD; Chen, Chin-Tin, PhD; Chiang, Chun-Pin, BDS, DMSc; "In Vivo Autofluorescence Spectroscopy of Oral Premalignant and Malignant Lesions: Distortion of Fluorescence Intensity by Submucous Fibrosis"; Lasers in Surgery and Medicine; bearing a date of 2003; pp. 40-47; vol. 33; Wiley-Liss, Inc.

Tseng, Chun-Chieh; Li, Chih-Shan; "Inactivation of Viruses on Surfaces by Ultraviolet Germicidal Irradiation"; Journal of Occupational and Environmental Hygiene; bearing a date of Jun. 2007; pp. 400-405; vol. 4; Joeh, LLC.

Tummala, R. Lal; Mukherjee, R.; Aslam, D.; Xi, Ning; Mahadevan, S.; Weng, J.; "Reconfigurable Adaptable Micro-robot"; IEEE; bearing a date of 1999; pp. 687-691.

Twardoch, U.M.; "Integrity of Ultramicro-Stimulation Electrodes Determined from Electrochemical Measurements"; Journal of Applied Electrochemistry; bearing a date of 1994; pp. 835-857; vol. 24; Chapman & Hall.

Van Der Veen, M.H.; Thomas, R.Z.; Huysmans, M.C.D.N.J.M.; De Soet, J.J.; "Short Communication: Red Autofluorescence of Dental Plaque Bacteria"; Caries Research; bearing a date of 2006; pp. 542-545; vol. 40; Karger AG.

Verbunt, Robert J.A.M.; Fitzmaurice, Mary Ann, MD, PhD; Kramer, John R., MD; Ratliff, Norman B., MD; Kittrell, Carter; Taroni, Paola, PhD; Cothren, Robert M., PhD; Baraga, Joe; Feld, Michael, PhD; "Characterization of Ultraviolet Laser-Induced Autofluorescence of Ceroid Deposits and Other Structures in Atherosclerotic Plaques as a Potential Diagnostic for Laser Angiosurgery"; American Heart Journal; bearing a date of Jan. 1992; pp. 208-216; vol. 123, No. 1; Mosby, Inc.

Wang, Bao-Gui; Halbhuber, Karl-Juergen; "Corneal Multiphoton Microscopy and Intratissue Optical Nanosurgery by Nanojoule Femtosecond Near-Infrared Pulsed Lasers"; Annals of Anatomy; bearing a date of 2006; pp. 395-409; vol. 188; Elsevier GmbH; located at: www.elsevier.de/aanat.

Warland, David K.; Reinagel, Pamela; Meister, Markus; "Decoding Visual Information from a Population of Retinal Ganglion Cells"; bearing a date of 1997; pp. 2336-2350; The American Physiological Society.

Weingandt, Helmut; Stepp, Herbert; Baumgartner, Reinhold; Diebold, Joachim; Xiang, Wei; Hillemanns, Peter; "Autofluorescence Spectroscopy for the Diagnosis of Cervical Intraepithelial Neoplasia"; BJOG: an International Journal of Obstetrics and Gynaecology; bearing a date of Aug. 2002; pp. 947-951; vol. 109; RCOG BJOG: an International Journal o fObstetrics and Gynaecology.

Weis, Rolf; Müller, Bernt; Fromherz, Peter; "Neuron Adhesion on a Silicon Chip Probed by an Array of Field-Effect Transistors"; Physical Review Letters; bearing a date of Jan. 8, 1996; pp. 327-330; vol. 76, No. 2; The American Physical Society.

Wessberg, Johan; Stambaugh, Christopher R.; Kralik, Jerald D.; Beck, Pamela D.; Laubach, Mark; Chapin, John K.; Kim, Jung; Biggs, S. James; Srinivasan, Mandayam A.; Nicolelis, Miguel A.L.; "Letters to Nature: Real-Time Prediction of Hand Trajectory by Ensembles of Cortical Neurons in Primates"; Nature; bearing a date of Nov. 16, 2000; pp. 361-365; vol. 408; Macmillan Magazines Ltd; located at: www.nature.com.

White, Dave; "Mini Robot Explores, Gives you Medicine from Within"; Mobile Magazine; bearing a date of Feb. 27, 2007; p. 1; located at: http://www.mobilemag.com/content/100/313/C11869/; printed on Mar. 8, 2007.

Wissing, Frank; Sanchez, Cecilia P.; Rohrback, Petra; Ricken, Sigrid; Lanzer, Michael; "Illumination of the Malaria Parasite Plasmodium Falciparum Alters Intracellular pH"; The Journal of Biological Chemistry; bearing a date of 2002; pp. 37747-37755; vol. 277, No. 40; The American Society for Biochemistry and Molecular Biology, Inc.; located at: http://www.jbc.org.

Wu, Yicong; Zheng, Wei; Qu, Jianan Y.; "Sensing Cell Metabolism by Time-Resolved Autofluorescence" Optics Letters; bearing a date of Nov. 1, 2006; pp. 3122-3124; vol. 31, No. 21; Optical Society of America.

Xie, L.; Li, Q.; Johnson, J.; Zhang, J.; Milhous, W.; Kyle, D.; "Development and Validation of Flow Cytometric Measurement for Parasitaemia using Autofluorescence and YOYO-1 in Rodent Malaria"; Parasitology; bearing a date of 2007; pp. 1151-1162; vol. 134; Cambridge University Press.

Yeo, C.B. Allen; Watson, Ian A.; Stewart-Tull, Duncan E.S.; Wardlaw, A.C.; Armstrong, Graham N.; "Bactericidal Effects of High-Power Nd:YAG Laser Radiation"; Pure App. Opt.; bearing a date of 1998; pp. 643-655; Vo. 7; IOP Publishing Ltd.

Yusa, Go; Muraki, Koji; Takashina, Kei; Hashimoto, Katsushi; Hirayama, Yoshiro; "Controlled multiple quantum coherences of nuclear spins in a nanometre-scale device"; Nature; Apr. 21, 2005; pp. 1001-1005; vol. 434; 2005 Nature Publishing Group; www.nature.com/nature.

Zipfel, Warren R.; Williams, Rebecca M.; Webb, Watt W.; "Review: Focus on Optical Imaging: Nonlinear Magic: Multiphoton Microscopy in the Biosciences"; Nature Biotechnology; bearing a date of Nov. 2003; pp. 1369-1377; vol. 21, No. 11; Nature Publishing Group; located at: http://www.nature.com/naturebiotechnology.

"Zyvex NanoEffector Microgrippers"; Nanotechnology at Zyvex; printed on Dec. 7, 2006; pp. 1-2; located at http://www.zyvex.com/Products/Grippers_Features.html.

"Zyvex NanoEffector Microgrippers"; Zyvex.com; bearing a date of 2006; pp. 1-2; Zyvex Corporation.

U.S. Appl. No. 13/136,680, Ferren et al.
U.S. Appl. No. 13/136,679, Ferren et al.
U.S. Appl. No. 13/136,677, Ferren et al.
U.S. Appl. No. 13/136,676, Ferren et al.
U.S. Appl. No. 13/136,675, Ferren et al.
U.S. Appl. No. 13/136,678, Ferren et al.
U.S. Appl. No. 13/136,674, Ferren et al.

Hammer-Wilson et al.; "Fluorescence Diagnostics of *Helicobacter pylori*-Infected Human Gastric Mucosa: Establishing Technique and Validity"; Scandinavian Journal of Gastroenterology; bearing a date of 2007, accepted Jan. 2, 2007; pp. 941-950; vol. 42; Taylor& Francis.

So, Peter TC; "Two-Photon Fluorescence Light Microscopy"; Encyclopedia of Life Sciences; bearing a date of 2002; pp. 1-5; Macmillan Publishers Ltd, Nature Publishing Group; located at: http://web.mit.edu/solab/Documents/Assets/So-2PF%20light%20microscopy.pdf.

Thomas et al.; "Detection and Analysis of Tumor Fluorescence Using a Two-Photon Optical Fiber Probe"; Biophysical Journal; bearing a date of Jun. 2004; 7 pages. (3959-3965); vol. 86, No. 6.

* cited by examiner

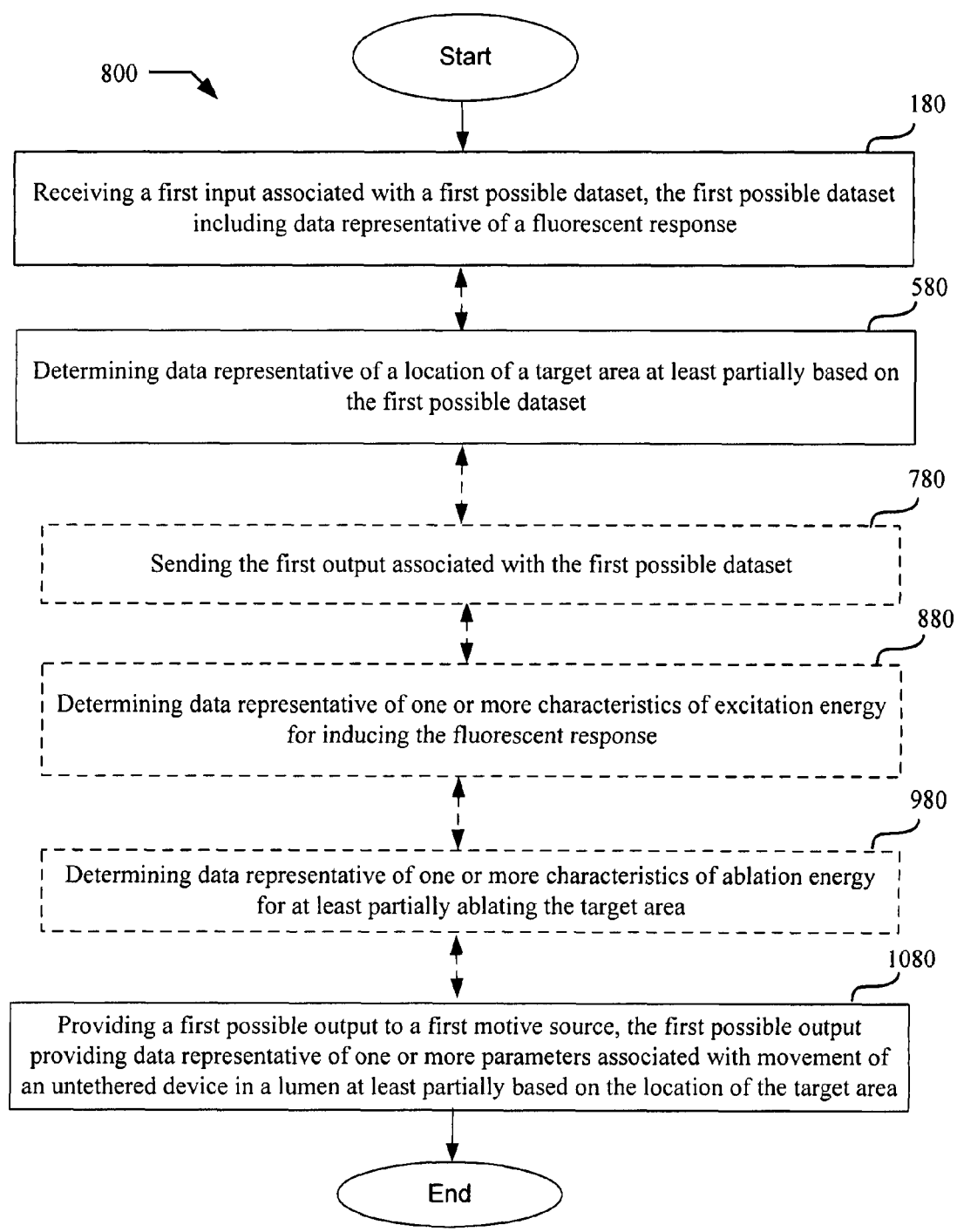

FIG.14

A computer program product 1200

A signal bearing medium 1210 at least one of one or more instructions 1215 including:

one or more instructions for receiving a first input associated with a first possible dataset, the first possible dataset including data representative of a target fluorescent response; and one or more instructions for accessing the first possible dataset in response to the first input; and one or more instructions for generating the first possible dataset in response to the first input; and one or more instructions for determining a graphical illustration of the first possible dataset; and one or more instructions for sending the first output associated with the first possible dataset; and one or more instructions for determining data representative of one or more characteristics of excitation energy for inducing the target fluorescent response; and one or more instructions for determining data representative of one or more characteristics of ablation energy for at least partially ablating the target; and one or more instructions for providing a first output to a first energy source in real time, the first output providing data associated with at least partial ablation of a target at least partially based on the first possible dataset

| a computer-readable medium 1220 | a recordable medium 1230 | a communications medium 1240 |

FIG. 32
A
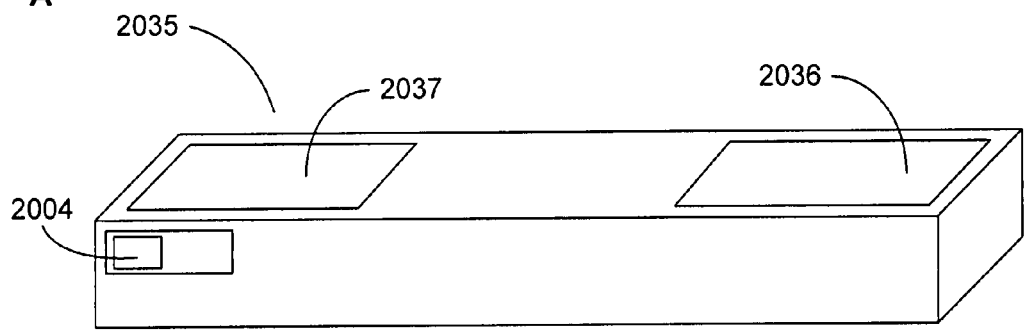
B
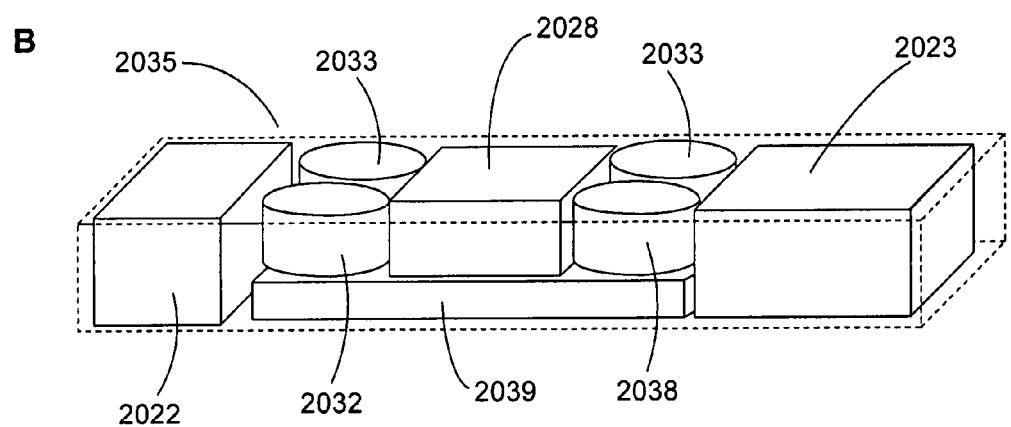
C
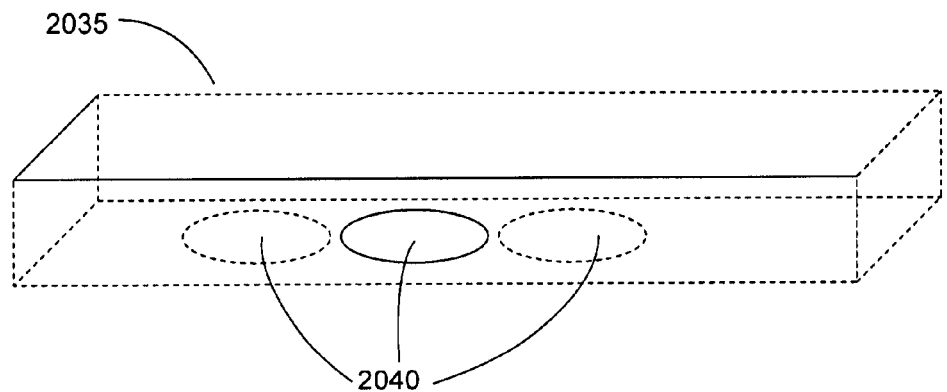

“AUTOFLUORESCENT IMAGING AND TARGET ABLATION”

AUTOFLUORESCENT IMAGING AND TARGET ABLATION

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/403,230, entitled LUMENALLY-ACTIVE DEVICE, naming Bran Ferren; W. Daniel Hillis; Roderick A. Hyde; Muriel Y Ishikawa; Edward K. Y. Jung; Nathan P. Myhrvold; Elizabeth A. Sweeney; Clarence T. Tegreene; Richa Wilson; Lowell L. Wood, Jr. and Victoria Y. H. Wood as inventors, filed 12 Apr. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/645,357, entitled LUMENALLY-TRAVELING DEVICE, naming Bran Ferren; W. Daniel Hillis; Roderick A. Hyde; Muriel Y Ishikawa; Edward K. Y. Jung; Eric C. Leuthardt; Nathan P. Myhrvold; Elizabeth A. Sweeney; Clarence T. Tegreene; Richa Wilson; Lowell L. Wood, Jr. and Victoria Y. H. Wood as inventors, filed 21 Dec. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/895,563, entitled AUTOFLUORESCENT IMAGING AND TARGET ABLATION, naming Edward S. Boyden; Roderick A. Hyde; Muriel Y. Ishikawa; Eric C. Leuthardt; Nathan P. Myhrvold; Dennis J. Rivet; Thomas A. Weaver; and Lowell L. Wood, Jr. as inventors, filed 24 Aug. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/895,564, entitled SYSTEMS FOR AUTOFLUORESCENT IMAGING AND TARGET ABLATION, naming Edward S. Boyden; Roderick A. Hyde; Muriel Y. Ishikawa; Eric C. Leuthardt; Nathan P. Myhrvold; Dennis J. Rivet; Thomas A. Weaver; and Lowell L. Wood, Jr. as inventors, filed 24 Aug. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/895,562, entitled SYSTEMS FOR AUTOFLUORESCENT IMAGING AND TARGET ABLATION, naming Edward S. Boyden; Roderick A. Hyde; Muriel Y. Ishikawa; Eric C. Leuthardt; Nathan P. Myhrvold; Dennis J. Rivet; Thomas A. Weaver; and Lowell L. Wood, Jr. as inventors, filed 24 Aug. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/895,565, entitled AUTOFLUORESCENT IMAGING AND TARGET ABLATION, naming Edward S. Boyden; Roderick A. Hyde; Muriel Y. Ishikawa; Eric C. Leuthardt; Nathan P. Myhrvold; Dennis J. Rivet; Thomas A. Weaver; and Lowell L. Wood, Jr. as inventors, filed 24 Aug. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/895,566, entitled SYSTEMS FOR AUTOFLUORESCENT IMAGING AND TARGET ABLATION, naming Edward S. Boyden; Roderick A. Hyde; Muriel Y. Ishikawa; Eric C. Leuthardt; Nathan P. Myhrvold; Dennis J. Rivet; Thomas A. Weaver; and Lowell L. Wood, Jr. as inventors, filed 24 Aug. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/895,561, entitled AUTOFLUORESCENT IMAGING AND TARGET ABLATION, naming Edward S. Boyden; Roderick A. Hyde; Muriel Y. Ishikawa; Eric C. Leuthardt; Nathan P. Myhrvold; Dennis J. Rivet; Thomas A. Weaver; and Lowell L. Wood, Jr. as inventors, filed 24 Aug. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/895,560, entitled AUTOFLUORESCENT IMAGING AND TARGET ABLATION, naming Edward S. Boyden; Roderick A. Hyde; Muriel Y. Ishikawa; Eric C. Leuthardt; Nathan P. Myhrvold; Dennis J. Rivet; Thomas A. Weaver; and Lowell L. Wood, Jr. as inventors, filed 24 Aug. 2007, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

The present application relates, in general, to apparatus and devices for fluorescent-based imaging and ablation of medical targets, as well as related methods and systems implementations. Such apparatus, devices, methods and/or systems are useful for ablating target cells and/or tissues as well as treatment, prevention, and/or amelioration of a variety of diseases and disorders. Apparatus and/or devices may be configured to be used externally or internally, to be handheld, intra-luminal, or ingestible, and/or to be tethered or untethered. Various methods and/or systems implementations include using one or more of the apparatus or devices for ablating target cells in wounds and/or surgical lesions, intra-lumenally, or in the digestive tract. Illustrative examples include using one or more of the apparatus, devices, methods and/or systems to treat *H. pylori* infection, and/or to test and ablate cancer margins.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 12 and FIG. 13 show an operational flow representing illustrative embodiments of operations related to providing a first possible output to a first motive source, the first possible output providing data representative of one or more parameters associated with movement of an untethered device in a lumen at least partially based on the location of the target area.

FIGS. 14-19 show a partial view of an illustrative embodiment of a computer program product that includes a computer program for executing a computer process on a computing device.

FIGS. 32A, 32B, and 32C show a schematic of an example of an illustrative embodiment of a handheld device.

DETAILED DESCRIPTION

Figure 1:
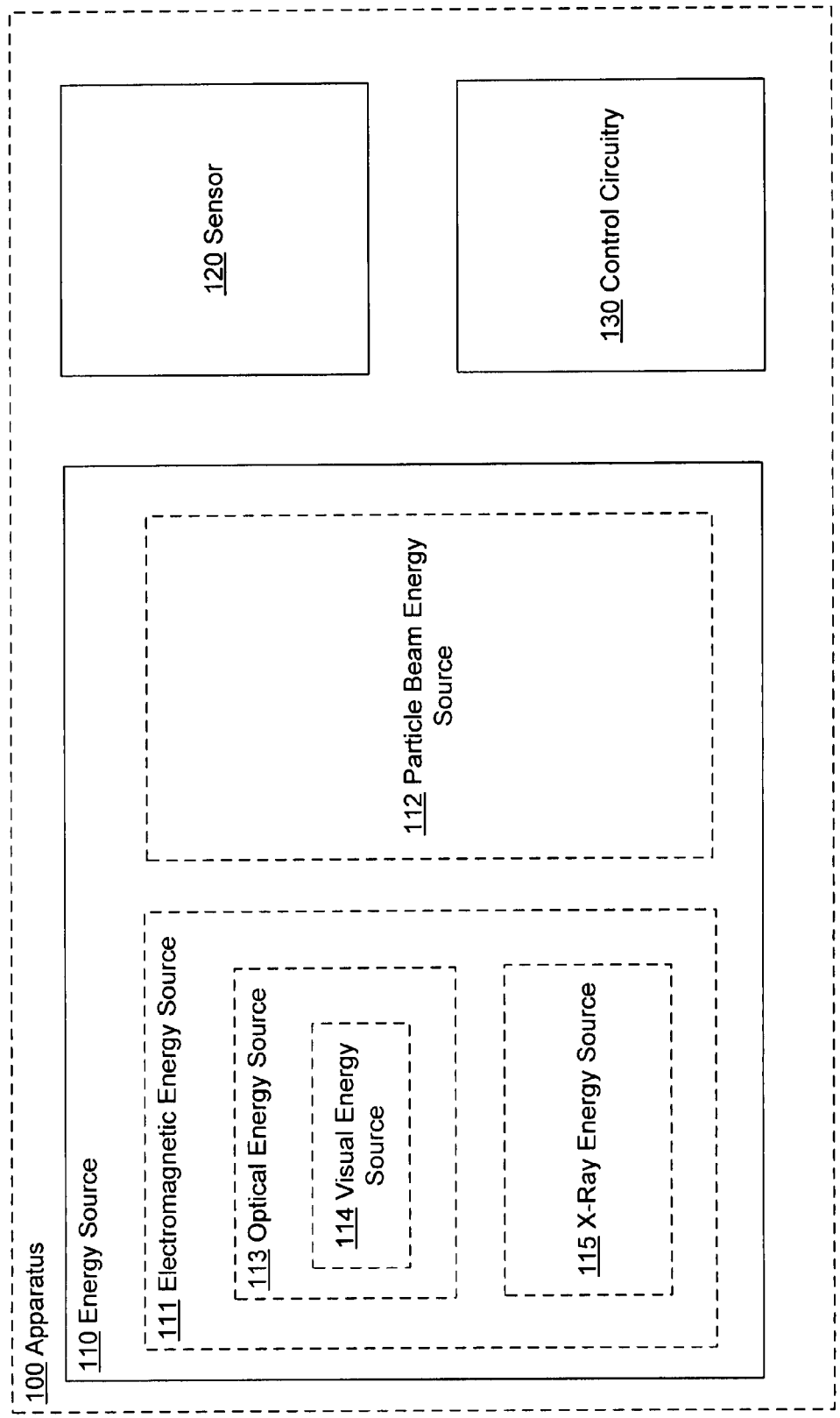
FIG. 1 shows a schematic of an illustrative apparatus in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application relates, in general, to apparatus, devices, systems, and methods of fluorescent imaging, optionally autofluorescent imaging, and ablation of medical targets. Those having skill in the art will appreciate that the specific systems, apparatus, devices, and methods described herein are intended as merely illustrative of their more general counterparts.

In one aspect, FIG. 1 through FIG. 7 depict one or more embodiments of one or more apparatus 100 and/or 500 and/or devices 200, 300, and/or 400 configured to detect and ablate targets at least partially based on a fluorescent response. Although one or more embodiments of one or more apparatus and/or devices may be presented separately herein, it is intended and envisioned that one or more apparatus and/or devices and/or embodiments of one or more apparatus and/or devices, in whole or in part, may be combined and/or substituted to encompass a full disclosure of the one or more apparatus and/or devices. In some embodiments, one or more apparatus and/or devices may include one or more system implementations including methods of operations, and/or include one or more computing devices and/or systems configured to perform one or more methods. As disclosed below, one or more apparatus and/or devices may be used in one or more methods of treatment and/or methods for ablating targets described herein.

Figure 2:
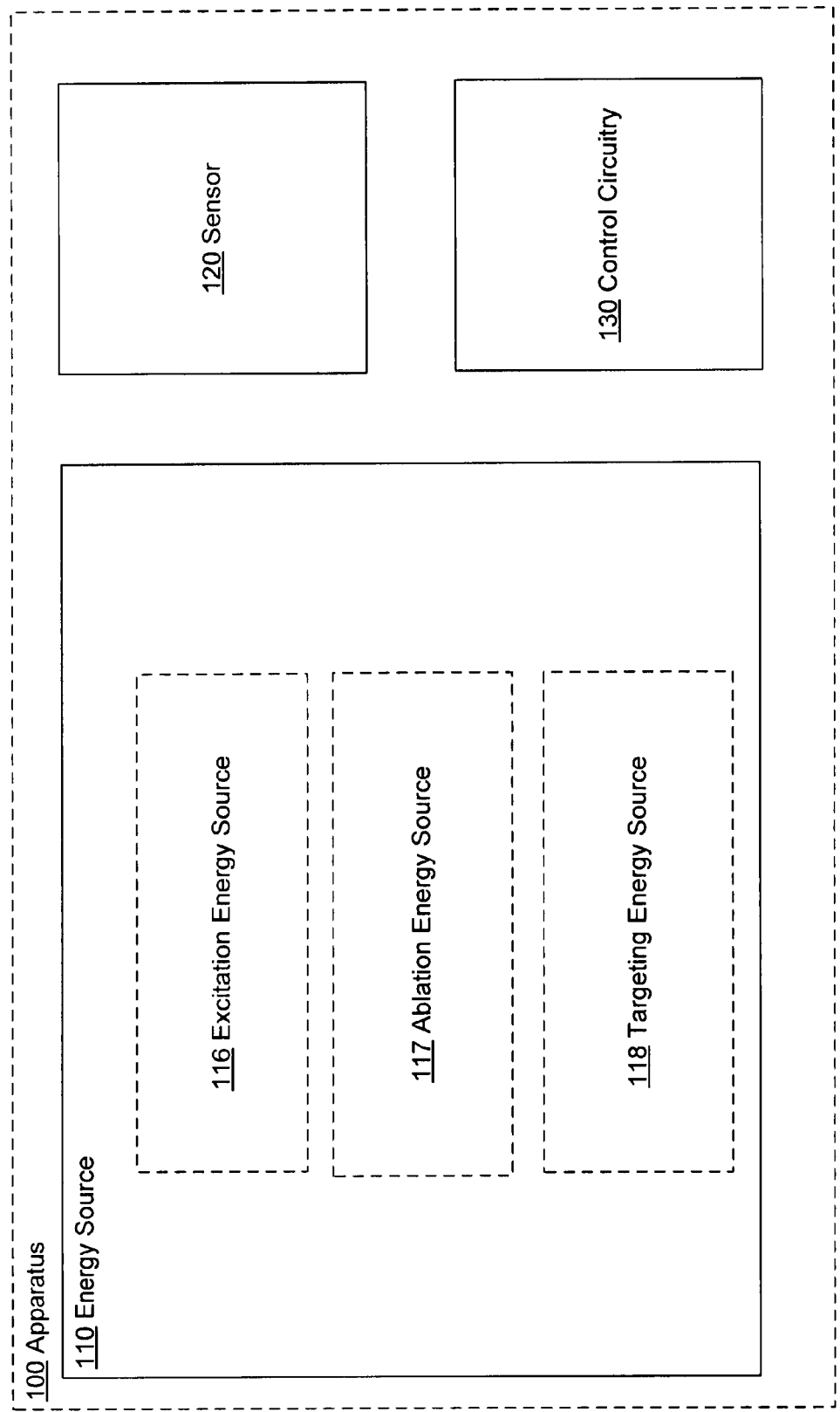
FIG. 2 shows a schematic of illustrative embodiments of the apparatus of FIG. 1, with illustrative examples of an energy source.
Figure 3:
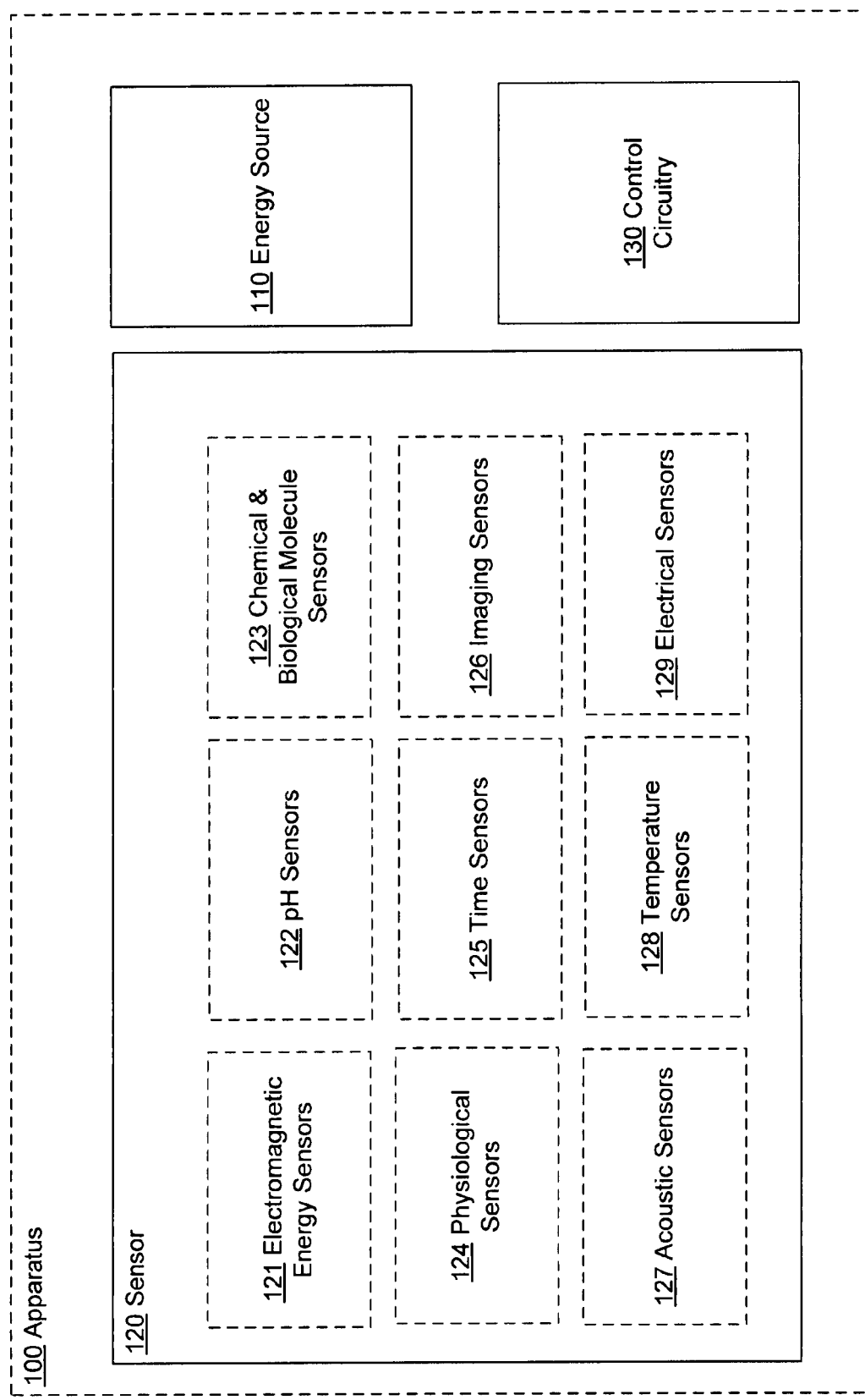
FIG. 3 shows a schematic of illustrative embodiments of the apparatus of FIG. 1, with illustrative examples of a sensor.

FIG. 1, FIG. 2, and FIG. 3 depict illustrative embodiments of one or more apparatus 100 having a first energy source 110 alignable to a lesion and configured to provide electromagnetic energy selected to induce a fluorescent response from a target area in the lesion; a sensor 120 configured to detect the fluorescent response; control circuitry 130 coupled to the sensor 120 and responsive to identify the target area; and a second energy source 110 responsive to the control circuitry 130 and configured to emit energy selected to at least partially ablate the target area.

Figure 4:
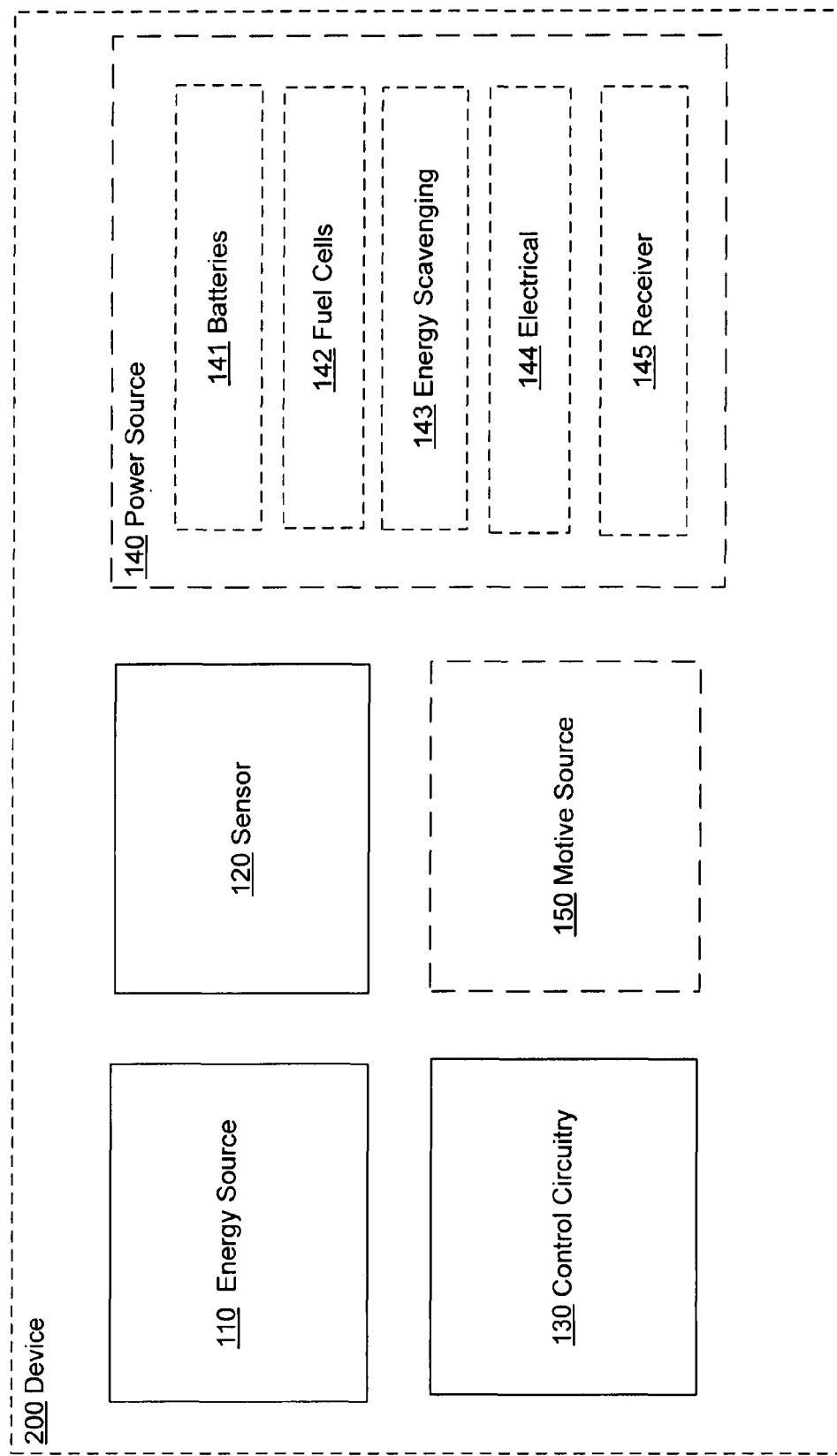
FIGS. 4-6 show a schematic of an illustrative untethered device in which embodiments may be implemented.
Figure 5:
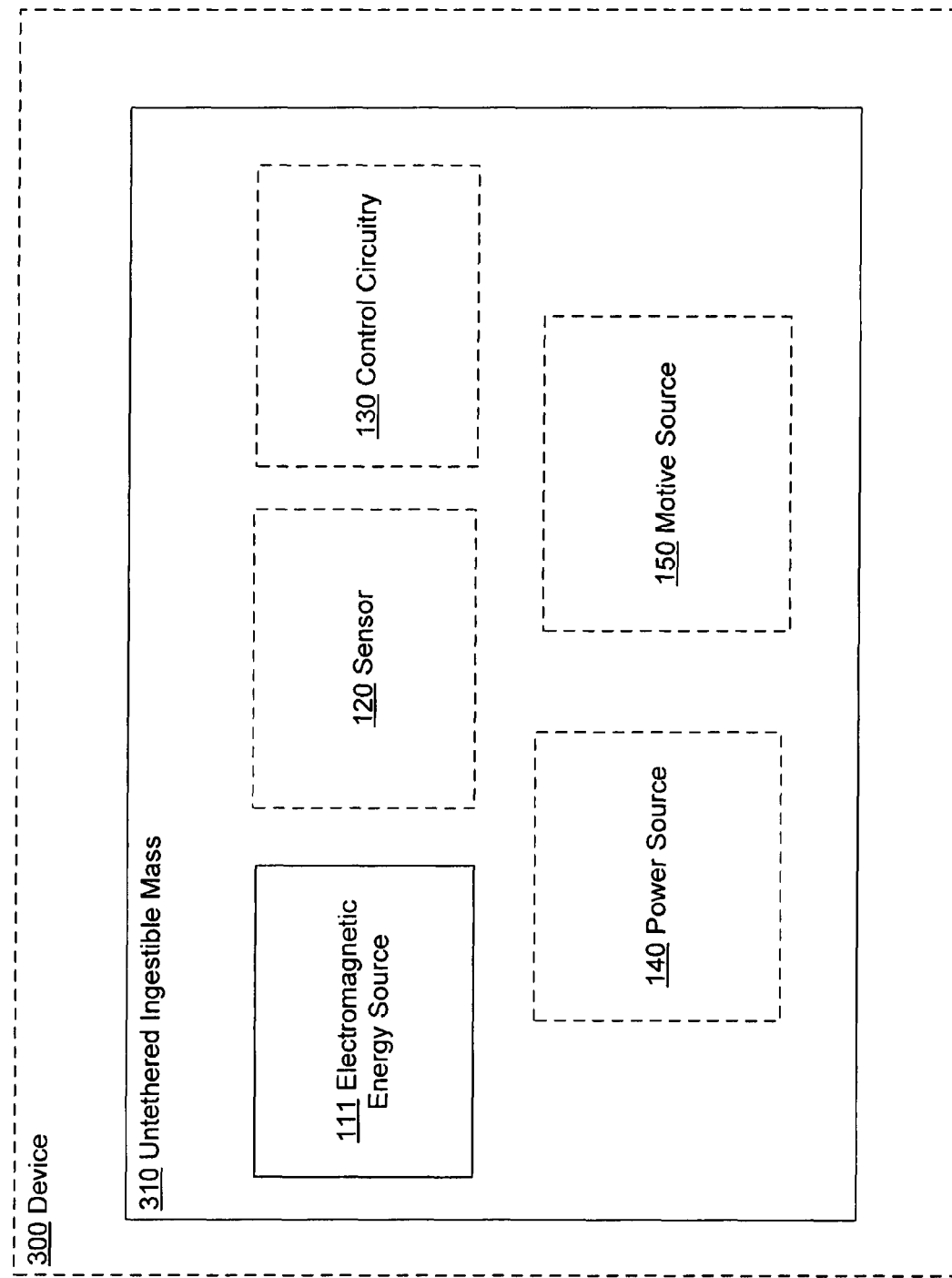
Figure 6:
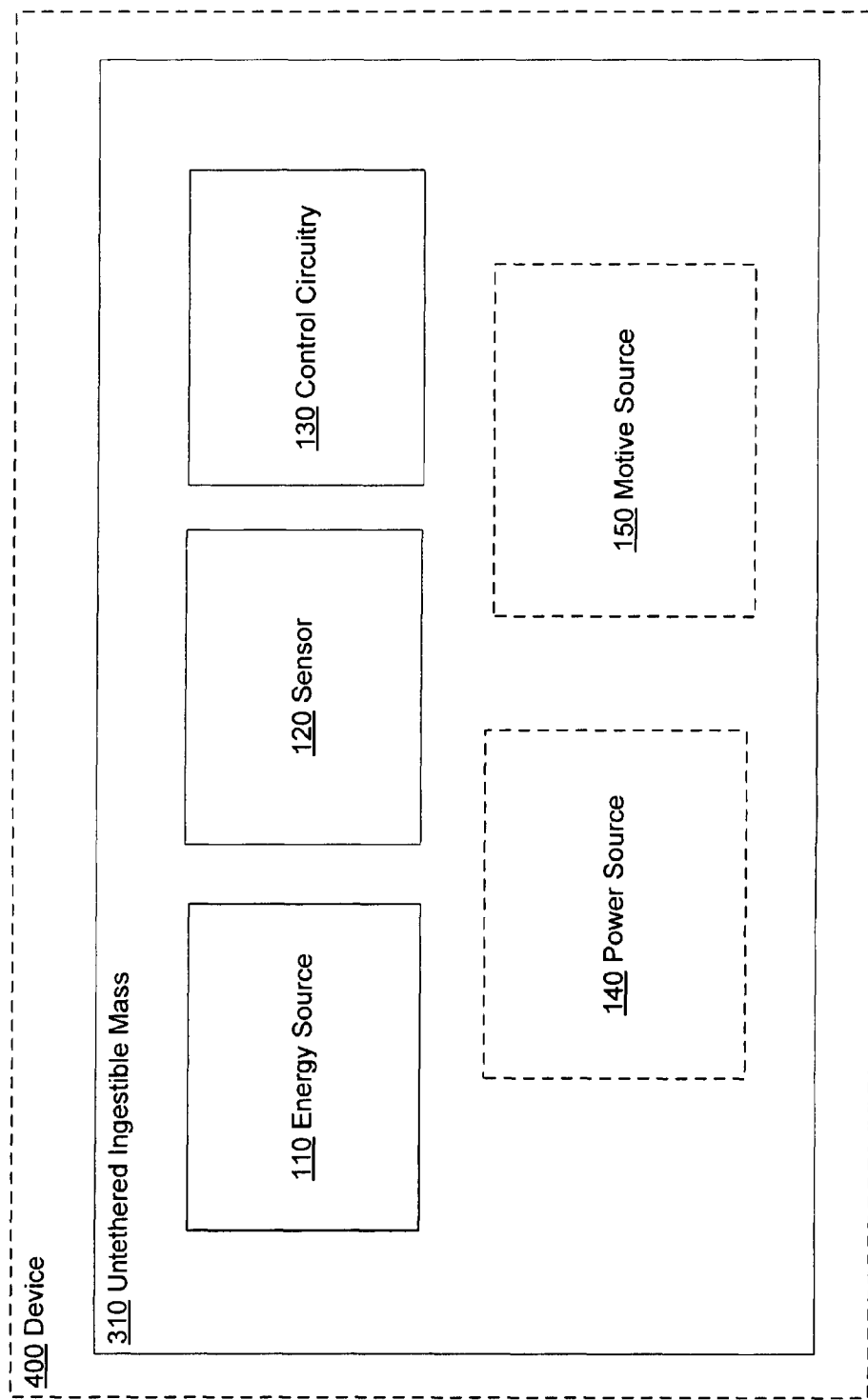

FIG. 4, FIG. 5, and FIG. 6 depict illustrative embodiments of one or more untethered device 200, 300, and 400, respectively.

FIG. 4 depicts illustrative embodiments of one or more untethered device 200 having an energy source 100, optionally a first electromagnetic energy source 111 configured to function in a lumen and configured to provide electromagnetic energy selected to induce an auto-fluorescent response in one or more target cells in proximity to the lumen; a sensor 120 configured to detect the auto-fluorescent response; control circuitry 130 coupled to the sensor 120 and responsive to identify a target area; optionally a second electromagnetic energy source 111 responsive to the control circuitry 130 and configured to emit energy selected to at least partially ablate the target area, optionally a power source 140, and optionally a motive source 150.

FIG. 5 depicts illustrative embodiments of one or more devices 300 for treating or ameliorating *H. pylori* infection including an untethered ingestible mass 310 optionally shaped for non-uniform movement having an electromagnetic energy source 111 optionally configured to emit variable directional electromagnetic energy in a manner selected to induce photodynamic cell death in *H. pylori*. In some embodiments, one or more devices 300 for ablating *H. pylori* include an untethered ingestible mass 310, optionally shaped for non-uniform movement, having an electromagnetic energy source 111 optionally configured to emit variable directional electromagnetic energy in a manner selected to induce photodynamic cell death in *H. pylori*.

FIG. 6 depicts illustrative embodiments of one or more devices 400 including an untethered ingestible mass 310 optionally configured to rotate, optionally shaped for non-uniform movement, wherein the untethered ingestible mass 310 includes: an energy source 110, optionally a first electromagnetic energy source 111 configured to provide electromagnetic energy selected to stimulate an auto-fluorescent response in one or more target cells in a digestive tract; a sensor 120 configured to detect the auto-fluorescent response; control circuitry 130 coupled to the sensor 120 and responsive to identify a target area; optionally a second electromagnetic energy source 111 responsive to the control circuitry 130 and configured to emit energy selected to at least partially ablate the target area, optionally a power source 140, and optionally a motive source 150.

Figure 7:
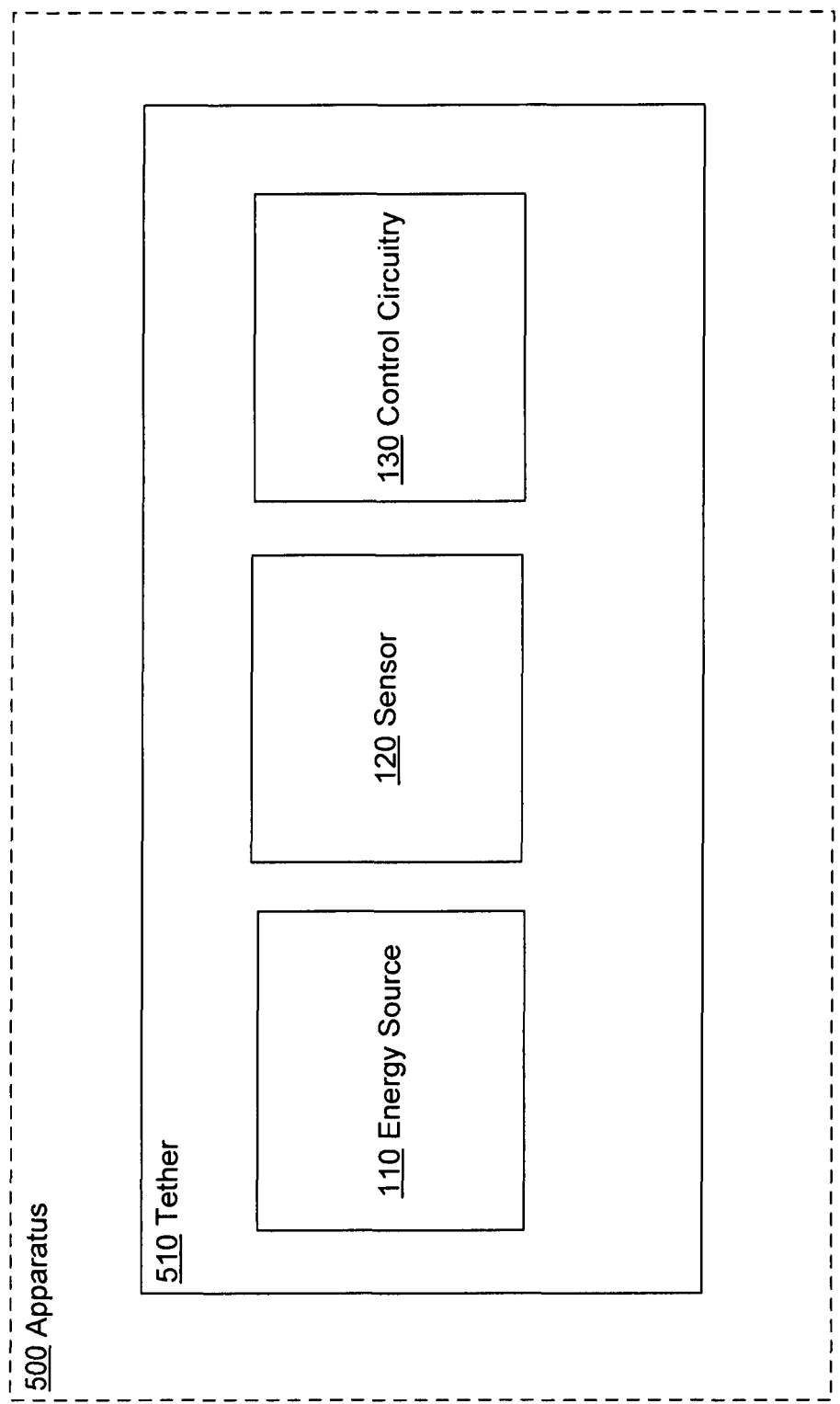
FIG. 7 shows a schematic of an illustrative tethered device in which embodiments may be implemented.

FIG. 7 depicts illustrative embodiments of one or more tethered 510 apparatus 500 including a first energy source 110 configured to provide electromagnetic energy selected to stimulate an auto-fluorescent response in one or more target cells in an internal location; a sensor 120 configured to detect the auto-fluorescent response; control circuitry 130 coupled to the sensor 120 and responsive to identify a target area in real time; and optionally a second energy source 110 responsive to the control circuitry 130 and configured to emit energy selected to at least partially ablate the target area.

Embodiments of one or more apparatus 100 and/or 500 and/or devices 200, 300, and/or 400 may be configured for use in one or more lesions, lumens, and/or internal locations of an organism. In illustrative embodiments, one or more apparatus 100, in part or in whole, is optionally a handheld device configured for detecting and ablating microbial and/or pathological contamination or cancer cells, for example, in lesions, optionally wounds or surgical incisions. In illustrative embodiments, one or more devices 200, in part or in whole, is an intra-lumenally sized device (e.g. small enough to be placed in a blood vessel while not obstructing the flow) configured for detecting and ablating microbial and/or pathogenic infections or cancer cells/metastases, for example, in the blood stream. In illustrative embodiments, one or more devices 300 and/or 400, in whole or in part, is an ingestibly-sized device (e.g. the size of a large vitamin pill) configured for detecting and ablating microbial and/or pathogenic infections or cancer cells, for example, in the digestive tract. In illustrative embodiments, one or more apparatus 500, in whole or in part, is part of or attached to a device, optionally handheld (e.g. an endoscope or fiber optic cable) and configured for detecting and ablating microbial and/or pathogenic infections or cancer cells, for example, in internal locations.

Embodiments of one or more apparatus 100 and/or 500 and/or devices 200, 300, and/or 400 may be configured as a self-contained unit that includes all functionalities necessary for operation of the device and/or apparatus, or configured as one or more subparts in one or more locations separate from one another, wherein one or more of the subparts includes one or more essential and/or non-essential functionalities. In illustrative examples, one subpart may be placed within a lumen of, for example, a blood vessel, and another subpart placed, for example, sub-cutaneously or within a larger or more accessible lumen. In illustrative embodiments, a remote portion may provide for monitoring of the lumen-based device or data collection or analysis. The remote portion may be at a separate location within the body of the subject, or outside the body of the subject. Data and/or power signals may be transmitted between the one or more subparts using electromagnetic signals, for example, or electrical or optical links. Methods of distributing functionalities of a system between hardware, firmware, and software at located at two or more sites are well known to those of skill in the art.

Embodiments of one or more apparatus 100 and/or 500 may be configured as a handheld unit, optionally self-contained and/or with one or more subparts in one or more other locations. In illustrative embodiments, a hand held unit includes one or more sources of energy 110, and at least one monitor to provide viewing of the lesion and targeting electromagnetic energy 118. In illustrative embodiments, a hand held unit includes control circuitry and at least one monitor for viewing lesion targeting information, as well as being connected to an energy source 110 and optionally one or more power sources 140 through one or more conduits. In illustrative embodiments, a handheld unit is wirelessly connected to control circuitry and to a monitor providing targeting information to an operator. In illustrative embodiments, apparatus 100 is a mounted, non-handheld, unit.

Embodiments of one or more apparatus 100 and/or 500 and/or devices 200, 300, and/or 400 may be described as having one or more subparts including, but not limited to, one or more energy sources 110, one or more sensors 120, one or more control circuitry 130, one or more power sources 140, and/or one or more motive sources 150. In some embodiments, one or more subpart may be a physically distinct unit. In some embodiments, one or more subpart is combined with one or more other subpart to form a single unit with no physically discernible separation. Some embodiments include a first, second, third, fourth, fifth, etc. energy source 110, sensor 120, control circuitry 130, power source 140, and/or motive source 150. One or more of the one, two three, four, five, etc. components may be the same component and/or physical entity, or one or more components may be a separate physical entity. For example, there may be two lasers in a device, or there may be one laser able to provide both excitation and ablation energy. For example, there may be two sensors in a device, or there may be one sensor able to detect a variety of energy wavelengths.

As used herein, the term "lesion" may include wounds, incisions, and/or surgical margins. In some embodiments, the term "lesion" may include, but is not limited to, cells and/or tissues, optionally including cells and/or tissues of the skin and/or retina. Wounds may include, but are not limited to, scrapes, abrasions, cuts, tears, breaks, punctures, gashes, slices, and/or any injury resulting in bleeding and/or skin trauma sufficient for foreign organisms to penetrate. Incisions may include those made by a medical professional, such as but not limited to, physicians, nurses, mid-wives, and/or nurse practitioners, dental professionals, such as but not limited to, dentists, orthodontists, dental hygienists, and veterinary professionals, including but not limited to, veterinarians during treatment optionally including surgery. As used herein, the term "surgical margins" may include the edges of incisions, for example, cancer margins.

As used herein, the term "lumen" may include, but is not limited to, part or all of a nostril or nasal cavity, the respiratory tract, the cardiovascular system (e.g., a blood vessel, including for example, arteries, veins, and capillaries), the lymphatic system, the biliary tract, the urogenital tract (e.g. a ureter), the oral cavity, the digestive tract, the tear ducts, a glandular system, a male or female reproductive tract (e.g. fallopian tubes, uterus, the epididymis, vas deferens, ductal deferens, efferent duct, ampulla, seminal duct, ejaculatory duct, and/or urethra), the cerebral-spinal fluid space (e.g. the cerebral ventricles, the subarachnoid space, and/or the spinal canal), the thoracic cavity, the abdominal cavity, and other fluid-containing structures of an organism. Other lumens may be found in the auditory or visual system, or in interconnections thereof, e.g., the Eustachian tubes.

Also included within the scope of the term "lumen" are man-made lumens within the body, including vascular catheters, spinal fluid shunts, vascular grafts, bowel re-anastomoses, bypass grafts, indwelling stents of various types (e.g., vascular, gastrointestinal, tracheal, respiratory, urethral, genitourinary, etc.) and surgically created fistulas. Other man-made lumens may be found associated with one or more implants, such as but not limited to, partial and/or complete joint replacements (knee, hip, shoulder, ankle, etc.) and/or partial and/or complete bone replacements (spinal vertebra, femur, shin, etc.).

As used herein, the term "internal location" may include locations within the body of a subject appropriate for the placement of one or more device and/or apparatus. Internal locations may be natural and/or man-made. In illustrative embodiments, one or more devices and/or subparts may be associated with one or more manmade objects within a subject, such as but not limited to, one or more stents, screws, rods, artificial joints, etc. Such internal locations are known to those with skill in the art and/or described herein.

As used herein, the term "in proximity to" may include, but is not limited to, a space and/or area near to a defined area, such as a lesion, lumen and/or internal location. Locations that are in proximity to a lumen may include, for example, locations internal to the lumen, parts, or all, of the width of the lumen wall, and locations external to the lumen wall. In some embodiments, "in proximity to" may include distances such as, but not limited to, approximately 0.1, 1.0, 10, and/or 100 µms and/or 0.1, 1.0, 10, and/or 100 mms, and may optionally include larger and/or smaller distances depending on the energy provided (e.g. electromagnetic energy, particle beam, two-photon, pulsed, etc.) and/or the sensitivity of detection. Those of skill in the art would know (and/or are able to calculate) the applicable distance for each form of energy.

As used herein, the term "subject" may include, but is not limited to, one or more living entities including, but not limited to, animals, mammals, humans, reptiles, birds, amphibians, and/or fish. The animals may include, but are not limited to, domesticated, wild, research, zoo, sports, pet, primate, marine, and/or farm animals. Animals include, but are not limited to, bovine, porcine, swine, ovine, murine, canine, avian, feline, equine, and/or rodent animals. Domesticated and/or farm animals include, but are not limited to, chickens, horses, cattle, pigs, sheep, donkeys, mules, rabbits, goats, ducks, geese, chickens, and/or turkeys. Wild animals include, but are not limited to, non-human primates, bear, deer, elk, raccoons, squirrels, wolves, coyotes, opossums, foxes, skunks, and/or cougars. Research animals include, but are not limited to, rats, mice, hamsters, guinea pigs, rabbits, pigs, dogs, cats and/or non-human primates. Pets include, but are not limited to, dogs, cats, gerbils, hamsters, guinea pigs and/or rabbits. Reptiles include, but are not limited to, snakes, lizards, alligators, crocodiles, iguanas, and/or turtles. Avian animals include, but are not limited to, chickens, ducks, geese, owls, sea gulls, eagles, hawks, and/or falcons. Fish include, but are not limited to, farm-raised, wild, pelagic, coastal, sport, commercial, fresh water, salt water, and/or tropical. Marine animals include, but are not limited to, whales, sharks, seals, sea lions, walruses, penguins, dolphins, and/or fish.

The dimensions and mechanical properties (e.g., rigidity) of the one or more apparatus 500 and/or devices 200, 300, and/or 400, and particularly of the structural elements of the one or more apparatus and/or device, may be selected for compatibility with the location of use in order to provide for reliable positioning and/or to provide for movement of the apparatus and/or device while preventing damage to the lesion, lumen, and/or internal location and its surrounding structure. In illustrative embodiments, an apparatus and/or device may be internal or external, tethered or untethered, motile or immobile, and/or optionally ingestible.

The choice of structural element size and configuration appropriate for a particular body lumen and/or internal location may be selected by a person of skill in the art. Structural elements may be constructed using a variety of manufacturing methods, from a variety of materials. Appropriate materials may include metals, ceramics, polymers, and composite materials having suitable biocompatibility, sterilizability, mechanical, and physical properties, as will be known to those of skill in the art. Examples of materials and selection criteria are described, for example, in *The Biomedical Engineering Handbook* (Second Edition, Volume I, J. D. Bronzino, Ed., Copyright 2000, CRC Press LLC, pp. IV-1-43-31). Manufacturing techniques may include injection molding, extrusion, die-cutting, rapid-prototyping, etc., and will depend on the choice of material and device size and configuration. Sensing and energy-emitting portions of the devices as well as associated control circuitry may be fabricated on the structural elements using various microfabrication and/or MEMS techniques (see, e.g., U.S. Patent Applications 2005/0221529, 2005/0121411, 2005/0126916, and Nyitrai, et al. "Preparing Stents with Masking & Etching Technology" (2003) $26^{th}$ International Spring Seminar on Electronics Technology pp. 321-324, IEEE), or may be constructed separately and subsequently assembled to the structural elements, as one or more distinct components. See also, U.S. patent application Ser. Nos. 11/403,230 and 11/645,357.

The choice of structural element size and configuration appropriate for a motile, optionally affixable, device may be selected by a person of skill in the art. Configurations for structural elements of motile devices include, but are not limited to, a substantially tubular structure, one or more lumens in fluid communication with the body lumen, and/or an adjustable diameter (see, e.g., U.S. patent application Ser. Nos. 11/403,230 and 11/645,357). Structural elements may have the form, for example, of a short cylinder, an annulus, a cylinder, and/or a spiral. A spiral structure is disclosed, for example, in Bezrouk et al, ("Temperature Characteristics of Nitinol Spiral Stents" (2005) Scripta Medica (BRNO) 78(4): 219-226. Elongated forms such as cylinders or spirals may be suitable for use in tubular lumen-containing structures such as, for example, blood vessels.

In additional to materials disclosed above, flexible material having adjustable diameter, taper, and length properties may be used as part of the structural material. For example, some materials may change from a longer, narrower configuration, to a shorter, wider configuration, or may taper over their length. Structural elements that may exhibit this type of expansion/contraction property may include mesh structures formed of various metals or plastics, and some polymeric materials, for example (see, e.g., "Agile new plastics change shape with heat" MIT News Office (Nov. 20, 2006) pp. 1-4; MIT Tech Talk (Nov. 22, 2006) p. 5; http://web.mit.edu/new-soffice/2006/triple-shape.html; and Shanpoor et al., Smart Materials and Structures (2005) 14:197-214, Institute of Physics Publishing).

In some embodiments, the structural element may include a self-expanding material, a resilient material, or a mesh-like material. Flexibility may also be conferred by configuration as well as material; the structural element may include a slotted structure and/or mesh-like material, for example. Structural elements may be formed from various materials, including metals, polymers, fabrics, and various composite materials, including ones of either inorganic or organic character, the latter including materials of both biologic and abiologic origin, selected to provide suitable biocompatibility and mechanical properties. The structural element may include a biocompatible material, and may include a bioactive component (such as a drug releasing coating or bioactive material attached to or incorporated into the structural element).

It is contemplated that additional components, such as energy sources 110, sensors 120, control circuitry 130, power sources 140, and/or motive sources 150 (e.g. propelling mechanisms), for example, will be attached, connected to, place within, manufactured on or in, and/or formed integrally with the structural element. Methods for manufacture and/or assembly are known in the art and/or described herein.

Embodiments of one or more apparatus 100 and/or 500 and/or devices 200, 300, and/or 400 may include one or more energy sources 110. One or more energy sources 110 may include, but are not limited to, one or more electromagnetic energy sources 111 and/or one or more charged particle energy sources 112. One or more electromagnetic energy sources 111 may include, but are not limited to, one or more optical energy sources 113 and/or one or more X-ray energy sources 115. One or more optical energy sources 113 may include, but are not limited to, one or more visual energy sources 114. In some embodiments one or more electromagnetic energy source 111 is a laser.

In some embodiments, one or more apparatus 100 and/or 500 is, in whole or in part, handheld. In some embodiments one or more energy source 110, optionally one or more electromagnetic energy source 111, is handheld. In some embodiments one or more energy source 110, optionally one or more electromagnetic energy source 111, is in the same handheld unit. In some embodiments one or more energy source 110, optionally one or more electromagnetic energy source 111, is in a different handheld unit.

In some embodiments, one or more energy sources 110 optionally provide energy for excitation of a fluorescent response 116, energy for targeting 118, and/or energy for ablation 117 of one or more targets. In some embodiments, one energy source 110 provides excitation energy 116, targeting energy 118, and ablation energy 117. In some embodiments, different energy sources 110 provide excitation energy 116, targeting energy 118, and ablation energy 117. In some embodiments, one energy source 110 provides excitation energy 116 and ablation energy 117, and optionally targeting energy 118. In some embodiments, more than one energy source 110 provides excitation energy 116. In some embodiments, more than one energy source provides ablation energy 117.

In some embodiments, one or more electromagnetic energy sources 111 provide one or more of excitation energy 116, ablation energy 117, and/or targeting energy 118. In some embodiments, one or more optical energy sources 113 (optionally visual energy sources 114) provide one or more of excitation energy 116, ablation energy 117, and/or targeting energy 118. In some embodiments, one or more X-ray energy sources 115 provide ablation energy. In some embodiments, one or more particle beam sources 112 provide ablation energy.

In some embodiments, one or more energy sources 110 are programmable, remote-controlled, wirelessly controlled, and or feedback-controlled.

As used herein, the term "electromagnetic energy" may include radio waves, microwaves, tetrahertz radiation, infrared radiation, visible light, X-rays, and gamma rays. In some embodiments, one or more of these frequencies may be explicitly excluded from the general category of electromagnetic energy (e.g. electromagnetic energy sources, but not including X-ray energy sources). Electromagnetic energy (or radiation) with a wavelength between approximately 400 nm and 700 nm is detected by the human eye and perceived as visible light. Optical light may also include near infrared (longer than 700 nm) and ultraviolet (shorter than 400 nm). In illustrative embodiments, electromagnetic energy is generated at one or more wavelengths of approximately 100-280 nm, 180-350 nm, 200-340 nm, 250-400 nm, 250-450 nm, 280-315 nm, 280-540 nm, 300-460 nm, 300-600 nm, 300-700 nm, 310-510 nm, 315-400 nm, 350-390 nm, 350-700 nm, 360-370 nm, 360-600 nm, 375-425 nm, 375-440 nm, 400-1000 nm, 407-420 nm, 410-430 nm, 445-470 nm, 450-490 nm, 450-560 nm, 455-490 nm, 465-495 nm, 490-690 nm, 505-550 nm, 515-555 nm, 580-600 nm, 600-1600 nm, 250 nm, 265 nm, 290 nm, 330 nm, 335 nm, 337 nm, 340 nm, 350 nm, 352 nm, 360 nm, 365 nm, 385 nm, 395 nm, 400 nm, 405 nm, 410 nm, 420 nm, 430 nm, 435 nm, 436 nm, 440 nm, 444 nm, 450 nm, 455 nm, 460 nm, 465 nm, 469 nm, 470 nm, 480 nm, 481 nm, 483 nm, 485 nm, 486 nm, 487 nm, 488 nm, 490 nm, 495 nm, 500 nm, 506 nm, 514 nm, 516 nm, 520 nm, 530 nm, 538 nm, 545 nm, 546 nm, 550 nm, 560 nm, 570 nm, 581 nm, 585 nm, 600 nm, 609 nm, 610 nm, 620 nm, 630 nm, 632 nm, 635 nm, 636 nm, 640 nm, 644 nm, 665 nm, 670 nm, 700 nm, 880 nm, 950 nm, 1064 nm, 1320 nm, 2070 nm, and/or 2940 nm, among others.

As used herein, the term "charged particle" may include particles generated using one or more particle beams. A particle beam is optionally an accelerated stream of charged particles or atoms that may be directed by magnets and focused by electrostatic lenses, although they may also be self-focusing. Particle beams may be high energy beams (e.g. created in particle accelerators), medium and/or low energy beams.

Electromagnetic or optical energy is made up of photons. Electromagnetic energy includes, but is not limited to, single photon electromagnetic energy, two photon electromagnetic energy, multiple wavelength electromagnetic energy, and extended-spectrum electromagnetic energy. Electromagnetic energy may be used for excitation of fluorescence, targeting, and/or for ablation of one or more targets. As used herein, the term "fluorescence" may include the production of light (emission) following excitation by electromagnetic energy. Fluorescence may result from emissions from exogenously provided tags and/or markers, and/or an inherent response of one or more targets to excitation with electromagnetic energy. As used herein, the term "auto-fluorescence" may include an inherent fluorescent response from one or more targets.

Electromagnetic energy sources 111 may be configured to emit energy as a continuous beam or as a train of short pulses. In the continuous wave mode of operation, the output is relatively consistent with respect to time. In the pulsed mode of operation, the output varies with respect to time, optionally having alternating 'on' and off periods. In illustrative examples, one or more energy sources are configured to emit pulsed energy to specifically ablate a limited area and/or a limited number of target cells. In illustrative examples, one or more energy sources are configured to emit continuous energy to excite endogenous fluorophores to emit fluorescence.

One or more electromagnetic energy sources 111 may include one or more lasers having one or more of a continuous or pulsed mode of action. One or more pulsed lasers may include, but are not limited to, Q-switched lasers, mode locking lasers, and pulsed-pumping lasers. Mode locked lasers emit extremely short pulses on the order of tens of picoseconds down to less than 10 femtoseconds, the pulses optionally separated by the time that a pulse takes to complete one round trip in the resonator cavity. Due to the Fourier limit, a pulse of such short temporal length may have a spectrum which contains a wide range of wavelengths.

In some embodiments, the electromagnetic energy is focused at a depth of approximately 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, or 3.0 mm below the surface of the lesion, beyond the surface of a wall of the lumen, and/or beyond a surface of an internal location. In some embodiments, the electromagnetic energy is focused at a depth of approximately 0.1 to 3 mm, 0.1 to 2.5 mm, 0.1 to 2.0 mm, 0.1 to 1.5 mm, 0.1 to 1.0 mm, 0.1 to 0.5 mm, 0.5 to 3.0 mm, 0.5 to 2.5 mm, 0.5 to 2.0 mm, 0.5 to 1.5 mm, 0.5 to 1.0 mm, 1.0 to 3.0 mm, 1.0 to 2.5 mm, 1.0 to 2.0 mm, 1.0 to 1.5 mm, 1.5 to 3.0 mm, 1.5 to 2.5 mm, 1.5 to 2.0 mm, 2.0 to 3.0 mm, 2.0 to 2.5 mm, or 2.5 to 3.0 mm below the surface of the lesion, beyond the surface of a wall of the lumen, and/or beyond a surface of an internal location.

In some embodiments, the electromagnetic energy is generated by two photons having the same wavelength. In some embodiments, the electromagnetic energy is generated by two photons having a different wavelength. Electromagnetic energy generated by two photons is optionally focused at a depth below the surface of the lesion, beyond the surface of a wall of the lumen, and/or beyond a surface of an internal location, optionally at one or more depths as described above and/or herein.

As used herein, the term "two-photon" may include excitation of a fluorophore by two photons in a quantum event, resulting in the emission of a fluorescence photon, optionally at a higher energy than either of the two excitatory photons, optionally using a femtosecond laser. In some embodiments, two photon electromagnetic energy is coupled through a virtual energy level and/or coupled through an intermediate energy level.

As used herein, the term "extended-spectrum" may include a range of possible electromagnetic radiation wavelengths within the full spectrum of possible wavelengths, optionally from extremely long to extremely short. One of skill in the art is able to select appropriate ranges for the devices and methods disclosed herein based on information publicly available and/or disclosed herein.

In some embodiments, the electromagnetic energy may be defined spatially and/or directionally. In some embodiments, the electromagnetic energy may be spatially limited, optionally spatially focused and/or spatially collimated. In illustrative embodiments, the electromagnetic energy optionally contacts less than less than an entire possible area, or an entire possible target, and/or is limited to a certain depth within a tissue.

In some embodiments, the electromagnetic energy may be directionally limited, directionally varied, and/or directionally variable. In illustrative embodiments, the electromagnetic energy may be provided only in a single direction, for example 90 degrees from the horizontal axis of a device, or toward a lumen wall, a lesion, or an internal location. In illustrative embodiments, the electromagnetic energy may be provided over a range of directions for example, through movement of the electromagnetic source, through movement of the entire device (e.g. rotation, random movement, wobbling, tumbling), and/or through illumination from a variety of sources in the device.

Electromagnetic energy configured to induce a fluorescent response in a target may be selected, optionally manually, remotely, programmably, wirelessly, and/or using feedback information. Frequencies that induce a fluorescent response in one or more targets are known in the art and/or discussed herein. In some embodiments, selection of excitation energy 116 may be performed in advance, or as a result of information received, optionally including feedback information, optionally from one or more sensors 120.

Electromagnetic energy and/or particle beam energy configured to ablate one or more targets may be selected, optionally manually, remotely, programmably, wirelessly, and/or using feedback information. Frequencies useful to at least partially ablate one or more targets are known in the art and/or discussed herein. In some embodiments, selection of ablation energy 117 may be performed in advance, or as a result of information received, optionally including feedback information, optionally from one or more sensors 120.

In addition to electromagnetic energy described herein, the ablation energy may be supplied by energetic charged particles, such as electrons, protons, or other ions. In one embodiment, the charged particles are directed towards the autofluorescent target in the form of particle beams. In another embodiment, the charged particles are emitted over relatively wide solid-angles, and address the designated autofluorescent target by virtue of spatial proximity.

In one embodiment, particle beams are generated outside the body by beam generators such as particle accelerators, cathode ray tubes, electrostatic accelerators, voltage-multiplier accelerators, Cockcroft-Walton accelerators, Van de Graaff accelerators, Alvarez accelerators, linear accelerators, circular accelerators, wakefield accelerators, collimated radioactive emitters, etc. The beams from these sources can be directed towards the autofluorescent target by mechanical, electrical, or magnetic methods. In some embodiments, the particle beams may be generated and directed from locations separate from the light source used to induce the autofluorescent response. In other embodiments, the particle beam may be generated in proximity to the autofluorescence inducing light source, by using compact particle sources such as electrostatic accelerators, Alvarez accelerators, linear accelerators, voltage-multiplier accelerators, Cockcroft-Walton accelerators, wakefield accelerators, collimated radioactive emitters, etc.

In some embodiments, particle beams are generated and delivered from inside the body. Compact particle beam generators such as electrostatic accelerators, Alvarez accelerators, linear accelerators, voltage-multiplier accelerators, Cockcroft-Walton accelerators, or wakefield accelerators can be used. In one embodiment of a voltage-multiplier accelerator, the staged voltage elements can use high-field-strength capacitors. In another embodiment, the staged voltages can be generated in an array of photocells by photogeneration using on-board or off-board light sources. In another embodiment of an in-vivo particle source, a radioactive emitter can be used to provide a charged particle source. One example of such a source is the Beta-Cath™ System, developed by Novoste Corp.

In one embodiment, in-vivo radioactive sources can be encapsulated within shielding which can be used to control charged particle exposure to nearby tissue. The shielding can have one or more portals, allowing for collimated emission. The shielding can be movable, either across all or part of its extent, or across one or more portal openings, in order to provide switchable particle sources. Shielding can be controllably moved by mechanical techniques such as valves, shutters, or similar devices, can utilize movable liquids, such as Hg, or utilize other methods. The particles from these in-vivo sources can be directed towards the autofluorescent target by mechanical, electrical, or magnetic methods, or may rely upon proximity.

Embodiments of one or more apparatus 100 and/or 500 and/or devices 200, 300, and/or 400 may include one or more targeting electromagnetic energy sources 118. Targeting electromagnetic energy is optionally from one or more optical energy sources 113, optionally from one or more visible light sources 114. In some embodiments, the one or more targeting energy source 118 is aligned with the excitation energy source 116 and/or the ablation energy source 117. In illustrative embodiments, the targeting energy source 118 provides a visual indication of the directional alignment of the excitation energy 116 to induce a fluorescent response, and/or the ablation energy 117 to at least partially ablate one or more targets.

In some embodiments, the one or more targeting energy source 118 has the same spatial extent as the excitation energy 116 and/or the ablation energy 117. In some embodiments, the one or more targeting energy source 118 has a different spatial extent than the excitation energy 116 and/or the ablation energy 117. In illustrative embodiments, the targeting energy is a visually detectable beam of light that is narrower than the excitation energy and/or ablation energy beam. In illustrative embodiments, the targeting energy is a visually detectable beam of light that is focused at the midpoint of the excitation and/or ablation energy beam. In illustrative embodiments, the targeting energy is a visually detectable beam of light that is broader than the excitation and/or ablation energy beam.

Embodiments of one or more apparatus 100 and/or 500 and/or devices 200, 300, and/or 400 may include one or more sensors 120. In some embodiments, one or more sensors 120 are the same sensor. In some embodiments, one or more sensors 120 are different sensors. In some embodiments, one or more sensors are in the same unit, optionally a handheld unit. In some embodiments, one or more sensors 120 are in separate units. In some embodiments, one or more sensors 120 are in the same and/or different units than one or more energy sources 110.

The one or more sensors may include, but are not limited to, electromagnetic energy detectors 121 (e.g. optical energy such as near IR, UV, visual), pH detectors 122, chemical and biological molecule detectors 123 (e.g. blood chemistry, chemical concentration, biosensors), physiological detectors 124 (e.g. blood pressure, pulse, peristaltic action, pressure sensors, flow sensors, viscosity sensors, shear sensors), time detectors 125 (e.g. timers, clocks), imaging detectors 126, acoustic sensors 127, temperature sensors 128, and/or electrical sensors 129. One or more sensors may be configured to measure various parameters, including, but not limited to, the electrical resistivity of the fluid, the density or sound speed of the fluid, the pH, the osmolality, or the index of refraction of the fluid at least one wavelength. The selection of a suitable sensor for a particular application or use site is considered to be within the capability of a person having skill in the art. One or more of these and/or other sensing capabilities may be present in a single sensor or an array of sensors; sensing capabilities are not limited to a particular number or type of sensors.

One or more biosensors 123 may detect materials including, but not limited to, a biological marker, an antibody, an antigen, a peptide, a polypeptide, a protein, a complex, a nucleic acid, a cell (and, in some cases, a cell of a particular type, e.g. by methods used in flow cytometry), a cellular component, an organelle, a gamete, a pathogen, a lipid, a lipoprotein, an alcohol, an acid, an ion, an immunomodulator, a sterol, a carbohydrate, a polysaccharide, a glycoprotein, a metal, an electrolyte, a metabolite, an organic compound, an organophosphate, a drug, a therapeutic, a gas, a pollutant, or a tag. A biosensor 123 may include an antibody or other binding molecule such as a receptor or ligand.

One or more sensors optionally include, in part or whole, a gas sensor such as an acoustic wave, chemiresistant, or piezoelectric sensors, or an electronic nose. One or more sensors are optionally small in size, for example a sensor or array that is a chemical sensor (Snow (2005) Science 307:1942-1945), a gas sensor (Hagleitner, et al. (2001) Nature 414:293-296.), an electronic nose, and/or a nuclear magnetic resonance imager (Yusa (2005), Nature 434:1001-1005). Further examples of sensors are provided in The Biomedical Engineering Handbook, Second Edition, Volume I, J. D. Bronzino, Ed., Copyright 2000, CRC Press LLC, pp. V-1-51-9, and U.S. Pat. No. 6,802,811).

One or more electromagnetic energy sensors 121 may be configured to measure the absorption, emission, fluorescence, or phosphorescence of one or more targets. Such electromagnetic properties may be inherent properties of all or a portion of one or more targets (e.g. auto-fluorescence), or may be associated with materials added or introduced to the body, surface, lumen, interior, and/or fluid, such as tags or markers for one or more targets. One or more targets may include, but are not limited to, at least a portion of one or more of a wound, a lesion, and/or an incision, one or more internal surfaces, one or more lumen fluids, one or more cells, one or more lumen walls, and/or one or more other interior locations.

In some embodiments, one or more sensors 120 are configured to detect a fluorescent response at a single wavelength of electromagnetic energy, at two wavelengths of electromagnetic energy, at multiple wavelengths of electromagnetic energy, or over extended-spectrum electromagnetic energy. In some embodiments, one or more sensors 120 are configured to detect excitation energy, ablation energy, and/or targeting energy. In illustrative embodiments, one or more sensors are configured to detect wavelengths of approximately 100-280 nm, 180-350 nm, 200-340 nm, 250-400 nm, 250-450 nm, 280-315 nm, 280-540 nm, 300-460 nm, 300-600 nm, 300-700 mm, 310-510 nm, 315-400 nm, 350-390 nm, 350-700 nm, 360-370 nm, 360-600 nm, 375-425 nm, 375-440 nm, 400-1000 nm, 407-420 nm, 410-430 nm, 445-470 nm, 450-490 nm, 450-560 nm, 455-490 nm, 465-495 nm, 490-690 nm, 505-550 nm, 515-555 nm, 580-600 nm, 600-1600 nm, 250 nm, 265 nm, 290 nm, 330 nm, 335 nm, 337 nm, 340 nm, 350 nm, 352 nm, 360 nm, 365 nm, 385 nm, 395 nm, 400 nm, 405 nm, 410 nm, 420 nm, 430 nm, 435 nm, 436 nm, 440 nm, 444 mm, 450 nm, 455 nm, 460 nm, 465 nm, 469 nm, 470 nm, 480 nm, 481 nm, 483 nm, 485 nm, 486 nm, 487 nm, 488 nm, 490 nm, 495 nm, 500 mm, 506 mm, 514 nm, 516 mm, 520 nm, 530 nm, 538 nm, 545 nm, 546 nm, 550 nm, 560 nm, 570 nm, 581 nm, 585 nm, 600 nm, 609 nm, 610 nm, 620 nm, 630 mm, 632 mm, 635 nm, 636 nm, 640 nm, 644 nm, 665 nm, 670 nm, 700 nm, 880 nm, 950 nm, 1064 nm, 1320 nm, 2070 nm, and/or 2940 nm.

In some embodiments, one or more sensors 120 are configured to detect a cumulative fluorescent response over a time interval. In some embodiments, one or more sensors 120 are configured to detect a fluorescent response at a specific time interval and/or at a specific time. In some embodiments, one or more sensors 120 are configured to detect a time-dependent fluorescent response. In illustrative embodiments, the cumulative fluorescent response is determined over milliseconds, seconds, and/or minutes following excitation. In some embodiments, the fluorescent response is detected over millisecond, second, and/or minute time intervals following excitation. In some embodiments, the fluorescent response is detected approximately femtoseconds, picoseconds, nanoseconds, milliseconds, seconds, and/or minutes after excitation.

In some embodiments, one or more sensors 120 are configured to be calibrated optionally at least partially based an expected baseline fluorescence (e.g. normal fluorescence) for the fluid, tissue, cells, internal location, lesion, and/or lumen. As used herein, the term "normal fluorescence" may include the intrinsic fluorescence of one or more fluid, tissue, cells, internal location, lesion, and/or lumen as determined by researchers and/or medical or veterinary professionals for subjects of a certain age, ethnicity, etc. who do not have pathological conditions (e.g. control subjects). "Normal fluorescence" may include the intrinsic fluorescence of fluid, tissue, cells, internal location, lesion, and/or lumen of a subject prior to a pathological condition and/or of a comparable location not affected by the pathological condition.

Embodiments of one or more apparatus 100 and/or 500 and/or devices 200, 300, and/or 400 may be configured to detect a condition of interest including, but not limited to, a temperature, a pressure, a fluid flow, an optical absorption, optical emission, fluorescence, or phosphorescence, an index of refraction at least one wavelength, an electrical resistivity, a density or sound speed, a pH, an osmolality, the presence of an embolism, the presence (or absence) of an object (such as a blood clot, a thrombus, an embolus, a plaque, a lipid, a kidney stone, a dust particle, a pollen particle, a gas bubble, an aggregate, a cell, a specific type of cell, a cellular component or fragment, a collection of cell, a gamete, a pathogen, or a parasite), and/or the presence (or absence) of a substance such as a biological marker, an antibody, an antigen, a peptide, a polypeptide, a protein, a complex, a nucleic acid, a cell (and, in some cases, a cell of a particular type, e.g. by methods used in flow cytometry), a cellular component, an organelle, a gamete, a pathogen, a lipid, a lipoprotein, an alcohol, an acid, an ion, an immunomodulator, a sterol, a carbohydrate, a polysaccharide, a glycoprotein, a metal, an electrolyte, a metabolite, an organic compound, an organophosphate, a drug, a therapeutic, a gas, a pollutant, or a tag, for example.

As used herein, the term "target" may include a condition and/or material of interest. Materials of interest may include, but are not limited to, materials identifiable by their autofluorescent emissions (individually or as an aggregate signal), or through the use of tags detectable through fluorescence. Such materials may include, but are not limited to, target cells, target tissues, and/or target areas. Such targets may include, but are not limited to, a blood clot, a thrombus, an embolus, a plaque, a lipid, a kidney stone, a dust particle, a pollen particle, an aggregate, a cell, a specific type of cell, a cellular component, an organelle, a collection or aggregation of cells or components thereof, a gamete, a pathogen, or a parasite.

One or more targets may include, but are not limited to, cancer, microbial cells, infected cells, and/or atherosclerotic cells. One or more cancer cells may include, but are not limited to, neoplastic cells, metastatic cancer cells, precancerous cells, adenomas, and/or cancer stem cells. Cancer types may include, but are not limited to, bladder cancer, breast cancer, colon cancer, rectal cancer, endometrial cancer, kidney (renal) cancer, lung cancer, leukemia, melanoma, non-Hodgkin's Lymphoma, pancreatic cancer, prostate cancer, skin (non-melanoma) cancer, and thyroid cancer. Cancers may include, but are not limited to, bone, brain, breast, digestive, gastrointestinal, endocrine, eye, genitourinary, germ line, gynecological, head and neck, hematologic/blood, leukemia, lymphoma, lung, musculoskeletal, neurologic, respiratory/thoracic, skin, and pregnancy-related. Microbial cells (microorganisms) may include, but are not limited to, bacteria, protists, protozoa, fungi, and/or amoeba. Pathogens may include, but are not limited to, bacteria, viruses, parasites, protozoa, fungi, and/or proteins. Bacteria may include, but are not limited to, *Escherichia coli, Salmonella, Mycobacterium* spp., *Bacillus anthracis, Streptococcus* spp., *Staphylococcus* spp., *Francisella tularensis*, and/or *Helicobacter pylori*. Viruses may include, but are not limited to, Hepatitis A, B, C, D, and/or E, Influenza virus, Herpes simplex virus, *Molluscum contagiosum*, and/or Human Immunodeficiency virus. Protozoa may include, but are not limited to, *Cryptosporidium, Toxoplasma* spp., *Giardia lamblia, Trypanosoma* spp., *Plasmodia* spp. and/or *Leishmania* spp. Fungi may include, but are not limited to, *Pneumocystis* spp., *Tinea, Candida* spp., *Histoplasma* spp., and/or *Cryptococcus* spp. Parasites may include, but are not limited to tapeworms and/or roundworms. Proteins may include, but are not limited to, prions.

As used herein, the term "fluid" may refer to liquids, gases, and other compositions, mixtures, or materials exhibiting fluid behavior. The fluid within the body lumen may include a liquid, or a gas or gaseous mixtures. As used herein, the term fluid may encompass liquids, gases, or mixtures thereof that also include solid particles in a fluid carrier. Liquids may include mixtures of two or more different liquids, solutions, slurries, or suspensions. Examples of liquids present within body lumens include, but are not limited to, blood, lymph, serum, urine, semen, digestive fluids, tears, saliva, mucous, cerebro-spinal fluid, intestinal contents, bile, epithelial exudate, or esophageal contents. Liquids present within body lumens may include synthetic or introduced liquids, such as blood substitutes, or drug, nutrient, fluorescent marker, or buffered saline solutions. Fluids may include liquids containing dissolved gases or gas bubbles, or gases containing fine liquid droplets or solid particles. Gases or gaseous mixtures found within body lumens may include inhaled and exhaled air, e.g. in the nasal or respiratory tract, or intestinal gases.

Embodiments of one or more apparatus 100 and/or 500 and/or device 200, 300, and/or 400 may include control circuitry 130. In some embodiments, the control circuitry is configured to control one or more of one or more energy sources 110, one or more sensors 120, and/or one or more power sources 140. In some embodiments, the control circuitry 130 may be directly coupled, indirectly coupled, and/or wirelessly coupled to one or more energy sources 110, one or more sensors 120, and/or one or more power sources 140. Control circuitry 130 may be electrical circuitry and/or other types of logic/circuitry including, for example, fluid circuitry, chemo-mechanical circuitry, and other types of logic/circuitry that provide equivalent functionality. The control circuitry 130 may include at least one of hardware, software, and firmware; in some embodiments the control circuitry may include a microprocessor. The control circuitry 130 may be located in or on the structural element of a device and/or at a location separate from the structural element. Various operation flows (e.g. 600, 700, and/or 800) operable on control circuitry 130 are described herein and/or known in the art.

In some embodiments, the control circuitry 130 is responsive to identify a target, target area, and/or target cells, molecules, and/or tissues. In some embodiments, the control circuitry 130 identifies a target, target area, and/or target cells, molecules, and/or tissues by determining one or more of the direction, the distance, the tissue depth, the time, and/or the coordinates from which a fluorescent response originated, optionally in relation to the excitation energy 116 and/or the targeting energy 118. In some embodiments, the control circuitry 130 identifies a target, target area, and/or target cells, molecules, and/or tissues by analysis of one or more characteristics of a fluorescent response (e.g. presence and/or absence of a fluorescent response and/or density of a fluorescent response—grouping of cells that if non-grouped would not be considered a target), optionally including but not limited to, the electromagnetic spectrum, or parts thereof, of a fluorescent response. In some embodiments, the control circuitry 130 identifies a target, target area, and/or target cells, molecules, and/or tissues in real time.

In some embodiments, the control circuitry 130 is responsive to select one or more characteristics of ablation energy 117 for at least partially ablating a target, target area, and/or target cells, molecules, and/or tissues. In some embodiments, the control circuitry 130 selects one or more characteristics of ablation energy 117 for at least partially ablating a target, target area, and/or target cells, molecules, and/or tissues responsive to one or more characteristics of the fluorescent response and/or the electromagnetic energy selected to elicit the fluorescent response. In some embodiments, the control circuitry 130 increases the ablation energy 117 responsive to an increase in the fluorescent response, and/or decreases the ablation energy 117 responsive to a decrease in the fluorescent response. In some embodiments, the control circuitry 130 selects one or more characteristics of the ablation energy 117 at least partially responsive to detection of one or more wavelengths of the fluorescent response.

In some embodiments, the control circuitry 130 is responsive to update targeting information on the basis of movement of part or all of an apparatus 100, and/or 500 and/or a device 100, 200, and/or 300 and/or a target and/or target area. In illustrative embodiments, such target updating may be useful when the ablating energy 117 may be delivered at a time substantially later than the time at which autofluorescence radiation is detected, or when the target is moving in relation to the ablation energy source 117. In this case, the detected location must be updated to take into account possible motion of the target area and/or the device.

Motion of the autofluorescence location can be updated by registering the detected autofluorescence location relative to other, updatable, location information. In one example, the detected autofluorescence location is registered relative to fiducials on or within the individual. Then, the location of the fiducials is updated, and the site of the autofluorescence location at such time can be predicted based upon its known registration relative to the fiducial locations. In another example, the detected autofluorescence location is registered relative to features within an image of a related portion of the individual. Then, the image is updated and the location of the autofluorescence location at such time can be predicted based upon its known registration relative to the image features.

Motion, which may include location and/or orientation, of the device can be updated by a variety of methods, including inertial navigation, measurements based on beacons or fiducials, measurements based on orientation sensors, or combinations of such techniques. Inertial navigation can be performed with the support of accelerometers on the device, and may also incorporate use of gyroscopic sensors on the device. Beacons and/or fiducials can be used to measure the device's motion; the beacons or fiducials may be on the device and their location or direction measured by remote sensors. Alternatively, measurements of remote beacons or fiducials may be made by sensors on the device. Combined systems may be used, with mixtures of remote and on-board sensors, measuring the location or direction of remote or on-board beacons or fiducials. Orientation sensors, such as tilt sensors may be used to provide information of one or more aspects of the device's orientation. Motion information obtained from different sources or methods can be combined together to give improved motion estimates, using techniques such as nonlinear filtering, least-squares filtering, Kalman filtering, etc.

The updated autofluorescence location may then be combined, via a coordinate translation and rotation, with the updated position and location of the device. This results in updated coordinates or directions of the autofluorescence location with respect to the device, and can be used to direct the delivery of ablation energy.

In some embodiments, control circuitry receives information from one or more sensors and/or one or more external sources. Information may include, but is not limited to, a location of an untethered device, allowable dose limits (e.g. of energy for excitation and/or ablation and/or targeting), release authority (e.g. for release of energy for excitation, ablation, and/or targeting, and/or release from a tethered location, or from an affixed and/or stationary location), control parameters (e.g. for energy release, for motion, for power, for sensors, etc.), operating instructions, and/or status queries.

In some embodiments, control circuitry is feedback controlled, optionally from information from one or more sensors, and/or one or more external sources. In some embodiments, control circuitry is monitored by one or more external sources, provides outputs to one or more sources, and/or sends outputs to one or more sources. In some embodiments control circuitry is remote-controlled, wirelessly controlled, programmed, and/or automatic.

Embodiments of one or more apparatus 100 and/or 500 and/or devices 200, 300 and/or 400 optionally include a power source 140. One or more power sources may be configured to provide power to one or more of one or more motive sources, one or more control circuitry, one or more sensor, and/or one or more energy source.

Power sources 140 may include, but are not limited to, one or more batteries 141, fuel cells 142, energy scavenging 143, electrical 144, and/or receivers 145 located on and/or in the one or more apparatus and/or devices or separately from the one or more apparatus and/or devices. The one or more batteries may include a microbattery such as those available from Quallion LLC (http://www.quallion.com), may be designed as a film (U.S. Pat. Nos. 5,338,625 and 5,705,293), or may be a nuclear battery. The one or more fuel cells may be enzymatic, microbial, or photosynthetic fuel cells or other biofuel cells (US2003/0152823A1; WO03106966A2 Miniature Biofuel cell; Chen T et al. J. Am. Chem. Soc. 2001, 123, 8630-8631, A Miniature Biofuel Cell), and may be of any size, including the micro- or nano-scale.

The one or more energy-scavenging devices may include a pressure-rectifying mechanism that utilizes pulsatile changes in blood pressure, for example, or an acceleration-rectifying mechanism as used in self-winding watches, or other types of flow rectifying mechanisms capable of deriving energy from other flow parameters. The one or more electrical power sources may be located separately from the structural element of the device and connected to the structural element by a wire, or an optical power source located separately from the structural element and connected to the structural element by a fiber-optic line or cable. The one or more power receivers may be capable of receiving power from an external source, acoustic energy from an external source, and/or a power receiver capable of receiving electromagnetic energy (e.g., infrared energy) from an external source.

In illustrative embodiments, one or more power sources 140 are optionally part of and/or are configured to propel, move, and/or provide power to one or more motive sources 150. One or more of the propelling mechanisms may include mechanical or micromechanical structures driven by at least one motor, micromotor, or molecular motor, or by expansion or change in configuration of a shape change polymer or metal. A molecular motor may be a biomolecular motor that runs on a biological chemical such as ATP, kinesin, RNA polymerase, myosin dynein, adenosinetriphosphate synthetase, rotaxanes, or a viral protein. In illustrative embodiments, one or more power sources 140 are configured to power one or more rotary motors, propellers, thrusters, and/or provide for jet propulsion, among others.

In some embodiments, the power source 140 optionally includes a power transmitter capable of transmitting power from one or more device to a secondary location. The power transmitter may be capable of transmitting at least one of acoustic power, electrical power, or optical power. The secondary location may be, for example, another device within the body, either in a body lumen or elsewhere that includes a power receiver and structures for using, storing and/or re-transmitting the received power.

Embodiments of one or more devices 200, 300 and/or 400 may include one or more motive sources 150. The one or more motive sources 150 are configured for the type and nature of the lumen and/or internal location to be traveled. A lumen and/or internal location having a relatively uniform cross-section (height and/or width) over the length to be traveled may be traversed by most propelling mechanisms including, but not limited to, mechanisms that engage the lumen wall on more than one and/or several sides, that engage the lumen wall on one side only, that are able to change shape/size (see, e.g., U.S. Patent Application 2005/0177223), and/or that employ more than one means of propulsion. A lumen and/or internal location that varies significantly in cross-section over the length to be traveled may be traversed using some propelling mechanisms including, but not limited to, those that walk or roll along one side of a lumen, those that are able to change shape/size, and/or those that employ more than one mode of propulsion.

In illustrative embodiments, one or more motive sources 150 may encompass part or all of the structural elements of one or more devices 200, 300, and/or 400. For example, one or more structural elements of one or more devices may be substantially cylindrical, and hollow and tubular in configuration, with a single central opening, optionally allowing the exterior of the cylindrical structural element to contact and engage the wall of a lumen, and the interior of the structural element (within the single central opening) to optionally form a fluid-contacting portion of the structural element. Optionally, one or more structural elements of one or more devices may be approximately hemi-spherical or hemi-elliptoid, optionally allowing a portion of its cross-section to contact and/or engage the wall of a lumen without obstructing the movement of fluid within the body lumen. Optionally, one or more structural elements of one or more devices may be pill- or capsule-shaped, and adapted to move through a central portion of a body lumen. Lumen wall engaging portions may include, but are not limited to, rotating wheels, projections (e.g. arms), springs, hooks (e.g. claws), and/or tissue adhesives that are configured to engage wall portions and optionally to provide mobility to one or more devices.

A variety of motive sources 150 applicable for one or more devices are known in the art and/or described herein. See, for example, U.S. Pat. Nos. 5,337,732; 5,386,741; 5,662,587; and 6,709,388; and Kassim, et al. "Locomotion Techniques for Robotic Colonoscopy"; IEEE Engineering in Med & Biol. Mag. (2006) pp. 49-56; Christensen "Musclebot: Microrobot with a Heart" (2004) Technolegy.com, pp. 1-2 located at http://www.technovelgy.com/ct/Science-Fiction-News.asp-?NewsNum=46; Ananthaswamy "First robot moved by muscle power" (2004), pp. 1-3; New Scientist; located at http://www.newscientist.com/article.ns?id=dn4714; and Freitas "8.2.1.2 Arteriovenous Microcirculation"; "9.4.3.5 Legged Ambulation"; "9.4.3.6 Tank-Tread Rolling"; "9.4.3.7 Amoeboid Locomotion"; "9.4.3.8 Inchworm Locomotion"; "Nanomedicine Volume I: Basic Capabilities" (1999) pp. 211-214, pp. 316-318; Landes Bioscience; Georgetown, Tex., USA.

One or more motive source 150 may include, but is not limited to, one or more propelling mechanisms such as one or more cilium-like structures (see, e.g., U.S. Patent Application 2004/0008853; Mathieu, et al. "MRI Systems as a Mean of Propulsion for a Microdevice in Blood Vessels" (2003) pp. 3419-3422, IEEE; Lu, et al. "Preliminary Investigation of Bio-carriers Using Magnetotactic Bacteria"; Proceedings of the 28th IEEE EMBS Annual International Conference (2006); pp. 3415-3418 IEEE, and Martel "Towards MRI-Controlled Ferromagnetic and MC-1 Magnetotactic Bacterial Carriers for Targeted Therapies in Arteriolocapillar Networks Stimulated by Tumoral Angiogenesis" Proceedings of the 28th IEEE EMBS Annual International Conference (2006) pp. 3399-3402 IEEE.

One or more motive source 150 may include propelling mechanisms such as, but not limited to, rollers or wheel-like structures (see, e.g., U.S. Pat. No. 7,042,184 and U.S. Patent Application 2006/0119304; screw-like structures (see, e.g., Ikeuchi, et al. "Locomotion of Medical Micro Robot with Spiral Ribs Using Mucus" Seventh International Symposium on Micro Machine and Human Science (1996) pp. 217-222 IEEE); and/or appendages capable of walking motion (see, e.g., U.S. Pat. No. 5,574,347; Shristensen "Musclebot: Microrobot with a Heart" Technovelgy.com; pp. 1-2; (2004); located at http://www.technovelgy.com/ct/Science-Fiction-News.asp?NewsNum=46; and Martel "Fundamentals of high-speed piezo-actuated three-legged motion for miniature robots designed for nanometer-scale operations" pp. 1-8), and others. Appendage-like structures may intermittently engage the lumen wall and push the structural element with respect to the lumen wall with a walking-type motion, or may push against fluid within the lumen in a paddling or swimming motion. In some embodiments, the propelling mechanism may drive rotational movement of a lumen-wall-engaging structure with respect to the structural element, e.g., as in turning of a wheel or a screw element to propel the structural element through a lumen.

One or more motive source 150 may include propelling mechanisms such as, but not limited to, an inchworm-type propulsion mechanism with suction mechanisms for engaging a surface (see, e.g., Patrick, et al. "Improved Traction for a Mobile Robot Traveling on the Heart", Proceedings of the 28$^{th}$ IEEE EMBS Annual International Conference (2006) pp. 339-342 IEEE; Dario, et al. "A Micro Robotic System for Colonoscopy" Proceedings of the 1997 IEEE International Conference on Robotics and Automation (1997) pp. 1567-1572 IEEE; and Dongxiang, et al. "An earthworm based miniature robot for intestinal inspection" Proceedings of SPIE (2001) 4601:396-400 SPIE).

One or more motive source 150 may include propelling mechanisms such as, but not limited to, multiple lumen wall engaging structures, operating in sequence to alternately engage and disengage the lumen wall, to produce "peristaltic" motion (see, e.g., U.S. Pat. No. 6,764,441; U.S. Patent Application 2006/0004395; Mangain, et al. "Development of a Peristaltic Endoscope" IEEE International Conference on Robotics & Automation 2002; pp. 1-6; http://biorobots.cwr-u.edu/publications/ICRA02_Mangan_Endoscope.pdf; and Meier, et al. "Development of a compliant device for minimally invasive surgery" Proceedings of the 28$^{th}$ IEEE EMBS Annual International Conference (2006) pp. 331-334 IEEE).

One or more motive source 150 may include propelling mechanisms such as, but not limited to, one or more paddles, propellers, or the like, which push against fluid contained within the lumen rather than engaging the wall of the body lumen (see, e.g., U.S. Pat. No. 6,240,312; and Behkam, et al. Proceedings of the 28$^{th}$ IEEE EMBS Annual International Conference (2006) pp. 2421-2424 IEEE.

One or more motive source 150 may include mechanisms configured to allow affixation to a lumen wall or other interior location, either permanent or temporary. In illustrative embodiments, configurations for affixing may include, but are not limited to, one or more anchors configured to attach at least temporarily to a wall of the lumen, one or more hooks and/or claws, one or more adhesive materials and/or glues, one or more brakes to oppose the action of the propelling mechanism, one or more expanding elements, one or more suction-generating elements, and/or or a shutoff for the propelling mechanism and/or for one or more power source 140.

In some embodiments, one or more configurations for affixing one or more devices may be activated responsive to control circuitry. In some embodiments, one or more configurations for affixing one or more devices may be fixed or movable. Movable structures may include, but are not limited to, mechanical elements and/or materials that change shape or rigidity in response to temperature, electric field, magnetic field, or various other control signals. Affixation may be permanent, for extended periods, and/or temporary. As used herein, the term "extended periods" may include weeks to months to years and subsets thereof. As used herein, the term "temporary" may include seconds, to minutes, to hours, to days and subsets thereof.

One or more motive source 150 may include mechanisms configured to allow one or more device to become stationary relative to a flow of fluid through a lumen and/or an internal location. In illustrative embodiments, configurations for becoming stationary include, but are not limited to, becoming affixed to a lumen or other internal location (e.g. by one or more mechanism described above), and/or reversing the propelling mechanism. Illustrative embodiments of configurations for reversing a propelling mechanism include, but are not limited to, reverse orientation of one or more motive source 150 (e.g. oriented to provide motive force in a reverse direction, such as against the flow of fluid, for example), one or more motive source 150 configured to allow bi-directional orientation (e.g. provide motive force in two directions, optionally 180 degrees apart (in opposition)), and/or one or more motive source configured to allow motive force to be applied in variable orientations.

In one aspect, the disclosure is drawn to one or more methods for ablating one or more targets optionally at least partially based on a fluorescent response, optionally using one or more apparatus 100 and/or 500 and/or device 200, 300 and/or 400 described herein. Although one or more methods may be presented separately herein, it is intended and envisioned that one or more methods and/or embodiments of one or more methods may be combined and/or substituted to encompass the full disclosure. In some embodiments, one or more methods may include one or more operations, and be implemented using one or more computing devices and/or systems.

In some embodiments, one or more methods of treatment include providing to a lesion electromagnetic energy selected to induce a fluorescent response from a target area; detecting the fluorescent response; identifying the target area at least partially based on an analysis of the detected fluorescent response; and providing energy to at least partially ablate the identified target area in real time. In some embodiments, one or more methods for ablating one or more target cells include providing to a lesion electromagnetic energy selected to induce a fluorescent response from a target area; detecting the fluorescent response; identifying the target area at least partially based on an analysis of the detected fluorescent response; and providing energy to at least partially ablate the identified target area in real time.

In some embodiments, one or more methods for detecting and ablating a target area include providing an untethered device to a lumen of a subject; providing from the untethered device electromagnetic energy selected to induce an auto-fluorescent response in one or more target cells in proximity to the lumen; detecting the auto-fluorescent response using a sensor in the untethered device; identifying the target area at least partially based on an analysis of the detected auto-fluorescent response; and providing from the untethered device energy configured to at least partially ablate the identified target area. In some embodiments, one or more methods of treatment include providing an untethered device to a lumen of a subject; providing from the untethered device electromagnetic energy selected to induce an auto-fluorescent response in one or more target cells in the lumen; detecting the auto-fluorescent response using a sensor in the untethered device; identifying the target area at least partially based on an analysis of the detected auto-fluorescent response; and providing from the untethered device electromagnetic energy configured to at least partially ablate the identified target area.

In some embodiments, one or more methods for treating or ameliorating *H. pylori* infection include providing to a digestive tract of a subject an untethered ingestible mass, the untethered ingestible mass configured for non-uniform movement; and emitting electromagnetic energy from the untethered ingestible mass in a manner selected to induce photodynamic cell death in *H. pylori*. In some embodiments, one or more methods for ablating *H. pylori* include providing to a digestive tract of a subject an untethered ingestible mass, the untethered ingestible mass configured for non-uniform movement; and emitting electromagnetic energy from the untethered ingestible mass in a manner selected to induce photodynamic cell death in *H. pylori*.

In some embodiments, one or more methods for detecting and ablating a target area in a digestive tract include providing to a subject an optionally rotating untethered ingestible mass and/or optionally configured for non-uniform movement; providing from the untethered ingestible mass electromagnetic energy selected to induce an auto-fluorescent response in one or more target cells in the digestive tract; detecting the auto-fluorescent response using a sensor in the untethered device; identifying the target area at least partially based on an analysis of the detected auto-fluorescent response; and providing from the untethered device electromagnetic energy configured to at least partially ablate the identified target area. In some embodiments, one or more methods for treating a disease or disorder in a digestive tract include providing to a subject a rotating untethered ingestible mass; providing from the untethered ingestible mass electromagnetic energy selected to induce an auto-fluorescent response in one or more target cells in the digestive tract; detecting the auto-fluorescent response using a sensor in the untethered device; identifying the target area at least partially based on an analysis of the detected auto-fluorescent response; and providing from the untethered device electromagnetic energy configured to at least partially ablate the identified target area. In some embodiments, one or more methods of treatment include providing to a subject a rotating untethered ingestible mass; providing from the untethered ingestible mass electromagnetic energy selected to induce an auto-fluorescent response in one or more target cells in the digestive tract; detecting the auto-fluorescent response using a sensor in the untethered device; identifying the target area at least partially based on an analysis of the detected auto-fluorescent response; and providing from the untethered device electromagnetic energy configured to at least partially ablate the identified target area.

In some embodiments, one or more methods for detecting and ablating one or more target cells include providing to an internal location a tethered device; providing from the tethered device electromagnetic energy selected to induce an auto-fluorescent response from the one or more target cells; detecting the auto-fluorescent response; identifying a target area at least partially based on an analysis of the detected auto-fluorescent response; and providing energy to at least partially ablate the identified target area in real time. In some embodiments, one or more methods of treatment include providing to an internal location a tethered device; providing from the tethered device electromagnetic energy selected to induce an auto-fluorescent response from one or more target cells; detecting the auto-fluorescent response; identifying a target area at least partially based on an analysis of the detected auto-fluorescent response; and providing energy to at least partially ablate the identified target area in real time.

Embodiments of one or more methods include affixing one or more devices 200, 300, and/or 400 to a location in a lumen and/or an interior location. As used herein, the term "affixing" may include, but is not limited to, one or more processes by which the one or more devices may be held stationary in the lumen or internal location. The affixation may be temporary and/or permanent as described herein. Mechanisms by which one or more device may become affixed are known in the art and/or described herein.

Embodiments of one or more methods include moving one or more devices 200, 300, and/or 400 from one location to another within a lumen and/or internal location. As used herein, the term "moving" may include, but is not limited to, one or more processes by which a device may traverse a lumen and or internal location in one or more directions. Movement may be with the flow of an optional moving fluid (and/or gravity), against the flow of an optional moving fluid (and/or gravity), and or at an angle oblique to a moving flow of fluid (and/or gravity). Movement may be irrespective of the presence and/or absence of fluid and/or moving fluid. Movement may be temporary, intermittent, and/or continuous. Movement may be random and/or non-uniform. Movement may be controlled by control circuitry, either internal or external to the device. Movement may be associated with identification and/or ablation of a target. Mechanisms for moving one or more device are known in the art and/or are described herein.

In illustrative embodiments, moving an untethered device includes moving an untethered device by providing a motive force to the untethered device. As used herein, the term "motive force" may include, but is not limited to, a mechanism that allows the untethered device to move within a lumen and/or internal location, such as for example, those described for a motive source and a power source herein. In some embodiments, a motive force is responsive to control circuitry, is remote-controlled, is programmable, and/or is feedback-controlled. In some embodiments, a motive force is powered by a battery, a capacitor, receives power from one or more external sources, and/or from one or more physiological sources. In some embodiments, a motive force is responsible for the random and or non-uniform movement of a device.

Embodiments of one or more methods include providing electromagnetic energy, optionally optical energy, to a target, target area, target cell, target tissue, lesion, incision, wound, internal location, and/or lumen, optionally selected to induce a fluorescent response. Providing electromagnetic energy optionally includes using a laser, optionally handheld, or other device to provide optical energy to a target.

Parameters associated with the selection of electromagnetic energy to induce a fluorescent response include, but are not limited to, the target, the environment associated with the target, the characteristics of the electromagnetic energy source, and/or the characteristics of the sensor.

The parameters associated with the target include, but are not limited to, the distance of the target from the electromagnetic source, the depth of the target beneath a surface (e.g. a lumen wall, an internal surface, a lesion surface), the inherent fluorescence of the target, the markers/tags used to identify the target, the size of the target, and/or the movement of the target (e.g. stationary, steady movement, variable movement, predictable movement, etc.).

The parameters associated with the environment include, but are not limited to, location (e.g. external, internal, lumen, wound, incision, etc.), milieu (e.g. fluid-filled, air-filled, blood, digestive contents, etc.), movement (e.g. stationary, steady movement, intermittent movement, predictable movement, etc.), physiologic parameters (e.g. pH, temperature, etc.), and/or non-target fluorescence (e.g. background fluorescence, non-specific fluorescence, intrinsic non-target fluoresce, etc.).

The parameters associated with the characteristics of the electromagnetic energy source include, but are not limited to, the wavelengths available for selection (e.g. single, two-photon, multiple, extended-spectrum, etc.), the strength of the emitted electromagnetic energy (e.g. limitations on distance and/or depth, etc.), the type of output (e.g. pulsed, two-photon, etc.), directionality (e.g. limited, variable, varied, etc.), and/or spatial parameters (e.g. limited, focused, collimated, etc.).

The parameters associated with the characteristics of the sensor include, but are not limited to, the detection limits associated with wavelength (e.g. single, two-photon, multiple, extended-spectrum, etc.), signal strength (e.g. sensitivity of detection, level above background, etc.), and/or time (e.g. detects cumulative readings over time, detects readings at certain time intervals, or at a certain time post excitation, etc.).

Embodiments of one or more methods include selecting the electromagnetic energy, optionally optical energy, to induce the fluorescent response. Methods for selecting include, but are not limited, manually, remotely, automatically, programmably, wirelessly, and/or using control circuitry. Manually selecting includes, but is not limited to, manually operating one or mechanism (e.g. a switch, dial, button, etc.) on one or more apparatus 100 and/or 500, and/or device 200, 300, and/or 400, that controls the emitted wavelength from one or more electromagnetic energy source. Remotely selecting includes, but is not limited to, optionally wirelessly interacting with circuitry on one or more apparatus 100 and/or 500, and/or device 200, 300, and/or 400 that controls the wavelength emitted from one or more electromagnetic energy source. Programmably selecting includes, but is not limited to, optionally using control circuitry, optionally part of one or more apparatus 100 and/or 500, and/or device 200, 300, and/or 400 (e.g. internal and/or external), programmed, optionally manually, remotely, and/or wirelessly, to select the wavelength emitted from one or more electromagnetic energy source. Methods for programming control circuitry are well-known to one of skill in the art, and some applicable control circuitry is described herein.

Embodiments of one or more methods include monitoring the electromagnetic energy selected to induce a fluorescent response, optionally an auto-fluorescent response, optionally a target fluorescent response, monitoring the energy selected to ablate the target, optionally electromagnetic energy, optionally particle beam energy, and/or monitoring the targeting electromagnetic energy, optionally visual light. Methods of monitoring electromagnetic energy and/or particle beam energy are known in the art and/or described herein. Methods include, but are not limited to, using sensors able to detect one or more characteristics of the energy.

Embodiments of one or more methods include detecting a fluorescent response. Methods of detecting a fluorescent response include, but are not limited to, detecting a fluorescent response using one or more sensors, detectors, and/or monitors. Sensors, detectors, and/or monitors appropriate for detection and/or monitoring of the fluorescent response are known in the art and/or described herein. As used herein, the term "detecting" may include any process by which one or more characteristics of a fluorescent response may be measured and/or quantified.

Embodiments of one or more methods include identifying a target for ablation (e.g. target area, target cells, and/or target tissues). As used herein, the term "identifying a target" may include, but is not limited to, processes including selecting a target and/or determining a target. One or more methods for identifying a target for ablation optionally include analyzing a fluorescent response and/or other information, optionally using control circuitry, optionally in real time.

Analyzing a fluorescent response to at least partially identify a target for ablation may include, but is not limited to, evaluating a fluorescent response at least partially in reference to baseline fluorescence, background fluorescence, expected fluorescence, normal fluorescence, reference fluorescence, non-specific fluorescence, and/or intrinsic non-target fluorescence, etc. Analyzing a fluorescent response may include, but is not limited to, subtractively determining a target fluorescent response (e.g. subtracting the non-target fluorescence from the total fluorescence to determine the target fluorescence). Analyzing a fluorescent response may include, but is not limited to, evaluating a fluorescent response at least partially based on detection at one or more wavelengths (e.g. single, multiple, extended-spectrum, etc.), based on time (e.g. one or more times, time intervals, and/or over time, etc.), based on direction (e.g. of origination of the emission, etc.), based on strength, and/or based on distance (e.g. of origination of emission from a sensor). In illustrative embodiments, analyzing a fluorescent response may include, but is not limited to, identifying "clumps" and/or "groups" of autofluorescent cells that in another context might be considered "normal", but that are not normally grouped and so may be a target for ablation.

In illustrative embodiments, an analyzed target fluorescent response is used to determine the direction from which the response originated in order to provide ablation energy to the location and/or general area. In illustrative embodiments, an analyzed target fluorescent response is used to determine the coordinates from which the response originated in order to provide ablation energy to the location and/or general area.

As used herein, the term "location" may include, but is not limited to, one or more of a direction, an area, a depth, a site, or a size, etc. A location may be defined by spatial coordinates and/or temporal coordinates. A location may be defined as precisely as the cellular level, for example, or as broadly as a general area, or a general direction. Methods of determining a location based on the detection of a fluorescent response are known in the art and/or described herein. In illustrative embodiments, a target location may be the cancerous and/or pre-cancerous cells remaining in a surgical margin. In illustrative embodiments, a target location may be the microbial cell contamination remaining in a wound following a sterile wash. In illustrative embodiments, a target location may be the lumen of a blood vessel following detection of a target fluorescent response. In illustrative embodiments, a target location may be the lumen of the digestive tract in a area with an acidic pH.

Analyzing other information to at least partially identify a target for ablation may include, but is not limited to, analyzing information optionally provided by one or more sensors (e.g. intrinsic and/or extrinsic to one or more device and/or apparatus) and/or provided by one or more external sources (e.g. remotely and/or wirelessly, etc.). Analyzing information optionally provided by one or more sensors may include analyzing information including, but not limited to, environmental information such as, but not limited to, pH, temperature, pressure, chemistry, physiological measurements, dietary measurements, biological measurements, etc. In illustrative embodiments, identifying a target fluorescent response is a least partially based on identifying the pH of the environment, optionally detecting an acidic pH. Analyzing information optionally provided by one or more external sources may include analyzing information including, but not limited to, environmental information and/or medical and/or veterinary professional information.

Analyzing a fluorescent response to at least partially identify a target for ablation may include, but is not limited to, evaluating a fluorescent response in real time. As used herein, the term "in real time" may include, but is not limited to, immediate, rapid, not requiring operator intervention, automatic, and/or programmed. In real time may include, but is not limited to, measurements in femtoseconds, picoseconds, nanoseconds, milliseconds, as well as longer, and optionally shorter, time intervals. In illustrative embodiments, analysis in real time is sufficiently rapid such that the target and the device have not moved and/or changed positions/locations significantly with respect to each other. In illustrative embodiments, a fluorescent response is detected and analyzed, and a target is identified without operator intervention and the target ablation information is provided to an energy source.

Embodiments of one or more methods include providing energy to at least partially ablate a target. One or more methods include providing energy to at least partially ablate a target in real time. As used herein the term "ablation or ablate" may include, but is not limited to, processes including destroying, modifying, removing, and/or eliminating, in part or in whole, a target and/or a material of interest. As used herein, ablation may include the process of removing material, optionally from a surface, by irradiating it, optionally with a laser beam. At low laser flux, the material is heated by the absorbed laser energy and evaporates or sublimes. At high laser flux, the material is typically converted to a plasma. Ablation may include the process of removing material with a pulsed laser, or a continuous wave laser.

Energy for ablation may include, but is not limited to, electromagnetic energy, X-ray energy, and particle beam energy. Electromagnetic energy such as light may cause, for example, a photoreaction, molecular bond breakage, heating, or other appropriate effect. Electromagnetic energy sources may include, but are not limited to, light sources such as light emitting diodes and laser diodes, or sources of other frequencies of electromagnetic energy, radio waves, microwaves, ultraviolet rays, infra-red rays, optical rays, terahertz beams, and the like.

As used herein, the term "at least partially ablate" may include partially and/or completely ablating a target. As used herein, the term "completely ablate" may include ablation of a target up to the applicable limits of detection (e.g. no longer detectable by the sensors used to detect the fluorescent response, no longer detectable over background, and/or no longer statistically significant). As used herein the term "partially ablate" may include ablation less than complete ablation, but where at least some detectable ablation occurs. At least some detection ablation includes, but is not limited to, ablation detectable by the sensors used to detect the fluorescent response, statistically significant ablation, detection by external sensors, and/or detection by inference from other measurements and/or sensor readouts.

Embodiments of one or more methods include providing targeting electromagnetic energy to a lesion, a lumen, an internal location, etc. methods for providing targeting electromagnetic energy are known in the art, and/or described herein. Targeting electromagnetic energy is optionally optical energy, optionally visible to the human eye. Targeting electromagnetic energy is optionally alignable with electromagnetic energy emitted to induce a fluorescent response and/or with energy emitted to at least partially ablate a target. In illustrative embodiments, targeting electromagnetic energy is aligned with the output from one or more energy sources as a visual aid to a medical and/or veterinary professional during treatment of a subject.

EXAMPLES

The following Examples are provided to illustrate, not to limit, aspects of the present invention. Materials and reagents described in the Examples are commercially available unless otherwise specified.

Example 1

Detection and Ablation of Pathogens Prior to Closing a Surgical Incision

A surgical incision is screened with a device that detects and ablates pathogens within the open lesion prior to closing to prevent postoperative infection. The device emits electromagnetic energy at wavelengths sufficient to induce autofluorescence of pathogens within the incision. The device detects the autofluorescence associated with the pathogens, and in real time automatically delivers energy sufficient to at least partially inactivate or ablate the pathogens. Optionally, the device detects the autofluorescence, collects and processes the data, and at the discretion of the surgeon or other medical practitioner (or veterinarian), a trigger mechanism, for example, is used to deliver energy sufficient to at least partially inactivate or ablate the pathogens at the coordinates associated with the autofluorescence. The device may be handheld, for example, and either self-contained or connected wirelessly or by wire to optionally a power supply, energy sources, control circuitry, and/or monitor. Alternatively, the device may be a fixed component of the surgical theater.

A pathogen or pathogens may be detected at the site of incision based on autofluorescence induced, for example, by electromagnetic energy. Naturally occurring autofluorescence in bacteria, for example, is derived from biomolecules containing fluorophores, such as porphyrins, amino acids tryptophan, tyrosine, and phenylalanine, and the coenzymes NADP, NADPH, and flavins (Koenig, et al. (1994) J. Fluoresc. 4:17-40; Kim, et al. (2004) IEEE/EMB Magazine January/February 122-129). The excitation maxima of these biomolecules lie in the range of 250-450 nm (spanning the ultraviolet/visible (UV/VIS) spectral range), whereas their emission maxima lie in the range of 280-540 (spanning the UV/VIS spectral range; Ammor (2007) J. Fluoresc. published on-line ahead of publication).

For example, two clinically important bacteria, *Enterococcus faecalis*, and *Staphylococcus aureus*, may be differentiated based on their respective autofluorescence in response to excitation spectra of 330-510 nm and emission spectra of 410-430 nm (Ammor (2007) J. Fluoresc. published on-line ahead of publication). Similarly, *Streptococcus pneumoniae, Moraxella catarrhalis*, and *Haemophilus influenzae* may be detected using fluorescence spectroscopy at excitation wavelengths of 250 and 550 nm and emission wavelengths of 265 and 700 nm (Ammor (2007) J. Fluoresc. published on-line ahead of publication). Bacteria associated with community acquired pneumonia, *Legionella anisa* and *Legionella dumoffii*, autofluoresce blue-white when exposed to long-wave (365-nm) UV light (Thacker, et al. (1990) J. Clin. Microbiol. 28:122-123). *Bacillus* spores will autofluoresce when excited by UV irradiation at a wavelength of 352 nm (Laflamme, et al. (2006) J. Fluoresc. 16:733-737). *Clostridium sporogenes, Pseuodomonas aeruginose, Pseudomonas fluorescens, Kocuria rhizophila, Bacteroides vulgatis, Serratia marcescens,* and *Burkholderia cepacia* emit yellow-green fluorescent signal when illuminated with blue light (Sage, et al. (2006) American Biotechnology Laboratory 24:20-23).

Autofluorescence of endogenous porphyrins may also be used to detect bacteria. A number of bacteria produce protoporphyrins, including *Propinibacterium acnes, Bacillus thuringiensis, Staphylococcus aureus,* and some strains of *Clostridium, Bifidobacterium,* and *Actinomyces* (Koenig, et al. (1994) J. Fluoresc. 4:17-40). Bacteria may also be detected using fluorescence lifetimes measured at 430, 487, and 514 nm after selective excitation at 340, 405, and 430 nm (Bouchard, et al. (2006) J. Biomed. Opt. 11:014011, 1-7).

Autofluorescence may also be used to detect members of the fungi family. For example, *Candida albicans* irradiated with electromagnetic energy at wavelengths of 465-495 nm autofluoresces at an emission wavelength of 515-555 nm (Mateus, et al. (2004) Antimicrob. Agents and Chemother. (2004) 48:3358-3336; Graham (1983) Am. J. Clin. Pathol. 79:231-234). Similarly, *Aspergillus niger* and *Aspergillus versicolor* may be detected using autofluorescence in response to excitation at 450-490 nm and emission at 560 nm (Sage, et al. (2006) American Biotechnology Laboratory 24:20-23; Graham (1983) Am. J. Clin. Pathol. 79:231-234).

A pathogen or pathogens at the site of incision may be inactivated or killed by energy emitted from a device in response to detection of the pathogen by autofluorescence using the same device. Many pathogens are inactivated or killed by UV germicidal irradiation (Anderson, et al. (2000) IEEE Transactions on Plasma Science 28:83-88; Hancock, et al. (2004) IEEE Transactions on Plasma Science 32:2026-2031). UV light ranges from UVA (400-315 nm), also called long wave or 'blacklight'; UVB (315-280 nm), also called medium wave; and UVC (<280 nm), also called short wave or 'germicidal'."

Optionally, a wavelength may be used that completely or partially inactivates pathogens but limits damage to surrounding tissue. For example, a wavelength of 630 nm partially inhibits growth of *Pseudomonas aeruginosa* and *Escherichia coli* (Nussbaum, et al. (2002) J. Clin. Laser Med. Surg. 20:325-333). Similarly, a number of oral bacteria, including *Acinobacillus actinomycetemcomitans, Fusobacterium nucleatum, Porphromonas gingivalis, Pnevotella intermedia,* and *Streptococcus sanguis,* may be partially inactivated using a diode 665 laser at 100 mW for 30 s (energy density 10.6 J/cm$^2$) or 60 s (energy density 21.2 J/cm$^2$) at a distance of 5 mm (Chan, et al. (2003) Lasers Surg. Med. 18:51-55).

Inactivation of bacteria by a diode 665 laser may be enhanced, for example, by pre-staining the bacteria with methylene blue (Chan, et al. (2003) Lasers Surg. Med. 18:51-55). Similarly, oral bacteria may be inactivated using a He—Ne laser at 30 mW for 30 s (energy density 3.2 J/cm$^2$) or 60 s (energy density 6.4 J/cm$^2$) in combination with methylene blue (Chan, et al. (2003) Lasers Surg. Med. 18:51-55).

Alternatively, a pathogen or pathogens may be inactivated or killed at the incision site with a form of laser thermal ablation using, for example, a $CO_2$ or Nd:YAG laser (Bartels, et al. SPIE Vol 2395:602-606). For example, *Staphylococcus aureus* may be partially inactivated or killed using high-power Nd:YAG laser radiation between 50 and 300 W with laser pulse frequencies of 5 to 30 Hz and pulse energies from 2 to 30 J, resulting in a range of energy densities from 800 to 270 J/cm$^2$ (Yeo, et al. (1998) Pure Appl. Opt. 7:643-655). *Escherichia coli* 0157:H7, for example, is extremely sensitive to heat with a maximum tolerance of approximately 35 degrees centigrade (U.S. Pat. No. 6,030,653).

Pathogens may be inactivated or killed using X-ray and gamma electromagnetic energy. For example, *Escherichia coli* 0157:H7, *Salmonella,* and *Campylobacter jejuni* may be at least partially inactivated or killed using cobalt-60 gamma radiation at doses of 0.5 to 3 kGy (Clavero, et al. (1994) Applied Environ. Microbiol. 60:2069-2075).

Alternatively, pathogens may be inactivated or killed using a form of particle beam irradiation. For example, *Salmonella, Yersinia,* and *Campylobacter* may be at least partially ablated using accelerated electrons with doses of irradiation ranging from 1-3 kGy (Sarjeant, et al. (2005) Poult. Sci. 84:955-958). Similarly, *Bacillus* endospores may be at least partially ablated using electron beam irradiation with doses ranging from 5 to 40 kGy (Helfinstine, et al. (2005) Applied Environ. Microbiol. 71:7029-7032).

Viruses may be inactivated on a surface using UV irradiation (Tseng & Li, (2007) J. Occup. Envirn. Hyg. 4:400-405). Fungi, for example *Aspergillus flavus* and *Aspergillus fumigatus,* may also be inactivated using UV germicidal irradiation at 12-98 mJ/cm$^2$ (Green, et al. (2004) Can. J. Microbiol. 50:221-224).

Alternatively, energy may be used that disrupts the function of heme iron porphyrins associated with iron uptake and utilization, inactivating iron dependent bacteria such as *Escherichia coli* and *Salmonella* (U.S. Pat. No. 6,030,653). Pathogens may be inactivated by irradiating the surface with visible and near infrared light having wavelengths of approximately 465 nm, 600 nm, and 950 nm, respectively.

In some instances, the entirety of the affected tissue may be irradiated to at least partially inactivate or kill pathogens. Alternatively, focused energy may be directed only to those sites emitting pathogen-associated autofluorescence or fluorescence. A pathogen or pathogens at the site of incision may be inactivated or killed by energy emitted from a device in either the presence or absence of prophylactic antibiotics (Dellinger, et al. (1994) Clin. Infect. Dis. 18:422-427).

There are a number of microbial pathogens of concern during surgical treatment that may lead to difficult to treat nosocomial or hospital acquired infection, including methicillin-resistant *Staphylococcus aureus* (MRSA), *Staphylococcus epidermidis, Streptococcus pyogenes, Pseudomonas aeruginosa,* vancomycin-resistant Enterococci (VRE), extended spectrum b-lactamase-producing bacteria (ESBL), multi-drug resistance in *Mycobacterium tuberculosis* (MDRTB) strains as well as multi-drug resistant Gram-negative bacteria (Lichtenstern, et al. (2007) Dig. Surg. 24: 1-11; NIAID (National Institute of Allergy and Infectious Disease) Profile Fiscal Year 2005, Selected Scientific Areas of Research, Antimicrobial Resistance, pages 52-55).

The Gram-positive bacteria *Staphylococcus aureus* is a common cause of superficial skin infections such as boils, furuncles, styes, impetigo. *S. aureus* is also a major cause of nosocomial and community-acquired infections, particularly in individuals debilitated by chronic illness, traumatic injury, burns or immunosuppression, as well as a common cause of postoperative infection. The infection may produce abscesses at the stitches or may cause extensive destruction of the incision site. Postoperative infections caused by *S. aureus* may appear a few days to several weeks after an operation but may develop more slowly in an individual taking antibiotics. Upon bloodstream dissemination or by continuous spread, *S. aureus* can readily survive in various deep tissues and can cause, among others, abscess formation, osteomyelitis, endocarditis, and sepsis. *S. aureus* may be detected by autofluorescence at the incision site using a device emitting electromagnetic energy at a wavelength, for example, of 488 nm (Hilton (1998) SPIE 3491:1174-1178). Optionally, *S. aureus* may be distinguished from, for example, *Escherichia coli* and *Enterococcus faecalis* based on emission spectra induced by excitations at 410-430 nm (Giana, et al. (2003) J. Fluoresc. 13:489-493; Ammor (2007) J. Fluoresc. published on-line ahead of publication).

*S. aureus* associated with the incision site may be killed or inactivated by irradiating the tissue with energy, for example, at a short UV "germicidal" wavelength as described above. Alternatively, *S. aureus* may be inactivated using a blue light with a wavelength, for example, of 405 nm at doses ranging from 1-20 Jcm$^{-2}$ (Guffey, et al. (2006) Photomed. Laser Surg. 24:680-683). Optionally, a blue light may be combined, for example, with an infrared light at a wavelength of 880 nm to promote tissue repair in combination with bacterial ablation (Guffey, et al. (2006) Photomed. Laser Surg. 24:680-683). In some instances, the entirety of the effected tissue may be irradiated. Alternatively, focused energy may be directed only to those sites emitting *S. aureus*-associated autofluorescence.

The Gram-negative bacteria *Pseudomonas aeruginosa* is another common cause of nosocomial infections, particularly in patients hospitalized with cancer, cystic fibrosis, and burns, and has a mortality rate of 50%. Other infections caused by *Pseudomonas* species include endocarditis, pneumonia, and infections of the urinary tract, central nervous system, wounds, eyes, ears, skin, and musculoskeletal system. *P. aeruginosa* is an opportunistic and ubiquitous pathogen with limited tissue penetration on its own, gaining entry to the host, for example, through burns, wounds, intravenous and urinary catheterization, and surgical procedures. *P. aeruginosa* may be detected by autofluorescence at the incision site using a device emitting electromagnetic energy at a wavelength, for example, of 488 nm (Hilton (1998) SPIE 3491:1174-1178). *P. aeruginosa* contains a pigment called pyocyanin which appears blue in visible light and may also be used for detection.

*P. aeruginosa* may be killed using a blue light with a wavelength, for example, of 405 nm at doses ranging from 1-20 Jcm$^{-2}$ (Guffey, et al. (2006) Photomed. Laser Surg. 24:680-683). Alternatively, irradiation using a wavelength, for example, of 630 nm at 1-20 Jcm$^{-2}$ may partially inactivate *P. aeruginosa* (Nussbaum, et al. (2002) J. Clin. Laser Med. Surg. 20:325-333).

Example 2

Detection and Ablation of Pathogens Prior to Closing and/or Bandaging a Wound

A wound may be screened with a handheld device that detects and ablates pathogens within the open lesion prior to closing (e.g. suturing) and/or bandaging to prevent possible microbial infection. The device emits electromagnetic energy at wavelengths sufficient to induce autofluorescence of pathogens within the wound. Alternatively, the device emits electromagnetic energy at wavelengths sufficient to induce fluorescence of reagents applied to the wound to selectively detect pathogens, such as, for example, a chemical dye or an antibody or aptamer conjugated to a fluorescent tag. Pathogens may include bacteria, fungi and/or viruses. The handheld device detects the autofluorescence or reagent-induced fluorescence associated with the pathogens and in real time automatically delivers energy sufficient to ablate or kill the pathogens. Optionally, the handheld device detects the autofluorescence, collects and processes the data, and at the discretion of the user, a trigger mechanism, for example, is used to deliver energy sufficient to at least partially inactivate or ablate the pathogens at the coordinates associated with the autofluorescence.

Pathogens commonly associated with wound infections include the Gram-positive cocci *Streptococcus pyogenes*, *Enterococcus faecalis*, and *Staphylococcus aureus*, the Gram-negative rods *Pseudomonas aeruginosa, Enterobacter* species, *Escherichia coli, Klebsiella* species, and *Proteus* species, the anaerobes *Bacteroides* and *Clostridium*, and the fungi *Candida* and *Aspergillus* (World Wide Wounds January 2004). Additional microbes of concern include *Burcella*, which infects cows, sheep, and goats, and can be transmitted through secretion and excretion to open wounds, *Bartonella henselae*, which is associated with cats and can cause "cat scratch fever", and *Clostridium tetani* which survives for years in soil and animal feces and can cause infection in both superficial wounds and deep in contaminated wounds of individuals not immunized against tetanus (Park, et al. (2001) J. Bacteriol. 183:5751-5755). In addition, *Vibrio vulnificus* is an emerging human pathogen which is found primarily in sea water and can be transmitted into open wounds and cause infection (Oliver, et al. (1986) Applied Environmental Microbiology 52:1209-1211). Among healthy individuals, ingestion of *V. vulnificus* can cause vomiting, diarrhea, and abdominal pain. In immunocompromised persons, particularly those with chronic liver disease, *V. vulnificus* can invade the bloodstream through a wound, causing primary septicemia and a 50% mortality rate.

A pathogen or pathogens may be detected at the wound site based on autofluorescence induced by electromagnetic energy at specific or multiple wavelengths, as described herein. *Bartonella henselae*, for example, has weak autofluorescence at an excitation wavelength of 485 nm and emission wavelength of 538 nm (Park, et al. (2001) J. Bacteriol. 183: 5751-5755). Some strains of *V. vulnificus* exhibit bioluminescence with maximal light emission at 483 nm (Oliver, et al. (1986) Applied Environmental Microbiology 52:1209-1211).

Alternatively, pathogens may be detected at the wound site based on addition of an agent or agents that fluoresces and binds selectively to the pathogen, allowing for detection and subsequent ablation of the pathogen. For example, a fluorescent stain such as BacLight™ Green or BacLight™ Red bacterial stain (absorption/emission: 480/516 and 581/644, respectively) may be used to detect, for example, *Staphylococcus aureus* and *Escherichia coli* (Invitrogen, Carlsbad, Calif.). *S. aureus* may also be detected at the wound site based on binding of immunoglobulins to the bacterial cell wall. Protein A on the surface of *S. aureus* readily binds the IgG class of immunoglobulins (Hjelm, et al. (1972) FEBS Lett. 28:73-76). To detect *S. aureus*, the incision site may be briefly sprayed with a sterile saline solution containing, for example, an IgG antibody conjugated to a fluorescent tag, for example FITC, Rhodamine, or Cy3, and rinsed. The fluorescence is detected by the handheld device. In response, energy is emitted specifically to the fluorescing site and the bacteria are killed.

Alternatively, pathogens may be detected at the wound site using fluorescently labeled antibodies. For example, *Streptococcus pyogenses*, one of the main pathogens associated with necrotizing fasciitis, may be detected using antibodies from commercial sources (e.g. AbD SEROTEC, Oxford, UK; Affinity BioReagents, Golden, Colo.; GeneTex, Inc. San Antonio, Tex.). Antibodies against *S. pyogenses* may be conjugated, for example, with a fluorescent tag such as the Alexa Fluors, FITC, Oregon Green, Texas Red, Rhodamine, Pacific Blue, Pacific Orange, Cy3, or Cy5 using labeling kits available from commercial sources (e.g. Invitrogen, Carlsbad, Calif.; Pierce, Rockford, Ill.). Alternatively, antibodies to *S. pyogenses* may be labeled with quantum dot nanocrystals using labeling kits from commercial sources (e.g. Invitrogen, Carlsbad, Calif.). Similarly, *P. aeruginosa* and *S. aureus*, for example, may be detected at the wound site using commercially available antibodies tagged with a fluorophore (e.g. Accurate Chemical & Scientific Co., Westbury, N.Y.; AbD SEROTEC, Oxford, UK; Cell Sciences Inc., Canton, Mass.).

The fluorescing bacterial stain, immunoglobulin, antibody, or aptamer may be administered to the wound in a sterile solution, rinsed and the wound subsequently screened with the handheld device. The handheld device may be placed in close proximity to a wound and emits electromagnetic energy at wavelengths ranging, for example, from 300 to 700 nm to excite autofluorescence of endogenous molecules or fluorescence of a probe associated with the pathogen. The resulting fluorescence is detected by the handheld device which subsequently emits energy sufficient to at least partially inactivate or ablate the pathogen. In some instances, the entirety of the effected tissue may be irradiated. Alternatively, focused energy may be directed only to those sites emitting pathogen-associated autofluorescence or fluorescence.

Autofluorescence may also be used to detect members of the fungi family. For example, *Candida albicans* irradiated with electromagnetic energy at wavelengths of 465-495 nm autofluoresces at an emission wavelength of 515-555 nm (Mateus, et al. (2004) Antimicrobial Agents and Chemotherapy 48:3358-3336; Graham (1983) Am. J. Clin. Pathol. 79:231-234). Similarly, *Aspergillus niger* and *Aspergillus versicolor* may be detected using autofluorescence in response to excitation at 450-490 nm and emission at 560 nm (Sage, et al. (2006) American Biotechnology Laboratory 24:20-23; Graham (1983) Am. J. Clin. Pathol. 79:231-234). Alternatively, fungi may be detected in a wound using the non-selective dye, Congo Red, which fluoresces at excitation maxima of 470 and 546 nm when irradiated with electromagnetic energy at wavelengths ranging from 450-560 nm (Slifkin, et al. (1988) J. Clin. Microbiol. 26:827-830).

A pathogen or pathogens at the wound site may be inactivated or killed by energy emitted from a handheld device in response to detection of the pathogen or pathogens by autofluorescence using the same handheld device. Energy in the form of UV irradiation may be used to at least partially inactivate or kill a pathogen or pathogens as described herein. Alternatively, a pathogen, for example *Escherichia coli*, may be at least partially inactivated or killed at a wound site in response to fluence doses ranging from 130-260 $J/cm^2$ using a 810 nm diode laser (Jawhara, et al (2006) Lasers Med. Sci. 21:153-159). Alternatively, a pathogen or pathogens may be at least partially inactivated or killed at the wound site with a form of laser thermal ablation using energy emitted, for example, from a $CO_2$ (10,600 nm) or a Nd:YAG (1064 nm) laser (Bartels, et al. SPIE Vol 2395:602-606). For example, *Staphylococcus epidermidis*, a common skin bacteria, may be killed using pulsed radiation from a Nd:YAG laser with an exposure of 1000-2000 $J/cm^2$ (Gronqvist, et al. (2000) Lasers Surg. Med. 27:336-340). Alternatively, a pathogen at a wound site may be at least partially inactivated or killed using electron beam or x-ray or gamma irradiation as described herein.

Optionally, energy emitted from the handheld device may be combined with a photosensitive agent applied directly to the wound (Maisch (2007) Lasers Med. Sci. 22:83-91; Jori, et al. (2006) Lasers Surg. Med. 38:468-481). As such, the photosensitive agent may be administered to the wound in a sterile solution, allowed to incubate for a certain interval, for example 1-30 minutes, rinsed and subsequently screened with the handheld device. The wound may be irradiated by the handheld device first with wavelengths sufficient to detect the photosensitive agent and second with energy sufficient to at least partially inactivate or kill the pathogens. For example, *Staphylococcus aureus* and *Pseudomonas aeruginosa* may be inactivated using either a 0.95-mW helium-neon laser (632 nm) or a 5-mW indium-gallium-aluminum-phosphate laser (670 nm) with exposure doses ranging from 0.1 to 10.0 $J/cm^2$ in combination with the bacterial sensitizing agent, toluidine blue O, (DeSimone, et al. (1999) Phys. Ther. 79:839-846). Alternatively, a diode laser with an emission wavelength, for example, of 808 nm may be used in combination with a topically applied fluorescing dye, for example, indocyanine green (ICG), to inactive a pathogen or pathogens (Bartels, et al. SPIE Vol 2395:602-606). ICG may be used to concentrate the diode laser energy to very specific "stained" areas with minimal damage to surrounding tissue. Optionally, a polycationic photosensitizer conjugated between, for example, poly-L-lysine and chlorin$_{e6}$, may be topically applied to a wound and subsequently irradiated with a diode laser at 665 nm at doses ranging from, for example, 40-160 $J/cm^2$ to kill bacteria (Hamblin, et al. (2002) Photochem. Photobiol. 75:51-57). Optionally, pathogens in a wound site, such as, for example, *Staphylococcus aureus* and *Staphylococcus epidermidis*, may be at least partially inactivated using energy from, for example, an argon-ion pumped dye laser (wavelength of 630 nm with total light dose of 180 $J/cm^2$) in combination with 5-aminolevulinic acid or Photofrin (Karrer, et al (1999) Lasers Med. Sci. 14:54-61; Nitzan, et al (1999) Lasers Med. Sci. 14:269-277).

Example 3

Detection and Ablation of Pathogens on Oral or Skin Surfaces

An oral cavity or surface of the skin may be screened with a device that detects and ablates pathogens associated with plaque and acne, respectively. The device emits electromagnetic energy at wavelengths sufficient to induce autofluorescence of pathogens on the surface. Alternatively, the device emits electromagnetic energy at wavelengths sufficient to cause fluorescence of reagents added to the surface to selectively detect pathogens, such as, for example, a chemical dye or an antibody or aptamer conjugated to a fluorescent tag. Pathogens may include bacteria, fungi and/or viruses. The device detects the autofluorescence or reagent-induced fluorescence associated with the pathogens and in real time automatically delivers energy sufficient to ablate or kill the pathogens. Optionally, the device detects the autofluorescence, collects and processes the data, and at the discretion of the physician or other medical practitioner, a trigger mechanism, for example, is used to deliver energy sufficient to at least partially inactivate or ablate the pathogens at the coordinates associated with the autofluorescence. The device may be handheld, for example, and either self-contained or connected wirelessly or by wire to optionally a power supply, energy sources, control circuitry, and/or monitor. Alternatively, the device may be a fixed component of, for example, a dentist's or doctor's office.

A device emitting energy may be used to detect and ablate the pathogens associated with dental plaque. For example, pathogens associated with caries and dental plaques, including *Actinomyces odontolyticus*, *Prevotella intermedia*, *Porphyromonas gingivalis*, *Peptostreptococcus*, *Candida albicans*, and *Corynebacterium*, all autofluoresce red in response to violet-blue light at a wavelength of 405 nm (van der Veen, et al. (2006) Caries Res. 40:542-545; Koenig, et al. (1994) J. Fluoresc. 4:17-40). Similarly, healthy dental tissue may be distinguished from carious lesions based on the autofluorescence of the associated pathogens (Koenig, et al. (1994) J. Fluoresc. 4:17-40). For example, healthy dental tissue irradiated with an excitation wavelength, for example, of 405 nm may exhibit a broad emission spectra in the short-wavelength portion of the visible spectrum while fluorescence spectra from a carious lesion may have a maxima in the red spectral region with a main band at 635 nm, for example (Koenig, et al. (1994) J. Fluoresc. 4:17-40). Once the autofluorescence is detected, energy emitted from the device may be used to at least partially inactivate or kill the fluorescing bacteria in real time using the methods and/or devices described herein.

A device emitting energy may be used to detect and ablate the pathogens associated with acne vulgaris. For example, the Gram-positive bacteria *Propionibacterium acnes*, which are involved in the pathogenesis of acne vulgaris, may be detected on the surface of the skin using autofluorescence (Koenig, et al. (1994) J. Fluoresc. 4:17-40; Shalita, et al (2001) SPIE Vol. 4244, p. 61-73). A laser emitting radiation at 407 nm, for example, may be used to detect fluorescent spots in the nasal area and in pimples of acne patients. The spots may differ in color, with their spectrum consisting of three main peaks, at about 580-600, 620, and 640 nm, and may be associated with autofluorescence induced by endogenous porphyrins such as protoporphyrin and coproporphyrin (Koenig, et al. (1994) J. Fluoresc. 4:17-40). Once the autofluorescence is detected, energy emitted from the device, for example, UV radiation, may be used to at least partially inactivate or kill the fluorescing bacteria in real time using the methods described herein. Alternatively, electromagnetic energy emitted from the device in the violet-blue range (407-420 nm) may be used to at least partially inactivate or kill pathogens associated with acne vulgaris by activating the endogenous porphyrins and causing photo-destructive ablation of the bacteria (Shalita, et al (2001) SPIE Vol. 4244, p. 61-73). For example, patients with acne vulgaris may be treated with a 400 w UV-free, enhanced blue (407-420 nm) metal halide lamp producing, for example, 90 mW/cm$^2$ homogeneous illumination (Shalita, et al (2001) SPIE Vol. 4244, p. 61-73).

Alternatively, a pathogen in the oral cavity or on the surface of the skin may be at least partially inactivated or killed using electron beam or x-ray or gamma irradiation as described herein.

Example 4

Detection and Ablation of Cancer and Cancer Margins

Tissue may be screened with a device that detects and ablates cancerous cells optionally in real time. The device emits electromagnetic energy at wavelengths to induce autofluorescence selected to differentiate between normal and cancerous cells. Alternatively, the device emits electromagnetic energy at wavelengths sufficient to cause fluorescence of reagents added to the tissue to selectively detect cancerous cells, such as, for example, a photosensitizer, a chemical dye, or an antibody or aptamer conjugated to a fluorescent tag. Autofluorescence or reagent-induced fluorescence associated with cancerous cells may be used to detect cancers and to aide in surgical intervention. In addition, autofluorescence or reagent-induced fluorescence associated with cancerous cells may be used to aide a medical practitioner in defining the margins of a solid tumor to ensure thorough excision of the lesion.

The device detects the autofluorescence or reagent-induced fluorescence associated with the cancerous cells and in real time delivers energy sufficient to at least partially inactivate or ablate the cancerous cells. Optionally, the device detects the autofluorescence, collects and processes the data, and at the discretion of the surgeon or other medical (or veterinary) practitioner, a trigger mechanism, for example, is used to deliver energy sufficient to at least partially inactivate or ablate the cancerous cells at the coordinates associated with the autofluorescence. The device may be handheld, for example, and either self-contained or connected wirelessly or by wire to optionally a power supply, energy sources, control circuitry, and/or monitor. Alternatively, the device may be a fixed component of a surgical theater, doctor's office, or other venue for patient treatment.

Electromagnetic energy emitted from a device may be used to induce autofluorescence of a tissue such as, for example, the surface of the skin or the surface of an internal organ exposed during surgery. The differences in the properties of emitted fluorescence may be used to distinguish between normal and pathological tissue. Tissue may be illuminated with electromagnetic energy at specific wavelengths of ultraviolet or visible light, for example. Endogenous fluorophores will absorb the energy and emit it as fluorescent light at a longer wavelength. Tissue autofluorescence may originate from aromatic amino acids such as tryptophan, tyrosine, and phenylalanine (excitation wavelengths of 200-340 nm, emission wavelengths of 360-370, 455 nm), from reduced pyridine nucleotides such as nicotinamide adenine dinucleotide (NADH, excitation wavelength of 360 nm, emission wavelength of 460 nm), from flavins and flavin nucleotides such as riboflavin and flavin mononucleotide (excitation wavelengths of 360 nm, 445-470 nm, emission wavelengths of 440 nm, 520 nm), from structural proteins such as collagen, and from lipopigments such as ceroid and lipofuscin (Chung, et al. (2005) Current Surgery 62:365-370; DaCosta, et al. (2005) J. Clin. Path. 58:766-774).

Differences in the properties of emitted autofluorescence may be used to distinguish, for example, between normal and cancerous cells and tissue in a variety of epithelial organ systems, including the cervix, colon, bladder, bronchus and oral mucosa (Ann. Surg. Oncol. (2003) 11:65-70; Weingandt, et al. (2002) BJOG 109:947-951; DaCosta, et al. (2005) J. Clin. Path. 58:766-775; Chiyo, et al. (2005) Lung Cancer 48:307-313). For example, changes in autofluorescence emission (350 to 700 nm) of premalignant or malignant lesions in the oral cavity relative to normal tissue may be detected using excitation wavelengths of 337 nm, 365 nm, and 410 nm (Gillenwater, et al. (1998) Arch. Otolaryngol. Head Neck Surg. 124:1251-1258). In this instance, the fluorescence intensity of normal mucosa may be greater than that of abnormal areas, while the ratio of red fluorescence (635 nm) to blue fluorescence (455-490 nm) intensities may be greater in abnormal areas. Autofluorescence may also be used to distinguish between normal and cancerous cells in non-epithelial organ systems, such as, for example, between normal white and gray matter and cancerous cells in the brain (U.S. Pat. No. 6,377,841).

Alternatively, cancerous cells may be detected using electromagnetic energy in combination with a light-activated dye. For example, Photofrin® (Axcan Pharma, Inc.) administered systemically to patients with cancer in the oral cavity, esophagus or bronchus accumulates preferentially in cancerous cells. Fluorescence of activated Photofrin® in cancer cells may be measured at 630 nm, for example, in response to excitation wavelengths of 405 nm and 506 nm 1-50 hours after administration (Braichotte, et al. (1995) Cancer 75:2768-2778).

As cancerous cells are identified based on differences in autofluorescence relative to normal cells using the device, the same device may be used in real time to ablate the identified cancerous cells. A cancerous cell or cells may be ablated by energy in the form of high-intensity light emitted, for example, by a laser. Lasers are commonly used to treat superficial cancers, such as basal cell skin cancer and the very early stages of some cancers, such as cervical, penile, vaginal, vulvar, and non-small cell lung cancer (National Cancer Institute (2004) Lasers in Cancer Treatment FactSheet). Energy emitted from a laser may also be used to relieve certain symptoms associated with cancer, such as bleeding or obstruction. For example, a laser may be used to shrink or destroy a tumor blocking the trachea or the esophagus or to remove polyps or tumors blocking the colon or stomach.

A variety of lasers with varied excitation wavelengths and penetration potential may be used to generate electromagnetic energy sufficient to ablate a cancer cell or cells (Burr Interventional Technologies for Tissue Volume Reduction, October 2004). For example, a cancer cell or cells may be ablated using a $CO_2$ laser (10,600 nm, 0.1-0.2 mm penetration depth). Alternatively, cancer cells may be ablated by a Yttrium-Aluminium-Garnet (YAG) laser with Neodymium (Nd, 1064 nm or 1320 nm, 3-4 mm penetration depth), Erbium (Eb, 2940 nm, with <0.1 mm penetration depth), or Holmium (Ho, 2070 nm). Alternatively, cancer cells may be ablated by diode lasers (600-1600 nm), argon laser (488 nm and 514 nm, 1-1.5 mm penetration depth), or an excimer laser (180-350 nm, cell/tissue disintegration). As such, the device may contain one or more of the lasers described herein as an optical energy source for use in exciting and/or ablating the target tissue.

Alternatively, a cancer cell or cells may be ablated by electromagnetic energy emitted from a laser in combination with a photosensitizing agent in a process termed photodynamic therapy (PDT; National Cancer Institute (2004) Lasers in Cancer Treatment FactSheet). For example, a patient may be injected with a photosensitizing agent such as, for example, Photofrin or 5-aminolevulinic acid, which after a few days concentrates in the cancerous cells. Electromagnetic energy from, for example, a laser is then used to activate the photosensitizing agent which has a subsequent toxic effect on the cancer cell or cells and results in cell death.

Alternatively, a cancer cell or cells may be ablated using x-ray energy. X-ray therapy or radiotherapy may be used to treat almost every type of solid tumor, including cancers of the brain, breast, cervix, larynx, lung, pancreas, prostate, skin, spine, stomach, uterus, or soft tissue sarcomas (National Cancer Institute (2004) Radiation Therapy for Cancer FactSheet). As such, the device may include a standard linear accelerator that emits X-ray electromagnetic energy at wavelengths sufficient for therapeutic ablation of cancerous cells. Alternatively, the device may contain a miniature X-ray emitter (see e.g. U.S. Patent Application 2004/218724 A1). Alternatively, the device may contain radioisotopes such as cobalt 60, cesium 137, or europium 152, for example, that emit strong gamma rays and may be used to ablate cancerous cells. Optionally, the device may contain other intrinsically radioactive isotope such as those that might be used for brachytherapy, including, for example, iodine 125, iodine 131, strontium 89, phosphorous, palladium, or phosphate (National Cancer Institute (2004) Radiation Therapy for Cancer FactSheet).

Alternatively, a cancer cell or cells may be ablated by using particle beam energy generated for example by a betatron, cyclotron or microton (Podgorsak, Chapter 5). Alternatively, particle beam energy may be generated using LINAC (linear accelerator)-based external beam radiotherapy. Medical LINACs accelerate electrons to kinetic energies from 4 to 25 MeV using microwave radiofrequency waves at $10^3$ to $10^4$ MHz (Podgorsak, Chapter 5). A LINAC may provide X-rays in the low megavoltage range (4 to 6 MV). Alternatively, a LINAC may provide both X-rays and electrons at various megavoltage energies, for example, two photon energies (6 and 18 MV) and several electron energies (6, 9, 12, 16, and 22 MeV; Podgorsak, Chapter 5).

Breast cancer may be detected using a device that emits electromagnetic energy at a wavelength or wavelengths sufficient to induce autofluorescence of malignant tissue. For example, an excitation-emission matrix of tissue autofluorescence generated using incremental excitation and emission wavelengths may be used to differentiate between normal and malignant breast tissue (Ann. Surg. Oncol. (2003) 11:65-70). Breast tissue may be irradiated with electromagnetic energy at excitation wavelengths of 300 to 460 nm, for example, in 10 to 20 nm increments and the resulting fluorescence emission recorded in 5 to 10 nm increments beginning with a wavelength, for example, 10 nm longer than the excitation wavelength, up to, for example, 600 nm (e.g. 360 to 600 nm for a 350 nm excitation). An excitation-emission matrix may be generated using this information and changes in peaks and valleys of fluorescence intensity may be used to distinguish between normal and malignant tissue. Optionally, a $N_2$ laser emitting 7 nsec pulses with a repetition rate of 10 Hz, pulse energy of 200 µJ, and filtered excitation wavelength of 337 nm may be used to distinguish between autofluorescence of normal and malignant breast tissue (Gupta, et al. (1997) Lasers Surg. Med. 21:417-422). Alternatively, cancerous breast tissue may be ablated using X-ray energy, for example, from a miniature electron beam-driven X-ray source at doses of 5 to 20 Gy (Ross, et al. (2005) Breast Cancer Res. 7:110-112). Alternatively, a breast tumor may be at least partially ablated using electron beam intra-operative radiotherapy with a radiation dose of 17 to 21 Gy (Ross, et al. (2005) Breast Cancer Res. 7:110-112).

Squamous intraepithelial lesions of the cervix may be differentiated from normal squamous tissue by autofluorescence using an electromagnetic energy emission wavelength of 460-nm (U.S. Pat. No. 5,623,932). Alternatively, cervical intraepithelial neoplasia may be differentiated from normal tissue by autofluorescence using a frequency tripled Nd:YAG laser with an excitation wavelength of 355 nm (Nordstrom, et al. (2001) Lasers Surg. Med. 29:118-127). Under these conditions, normal tissue may have an autofluorescence maxima (~460 nm) that is shifted to the left relative to neoplastic tissue (~470 nm) and is of higher intensity, allowing for differentiation between normal and abnormal tissue (Nordstrom, et al. (2001) Lasers Surg. Med. 29:118-127). Optionally, excitation wavelengths between 375 and 440 nm to induce autofluorescence may be used to distinguish between normal and precancerous lesions of the cervix (Weingandt, et al. (2002) BJOG 109:947-951). Alternatively, a fluorophore synthesized in the tissue after administration of a precursor molecule may be used in combination with electromagnetic energy to detect cancerous cells, for example, in the cervix (Andrejevic-Blant, et al. (2004) Lasers Surg. Med. 35:276-283). For example, cervical intraepithelial neoplasia may be detected by first applying 5-aminolevulinic acid topically to the cervix followed by porphyrin fluorescence spectroscopy (Keefe, et al. (2002) Lasers Surg. Med. 31:289-293). Cervical cancer may be ablated using laser conization or vaporization using, for example, a $CO_2$ laser focused to spot size of 0.1-0.2 mm with a continuous beam of 40-60 W and a power density of 80,000-165,000 W/cm2 (Bekassy, et al. (1997) Lasers Surg. Med. 20:461-466) or a garnet (Nd:YAG) laser.

The early stages of melanoma may be detected using a device that emits electromagnetic energy at incremental wavelengths ranging, for example, from 400-1000 nm using, for example, an acoustic-optic tunable filter (ACTF) in combination with, for example, a white light generated with an Kr—Ar laser (Farkas, et al. (2001) Pigment Cell Res. 14:2-8). Spectral imaging of this sort may also be accomplished, for example, using rotating interference filters, the Fabry-Perot interferometer, liquid crystal tunable filters (LCTF), gratings or prisms, or Fourier transform spectroscopy (Chung, et al. (2005) Current Surgery 62:365-370). The reflected light from the potentially cancerous pigmented tissue is collected at specific wavelengths. A microprocessor may be used to generate a profile of emission intensity across the electromagnetic energy spectrum. The resulting profile may be compared with that of normal pigmented tissue to identify specific areas of dysplasia. Autofluorescence may also be used to differentiate between normal skin and non-melanoma skin lesions. For example, autofluorescence induced by an excitation wavelength of 410 nm may be used to distinguish between normal tissue, basal cell carcinoma, squamous cell carcinoma, and actinic keratosis (Panjepour, et al. (2002) Lasers Surg. Med. 31:367-373). Optionally, autofluorescence may be used to distinguish between sun-exposed and sun-protected areas of skin and may also indicate regions of sun damage (Davies, et al. (2001) Applied Spectroscopy 55:1489-1894). Once the areas of dysplasia or sun damage are identified, the device may emit in real time energy sufficient to ablate the abnormal cell or cells. For example, the lesion may be ablated using a carbon dioxide laser with a wavelength of 10,600 nm and a power output of 80 W (Gibson, et al. (2004) Br. J. Surg. 91:893-895).

Example 5

Detection and Ablation of Gastrointestinal Pathogens with an Untethered Ingestible Device An untethered ingestible device may be used to detect and ablate gastrointestinal pathogens optionally in real time. The device emits electromagnetic energy at wavelengths sufficient to induce autofluorescence of pathogens within the gastrointestinal tract. Alternatively, the device emits electromagnetic energy at wavelengths sufficient to induce fluorescence of reagents added to the gastrointestinal tract to selectively detect pathogens, such as, for example, a chemical dye or an antibody or aptamer conjugated to a fluorescent tag. Pathogens may include bacteria, fungi and/or viruses. The untethered ingestible device detects the autofluorescence or reagent-induced fluorescence associated with the pathogens and in real time delivers energy sufficient to inactivate or ablate the pathogens. Optionally, the untethered ingestible device detects the autofluorescence, wirelessly transmits data to an external source, and at the discretion of the physician or other medical practitioner, a trigger mechanism, for example, is used to deliver energy sufficient to at least partially inactivate or ablate the pathogens at the coordinates associated with the autofluorescence.

Pathogens commonly associated with gastrointestinal disorders include bacteria, such as certain strains of *Escherichia coli* (e.g. *Escherichia coli* O157:H7), various strains of *Salmonella*, *Vibrio cholera*, *Campylobacter*, *Listeria monocytogenes*, *shigella*, and *Helicobacter pylori*, viruses such as rotovirus and Calicivirus, and parasites such as *Giardia lamblia*, *Entamoeba histolytica* and *Cryptosporidium*.

A pathogen may be detected in the gastrointestinal tract based on autofluorescence induced, for example, by electromagnetic energy. In general, pathogens such as bacteria and fungi may be detected by autofluorescence as described herein. For example, *Escherichia coli* autofluorescence may be detected using excitation wavelengths of 250-400 nm and examined at an emission wavelength of 495 nm and higher through, for example, a long pass optical filter (Glazier, et al. (1994) J. Microbiol. Meth. 20:23-27; Hilton, et al. (2000) Proc. SPIE 4087:1020-1026). Alternatively, *Escherichia coli* autofluorescence maxima of 350 nm and 485 nm may be detected following excitation at 290 nm (Cabreda, et al. (2007) J. Fluoresc. 17:171-180). Alternatively, *Salmonella* as well as *Escherichia coli* autofluoresce when irradiated with electromagnetic energy at a wavelength of 488 nm (Hilton (1998) SPIE 3491:1174-1178). The Coccidia class of bacteria, which are transmitted through a fecal-oral route via contaminated water and food and are associated with watery diarrhea, may also be detected based on autofluorescence (Bialek, et al. (2002) Am. J. Trop. Med. Hyg. 67:304-305). For example, *Isospora belli* and *Cyclospora* fluoresce a bluish violet color under UV excitation (365 nm) and fluoresce a bright green under violet excitation (405 nm).

A pathogen within the gastrointestinal tract may be inactivated or killed by energy emitted from an untethered ingestible device in response to detection of the pathogen by autofluorescence using the same untethered ingestible device. In general, pathogens such as bacteria and fungi may be inactivated or killed by various wavelengths of electromagnetic energy as described herein. For example, *Escherichia coli* may be partially or completely inactivated, for example, by a 60 s exposure to a UV electromagnetic energy source at wavelengths of 100-280 nm (Anderson, et al. (2000) IEEE Transactions on Plasma Science 28:83-88). The intestinal parasites *Cryptosporidium* and *Giardia* may also be at least partially inactivated or killed using UV irradiation from, for example, a mercury arc lamp at a fluence of 40 mJ/cm$^2$ (Li, et al. (2007) Appl. Environ. Microbiol. 73:2218-2223). Alternatively, *Escherichia coli* and *Salmonella enteritidis* may be inactivated using pulsed broad-spectrum electromagnetic energy with high UV content from, for example, a Xenon lamp (Anderson, et al. (2000) IEEE Transactions on Plasma Science 28:83-88). In this instance, targeted bacteria are subjected to 100-1000 pulses of broad-spectrum light with each pulse lasting, for example, 85 ns and having, for example, a power output of 10 MW. Alternatively, a pathogen within the gastrointestinal tract may be inactivated or killed by a particle beam, or x-ray, or gamma ray electromagnetic energy, as described herein.

*Helicobacter pylori* is a gram-negative bacterium which selectively colonizes the stomach and duodenum and is associated with chronic gastritis, gastric ulcer and increased risk for gastric adenocarcinoma. *H. pylori* may be detected in the antrum of the stomach by autofluorescence using an excitation wavelength, for example, of 405 nm (Hammer-Wilson, et al. (2007) Scand. J. Gastroenterol. 42:941-950). *H. pylori* naturally accumulates coproporphyrin and protoporphyrin which sensitize the bacteria to inactivation by visible light at wavelengths ranging from 375 to 425 nm (Hamblin, et al. (2005) Antimicrob. Agents Chemother. 49:2822-2827; U.S. Patent Application 2004/0039232 A1). As such, an untethered ingestible device emitting electromagnetic energy as described herein may be used to detect and at least partially inactivate or kill *H. pylori* in the gastrointestinal tract.

The untethered ingestible device may transit through the gastrointestinal tract by natural peristalsis after ingestion. Transit times may vary depending, for example, on the time required for gastric emptying and for transit through the small bowel. For example, transit time of an untethered ingestible device out of the stomach may range from 20-160 minutes depending upon, for example, the age of the patient and whether polyethylene glycol (PEG 400) or erythromycin are administered prior to and following ingestion of the device (Fireman, et al. (2005) World J. Gastroenterol 11:5863-5866). Similarly, transit time through the small bowel may range from 220-320 minutes depending, for example, upon the age of the patient and co-administered agents (Fireman, et al. (2005) World J. Gastroenterol 11:5863-5866).

The untethered ingestible device may be affixed to a specific site within the gastrointestinal tract, for example, by expanding to fill the lumen of the tract (U.S. Patent Application 2007/015621 A1). As such, the untethered ingestible device may be cylindrical in shape with a central core enabling free flow of fluids within the digestive tract.

Optionally, the untethered ingestible device may contain a means of locomotion with internal or external control that allows an operator to control movement of the device within the gastrointestinal tract. The device may use a locomotion system based on "inch-worm" motion using, for example, grippers and extensors, rolling tracks, or rolling stents (Rentshcler, et al. (2006) SAGES Meeting; Rentschler, et al. (2007) Surg. Endosc. on-line ahead of publication). Alternatively, the device may use a helical wheel configuration on its surface with, for example, two independent motors that control the wheels, providing forward, backward, and turning capacity (see, e.g., Rentshcler, et al. (2006) SAGES Meeting; Rentschler, et al. (2007) Surg. Endosc. on-line ahead of publication; U.S. Patent Application 2006/119304 A1). Alternatively, the device may use a locomotion system based on wheels or expanding and contracting components (see, e.g., U.S. Patent Application 2006/119304 A1).

Example 6

Detection and Ablation of Pathological Gastrointestinal Tissue with an Untethered Ingestible Device An untethered ingestible device may be used to detect and ablate pathological gastrointestinal tissue in real time. The device emits electromagnetic energy at wavelengths sufficient to induce autofluorescence of pathological tissue within the gastrointestinal tract. Alternatively, the device emits electromagnetic energy at wavelengths sufficient to cause fluorescence of reagents added to the gastrointestinal tract to selectively detect pathological tissue, such as, for example, a chemical dye or an antibody or aptamer conjugated to a fluorescent tag. Pathological tissue may include, for example, cancer or lesions associated with Crohns disease. The untethered ingestible device detects the autofluorescence or reagent-induced fluorescence associated with the pathological tissue and in real time delivers energy sufficient to at least partially ablate the pathological tissue. Optionally, the untethered ingestible device detects the autofluorescence, wirelessly transmits data to an external source, and at the discretion of the physician or other medical practitioner, a trigger mechanism, for example, is used to deliver energy sufficient to at least partially ablate the pathological tissue at coordinates associated with the autofluorescence.

For example, changes in autofluorescence emission (350 to 700 nm) of premalignant or malignant lesions in the oral cavity relative to normal tissue may be detected using excitation wavelengths of 330, nm, 337 nm, 365 nm, and 410 nm (Gillenwater, et al. (1998) Arch. Otolaryngol. Head Neck Surg. 124:1251-1258; Tsai, et al. (2003) Lasers Surg. Med. 33:40-47). In this instance, the fluorescence intensity of normal mucosa may be greater than that of abnormal areas, while the ratio of red fluorescence (635 nm) to blue fluorescence (455-490 nm) intensities may be greater in abnormal areas. Alternatively, autofluorescence induced by excitation wavelengths of 365, 385, 405, 420, 435, and 450 nm may be combined with diffuse reflectance spectroscopy to detect premalignant and malignant lesions in the oral mucosa (de Veld, et al. (2005) Lasers Surg. Med. 36:356-364). Based on the relative autofluorescence, the cancerous cells may be identified and irradiated with electromagnetic energy sufficient to ablate the cell or cells, as described herein.

Autofluorescence may be used to distinguish between normal and neoplastic tissue in patients with Barrett's esophagus (Borovika, et al. (2006) Endoscopy 38:867-872; Pfefer, et al. (2003) Lasers Surg. Med. 32:10-16) For example, fluorescence spectra excited at 337 nm and 400 nm may be used to distinguish between normal and neoplastic tissue (Pfefer, et al. (2003) Lasers Surg. Med. 32:10-16). Alternatively, fluorescence maxima may be compared at various emission wavelengths, for example, 444, 469, 481, 486, 545, 609, and 636 nm following excitation at 337 nm and 400 nm. Autofluorescence may be observed with a long-pass filter with a cut-off wavelength >470 nm to optimize fluorescence detection and minimize excitation light (Borovika, et al. (2006) Endoscopy 38:867-872). Alternatively, adenocarcinoma in patients with Barrett's esophagus may be detected using electromagnetic energy in combination with an agent that concentrates in cancerous cells and that fluoresces upon laser excitation, such as, for example, Photofrin® (von Holstein, et al. (1999) Gut 39:711-716).

Autofluorescence may be used to distinguish between normal, hyperplastic and adenomatous colonic mucosa (DaCosta, et al. (2005) J. Clin. Path. 58:766-774; Eker, et al. (1999) Gut 44:511-518). Irradiation of colon mucosa with ultraviolet light or blue light with a wavelength of 488 nm, for example, induces emission of green and red regions of autofluorescence. In normal tissue, collagen and elastin emit weak green fluorescence. In hyperplastic tissue or polyps, increased collagen produces intense green fluorescence. Dysplastic or malignant lesions may have enhanced red fluorescence compared with either normal or hyperplastic polyps (DaCosta, et al. (2005) J. Clin. Path. 58:766-774).

An untethered ingestible device emitting electromagnetic energy at a wavelength or wavelengths sufficient to induce autofluorescence such as ultraviolet or blue light, for example, is used to irradiate the colon. Fluorescence emission is detected at wavelengths of 505-550 nm and >585 nm, for example, to detect the green and red autofluorescence, respectively. Alternatively, shifts in the autofluorescence emission maxima following excitation at 337 nm may be used to distinguish normal from adenomatous tissue (Eker, et al. (1999) Gut 44:511-518).

Optionally, electromagnetic energy may be combined with 5-aminolevulinic acid (ALA) to differentiate between normal colon tissue and adenomatous polyps (Eker, et al. (1999) Gut 44:511-518). For example, ALA at a dose of 5 mg/kg body weight may be administered orally to patients 2 to 3 hours prior to investigation followed by irradiation of the colon tissue with excitation wavelengths of 337 nm, 405 nm, and 436 nm. Normal versus abnormal tissue may be distinguished based on relative shifts in the emission maxima (Eker, et al. (1999) Gut 44:511-518).

Based on the relative autofluorescence, the cancerous cells are identified and may be irradiated with energy sufficient to ablate the cell or cells, as described herein. For example, colorectal adenomas may be ablated using an Nd:YAG (1064 nm) with maximal power output of 100 W (Norberto, et al. (2005) Surg. Endosc. 19:1045-1048). Alternatively, X-ray energy administered at a total dose of 20 Gy may be used to treat colon cancer (Kosmider, et al. (2007) World J. Gastroenterol. 13:3788-3805).

Autofluorescence imaging may be used to detect the severity of ulcerative colitis (Fujiya, et al. (2007) Dig. Endoscopy 19 (Suppl. 1):S145-S149). For example, differences in inflammatory state may be distinguished by autofluorescence, with severely inflamed mucosa associated with purple autofluorescence, atrophic regenerative mucosa associated with faint purple autofluorescence with green spots, and normal mucosa associated with green autofluorescence.

Example 7

Detection and Ablation of Pathogens in a Lumen with an Untethered Device

An untethered device may be used to detect and ablate pathogens within a lumen in real time. The device emits electromagnetic energy at wavelengths sufficient to induce autofluorescence of pathogens within the lumen. Alternatively, the device emits electromagnetic energy at wavelengths sufficient to cause fluorescence of reagents added to the lumen to selectively detect pathogens, such as, for example, a chemical dye or an antibody or aptamer conjugated to a fluorescent tag. Pathogens may include bacteria, fungi and/or viruses. A lumen may include that associated with blood vessels, the urogenital tract, and the respiratory tract, for example. The untethered luminal device detects the autofluorescence or reagent-induced fluorescence associated with the pathogens and in real time delivers energy sufficient to inactivate or ablate the pathogens. Optionally, the untethered luminal device detects the autofluorescence, wirelessly transmits data to an external source, and at the discretion of the physician or other medical practitioner, a trigger mechanism, for example, is used to deliver energy sufficient to at least partially ablate the pathogen at coordinates associated with the autofluorescence.

An untethered device in the lumen of a blood vessel may be used to detect and ablate pathogens associated with blood infections or septicemia. Gram-negative enteric bacilli, *Staphylococcus aureus*, and *Streptococcus pneumoniae* are the most common pathogens in the United States associated with micronemia and sepsis. As such, electromagnetic energy emitted from a luminal device may be used to detect autofluorescence associated, for example, with blood borne bacteria as described herein. The pathogens are subsequently ablated using, for example, UV electromagnetic energy as described herein.

An untethered device in the lumen of a blood vessel may be used to detect and ablate parasites in the blood stream. For example, autofluorescence associated with the food vacuole of the malaria parasite *Plasmodium* spp. may be used to detect infected erythrocytes with in the blood stream (Wissing, et al. (2002) J. Biol. Chem. 277:37747-37755). As such, an untethered luminal device may induce autofluorescence of parasites at a wavelength of, for example, of 488 nm (Wissing, et al. (2002) J. Biol. Chem. 277:37747-37755). Alternatively, erythrocytes infected with *Plasmodium* spp. may be detected by pre-staining the cells with acridine orange, which when excited at 490 nm emits green light at 530 nm (Wissing, et al. (2002) J. Biol. Chem. 277:37747-37755). Other nucleic-acid binding dyes may be used for this purpose including Hoechst 33258, thiazole orange, hydroethidine, and YOYO-1 (Li, et al. (2007) Cytometry 71A:297-307). As such, the dyes bind to parasite DNA in the infected erythrocytes which are otherwise free of DNA. Erythrocytes autofluoresce upon excitation at a wavelength of 545 nm with an emission wavelength of 610 nm associated with the heme porphyrin (Liu, et al. (2002) J. Cereb. Blood Flow Metab. 22:1222-1230). As such, the untethered luminal device may optionally first identify an erythrocyte based on autofluorescence at one wavelength, followed by detection of a parasite within the erythrocyte based on autofluorescence or dye induced fluorescence at a second wavelength. The untethered luminal device may detect fluorescence associated with infected erythrocytes and in real time emit energy at wavelengths sufficient to at least partially ablate the infected cells.

An untethered luminal device may be used to detect and ablate pathogens associated with urinary tract infections (UTI), for example, in the lumen of the bladder. For example, *Escherichia coli* uropathogenic strains are the most common cause of urinary tract infections (Finer, et al. (2004) Lancet Infect. Dis. 4:631-635). *Escherichia coli* may be detected in the bladder, for example, using electromagnetic energy to induce autofluorescence as described herein. An untethered luminal device may be inserted into the bladder via a catheter. Once inserted, the untethered luminal device may scan the internal surface of the bladder with electromagnetic energy sufficient to induce autofluorescence of pathogens. In response to autofluorescence, the untethered luminal device may emit energy sufficient to at least partially inactivate pathogens, as described herein.

Optionally, the untethered luminal device may be affixed to a specific site within a lumen, for example, by expanding to fill the lumen (see, e.g., U.S. Patent Application 2007/015621 A1). As such, the untethered luminal device may be cylindrical in shape with a central core enabling free flow of fluids within the lumen. Alternatively, the untethered luminal device may be affixed to a specific site within a lumen using, for example, a hook or claw-like structure, an adhesive or glue-like material, or suction (see, e.g., U.S. Patent Application 2007/015621 A1).

Optionally, the untethered luminal device may contain a means of locomotion with internal or external control that allows an operator to control movement of the device within the lumen by means described herein. Alternatively, the untethered luminal device may be controlled by external magnetic energy. For example, an untethered luminal device in an artery, for example, may be manipulated using a clinical magnetic resonance imaging system (see, e.g., Mathieu, et al. Proceedings of the 2005 IEEE, Engineering in Medicine and Biology $27^{th}$ Annual Conference, Shanghai, China, Sep. 1-4, 2005, 4850-4853; Martel, et al. (2007) Applied Physics Letters 90:114105-1-3). As such, the untethered luminal device may be constructed, at least in part, with ferromagnetic material.

Example 9

Detection and Ablation of Pathological Tissue in a Lumen with an Untethered Device An untethered device may be used to detect and ablate pathological tissue or cells within a lumen in real time. The device emits electromagnetic energy at wavelengths sufficient to induce autofluorescence of pathological tissue within the lumen. Alternatively, the device emits electromagnetic energy at wavelengths sufficient to cause fluorescence of reagents added to the lumen to selectively detect pathological tissue, such as, for example, a chemical dye or an antibody or aptamer conjugated to a fluorescent tag. Pathological tissue may include cancer, atherosclerosis, and inflammation, for example. A lumen may include that associated with blood vessels, the urogenital tract, and the respiratory tract, for example. The untethered luminal device detects the autofluorescence or reagent-induced fluorescence associated with the pathogens and in real time delivers energy sufficient to inactivate or ablate the pathological tissue. Optionally, the untethered luminal device detects the autofluorescence, wirelessly transmits data to an external source, and at the discretion of the physician or other medical practitioner, a trigger mechanism, for example, is used to deliver energy sufficient to at least partially ablate the pathological tissue at coordinates associated with the autofluorescence.

An untethered device in the lumen of a blood vessel, for example, may be used to detect and ablate tissue and cells associated with, for example, an atherosclerotic plaque. For example, autofluorescence associated with macrophages in a plaque may be used to characterize an atherosclerotic lesion (Marcu, et al. (2005) Atherosclerosis 181:295-303). The accumulation of macrophages in the fibrous cap of an atherosclerotic plaque are indicative of inflammation as well as instability of the plaque. The lumen of a blood vessel may be irradiated, for example, with 1 ns pulses of electromagnetic energy at a wavelength of 337 nm. The resulting autofluorescence may be detected at specific maxima wavelengths, for example, 395 nm and 450 nm, or over a range of wavelengths, for example, from 300-600 nm (Marcu, et al. (2005) Atherosclerosis 181:295-303). Differences in the autofluorescence spectra may be used to differentiate between normal, collagen thick and macrophage thick plaques (Marcu, et al. (2005) Atherosclerosis 181:295-303). Alternatively, the lumen of a blood vessel may be irradiated with electromagnetic energy ranging in wavelength from 350 to 390 nm and the resulting autofluorescence detected at critical wavelengths, for example, of 570, 600, 480, or 500 nm may be sufficient to differentiate between structurally viable tissue and an atherosclerotic plaque (U.S. Pat. No. 5,046,501).

The untethered device may subsequently in real time emit energy sufficient to at least partially ablate the atherosclerotic plaque based on the differential autofluorescence. An eximer laser operating in the ultraviolet range may be used to ablate an atherosclerotic plaque (Morguet, et al. (1994) Lasers Surg. Med. 14:238-248). Alternatively, other laser systems may be used to ablate an atherosclerotic plaque, including, for example, a CO2 laser, Nd:YAG laser or an argon laser (Morguet, et al. (1994) Lasers Surg. Med. 14:238-248).

An untethered device in the lumen of a blood vessel, for example, may be used to detect and ablate cells associated with, for example, a hematological form of cancer. For example, leukemia is characterized by an increase in immature lymphoblasts in circulation. These cells may have a distinct autofluorescence relative to normal lymphocytes. As such, fluorescence associated with the lymphoblasts may be detected and the cells subsequently ablated using the methods described herein.

An untethered device in the lumen of a blood vessel may be used to detect and ablate cells that have migrated from a solid tumor and are on route to metastasis elsewhere in the body. These cells may be identified using the untethered device to generate and detect autofluorescence. Alternatively, these cells may be identified using the untethered device to induce and detect fluorescence associated with a reagent that specifically binds to a cancer cell, such as a fluorescent antibody or aptamer. For example, circulating tumor cells associated with breast cancer may be detected using a fluorescently tagged antibody or aptamer to a tumor specific cell-surface antigen such as, for example, the Her2/Neu epidermal growth factor receptor (Gilbey, et al. (2004) J. Clin. Pathol. 57:903-911). Patients with increased breast epithelial cells in circulation have a higher rate of metastasis and poorer outcome. As such, fluorescence associated with the breast cancer cell may be detected and the cell subsequently ablated by the untethered luminal device using the methods described herein.

Example 10

Detection and Ablation of Pathogens in a Lumen with a Tethered Device

A tethered device may be used to detect and ablate pathogens within a lumen in real time. The device emits electromagnetic energy at wavelengths sufficient to induce autofluorescence of pathogens within the lumen. Alternatively, the device emits electromagnetic energy at wavelengths sufficient to cause fluorescence of reagents added to the lumen to selectively detect pathogens, such as, for example, a chemical dye or an antibody or aptamer conjugated to a fluorescent tag. Pathogens may include bacteria, fungi and/or viruses. A lumen may include that associated with blood vessels, gastrointestinal tract, the urogenital tract, or the respiratory tract, for example. The tethered luminal device detects the autofluorescence or reagent-induced fluorescence associated with the pathogens and in real time delivers energy sufficient to inactivate or ablate the pathogens.

A tethered device in the lumen of a blood vessel, for example, may be used to detect and ablate pathogens in the blood such as those associated with septicemia and malaria using electromagnetic energy, as described herein.

A tethered device in the lumen of the lung, for example, may be used to detect and ablate pathogens associated with bronchial infections, such as bronchitis, pneumonia, and tuberculosis. *Streptococcus pneumoniae* is the most common cause of community-acquired pneumonias whereas *Pseudomonas aeruginosa, Escherichia coli, Enterobacter, Proteus,* and *Klebsiella* are commonly associated with nosocomial-acquired pneumonia. Although the incidence of tuberculosis is low in industrialized countries, *M tuberculosis* infections still continue to be a significant public health problem in the United States, particularly among immigrants from developing countries, intravenous drug abusers, patients infected with human immunodeficiency virus (HIV), and the institutionalized elderly. Autofluorescence induced by electromagnetic energy may be used to detect various bacterial pathogens, as described herein. A tethered device may be inserted into the lung comparable, for example, to a bronchoscope, and used to detect pathogens. In response to autofluorescence, the same tethered device may emit in real time energy sufficient to at least partially inactivate pathogens, as described herein.

Example 11

Detection and Ablation of Pathological Tissue in a Lumen with Tethered Device

A tethered device may be used to detect and ablate pathological tissue or cells within a lumen in real time. The device emits electromagnetic energy at wavelengths sufficient to induce autofluorescence of pathological tissue within the lumen. Alternatively, the device emits electromagnetic energy at wavelengths sufficient to cause fluorescence of reagents added to the lumen to selectively detect pathological tissue, such as, for example, a chemical dye or an antibody or aptamer conjugated to a fluorescent tag. Pathological tissue may include cancer, atherosclerosis, and inflammation, for example. A lumen may include those associated with blood vessels, the urogenital tract, the gastrointestinal tract, or the respiratory tract, for example. The tethered luminal device detects the autofluorescence or reagent-induced fluorescence associated with the pathological tissue and in real time automatically delivers energy sufficient to at least partially ablate the pathological tissue.

Autofluorescence induced by an optical energy source may be used to detect pathological tissue as described herein. Alternatively, fluorescence associated with a selective marker may be induced by an optical energy source to detect pathological tissue as described herein. A tethered device that emits optical energy to induce autofluorescence of pathological tissue may be configured, for example, like an endoscope (see, e.g., U.S. Pat. No. 5,507,287; U.S. Pat. No. 5,590,660; U.S. Pat. No. 5,647,368; U.S. Pat. No. 5,769,792; U.S. Pat. No. 6,061,591; U.S. Pat. No. 6,123,719; U.S. Pat. No. 6,462,770B1). As such, a flexible optical tube sufficiently small enough to be inserted into a lumen may be attached to an optical energy source that emits wavelengths sufficient to induce autofluorescence such as for example, a nitrogen laser. The same flexible tube may transmit the emitted autofluorescence back to a CCD camera and control circuitry. Immediately upon receiving the emitted autofluorescence indicative of pathological tissue, a second emission of energy, from for example an Nd:YAG laser, is released to at least partially ablate the pathological tissue. Alternatively, the head of the flexible tube may contain a photodiode array sensor that directly detects the autofluorescence and triggers a second emission of energy sufficient to at least partially ablate the pathological tissue. Alternatively, the head of the flexible tube may contain shielded gamma emitting isotopes that exposure the tissue to radiation in real time in response to the detected autofluorescence.

A tethered device in the lumen of a blood vessel, for example, may be used to detect and ablate pathological tissue, for example, atherosclerotic plaques or circulating cancer cells as described herein.

Autofluorescence in combination with reflected light may be used to differentiate between normal, inflamed and pre-invasive lesions in the lung (Chiyo, et al. (2005) Lung Cancer 48:307-313; Gabrecht, et al. (2007) SPIE-OSA Vol. 6628, 66208C-1-8; U.S. Pat. No. 5,507,287). For example, bronchial tissue may be irradiated with excitation wavelengths of 395-445 nm and autofluorescence detected at wavelengths of 490-690 nm. Simultaneously or subsequently, reflected light at 550 nm (green) and at 610 nm (red) may be collected and combined with the autofluorescence data to form a composite image. As such, the ratios of green/red and green/autofluorescence may be greater in squamous dysplasia relative to inflamed lung tissue associated with bronchitis, allowing for differentiation between these two disease states (Chiyo, et al. (2005) Lung Cancer 48:307-313). Based on the relative autofluorescence detected, the tethered device emits energy sufficient to at least partially ablate the cancerous tissue. For example, electromagnetic energy sufficient to ablate cancerous cells in the lung may be generated by a Neodynium YAG laser (1064 nm) with power output up to 100 W and tissue penetration of 1-5 mm (Hansen, et al. (2006) Minim. Invasive Ther. Allied Technol. 15:4-8).

Example 12

An Apparatus for Detection and Ablation of Pathogens and Pathological Tissue

Figure 26:
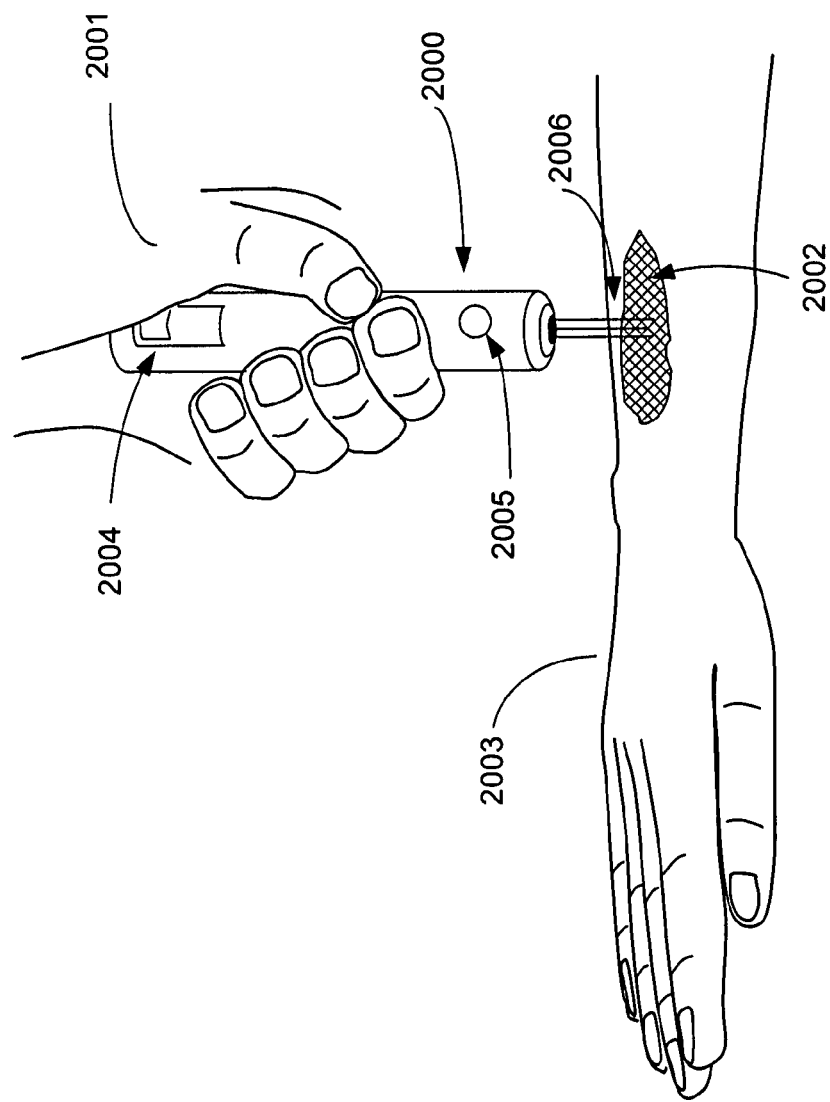
FIG. 26 shows a schematic of an example of an illustrative embodiment of a handheld device in use on an illustrative subject.
Figure 27:
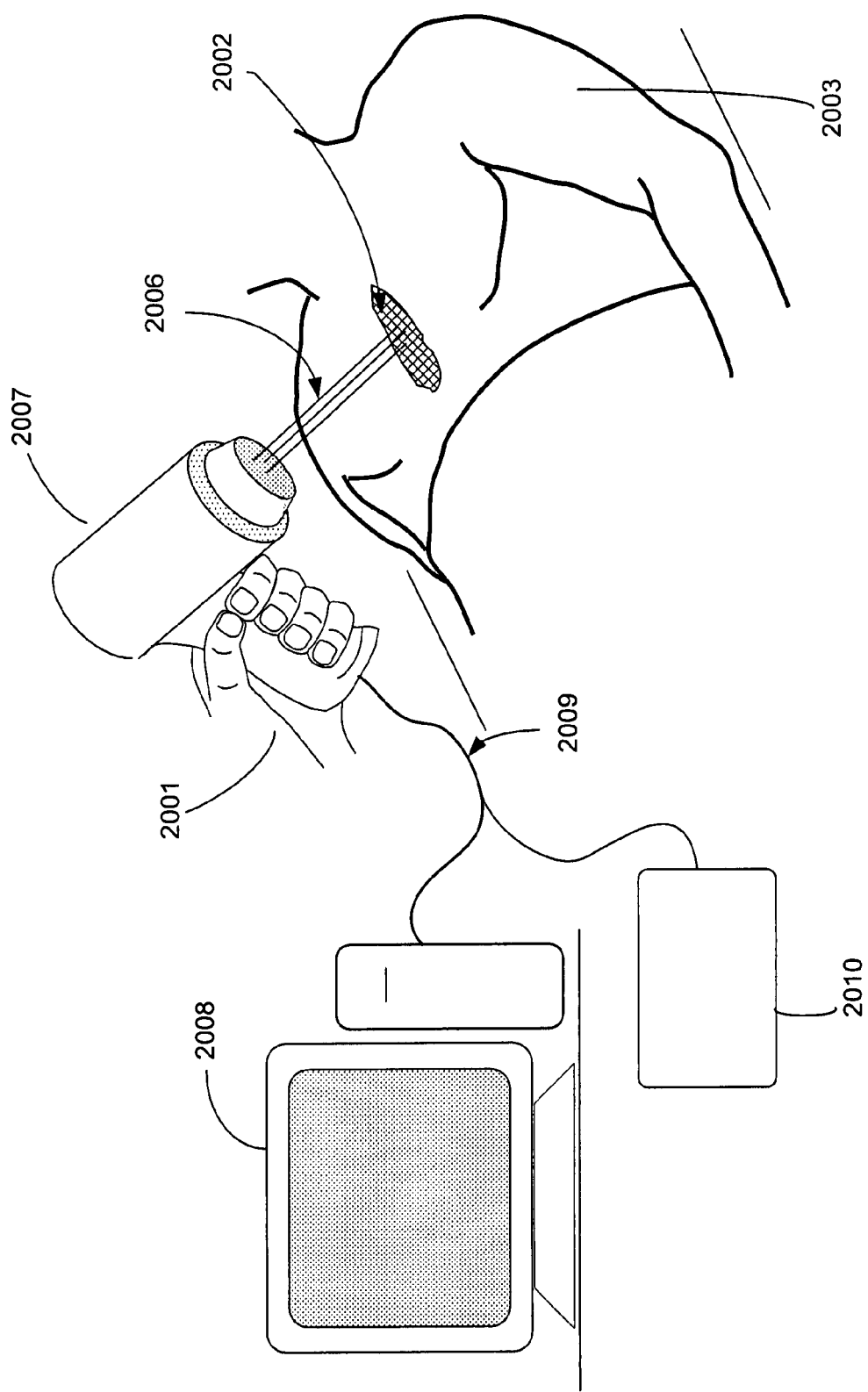
FIG. 27 shows a schematic of an example of an illustrative embodiment of a device in use on an illustrative subject.
Figure 28:
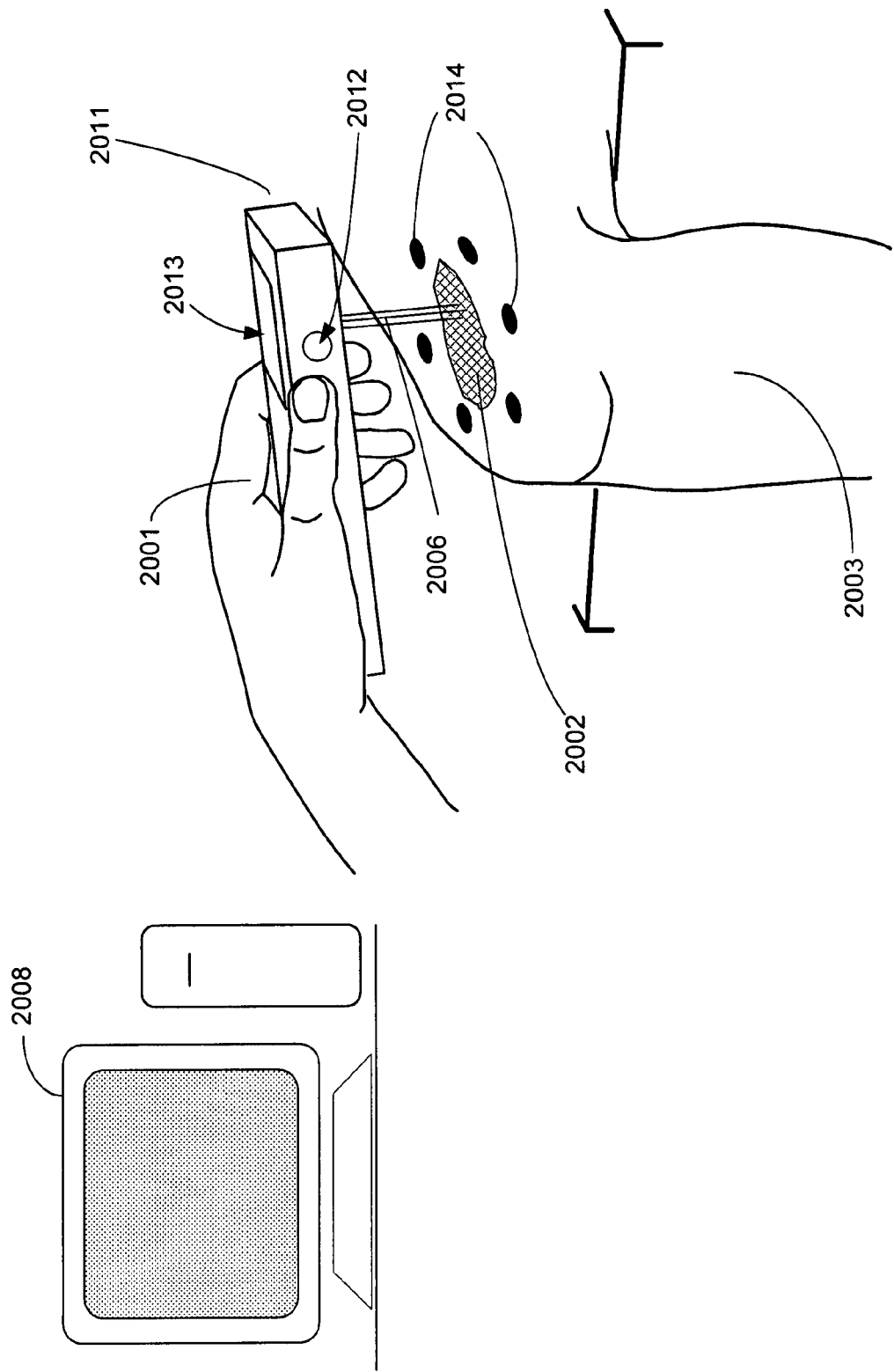
FIG. 28 shows a schematic of an example of an illustrative embodiment of a handheld device in use on an illustrative subject.

FIG. 26, FIG. 27, and FIG. 28 show illustrative configurations of handheld versions of an apparatus 100 of FIG. 1. for the detection and ablation of pathogens and pathological tissue.

FIG. 26 shows an illustrative configuration of a handheld device 2000 which is completely self-contained and easily held in the hand of the user 2001. The user 2001 may be, for example, a surgeon or other medical practitioner and/or a veterinarian, using the handheld device 2000, for example, in a surgical theater, a hospital emergency room, a doctor, dentist, veterinary, or nurse practitioner's office. Alternatively, the user 2001 may be an emergency responder, using the hand held device 2000, for example, out in the field at the site of an accident or on the battlefield. The user 2001 may hold the handheld device 2000 in proximity to a lesion or lesions 2002 on a patient 2003. The lesion 2002 may be a surgical incision or a wound. A wound, for example, may be an abrasion, a burn, a puncture, or a deep gouge. Alternatively, the lesion 2002 may be on the surface of the skin or the surface of the oral cavity. The user 2001 turns on the handheld device 2000 using an on/off switch 2004. Optionally, the user 2001 may use a button 2005 on the handheld device 2000 to activate or enable a beam of energy 2006 (optionally the same as 110). The user 2001 activates a beam of energy 2006 in proximity to the lesion 2002 to detect and ablate pathogens and pathological tissue.

FIG. 27 shows an illustrative configuration of a handheld device 2007 which is held in the hand of the user 2001 and is optionally wirelessly connected to optional external control circuitry 2008. Optionally, the handheld device 2007 is connected via a wire 2009 to external control circuitry 2008 or an external power source 2010, or both. The user 2001 activates a beam of energy 2006 in proximity to the lesion 2002 to detect and ablate pathogens and pathological tissue.

FIG. 28 shows an illustrative configuration of a handheld device 2011 which is held in the hand of the user 2001, and is used in conjunction with targeting aids 2014 surrounding the lesion 2002 on the surface of the patient 2003. The targeting aids 2014 are used, for example, to register the position of autofluorescence associated with pathogens or pathological tissue within the lesion 2002 with respect to the surface of the patient 2003. As such, the user 2001 may screen the entire lesion 2002, noting the position of possible pathogens or pathological tissue. The user 2001 may subsequently return to specific regions of concern and at the discretion of the user 2001, manually initiate ablation using, for example, a trigger 2012. The handheld device 2011 may include a monitor 2013 that allows the user 2001 to observe the autofluorescence emitted from the lesion 2002 in real time and/or to observe a targeting beam of optionally visual light indicating the location of emitted energy for excitation and/or ablation.

Alternatively, the handheld device may be connected to an external display device and control circuitry 2008 as described in FIG. 27. The user 2001 places at least three targeting aids around the lesion 2002 on the patient 2003. The user 2001 scans the surface of the lesion 2002 with the handheld device 2011 and data is collected regarding the position of autofluorescence associated with a pathogen or pathological tissue. The user 2001 may analyze the accumulated data and at the discretion of the user 2001, return to specific regions of the lesion 2002 and use the trigger 2012 to initiate or enable irradiation with a beam of energy 2006 to ablate pathogens or pathological tissue. Alternatively, the targeting aids 2014 may be placed on fixed surfaces, for example, of the examination room. As such, the extremity with the lesion 2002 is immobilized to an examining surface, for example, to aide in location registration.

Figure 29:
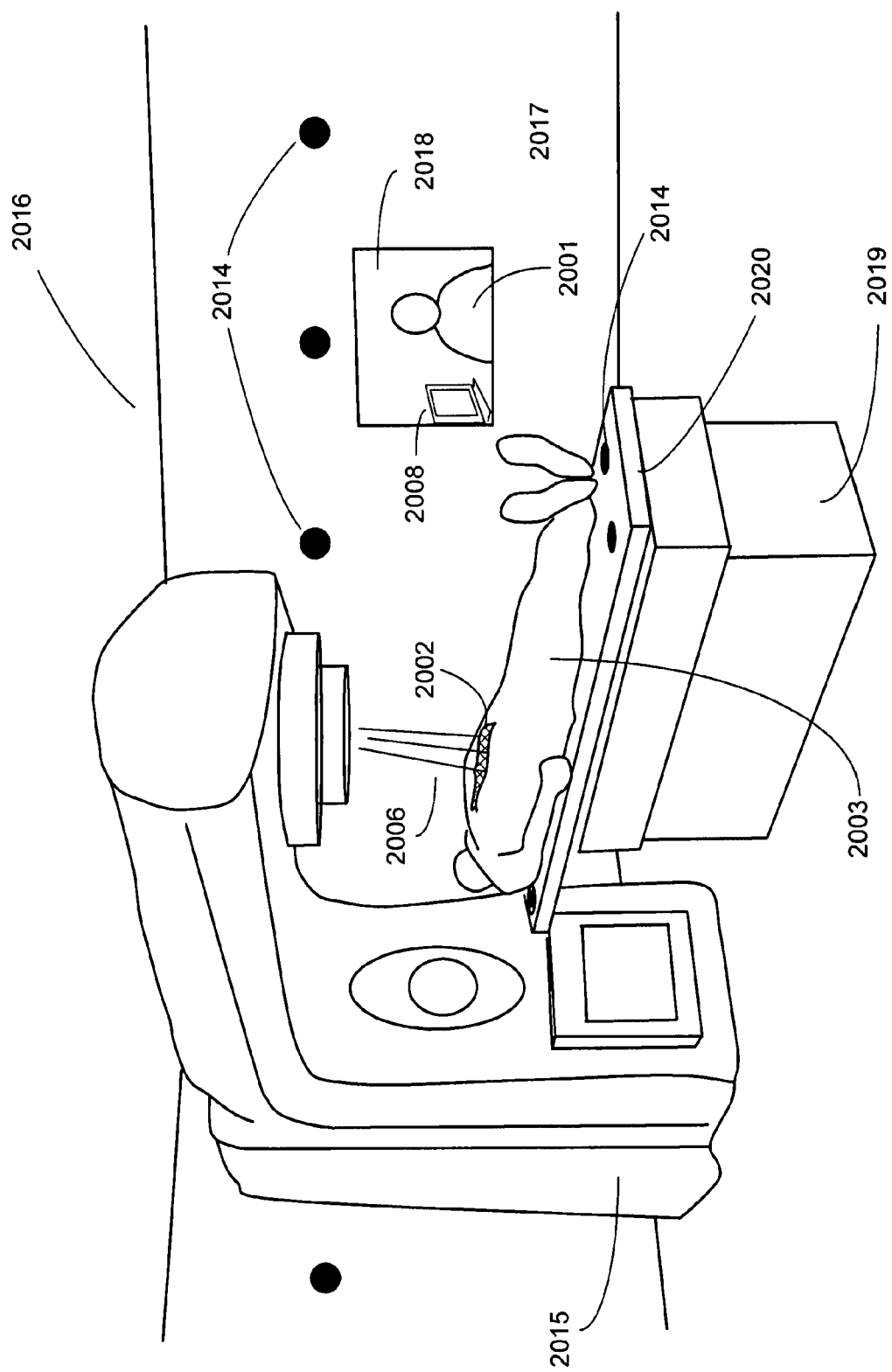
FIG. 29 shows a schematic of an example of an illustrative embodiment of a device in use on an illustrative subject.

FIG. 29 shows an illustrative configuration of a stationary version of the apparatus 100 for the real time detection and ablation of pathogens and pathological tissue. The stationary device 2015 may be a component of a room 2016 that is, for example, part of a surgical theater, an imaging and treatment facility, or a doctor's or dentist's or veterinarian's office. The stationary device 2015 may be used in conjunction with targeting aids 2014 placed at various locations around the room 2016. In the example shown in FIG. 29, the targeting aids 2014 are affixed to the walls 2017 of the room 2016. Alternatively, the targeting aids 2014 may be affixed to the ceiling, to the floor or to objects within the room, or a combination thereof.

The user 2001 may control the stationary device 2015 using control circuitry 2008 optionally in an auxiliary room 2018 optionally visually connected to the main room 2016 by a window or other viewing means, for example. The room 2016 may also contain a table 2019 upon which there is optionally a sliding platform 2020 for moving the patient 2003 into position relative to the stationary device 2015. The sliding platform 2020 may also have strategically placed targeting aids 2014. Alternatively, targeting aids 2014 may be placed on the patient 2003 in proximity to the lesion 2002 as described herein. In an alternative configuration, the patient 2003 may remain stationary on a table 2019 while some component of the stationary device 2015 is moved into the appropriate position relative to the lesion 2002.

The user 2001 may scan a lesion 2002 with the stationary device 2015 using a beam of energy 2006 to detect autofluorescence associated with pathogens or pathological tissue. The beam of energy 2006 exciting the autofluorescence associated with the pathogen or pathological tissue may be emitted, for example, from a mercury arc lamp, a Xenon lamp, a UV eximer, a halogen lamp, a laser or light emitting diode at wavelengths ranging, for example, from 200 nm to 1000 nm. The stationary device 2015 may automatically ablate the pathogen or pathological tissue based on the emitted autofluorescence. Alternatively, data may be collected regarding the position of autofluorescence associated with a pathogen or pathological tissue. The user 2001 may analyze the accumulated data and at the discretion of the user 2001, return to a specific region of the lesion 2002 based on orientation from the targeting aids 2014 and instruct the stationary device 2015 to emit a second beam of energy 2006 to ablate pathogens or pathological tissue. The second beam of energy 2006 may or may not be of the same wavelength and intensity as the first beam of energy 2006 used to excite fluorescence. The beam of energy 2006 inducing ablation of pathogens or pathological tissue may be an optical energy source, such as those described above, an X-ray energy source, a particle beam energy source, or a combination thereof.

Figure 30:
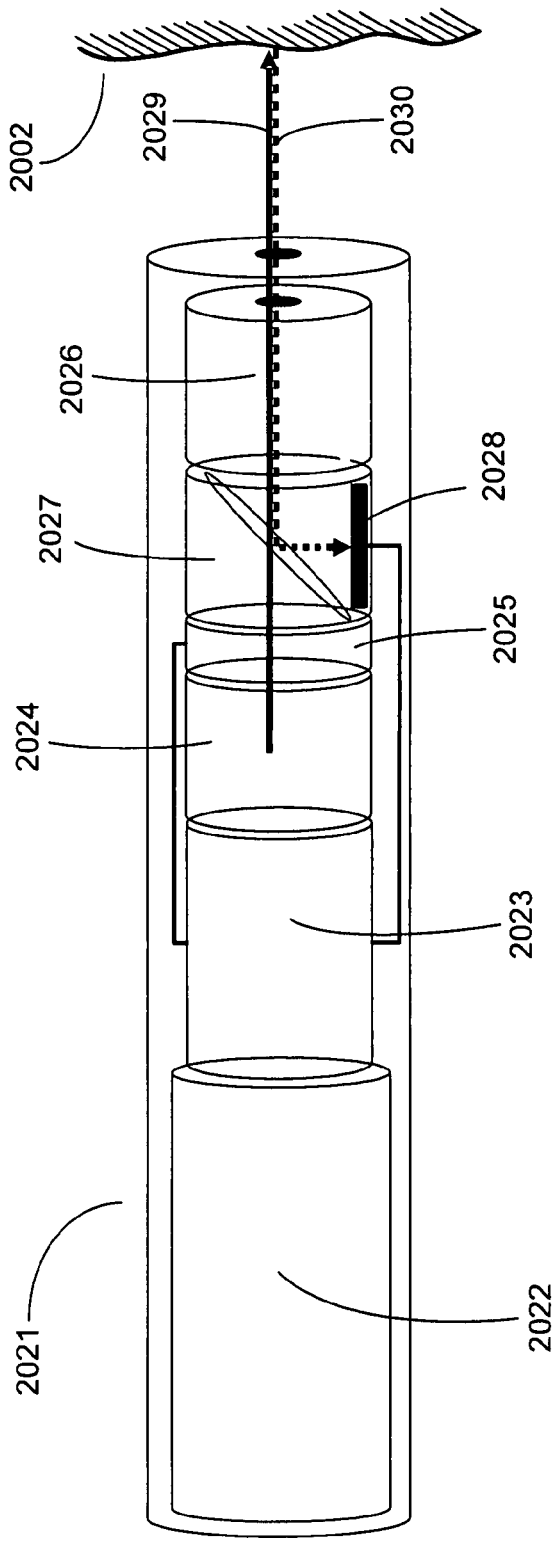
FIGS. 30-31 show a schematic of an example of an illustrative embodiment of a handheld device.
Figure 31:
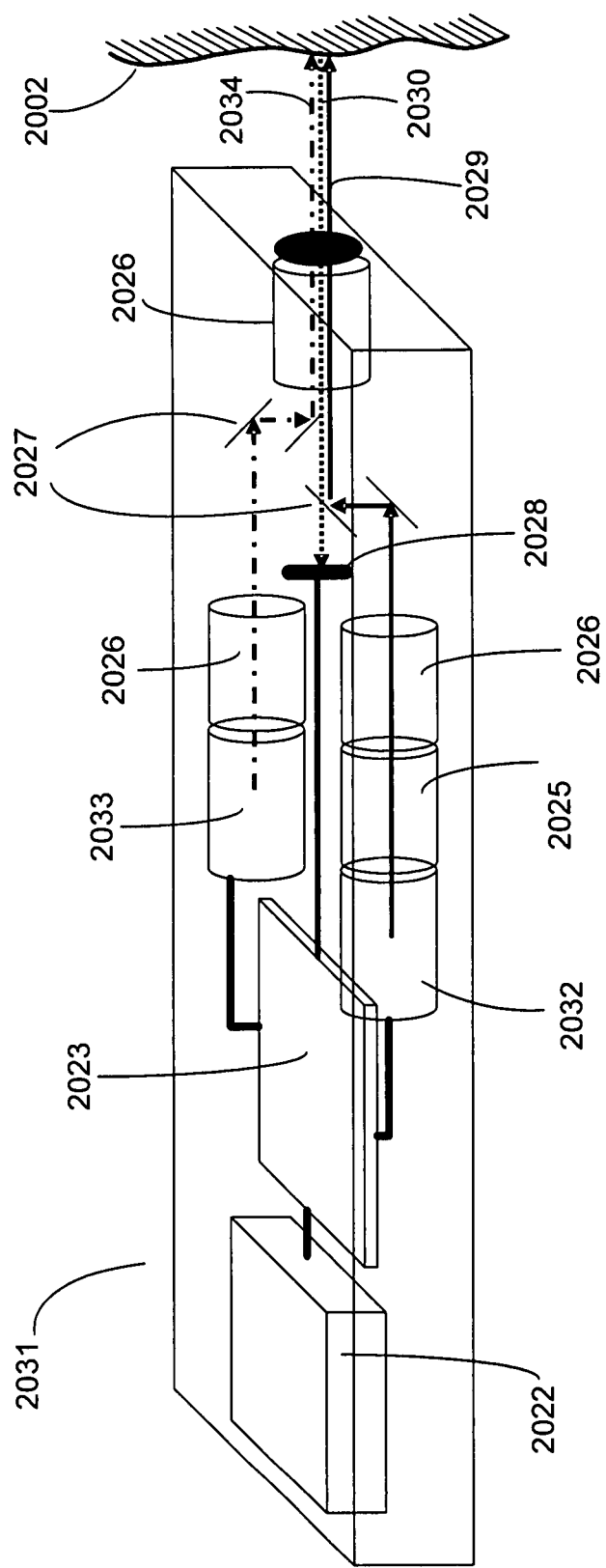

FIG. 30, FIG. 31, and FIG. 32 show schematic representations of illustrative configurations of handheld versions of an apparatus 100 for the detection and ablation of pathogens and pathological tissue.

FIG. 30 shows a schematic representation of an illustrative configuration of a completely self-contained handheld device 2021 for the detection and ablation of pathogens and pathological tissue. The handheld device 2021 contains a power source 2022 which powers the control circuitry 2023, the optical energy source 2024, and other components of the device 2021. The optical energy source 2024 may be, for example, a mercury arc lamp, a Xenon lamp, a UV eximer, a halogen lamp, a nitrogen laser or a laser diode. The electromagnetic energy 2029 emitted from the optical energy source 2024 may pass through a filter 2025 that allows for emission of specific wavelengths appropriate for inducing autofluorescence of pathogens or pathological tissue as described herein. The electromagnetic energy 2029 may pass through a lens 2026 to focus the energy and optionally through a chromatic beam splitter 2027. The electromagnetic energy 2029 hits the lesion 2002 resulting in emission of autofluorescence 2030. The autofluorescence 2030 is detected by a sensor 2028 and as a result a second wave of electromagnetic energy 2029 is emitted in real time from the optical energy source 2024 at a wavelength and intensity sufficient to ablate the detected pathogen or pathological tissue as described herein.

FIG. 31 shows a schematic representation of an illustrative configuration of a handheld device 2031 in which separate energy sources are optionally used for detection and ablation of pathogens or pathological tissue. The handheld device 2031 may be powered by an internal power supply 2022. Optionally, the handheld device may be connected to an external power supply. The handheld device 2031 may be controlled by internal control circuitry 2023. Optionally, the handheld device 2031 may be connected either with or without wires to external control circuitry. The handheld device 2031 contains at least one optical energy source 2032. The handheld device 2031 may also contain a least one additional energy source 2033 for the ablation of pathogens or pathological tissue. The energy source 2033 may be an optical energy source, an X-ray source, or a particle beam source, or a combination thereof.

Electromagnetic energy 2029 emitted from the optical energy source 2032 may pass through a filter 2025 that allows for emission of specific wavelengths appropriate for inducing autofluorescence of pathogens or pathological tissue as described herein. The electromagnetic energy 2029 may pass through a lens 2026, a series of beam splitters 2027, and through a final lens 2026 prior to hitting the lesion 2002. The autofluorescence 2030 emitted by pathogens or pathological tissue in the lesion 2002 is detected by the sensor 2028. As a result, a second beam of electromagnetic energy 2029 may be emitted from the first optical energy source 2032. Alternatively, a second beam of energy 2034 may be emitted from the second energy source 2033 which is a level of energy sufficient to ablate a pathogen or pathological tissue as described herein. The ablation energy may pass through portions of the same beam path, or may use a fully or partially dedicated beam path.

FIG. 32 shows a schematic representation of an illustrative configuration of a handheld device 2035 in which multiple energy sources are optionally used for position, detection and ablation of pathogens or pathological tissue. As shown in FIG. 32A, the handheld device 2035 may include a monitor 2036 for observing the autofluorescence associated with a pathogen or a pathological tissue. Optionally, the handheld device 2035 may be connected with or without wires to an external display device. The handheld device 2035 may include a control panel 2037 allowing for entry of commands by the user. Optionally, the handheld device 2035 may be connected with or without wires to an external control panel associated, for example, with a computer. The handheld device may be turned on and off via a switch 2004.

As shown in FIG. 32B, the handheld device 2035 may be powered by an internal power supply 2022. Optionally, the handheld device may be connected to an external power supply. The handheld device 2035 may be controlled by internal control circuitry 2023. Optionally, the handheld device 2035 may be connected either with or without wires to external control circuitry. The handheld device 2035 contains at least one optical energy source 2032. The handheld device 2035 may also contain at least two additional energy sources 2033 for the ablation of pathogens or pathological tissue. The energy source 2033 may be an optical energy source, an X-ray source, or a particle beam source, or a combination thereof. The handheld device 2035 may also contain at least one targeting energy source 2038 for positioning the autofluorescence associated with a pathogen or pathological tissue relative to one or more targeting sensors, as described herein.

Energy emitted from the optical energy source 2032 may pass through a filter/focus unit 2039 that allows for emission of specific wavelengths appropriate for inducing autofluorescence of pathogens or pathological tissue as described herein. The autofluorescence emitted by pathogens or pathological tissue in a lesion is detected by the sensor 2028. The position of the autofluorescence in the lesion may be determined with the aide of the targeting energy source 2038 and targeting sensors positioned, for example, on the surface of the patient in proximity to the lesion or on various surfaces in a room or a combination thereof as described herein. After the autofluorescence is detected, a second beam of electromagnetic energy may be emitted from the first optical energy source 2032. Alternatively, a second beam of energy may be emitted from the second or third energy source 2033 at a level of energy sufficient to ablate a pathogen or pathological tissue as described herein.

As shown in FIG. 32C, energy emitted from or detected by the device 2035 passes through one or more openings 2040 at the bottom of the device 2035.

Figure 33:
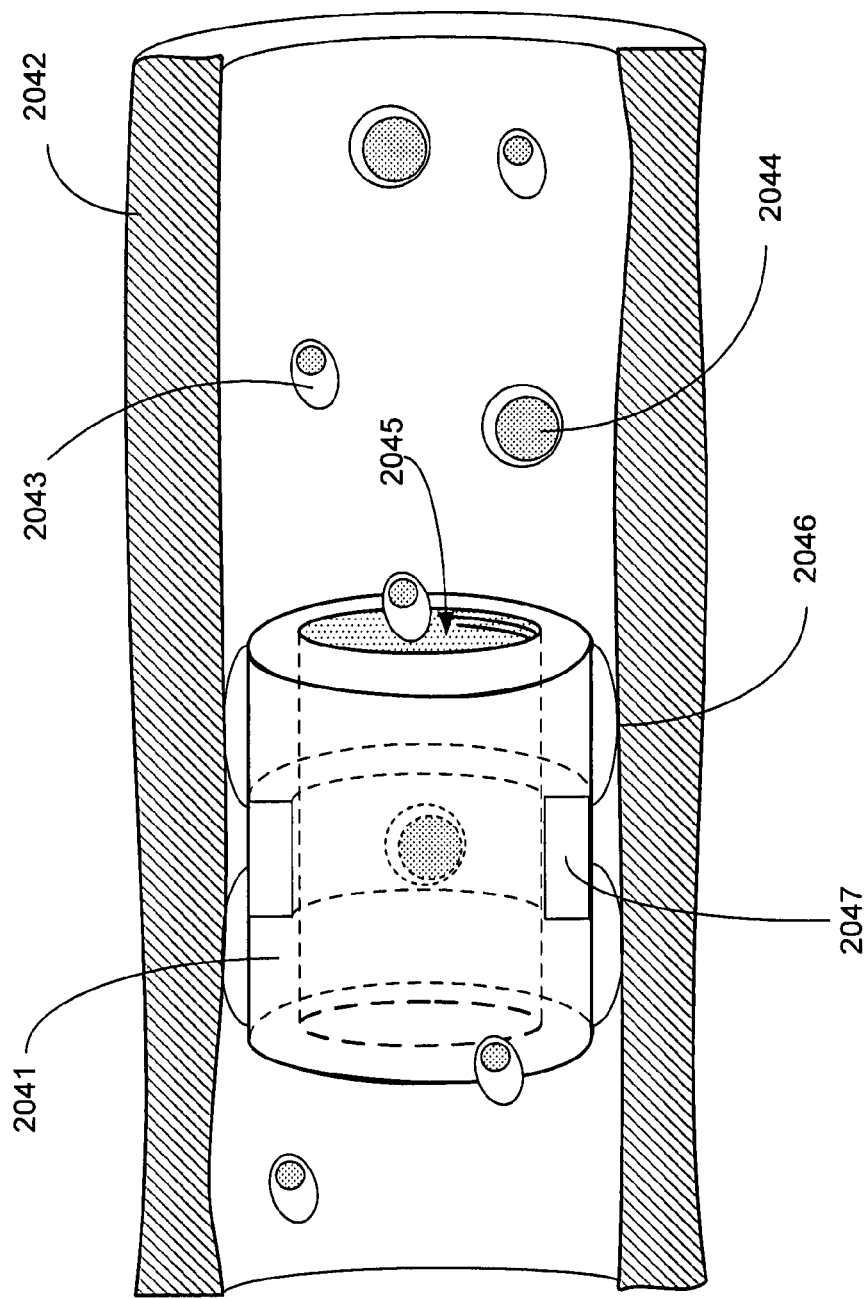
FIG. 33 shows a schematic of an example of an illustrative embodiment of an untethered device in use on an illustrative subject.
Figure 34:
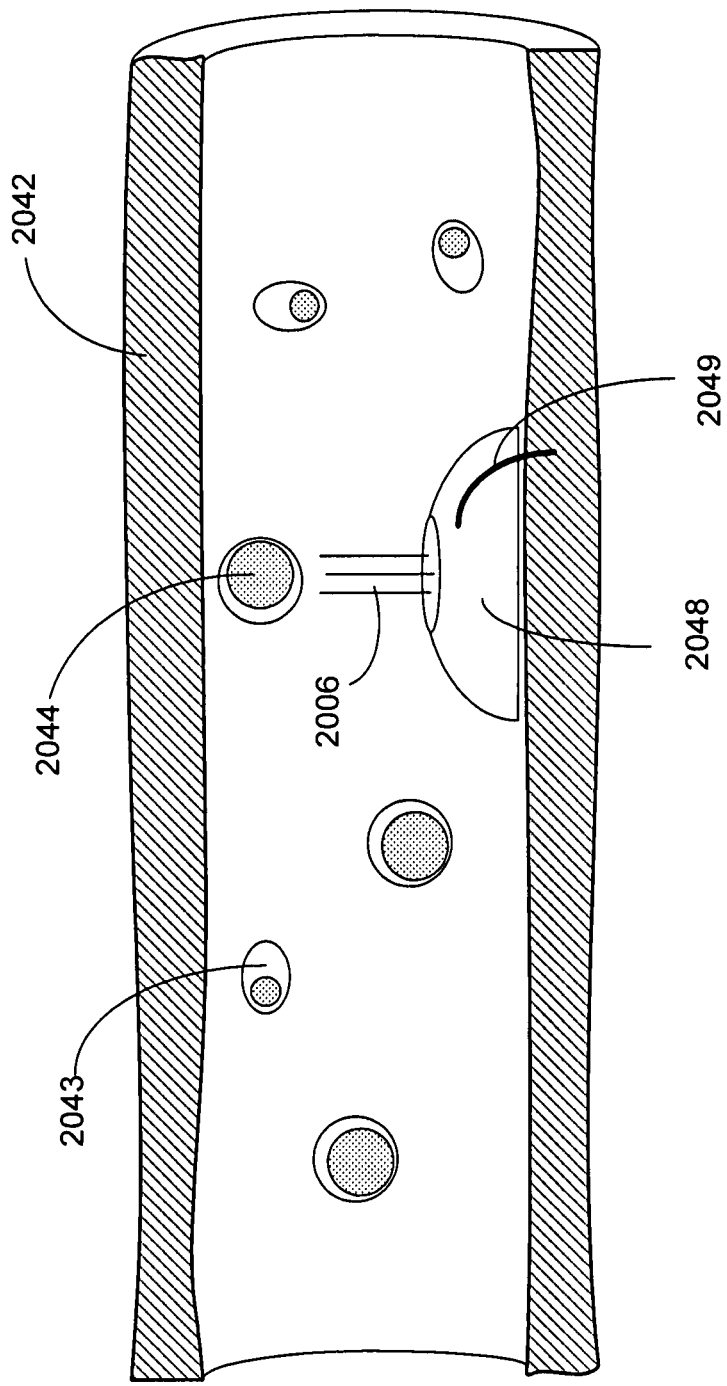
FIGS. 34-40 show a schematic of an example of an illustrative embodiment of an untethered device in use on an illustrative subject.

FIG. 33 and FIG. 34 show illustrative configurations of untethered versions of a device 200, 300 and/or 400 for the detection and ablation of pathogens and pathological tissue in the lumen, for example, of a blood vessel.

FIG. 33 shows an illustrative configuration of an untethered device 2041 for the detection and ablation of pathogens and pathological tissue in the lumen 2042 of a blood vessel, for example. Alternatively, the untethered device 2041 may be used in other lumens including those associated with the gastrointestinal tract, the respiratory tract, and the urogenital tract, for example. In this configuration, the untethered device 2041 may be a hollow cylinder that when placed in a lumen 2042 allows for the flow of fluid and cells 2043 through the central core 2045 of the cylinder. The hollow cylinder contains a detection and ablation unit 2047, which optionally contains a power source, control circuitry, one or more energy sources, and a sensor. Control of the device may be completely self-contained or controlled wirelessly by an external user.

As normal cells 2043 and abnormal cells 2044 pass through the central core 2045 of the untethered device 2041, the detection and ablation unit 2047 detects autofluorescence associated with the abnormal cells 2044 and in real time ablates the abnormal cells 2044. Abnormal cells 2044 may be, for example, pathogens, pathological cells or cancerous cells as described herein. The untethered device 2041 may be reversibly fixed in a specific region of the lumen by virtue of inflatable pouches 2046 or other means.

FIG. 34 shows an illustrative configuration of an untethered device 2048 for the detection and ablation of pathogens and pathological tissue in the lumen 2042, for example, of a blood vessel. Alternatively, the untethered device 2048 may be used in other lumens including those associated with the gastrointestinal tract, the respiratory tract, and the urogenital tract, for example. In this configuration, the untethered device 2048 may be fixed to the surface of a lumen by virtue of a hook 2049 which at the appropriate time and location latches on to the surface of the lumen. Control of the untethered device 2048 may be completely self-contained or controlled wirelessly by an external user. The untethered device 2048 may sit on the surface of a lumen and monitor the flow of fluid and normal cells 2043 and abnormal cells 2044. The untethered device 2048 emits a beam of energy 2006 which detects abnormal cells 2044 based on autofluorescence and in real time ablates the abnormal cells.

Figure 35:
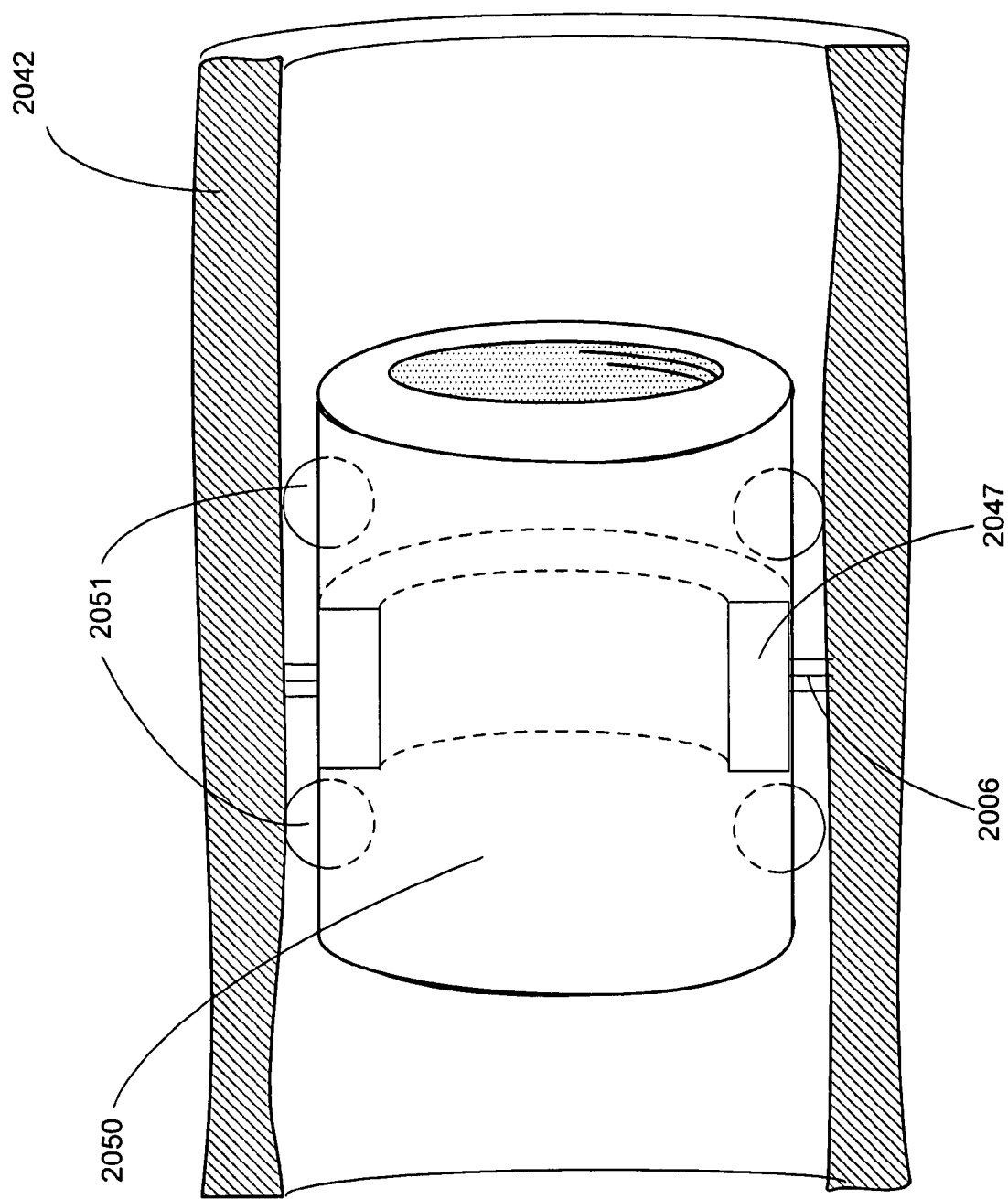
Figure 36:
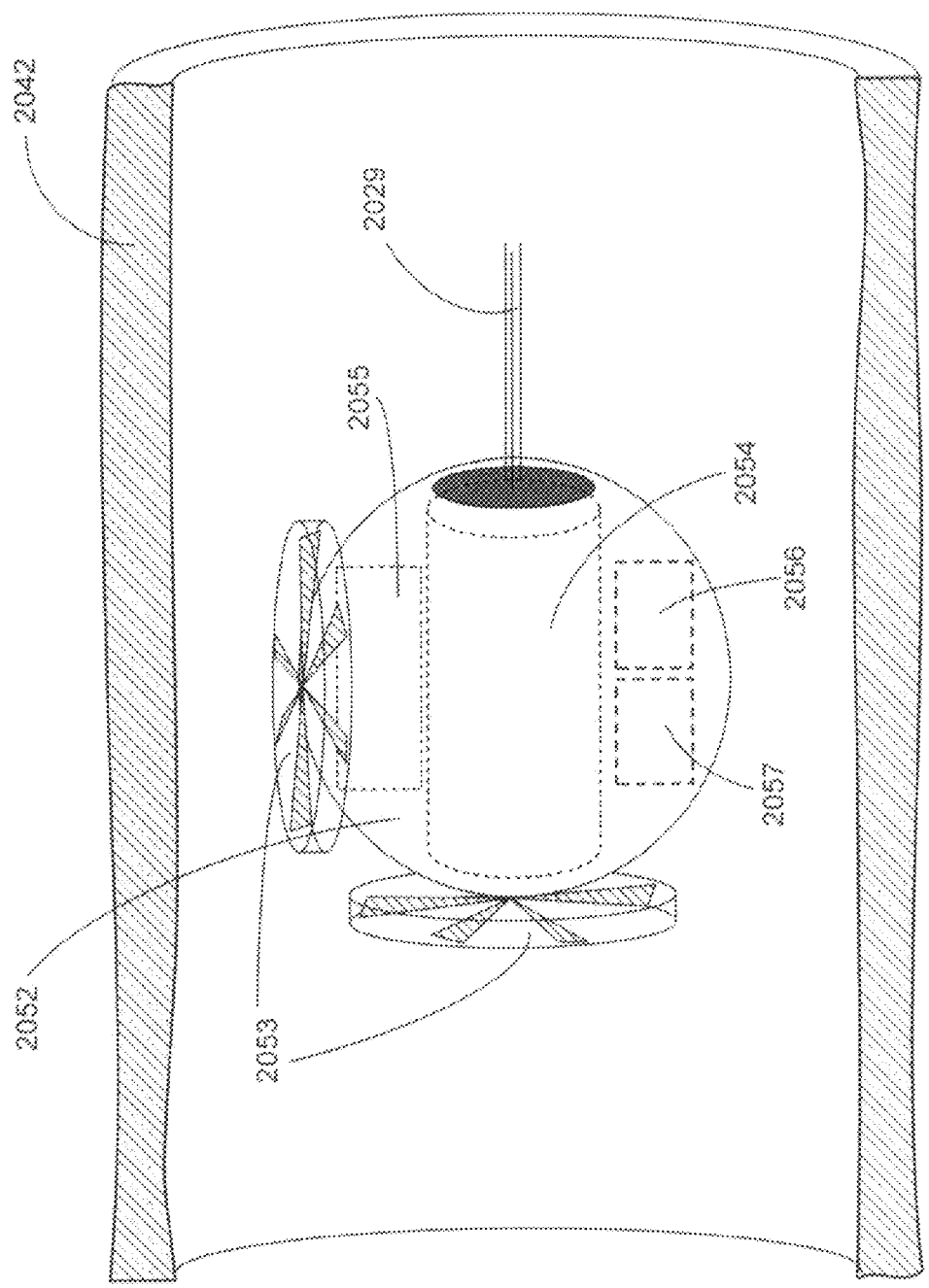
Figure 37:
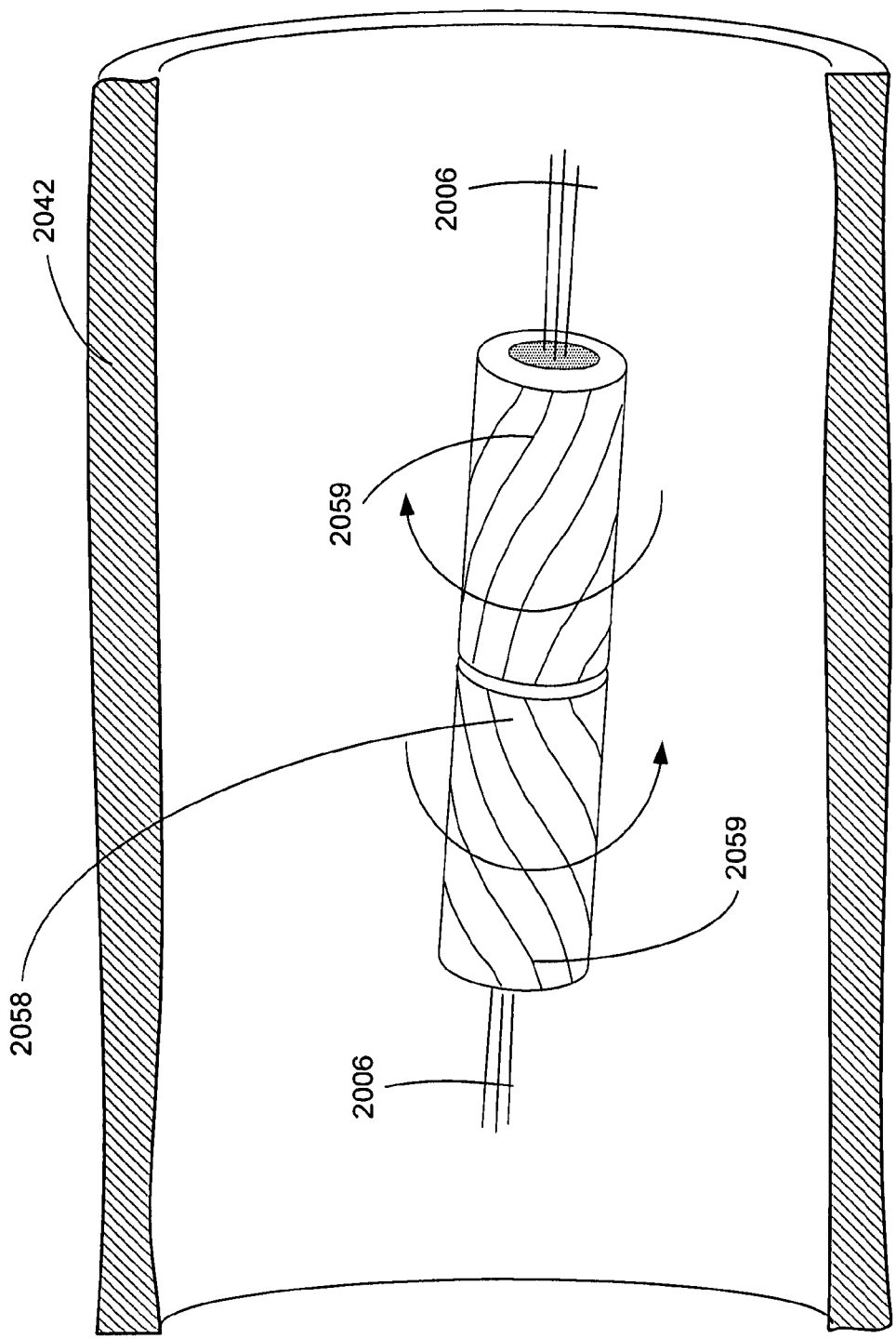

FIG. 35, FIG. 36, and FIG. 37 show illustrative configurations of untethered versions of an apparatus 100 with controlled locomotion for the detection and ablation of pathogens and pathological tissue in a lumen associated with, for example, the circulatory system, the gastrointestinal tract, the respiratory tract, or the urogenital tract.

FIG. 35 shows an illustrative configuration of an untethered device 2050 with controlled locomotion for the detection and ablation of pathogens and pathological tissue in a lumen 2042. In this configuration, the untethered device 2050 is a hollow cylinder and has two or more controllable wheels 2051 that allow the device to move along the surface of a lumen. Control of the movement of the untethered device 2050 may be completely self-contained or controlled wirelessly by an external user. The hollow cylinder contains a detection and ablation unit 2047, which optionally contains a power source, control circuitry, one or more energy sources, and a sensor. As the untethered device moves along the surface of a lumen, a beam of energy 2006 is emitted towards the surface, for example, scanning for autofluorescence associated with a pathogen or pathological tissue. Once autofluorescence is detected, the untethered device 2050 emits a beam of energy 2006 from the detection and ablation unit 2047 sufficient to ablate the pathogen or pathological tissue.

FIG. 36 shows an illustrative configuration of an untethered device 2052 with controlled locomotion for the detection and ablation of pathogens and pathological tissue in a lumen 2042. In the configuration shown, the untethered device 2052 is a sphere. Optionally, the untethered device 2052 may be any configuration that is compatible with housing the components necessary for detection and ablation of pathogens or pathological tissue in a lumen 2042. The untethered device 2052 has two propellers 2053 mounted on the top and on the side of the sphere to allow the controlled movement of the device in all directions. Optionally, more or less propellers 2053 may be mounted on the device. Optionally, the one or more propellers 2053 may be mounted in different locations on the device. Control of the movement of the untethered device 2052 may be completely self-contained or controlled wirelessly by an external user. As shown, the untethered device 2052 contains an energy source 2054, control circuitry, 2055, a sensor 2056, and a power source 2057. The energy source 2054 may be an optical energy source, an x-ray energy source, a particle beam energy source, or a combination thereof. The untethered device 2052 moves through a lumen 2042 scanning the surface of the lumen or cells flowing in the lumen with electromagnetic energy 2029 (optionally the same as 111) sufficient to induce autofluorescence associated with a pathogen or pathological cell or tissue. Once autofluorescence is detected by the sensor 2056, the untethered device 2052 emits energy sufficient to ablate the pathogen or pathological tissue.

FIG. 37 shows an illustrative configuration of an untethered device 2058 with controlled locomotion for the detection and ablation of pathogens and pathological tissue in a lumen 2042. In this configuration, the two halves of the untethered device 2058 have grooves 2059 cut in opposite directions. The two halves of the untethered device 2058 rotate independently in opposite directions. Control of the movement of the untethered device 2058 may be completely self-contained or controlled wirelessly by an external user. Each half of the untethered device may have the independent capability of emitting and detecting a beam of energy 2006 sufficient to detect and ablate pathogens or pathological tissue.

Figure 38:
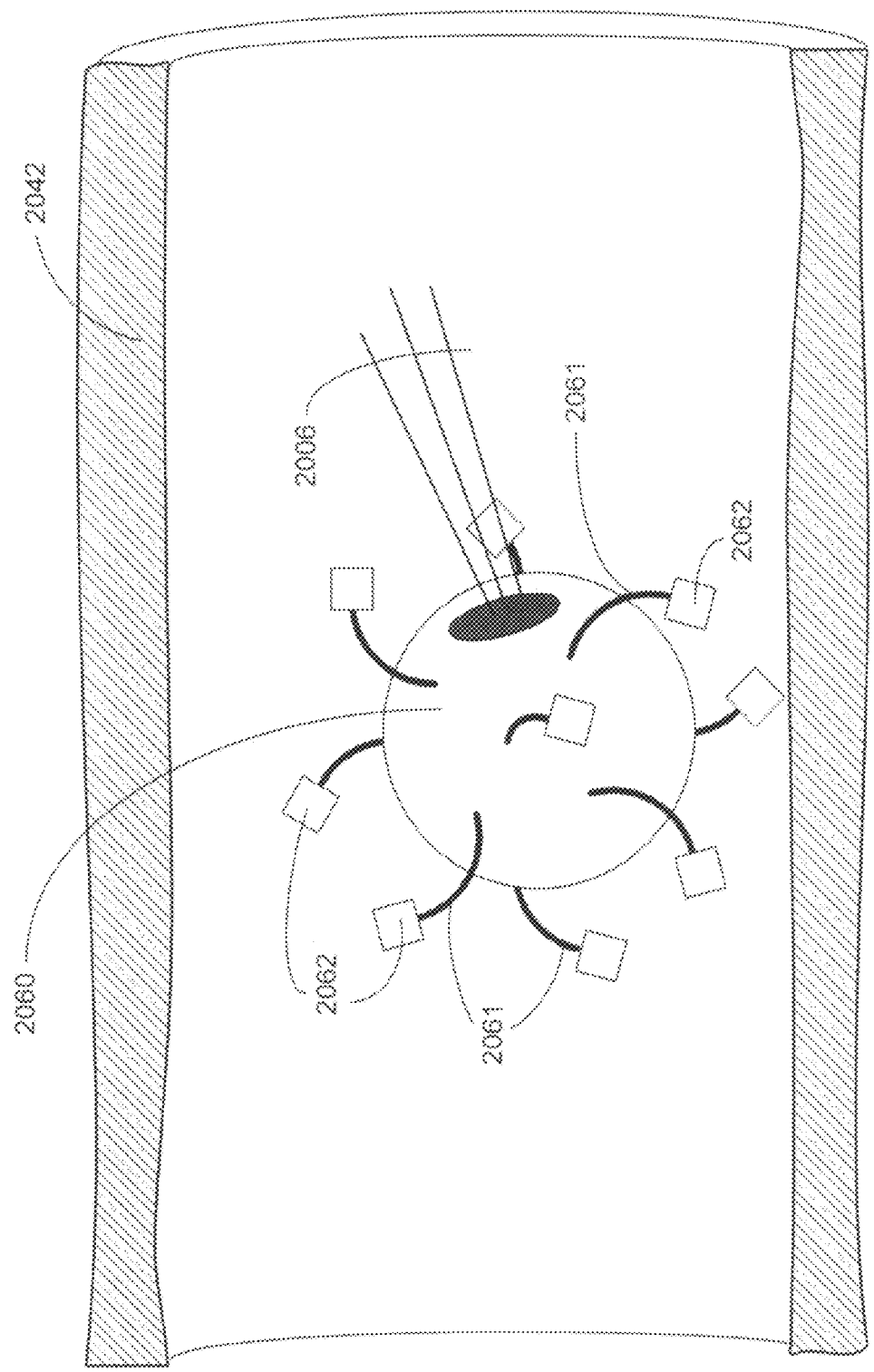
Figure 39:
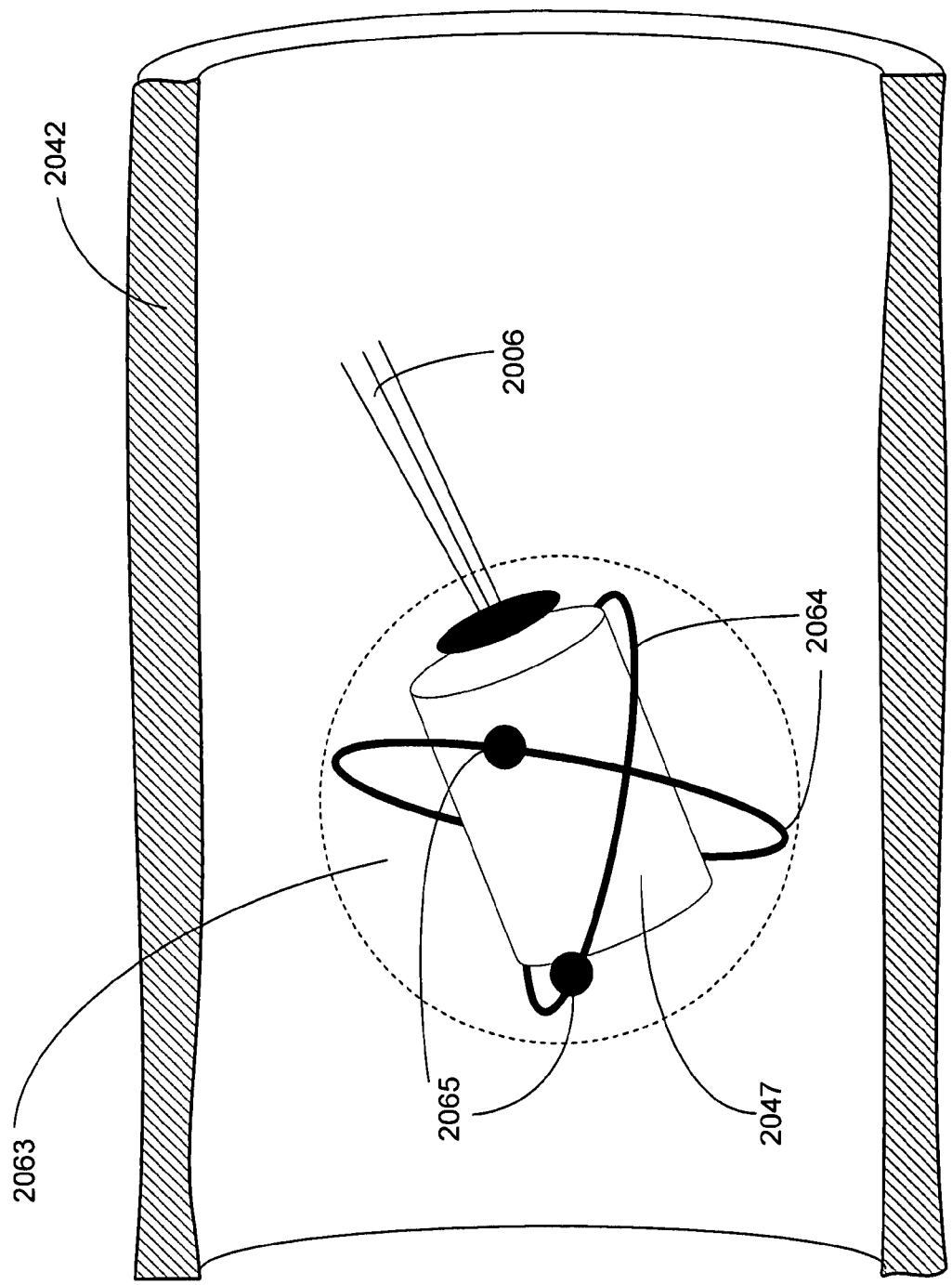

FIG. 38 and FIG. 39 show illustrative configurations of untethered versions of an apparatus 100 with random movement for the detection and ablation of pathogens and pathological tissue in a lumen associated with, for example, the circulatory system, the gastrointestinal tract, the respiratory tract, or the urogenital tract.

FIG. 38 shows an illustrative configuration of an untethered device 2060 with random movement for the detection and ablation of pathogens and pathological tissue in a lumen. In this configuration, the untethered device 2060 is a sphere. Optionally, the untethered device 2060 may be any configuration that is compatible with housing the components necessary for detection and ablation of pathogens or pathological tissue in a lumen 2042. The untethered device 2060 has one or more controllable arms 2061 attached to the surface. A paddle 2062 is attached to the end of each controllable arm 2061. The one or more arms 2061 may move in varied directions relative to the surface of the untethered device and as such, randomly turn the untethered device 2060. Control of the movement of the arms 2061 of the untethered device 2060 may be completely self-contained or controlled wirelessly by an external user. The untethered device 2060 randomly rotates based on the motion of the arms 2061 and associated paddles 2062, scanning the surface of a lumen 2042 with a beam of energy 2006 sufficient to induce autofluorescence. Once autofluorescence associated with a pathogen or pathological tissue is detected, the untethered device 2060 emits energy sufficient to ablate the pathogen or pathological tissue.

FIG. 39 shows an illustrative configuration of an untethered device 2063 with random movement for the detection and ablation of pathogens and pathological tissue in a lumen. In this configuration, the untethered device 2063 is a sphere with two or more tracks 2064 within the interior of the sphere. Each track 2064 has at least one associated weighted bead 2065 that is propelled along the track 2064. Differential movement of the weighted beads will cause random rotation of the untethered device 2063. The untethered device 2063 randomly rotates based on the motion of the two or more weighted beads, scanning the surface of a lumen 2042 with a beam of energy 2006, optionally electromagnetic energy 2029 from a detection and ablation unit 2047 sufficient to induce autofluorescence. Once autofluorescence associated with a pathogen or pathological tissue is detected, the untethered device 2063 emits a beam of energy 2006 from the detection and ablation unit 2047 sufficient to ablate the pathogen or pathological tissue.

Figure 40:
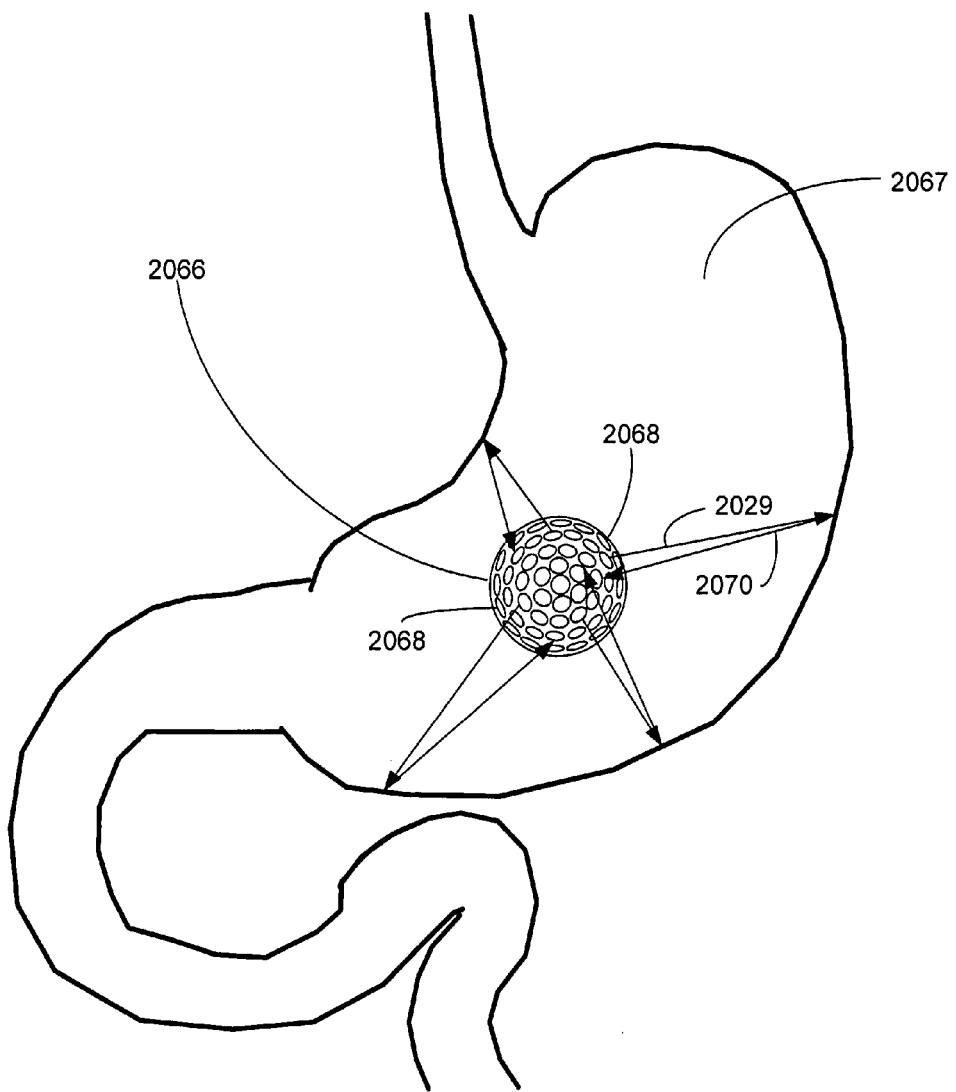

FIG. 40 shows an illustrative configuration of an untethered ingestible device 2066 for the detection and ablation of pathogens and pathological tissue in the lumen of the gastrointestinal tract 2067. In the configuration shown, the untethered ingestible device is a sphere with multiple openings 2068 covering the surface of the sphere. The multiple openings 2068 may emit electromagnetic energy 2029 sufficient to induce autofluorescence of a pathogen or pathological tissue and/or pathogen cell death. The emitted autofluorescence 2070 induced by the electromagnetic energy 2029 is detected through one or more of the multiple openings 2068. Once autofluorescence associated with a pathogen or pathological tissue is detected, the untethered ingestible device 2066 emits energy sufficient to ablate the pathogen or pathological tissue.

In one aspect, the disclosure is drawn to systems implementations including methods, computer programs, and systems for controlling optionally the detection and ablation and/or movement of targets optionally at least partially based on a fluorescent response. One or more of these systems implementations may be used as part of one or more methods for optionally detecting and ablating one or more targets optionally at least partially based on a fluorescent response, and/or implemented on one or more apparatus 100 and/or 500 and/or devices 200, 300, and/or 400 optionally configured to detect and/or to ablate one or more target cells. One or more of the operations, computer programs, and/or systems implementations described in association with one or more embodiments are envisioned and intended to also make part of other embodiments unless context indicates otherwise.

The operational flows may also be executed in a variety of other contexts and environments, and or in modified versions of those described herein. In addition, although some of the operational flows are presented in sequence, the various operations may be performed in various repetitions, concurrently, and/or in other orders than those that are illustrated. Although several operational flow sequences are described separately herein, these operational flows may be performed in sequence, in various repetitions, concurrently, and in a variety of orders not specifically illustrated herein. In addition, one or more of the steps described for one or more operational flow sequence may be added to another flow sequence and/or used to replace one or more steps in the flow sequence, with or without deletion of one or more steps of the flow sequence.

Operations may be performed with respect to a digital representation (e.g. digital data) of, for example, one or more characteristics of a fluorescent response, one or more characteristics of excitation energy 116, one or more characteristics of ablation energy 117, one or more movement parameters, and/or one or more targeting parameters. The logic may accept a digital or analog (for conversion into digital) representation of an input and/or provide a digitally-encoded representation of a graphical illustration, where the input may be implemented and/or accessed locally or remotely. The logic may provide a digital representation of an output, wherein the output may be sent and/or accessed locally or remotely.

Operations may be performed related to either a local or a remote storage of the digital data, or to another type of transmission of the digital data. In addition to inputting, accessing querying, recalling, calculating, determining or otherwise obtaining the digital data, operations may be performed related to storing, assigning, associating, displaying or otherwise archiving the digital data to a memory, including for example, sending, outputting, and/or receiving a transmission of the digital data from (and/or to) a remote memory and/or unit, device, or apparatus. Accordingly, any such operations may involve elements including at least an operator (e.g. human or computer) directing the operation, a transmitting computer, and/or receiving computer, and should be understood to occur in the United States as long as at least one of these elements resides in the United States.

Figure 8:
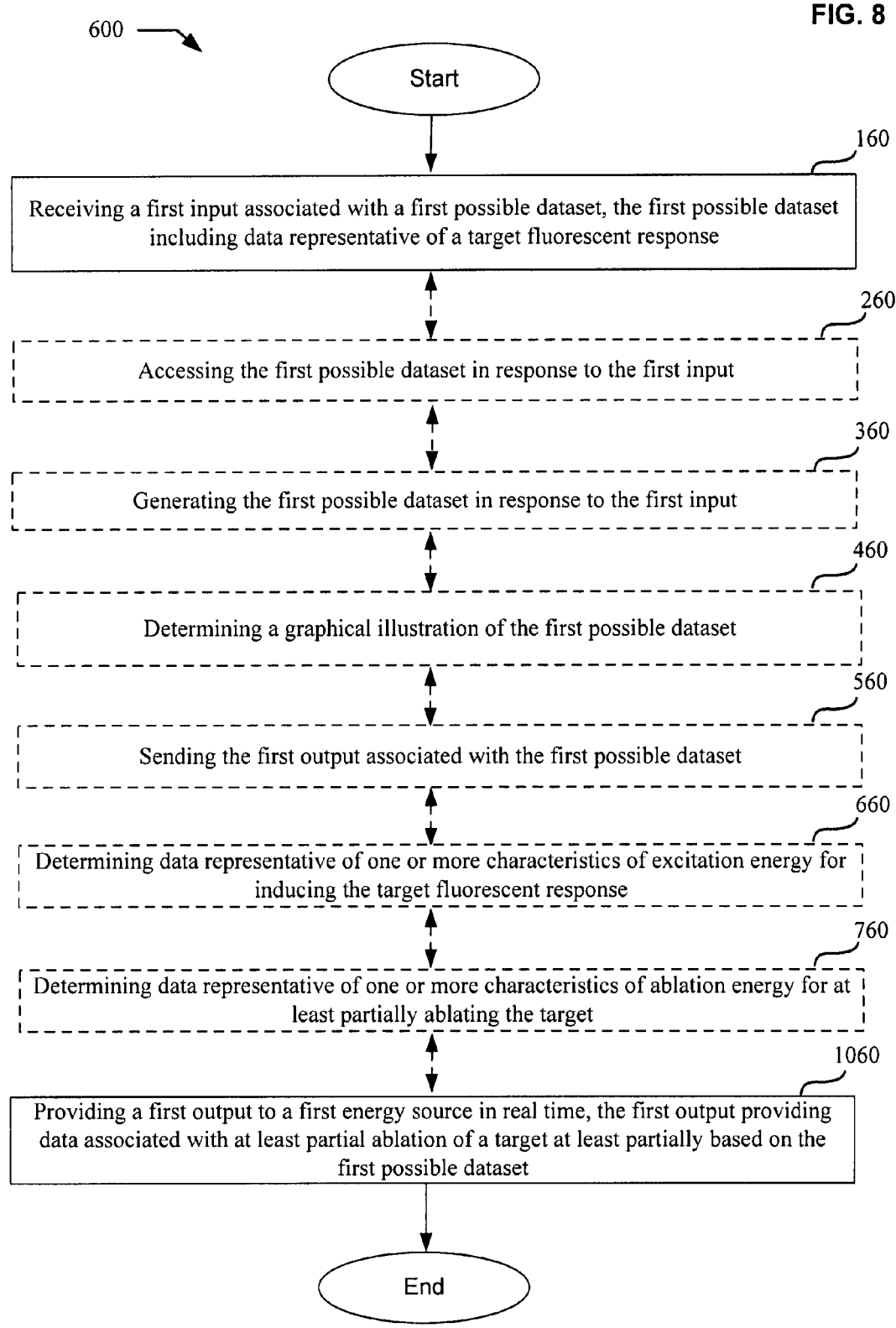
FIG. 8 and FIG. 9 show an operational flow representing illustrative embodiments of operations related to providing a first output to a first energy source in real time, the first output providing data associated with at least partial ablation of a target at least partially based on the first possible dataset.
Figure 9:
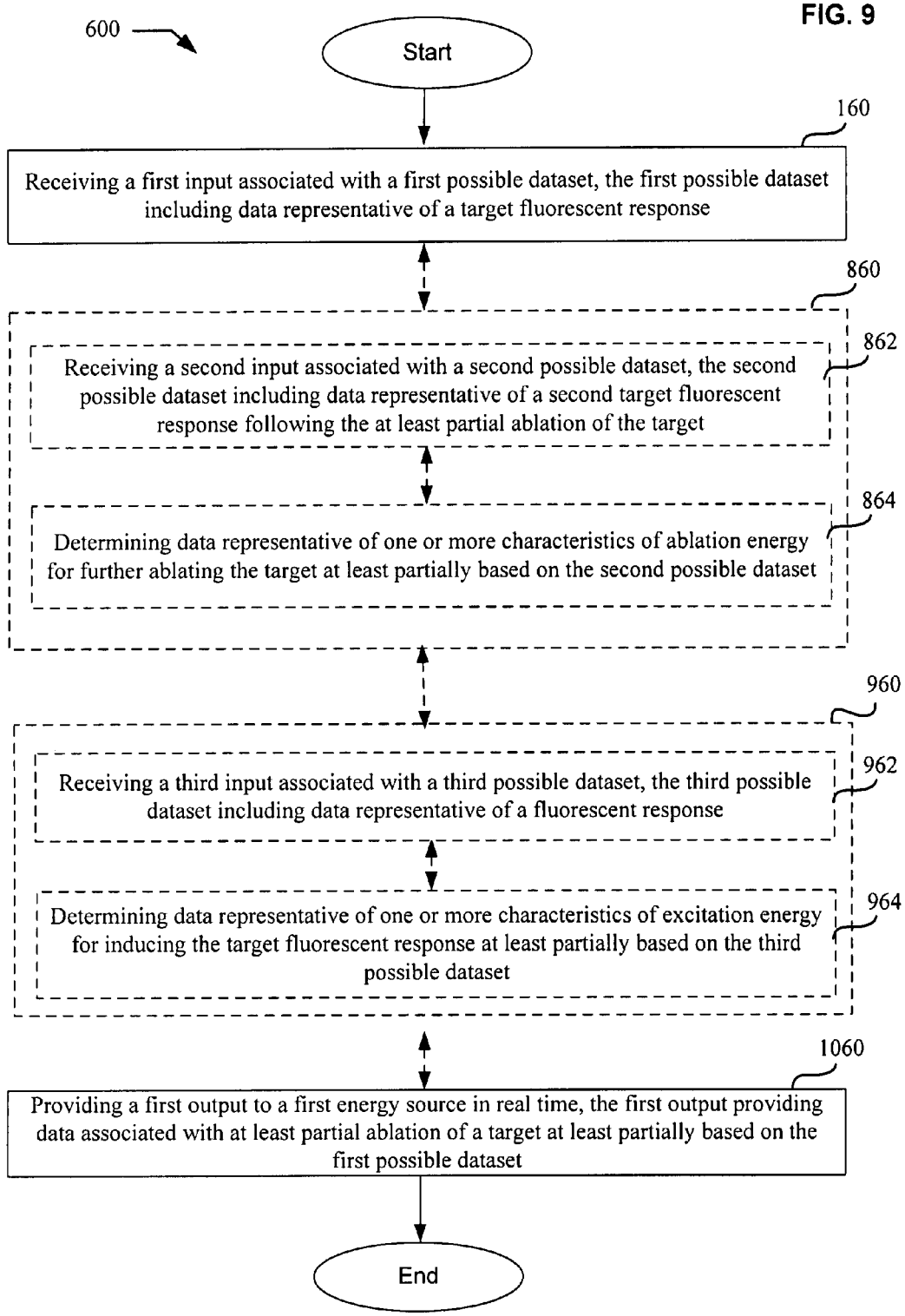

FIG. 8 and/or FIG. 9 depict embodiments of an operational flow 600 representing illustrative embodiments of operations related to providing a first output to a first energy source in real time, the first output providing data associated with at least partial ablation of a target at least partially based on the first possible dataset. In FIG. 8 and/or FIG. 9, discussion and explanation may be provided with respect to one or more apparatus 100 and/or 500 and/or device 200, 300 and/or 400 and methods described herein, and/or with respect to other examples and contexts.

In some embodiments, one or more methods include receiving a first input associated with a first possible dataset, the first possible dataset including data representative of a target fluorescent response; and providing a first output to a first energy source in real time, the first output providing data associated with at least partial ablation of a target at least partially based on the first possible dataset.

In illustrative embodiments, operational flow 600 may be employed in the process of target ablation to receive information associated with a target fluorescent response optionally from one or more apparatus 100 and/or 500 and/or devices 200, 300, and/or 400, optionally including, but not limited to, information relating to the wavelength, intensity, strength, directionality, and/or spatial extent of the fluorescent response. In illustrative embodiments, operational flow 600 may be employed in the process of target ablation to analyze information associated with a target fluorescent response, optionally from one or more apparatus 100 and/or 500 and/or devices 200, 300, and/or 400, to determine one or more characteristics of one or more energy source 110 and/or ablation energy 117 associated with at least partially ablating one or more target.

After a start operation, the operational flow 600 moves to a receiving operation 160, receiving a first input associated with a first possible dataset, the first possible dataset including data representative of one or more target fluorescent response. For example, a first input may include, but is not limited to, data representative of one or more wavelengths of excitation energy, direction, pulse time, timing, as well as detection wavelengths and timing. For example, a first input may include, but is not limited to, a condition, an illness, a cell and/or tissue type under investigation, and/or other disease and/or preventive medicine information An optional accessing operation 260 accesses the first possible dataset in response to the first input. For example, data representative of one or more fluorescent responses, one or more autofluorescent responses, and/or one or more target fluorescent responses may be accessed. For example, data representative of background fluorescence, fluorescent tags and/or markers, and/or limits of detection may be accessed.

An optional generating operation 360 generates the first possible dataset in response to the first input. For example, data representative of one or more target fluorescent response may be generated optionally by eliminating and/or controlling for endogenous non-target fluorescence and/or non-specific fluorescence. For example, data representative of direction and/or location of a target, the presence or absence of a target, and/or the risk to non-target cells and tissues of ablation may be generated.

An optional determining operation 460 determines a graphical illustration of the first possible dataset. For example, data representative of one or more fluorescent responses, one or more autofluorescent responses, and/or one or more target fluorescent response may be graphically represented. For example, data representative of direction and/or location of a target optionally in relation to other non-target areas and/or the likelihood of collateral damage may be graphically represented.

An optional sending operation 560 sends the first output associated with the first possible dataset. For example, data representative of one or more fluorescent responses, one or more autofluorescent responses, and/or one or more target fluorescent response may be sent as part of the first output. For example, data representative of direction and/or location of a target may be sent optionally to an external source and/or to an ablation device.

An optional determining operation 660 determines data representative of one or more characteristics of excitation energy 116 for inducing the target fluorescent response. For example, data representative of one or more characteristics of excitation energy 116, optionally including, but not limited to, wavelength, strength, mode, directionality, and/or spatial limitations may be determined.

An optional determining operation 760 determines data representative of one or more characteristics of ablation energy 117 for at least partially ablating a target. For example, data representative of one or more characteristics of ablation energy 117, optionally including, but not limited to, wavelength, strength, mode, directionality, and/or spatial limitations may be determined.

An optional operation 860 includes an optional receiving operation 862 and an optional determining operation 864. The optional receiving operation 862 receives a second input associated with a second possible dataset, the second possible dataset including data representative of a second target fluorescent response following the at least partial ablation of the target. The optional determining operation 864 determines data representative of one or more characteristics of ablation energy 117 for further ablating a target at least partially based on the second possible dataset. For example, data representative of a second target fluorescent response may include one or more characteristics different from the first, previous and/or original target fluorescent response, optionally as a result of the at least partial ablation of the target. For example, the one or more characteristics may include, but are not limited to, presence, absence and/or reduction in the target fluorescent response.

An optional operation 960 includes an optional receiving operation 962 and an optional determining operation 964. The optional receiving operation 962 receives a third input associated with a third possible dataset, the third possible dataset including data representative of a fluorescent response. The optional determining operation 964 determines data representative of one or more characteristics of excitation energy 116 for inducing a target fluorescent response at least partially based on the third possible dataset. For example, data representative of a fluorescent response may indicate the presence or absence of a target fluorescent response.

Then, a providing operation 1060, provides a first output to a first energy source in real time, the first output providing data associated with at least partial ablation of a target at least partially based on the first possible dataset. For example, data representative of one or more characteristics of ablation energy 117, one or more characteristics of the excitation energy 116, one or more characteristics of the fluorescent response, one or more environmental parameters, and/or one or more targeting parameters.

Figure 10:
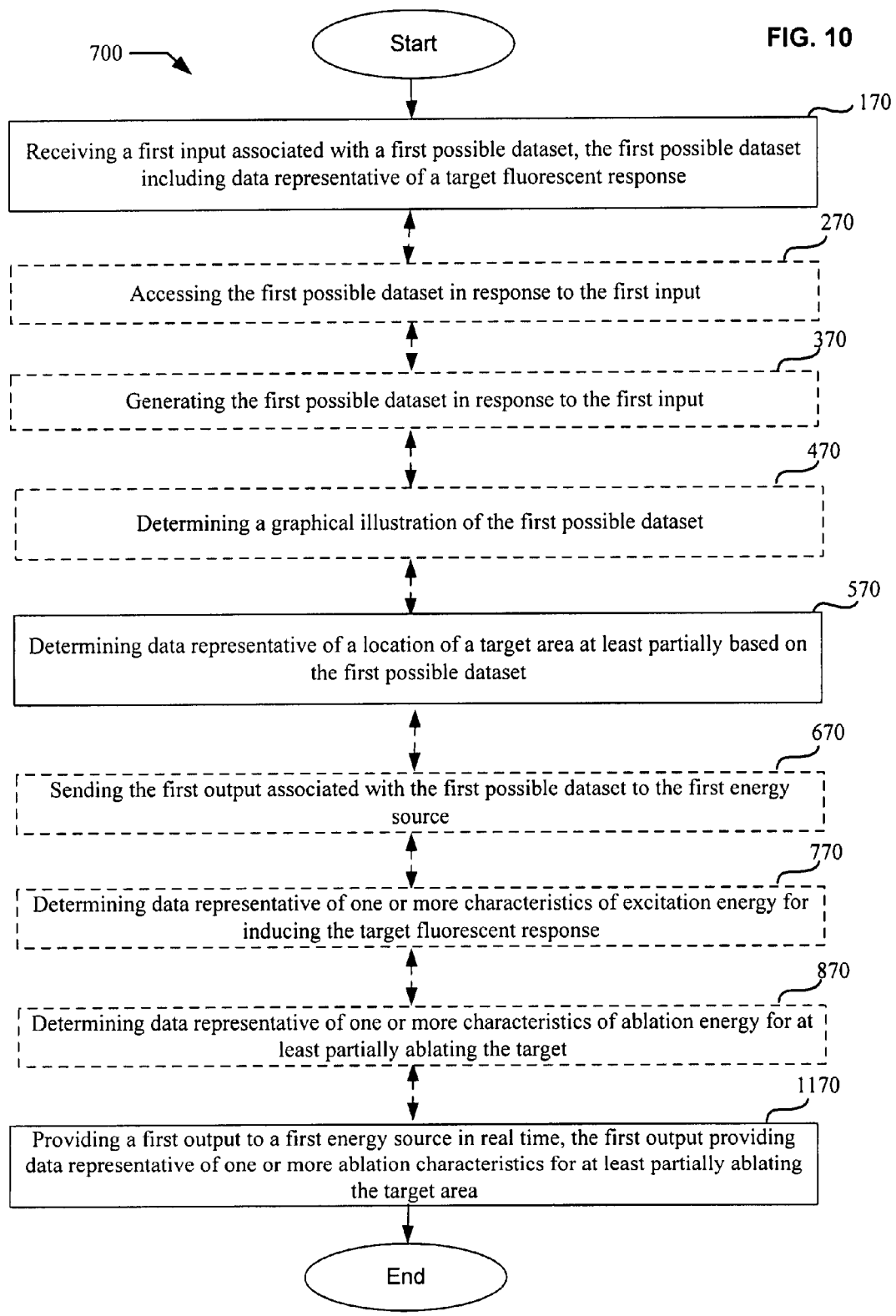
FIG. 10 and FIG. 11 show an operational flow representing illustrative embodiments of operations related to providing a first output to a first energy source in real time, the first output providing data representative of one or more ablation characteristics for at least partially ablating a target area.
Figure 11:
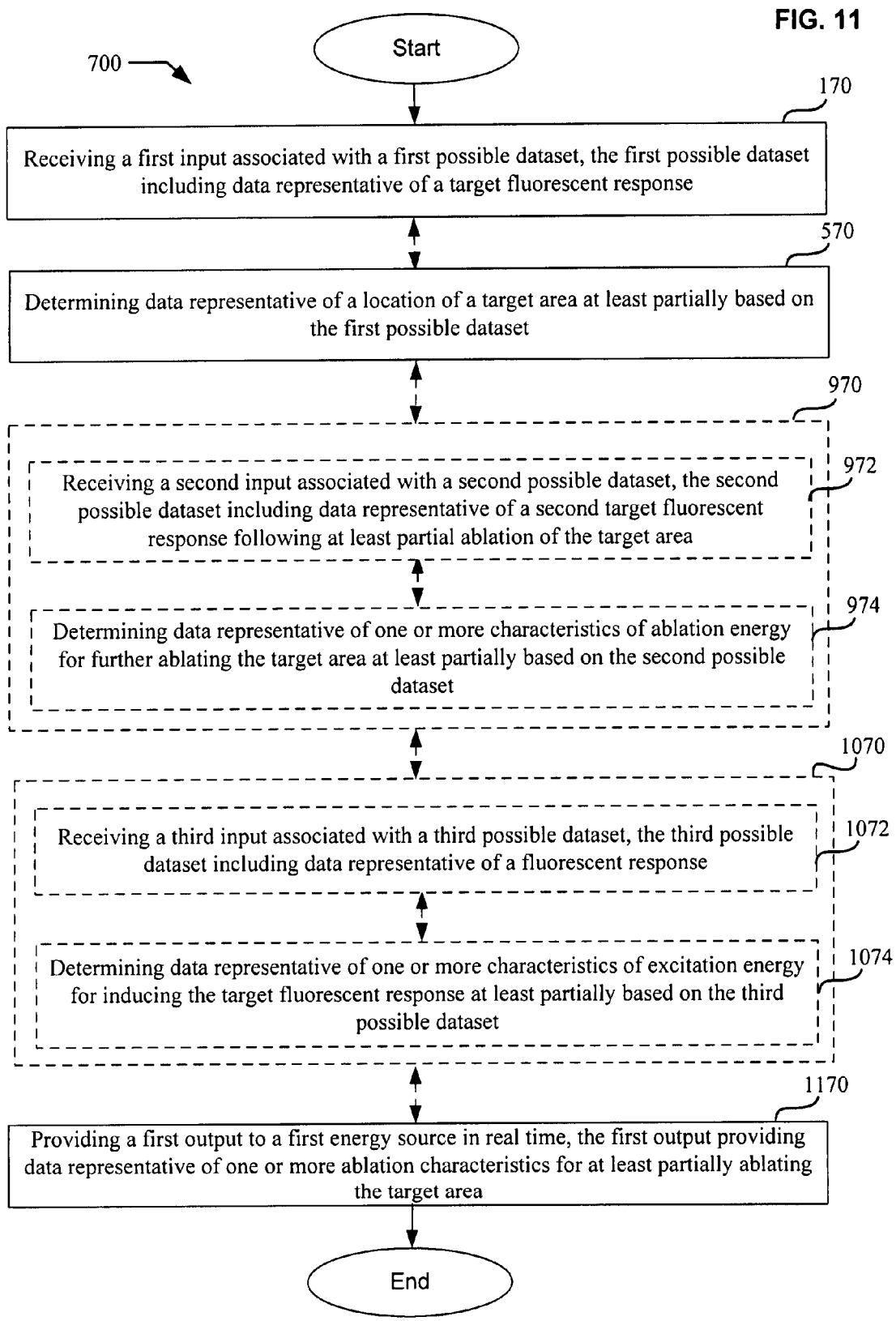

FIG. 10 and/or FIG. 11 depict embodiments of an operational flow 700 representing illustrative embodiments of operations related to providing a first output to a first energy source in real time, the first output providing data representative of one or more ablation characteristics for at least partially ablating a target area. In FIG. 10 and/or FIG. 11, discussion and explanation may be provided with respect to one or more apparatus 100 and/or 500 and/or device 200, 300 and/or 400 and methods described herein, and/or with respect to other examples and contexts.

In some embodiments, one or more methods include receiving a first input associated with a first possible dataset, the first possible dataset including data representative of a target fluorescent response; determining data representative of a location of a target area at least partially based on the first possible dataset; and providing a first output to a first energy source in real time, the first output providing data representative of one or more ablation characteristics for at least partially ablating the target area.

In illustrative embodiments, operational flow 700 may be employed in the process of target ablation to receive information associated with a target fluorescent response optionally from one or more apparatus 100 and/or 500 and/or devices 200, 300, and/or 400, optionally including, but not limited to, information relating to the wavelength, intensity, strength, directionality, and/or spatial extent of the fluorescent response. In illustrative embodiments, operational flow 700 may be employed in the process of target ablation to analyze information associated with a target fluorescent response to determine data associated with the location of a target and one or more characteristics of one or more energy source 110 and/or ablation energy 117 associated with at least partially ablating one or more target.

After a start operation, the operational flow 700 moves to a receiving operation 170, receiving a first input associated with a first possible dataset, the first possible dataset including data representative of one or more target fluorescent response. For example, a first input may include, but is not limited to, data representative of one or more wavelengths of excitation energy, direction, pulse time, timing, as well as detection wavelengths and timing. For example, a first input may include, but is not limited to, a condition, an illness, a cell and/or tissue type under investigation, and/or other disease and/or preventive medicine information An optional accessing operation 270 accesses the first possible dataset in response to the first input. For example, data representative of one or more fluorescent responses, one or more autofluorescent responses, and/or one or more target fluorescent responses may be accessed. For example, data representative of background fluorescence, fluorescent tags and/or markers, and/or limits of detection may be accessed.

An optional generating operation 370 generates the first possible dataset in response to the first input. For example, data representative of one or more target fluorescent response may be generated optionally by eliminating and/or controlling for endogenous non-target fluorescence and/or non-specific fluorescence. For example, data representative of emissions as a function of wavelength in relation to time and/or distance may be generated.

An optional determining operation 470 determines a graphical illustration of the first possible dataset. For example, data representative of one or more fluorescent responses, one or more autofluorescent responses, and/or one or more target fluorescent response may be graphically represented. For example, data representative of possible results associated with (and/or corresponding to) one or more possible ablation parameters, optionally including use of particle beam and/or electromagnetic energy for target ablation, optionally in relation to other non-target areas and/or the likelihood of collateral damage may be graphically represented.

An optional determining operation 570 determining data representative of a location of one or more target area at least partially based on the first possible dataset. For example, data representative of a location of one or more target area may include, but is not limited to, direction, spatial extent, environment, and/or depth, optionally in relation to one or more excitation energy source 116, one or more targeting energy source 118, and/or one or more ablation energy source 117.

An optional sending operation 670 sends the first output associated with the first possible dataset optionally to the first energy source, optionally the ablation energy source 117. For example, data representative of one or more target fluorescent response, one or more characteristics of ablation energy 117, and/or one or more targeting parameters may be sent as part of the first output.

An optional determining operation 770 determines data representative of one or more characteristics of excitation energy 116 for inducing the target fluorescent response. For example, data representative of one or more characteristics of excitation energy 116, optionally including, but not limited to, wavelength, strength, mode, directionality, and/or spatial limitations may be determined.

An optional determining operation 870 determines data representative of one or more characteristics of ablation energy 117 for at least partially ablating a target. For example, data representative of one or more characteristics of ablation energy 117, optionally including, but not limited to, wavelength, strength, mode, directionality, and/or spatial limitations may be determined.

An optional operation 970 includes an optional receiving operation 972 and an optional determining operation 974. The optional receiving operation 972 receives a second input associated with a second possible dataset, the second possible dataset including data representative of a second target fluorescent response following the at least partial ablation of the target. The optional determining operation 974 determines data representative of one or more characteristics of ablation energy 117 for further ablating a target at least partially based on the second possible dataset. For example, data representative of a second target fluorescent response may include one or more characteristics different from the first, previous and/or original target fluorescent response, optionally as a result of the at least partial ablation of the target. For example, the one or more characteristics may include, but are not limited to, presence, absence and/or extent of reduction in the target fluorescent response.

An optional operation 1070 includes an optional receiving operation 1072 and an optional determining operation 1074. The optional receiving operation 1072 receives a third input associated with a third possible dataset, the third possible dataset including data representative of a fluorescent response. The optional determining operation 1074 determines data representative of one or more characteristics of excitation energy 116 for inducing a target fluorescent response at least partially based on the third possible dataset. For example, data representative of a fluorescent response may indicate the presence, absence, or extent of reduction of a target fluorescent response.

Then, a providing operation 1170, provides a first output to a first energy source in real time, the first output providing data representative of one or more ablation characteristics for at least partially ablating the target area. For example, data representative of one or more characteristics of ablation energy 117, one or more characteristics of the excitation energy 116, one or more characteristics of the fluorescent response, one or more environmental parameters, and/or one or more targeting parameters.

Figure 12:
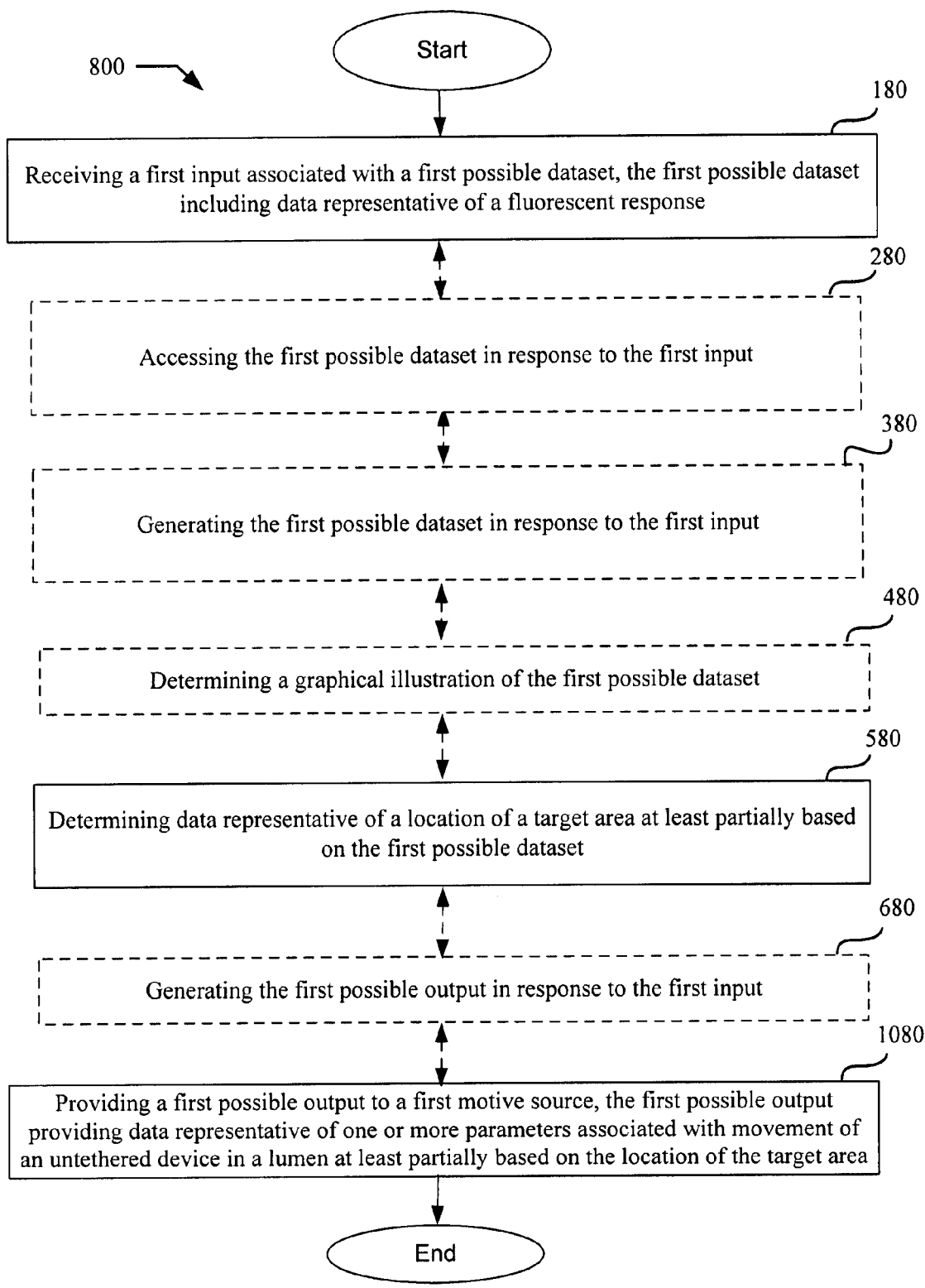

FIG. 12 and/or FIG. 13 depict embodiments of an operational flow 800 representing illustrative embodiments of operations related to providing a first possible output to a first motive source, the first possible output providing data representative of one or more parameters associated with movement of an untethered device in a lumen at least partially based on the location of the target area. In FIG. 12 and/or FIG. 13, discussion and explanation may be provided with respect to one or more device 200 and/or 300 and methods described herein, and/or with respect to other examples and contexts.

In some embodiments, one or more methods include receiving a first input associated with a first possible dataset, the first possible dataset including data representative of a fluorescent response; determining data representative of a location of a target area at least partially based on the first possible dataset; and providing a first possible output to a first motive source, the first possible output providing data representative of one or more parameters associated with movement of an untethered device in a lumen at least partially based on the location of the target area.

In illustrative embodiments, operational flow 800 may be employed in the process of moving an untethered device in a lumen, optionally associated with target ablation, to receive information associated with a fluorescent response optionally from one or more devices 200 and/or 300, optionally including, but not limited to, information relating to the wavelength, intensity, strength, directionality, and/or spatial extent of the fluorescent response. In illustrative embodiments, operational flow 800 may be employed in the process of moving an untethered device in a lumen to analyze information associated with a target fluorescent response to determine data associated with the location of a target and one or more characteristics of one or more power source 140 and/or motive force, optionally associated with at least partially ablating one or more target.

After a start operation, the operational flow 800 moves to a receiving operation 180, receiving a first input associated with a first possible dataset, the first possible dataset including data representative of one or more fluorescent response. For example, data representative of one or more fluorescent response may include, but is not limited to, data representative of a target fluorescent response, a non-target fluorescent response, and/or a autofluorescent response. For example, a first input may include, but is not limited to, one or more characteristics of excitation energy, one or more characteristics of targeting energy, and/or one or more characteristics of ablation energy.

An optional accessing operation 280 accesses the first possible dataset in response to the first input. For example, data representative of one or more fluorescent responses, optionally data representative of one or more target fluorescent response and/or one or more autofluorescent response, may be accessed. For example, data representative of the presence and/or absence of a target fluorescent response and/or presence or absence of other non-target fluorescent responses may be accessed.

An optional generating operation 380 generates the first possible dataset in response to the first input. For example, data representative of one or more target fluorescent response may be generated optionally based on calculations associated with background fluorescent, signal to noise ratios, non-specific fluorescence, and/or endogenous non-target autofluoresce. For example, data representative of a location of a target area determined at least partially based on the fluorescent response may also be generated.

An optional determining operation 480 determines a graphical illustration of the first possible dataset. For example, data representative of one or more target fluorescent response may be graphically represented. For example, data representative of a location of one or more target area optionally in relation to the current device location may be graphically represented. For example, data representative of one or more parameters associated with the movement of the untethered device associated with target ablation and/or target detection may be determined and/or generated.

A determining operation 580 determines data representative of a location of one or more target area at least partially based on the first possible dataset. For example, data representative of a location of one or more target area may include, but is not limited to, direction, spatial extent, environment, and/or depth, optionally in relation to one or more excitation energy source 116, one or more targeting energy source 118, and/or one or more ablation energy source 117. For example, data representative of a location of one or more target area may include, but is not limited to, one or more characteristics associated with movement of an untethered device for target ablation and/or target detection.

An optional generating operation 680 generates the first possible output in response to the first input. For example, a first possible output may include data representative of a location of one or more target area at least partially based on the first possible dataset. For example, a first possible output may include, but is not limited to, data representative of a direction of movement, a rate of movement, a speed of movement, a time of movement, a mechanism of movement, and/or a power source.

An optional sending operation 780 sends the first output associated with the first possible dataset optionally to a motive source 150 and/or a power source 140. For example, data representative of a direction of movement, a rate of movement, a speed of movement, a time of movement, a mechanism of movement, and/or a power source may be sent as part of the first output.

An optional determining operation 880 determines data representative of one or more characteristics of excitation energy 116 for inducing the fluorescent response. For example, data representative of one or more characteristics of excitation energy 116, optionally including, but not limited to, wavelength, strength, mode, directionality, and/or spatial limitations may be determined.

An optional determining operation 980 determines data representative of one or more characteristics of ablation energy 117 for at least partially ablating a target. For example, data representative of one or more characteristics of ablation energy 117, optionally including, but not limited to, wavelength, strength, mode, directionality, and/or spatial limitations may be determined.

Then, a providing operation 1080, provides a first possible output to a first motive source, the first possible output providing data representative of one or more parameters associated with movement of an untethered device in a lumen at least partially based on the location of the target area. For example, data representative of one or more characteristics of ablation energy 117, one or more characteristics of the excitation energy 116, one or more characteristics of the fluorescent response, one or more environmental parameters, and/or one or more targeting parameters.

The following include illustrative embodiments of one or more operations of operational flow 600, operational flow 700 and/or operational flow 800.

In illustrative embodiments, a target fluorescent response is optionally an auto-fluorescent response and/or elicited from one or more extrinsically provided markers.

In illustrative embodiments, a first input is from a sensor configured to detect one or more of a target fluorescent response, a fluorescent response, and/or an autofluorescent response. In illustrative embodiments, a first input is from one or more external sources, optionally remotely, programmably, and/or wirelessly received. The one or more external sources may include, but are not limited to, sensors, control circuitry, databases, and/or user interfaces.

In illustrative embodiments, a first input includes data representative of one or more measurements of electromagnetic energy. One or more measurements of electromagnetic energy optionally include, but are not limited to, one or more measurements of one or more wavelengths of the electromagnetic energy and/or measurements of an extended-spectrum of the electromagnetic energy. One or more measurements of electromagnetic energy optionally include, but are not limited to, measurements over a cumulative time interval and/or time dependent electromagnetic energy measurements. One or more time dependent measurements may include, but are not limited to, measurements at one or more times and/or measurements at one or more time intervals following excitation of a fluorescent response. One or more measurements of electromagnetic energy optionally include, but are not limited to, one or more measurements of the location of the source and/or incidence of electromagnetic energy (e.g. a fluorescent response, excitation energy 116, ablation energy 117, and/or targeting energy 118). One or more measurements of the location of the source and/or incidence of electromagnetic energy include, but are not limited to, one or more measurements of a direction of incidence electromagnetic energy, and/or one or more measurements of a tissue depth of incidence electromagnetic energy. One or more measurements of electromagnetic energy optionally include, but are not limited to, one or more measurements of a strength of the electromagnetic energy.

In illustrative embodiments, a first input includes dara representative of one or more characteristics of one or more targets and/or one or more diseases and/or disorders. In illustrative embodiments, a first input includes data representative of the target fluorescent response. Data representative of the target fluorescent response may include, but is not limited to, one or more measurements of electromagnetic energy, and/or one or more measurements of one or more temporal-spatial locations of the target fluorescent response. As used herein, the term "temporal-spatial locations" may include one or more temporal locations and/or one or more spatial locations. Data representative of a target fluorescent response may include, but is not limited to, a clustering of fluorescent responses that would otherwise be considered a normal response in the absence of clustering, or with limited clustering, or non-significant clustering. In illustrative embodiments, clustering might include cells forming a plaque, bacterial cells forming a colony, blood cells forming a clot, malaria-infected red blood cells aggregating, among others.

In illustrative embodiments, a first possible dataset includes data representative of one or more fluorescence characteristics of one or more possible constituents of the target area. As used herein, the term "constituents" may include, but is not limited to, cells, tissues, lumen, proteins, plaques, membranes, pathogens, microorganisms, and/or parasites, among others.

In illustrative embodiments, a first possible dataset includes data representative of one or more numerical measurements for one or more possible constituents of the target area. One or more numerical measurements may include, but are not limited to, one or more numerical measurements for normal levels of one or more possible constituents of the target area and/or for abnormal levels of one or more possible constituents of the target area.

In illustrative embodiments, a first possible dataset includes data representative of excitation energy 116. Data representative of excitation energy 116 includes, but is not limited to, data representative of one or more characteristics of excitation energy 116. Data representative of one or more characteristics of excitation energy 116 include, but are not limited to, strength of the excitation energy, one or more wavelengths of the excitation energy, one or more spatial parameters of the excitation energy, and/or one or more directional parameters of the excitation energy. One or more spatial parameters of the excitation energy include, but are not limited to, one or more spatial limitations of the excitation energy, optionally including, but not limited to, spatially focused and spatially collimated. One or more directional parameters of the excitation energy include, but are not limited to, directionally limited, directionally varied and directionally variable.

One or more characteristics of the excitation energy include, but are not limited to, manual, programmable, automatic, remote-controlled, and feedback-control. In illustrative embodiments, for example, subsequent excitation energy characteristics may be determined based on one or more characteristics of the fluorescent emissions associated with the characteristics of the previous excitation energy selected. For example, if the previous excitation energy induced a fluorescent response with high background and/or non-specific emissions, or without a target signal, a different excitation energy might be selected. In illustrative embodiments, for example, excitation energy may be at least partially determined by the location, and/or as a result of a prior ablation.

In illustrative embodiments, a first possible dataset includes data representative of ablation energy 117. Data representative of ablation energy 117 optionally includes, but is not limited to data representative of one or more characteristics of the ablation energy 117. One or more characteristics of the ablation energy include, but are not limited to, strength of the ablation energy, one or more wavelengths of the ablation energy, one or more spatial parameters of the ablation energy, and/or one or more directional parameters of the ablation energy. One or more spatial parameters of the ablation energy include, but are not limited to, one or more spatial limitations of the ablation energy, optionally including, but not limited to, spatially focused and spatially collimated. One or more directional parameters of the ablation energy include, but are not limited to, directionally limited, directionally varied and directionally variable.

One or more characteristics of the ablation energy include, but are not limited to, manual, programmable, automatic, remote-controlled, and feedback-controlled. One or more characteristics of the ablation energy include, but are not limited to, the minimum energy associated with at least partially ablating one or more target areas and/or one or more non-target areas. One or more characteristics of the ablation energy include, but are not limited to, the one or more characteristics of the optimum energy associated with at least partially ablating one or more target areas while minimizing and/or reducing the ablation of one or more non-target areas (e.g. reducing collateral damage). In illustrative embodiments, one or more characteristics of ablation energy may be determined based on detection of only partial ablation from a prior ablation.

In some embodiments, ablation energy 117 is one or more of charged particles (e.g. from a particle beam) 112 or electromagnetic energy 111. In some embodiments, particle beam energy 112 may include, but is not limited to, electrons, protons, alpha particles, beta particles and/or gamma particles. In some embodiments, electromagnetic energy 111 may include, but is not limited to, optical energy 113 and/or X-ray 115 energy. In some embodiments, ablation energy 117 is pulsed energy.

In illustrative embodiments of a receiving operation 160, 170, and/or 180, receiving a first input associated with a first possible dataset includes, but is not limited to, receiving a first data entry associated with the first possible dataset. In illustrative embodiments, a first data entry may include, but is not limited to, one or more measurements of energy (optionally electromagnetic energy) and/or one or more measurements of one or more temporal-spatial locations of a fluorescent response (e.g. a target fluorescent response). In illustrative embodiments, a first data entry may include, but is not limited to, data representative of one or more characteristics of one or more targets, one or more diseases, and/or one or more disorders.

In illustrative embodiments of a receiving operation 160, 170, and/or 180, receiving a first input associated with a first possible dataset includes, but is not limited to, receiving a first data entry from a sensor, from a database, and/or from a user interface (e.g. from at least one submission element of a graphical user interface).

In illustrative embodiments of a receiving operation 160, 170, and/or 180, receiving a first input associated with a first possible dataset includes, but is not limited to, receiving a first data entry at least partially identifying one or more elements of the first possible dataset. In illustrative embodiments, one or more elements of the first possible dataset include one or more of one or more measurements of electromagnetic energy, one or more measurements of one or more temporal-spatial locations of a target fluorescent response, data representative of excitation energy, and/or data representative of ablation energy 117.

In illustrative embodiments of a receiving operation 160, 170, and/or 180, receiving a first input associated with a first possible dataset includes, but is not limited to, receiving a first request associated with the first possible dataset. In illustrative embodiments, the first request includes, but is not limited to, selecting and/or determining data representative of one or more measurements of electromagnetic energy, data representative of one or more measurements of one or more temporal-spatial locations of the target fluorescent response, and/or data representative of one or more characteristics of ablation energy.

In illustrative embodiments of a receiving operation 160, 170, and/or 180, receiving a first input associated with a first possible dataset includes, but is not limited to, receiving a first request from a user interface (e.g. at least one submission element of a graphical user interface). In illustrative embodiments, the first request at least partially identifies and/or selects one or more elements of the first possible dataset. In illustrative embodiments, the first request provides instructions identifying, specifying, and/or determining data representative of one or more elements of the first possible dataset.

In illustrative embodiments of an optional accessing operation 260, 270, and/or 280 accessing the first possible dataset in response to the first input includes, but is not limited to, accessing the first possible dataset using a database management system engine. In some embodiments, the database management system engine is configured to query a first database to retrieve the first possible dataset therefrom. In illustrative embodiments, accessing the first possible dataset in response to the first input includes, but is not limited to, accessing the first possible dataset by querying a first database to retrieve data representative of one or more characteristics of one or more targets associated with one or more diseases and/or disorders.

In illustrative embodiments of an optional accessing operation 260, 270, and/or 280 accessing the first possible dataset in response to the first input includes, but is not limited to, accessing the first possible dataset from within a first database associated with a plurality of measurements of electromagnetic energy, a plurality of measurements of one or more temporal-spatial locations of the target fluorescent response, and/or a plurality of characteristics of ablation energy.

In illustrative embodiments of an optional accessing operation 260, 270, and/or 280 accessing the first possible dataset in response to the first input includes, but is not limited to, accessing the first possible dataset by associating data representative of one or more measurements of electromagnetic energy, data representative of one or more temporal-spatial locations of the target fluorescent response, and/or data representative of one or more characteristics of ablation energy with one or more elements of the first possible dataset.

In illustrative embodiments of an accessing operation 260, 270, and/or 280 accessing the first possible dataset in response to the first input includes, but is not limited to, accessing the first possible dataset by corresponding data representative of one or more measurements of electromagnetic energy, data representative of one or more temporal-spatial locations of the target fluorescent response, and/or data representative of one or more characteristics of ablation energy with one or more elements of the first possible dataset.

In illustrative embodiments of an accessing operation 260, 270, and/or 280 accessing the first possible dataset in response to the first input includes, but is not limited to, accessing the first possible dataset as being associated with data representative one or more measurements of electromagnetic energy, data representative of one or more measurements of one or more temporal-spatial locations of the target fluorescent response, and/or data representative of one or more characteristics of ablation energy.

In illustrative embodiments of an optional generating operation 360, 370, and/or 380, generating the first possible dataset in response to the first input includes, but is not limited to, generating the first possible dataset using a database management system engine. In illustrative embodiments, generating the first possible dataset in response to the first input includes, but is not limited to, generating the first possible dataset using a database management system engine to retrieve data representative of one or more characteristics of one or more targets associated with one or more diseases and/or disorders.

In illustrative embodiments of an optional generating operation 360, 370, and/or 380, generating the first possible dataset in response to the first input includes, but is not limited to, generating the first possible dataset by corresponding and/or associating data representative of one or more measurements of electromagnetic energy, data representative of one or more measurements of temporal-spatial locations of the target fluorescent response, and/or data representative of one or more characteristics of ablation energy with one or more elements of the first possible dataset.

In illustrative embodiments of an optional generating operation 360, 370, and/or 380, generating the first possible dataset in response to the first input includes, but is not limited to, receiving a first request associated with the first possible dataset; and generating the first possible dataset in response to the first request, the first request specifying data representative of one or more measurements of electromagnetic energy, data representative of one or more measurements of one or more temporal-spatial locations of the target fluorescent response and/or data representative of one or more characteristics of ablation energy. In illustrative embodiments, the first request specifies one or more characteristics of one or more targets.

In illustrative embodiments of an optional generating operation 360, 370, and/or 380, generating the first possible dataset in response to the first input includes, but is not limited to, receiving a first request, the first request specifying data representative of one or more measurements of electromagnetic energy; and generating the first possible dataset in response to the first request at least partially by performing an analysis of data representative of one or more measurements of one or more temporal-spatial locations of the target fluorescent response.

In illustrative embodiments of an optional generating operation 360, 370, and/or 380, generating the first possible dataset in response to the first input includes, but is not limited to, receiving a first request, the first request specifying data representative of one or more measurements of one or more temporal-spatial locations of the target fluorescent response; and generating the first possible dataset in response to the first request at least partially by performing an analysis of data representative of one or more measurements of electromagnetic energy.

In illustrative embodiments of an optional generating operation 360, 370, and/or 380, generating the first possible dataset in response to the first input includes, but is not limited to, receiving a first request, the first request specifying data representative of one or more characteristics of ablation energy; and generating the first possible dataset in response to the first request at least partially by performing an analysis of data representative of one or more measurements of electromagnetic energy.

In illustrative embodiments of an optional generating operation 360, 370, and/or 380, generating the first possible dataset in response to the first input includes, but is not limited to, receiving a first request, the first request specifying data representative of one or more characteristics of ablation energy; and generating the first possible dataset in response to the first request at least partially by performing an analysis of data representative one or more measurements of one or more temporal-spatial locations of the target fluorescent response.

In illustrative embodiments of an optional determining operation 460, 470, and/or 480, determining a graphical illustration of the first possible dataset includes, but is not limited to, determining the graphical illustration of the first possible dataset for inclusion in a display element of a graphical user interface. In illustrative embodiments, determining a graphical illustration of the first possible dataset includes, but is not limited to, determining a graphical illustration of data representative of one or more characteristics of one or more targets associated with one or more diseases and/or disorders.

In illustrative embodiments of an optional determining operation 460, 470, and/or 480, determining a graphical illustration of the first possible dataset includes, but is not limited to, performing an analysis of one or more elements of the first possible dataset to determine the location of the target area; and determining the graphical illustration based on the analysis.

In illustrative embodiments of an optional determining operation 460, 470, and/or 480, determining a graphical illustration of the first possible dataset includes, but is not limited to, performing an analysis of one or more elements of the first possible dataset to determine the location of the target area; and determining the graphical illustration including data representative of one or more measurements of electromagnetic energy, data representative of one or more measurements of one or more temporal-spatial locations of the target fluorescent response, and/or data representative of one or more characteristics of ablation energy in association with a visual indicator related to the location of the target area.

In illustrative embodiments of an optional determining operation 460, 470, and/or 480, determining a graphical illustration of the first possible dataset includes, but is not limited to, performing an analysis of one or more elements of the first possible dataset to determine a first possible outcome; and determining the graphical illustration based on the analysis. In illustrative embodiments, the first possible outcome optionally includes, but is not limited to, one or more of a possible risk, a possible result, or a possible consequence.

In illustrative embodiments of an optional determining operation 460, 470, and/or 480, determining a graphical illustration of the first possible dataset includes, but is not limited to, performing an analysis of one or more elements of the first possible dataset to determine a first possible outcome; and determining the graphical illustration including data representative of one or more measurements of electromagnetic energy, data representative of one or more measurements of one or more temporal-spatial locations of the target fluorescent response, and/or data representative of one or more characteristics of ablation energy in association with a visual indicator related to the first possible outcome.

In illustrative embodiments of an optional determining operation 460, 470, and/or 480, determining a graphical illustration of the first possible dataset includes, but is not limited to, determining a correlation between a first possible outcome and a type or characteristic of a visual indicator used in the graphical illustration to represent the first possible outcome.

In illustrative embodiments of an optional determining operation 460, 470, and/or 480, determining a graphical illustration of the first possible dataset includes, but is not limited to, determining the graphical illustration of a first possible outcome based on use of ablation energy having one or more characteristics. A first possible outcome may include, but is not limited to, partial ablation, complete ablation, non-target partial ablation, and/or non-target complete ablation, among others.

In illustrative embodiments of a determining operation 570 and/or 580, determining data representative of a location of a target area at least partially based on the first possible dataset includes, but is not limited to, determining data representative of the location of the target area at least partially based on the first possible dataset, the first possible dataset including one or more measurements of electromagnetic energy, and/or one or more measurements of the target fluorescent response. In illustrative embodiments, determining data representative of a location of a target area at least partially based on the first possible dataset includes, but is not limited to, determining data representative of one or more characteristics of one or more targets associated with one or more diseases and/or disorders.

In illustrative embodiments of a determining operation 570 and/or 580, determining data representative of a location of a target area at least partially based on the first possible dataset includes, but is not limited to, performing an analysis of one or more elements of the first possible dataset; and determining data representative of the location of the target area at least partially based on the analysis. In illustrative embodiments, analysis of the first possible dataset my include a determination of coordinates for ablation, and/or a determination that one or more target locations are not within range of ablation energy, and/or a determination that ablation of one or more targets has a possibility of causing non-target damage.

In illustrative embodiments of a determining operation 570 and/or 580, determining data representative of a location of a target area at least partially based on the first possible dataset includes, but is not limited to, performing an analysis of one or more elements of the first possible dataset and at least one additional instruction; and determining data representative of the location of the target area at least partially based on the analysis.

In illustrative embodiments of an optional generating operation 680, generating the first possible output in response to the first input includes, but is not limited to, generating the first possible output at least partially based on information associated with the location of a target and movement of an untethered device associated with ablation. In illustrative embodiments, one or more target is identified, optionally in a location too distant and/or obstructed for ablation and one or more parameters associated with movement of the untethered device to a location optionally to facilitate ablation are generated. In illustrative embodiments, no targets are identified in a particular location and one or more parameters associated with movement of the untethered device to another location optionally to facilitate further screening are generated.

In illustrative embodiments of an optional sending operation 560, 670, and/or 780, sending a first output associated with the first possible dataset includes, but is not limited to, sending a first output to one or more of a motive source 150, a power source 140, and/or an energy source 110, optionally an excitation energy source 116 and/or an ablation energy source 117. In some embodiments, sending a first output associated with the first possible dataset includes, but is not limited to, sending a first output to one or more external sources, optionally to one or more control circuitry 130, optionally in an external and/or remote location, that optionally provide a graphical illustration of the output, and/or that provide analysis and feedback at least partially based on the output.

In illustrative embodiments of an optional determining operation 660, 770, and/or 880, determining data representative of one or more characteristics of excitation energy 116 for inducing the target fluorescent response includes, but is not limited to, determining one or more characteristics of excitation energy 116 based at least partially on one or more of, but not limited to, the location of the lesion, the lumen, and/or the internal location, the environmental characteristics of the location, the distance, depth of tissue, and putative target, as well as the characteristics of the expected surrounding constituents.

In illustrative embodiments, one or more characteristics of the excitation energy 116 include, but are not limited to, one or more of strength of the excitation energy, wavelengths of the excitation energy, spatial parameters of the excitation energy, and/or directional parameters of the excitation energy. In some embodiments, one or more spatial parameters of the excitation energy include, but are not limited to, one or more spatial limitations of the excitation energy and/or a depth of focus of the excitation energy. In some embodiments, one or more spatial limitations include, but are not limited to, spatially focused and spatially collimated. In some embodiments, one or more characteristics of the depth of focus of the excitation energy includes, but are not limited to, a depth of focus is below a surface of a lesion, beyond a surface of a wall of a lumen, and/or beyond a surface of an internal location. In illustrative embodiments, a depth of focus is approximately 0.1 mm to 3 mm below a surface of a lesion, beyond a surface of a wall of a lumen, and/or beyond a surface of an internal location. In some embodiments, one or more directional parameters include, but are not limited to, directionally limited, directionally varied and directionally variable.

In illustrative embodiments, one or more characteristics of the excitation energy 116 include, but are not limited to, manual, programmable, automatic, remote-controlled, and feedback-controlled. In illustrative embodiments, a caregiver (physician, veterinarian, dentist, etc.) makes the final determination for ablation based on information determined by one or more program, and manually releases the programmably determined ablation energy.

In illustrative embodiments, excitation energy 116 is electromagnetic energy, optionally optical energy. In illustrative embodiments, excitation energy 116 is pulsed energy. In illustrative embodiments, excitation energy 116 is optionally single photon electromagnetic energy, two photon electromagnetic energy, multiple wavelength electromagnetic energy, and/or extended-spectrum electromagnetic energy. In some embodiments, two photon electromagnetic energy is coupled through a virtual energy level and/or through an intermediate energy level. In some embodiments, two photon electromagnetic energy is generated by two photons having the same wavelength or by two photons having a different wavelength.

In Illustrative embodiments of an optional determining operation 760, 870, and/or 980, determining data representative of one or more characteristics of ablation energy for at least partially ablating the target area includes, but is not limited to, assessing one or more characteristics of one or more constituents, assessing one or more characteristics of the target (e.g. location, size, depth, distance, etc.), and/or selecting one or more energy sources. In illustrative embodiments, the one or more characteristics of the ablation energy are selected to optimally ablate the target area while minimizing ablation outside the target area.

In illustrative embodiments, optional receiving and determining operations 860 and/or 970 include receiving a second input associated with a second possible dataset, the second possible dataset including data representative of a second target fluorescent response following at least partial ablation of the target area; and determining data representative of one or more characteristics of ablation energy for further ablating the target area at least partially based on the second possible dataset. In illustrative embodiments, excitation energy is optionally provided following at least partial ablation of one or more target optionally to determine the extent of ablation of target and/or non-target tissues and/or cells. Emission information detected by one or more sensor is optionally used to determine locations (optionally coordinates) for additional ablation, as necessary.

In illustrative embodiments, optional receiving and determining operations 960 and/or 1070 include receiving a third input associated with a third possible dataset, the third possible dataset including data representative of a fluorescent response; and determining data representative of one or more characteristics of excitation energy for inducing the target fluorescent response at least partially based on the third possible dataset. In illustrative embodiments, excitation energy of one or more characteristics may not elicit an identifiable and/or detectable target fluorescent response by the sensor. At least partially based on the lack of detection of a target fluorescent response (and the characteristics of the excitation energy released), characteristics of an additional excitation energy for release are selected, and optionally provided to the electromagnetic energy source 111, optionally one or more excitation energy source 116.

In illustrative embodiments of a providing operation 1060 and/or 1170, providing a first output to a first energy source in real time includes, but is not limited to, sending the first output to the first energy source in real time.

In illustrative embodiments of a providing operation 1060 and/or 1170, providing a first output to a first energy source in real time includes, but is not limited to, sending a first instruction associated with the first possible dataset to the first energy source. In illustrative embodiments, the first instruction contains data representative of one or more measurements of electromagnetic energy, data representative of one or more measurements of target fluorescent energy, data representative of one or more characteristics of ablation energy, data representative of one or more characteristics of targeting energy, and/or data representative of the location of the target area to be at least partially ablated.

In illustrative embodiments of a providing operation 1060 and/or 1170, providing a first output to a first energy source in real time includes, but is not limited to, sending the first output to the first targeting energy source in real time, the first output providing data representative of the one or more ablation characteristics for at least partially ablating the target area.

In illustrative embodiments, a first energy source 110 is an electromagnetic energy source 111, optionally an optical energy source 113 and/or an X-ray energy source 115. In some embodiments, the first energy source 110 is a laser. In illustrative embodiments, a first energy source 110 is a charged particle source 112 that optionally provides particles including, but not limited to, electrons, protons, alpha particles, beta particles, and/or gamma particles.

In illustrative embodiments, a first output includes data representative of one or more characteristics of ablation energy 117 for at least partially ablating the target area. In illustrative embodiments, ablation energy 117 is electromagnetic energy and/or charged particles. In illustrative embodiments, a first output includes targeting data for at least partially ablating the target area. In illustrative embodiments, a first output includes data representative of the location of the target area to be at least partially ablated.

In illustrative embodiments, a first targeting energy 118 has a different spatial irradiation extent than the first energy source 110. in some embodiments, the first targeting energy source provides electromagnetic targeting energy, optionally optical targeting energy, optionally visual targeting energy.

In illustrative embodiments of a providing operation 1080, providing a first output to a first motive source includes, but is not limited to, providing a first output to a first motive source in real time. In illustrative embodiments of a providing operation 1080, providing a first output to a first motive source includes, but is not limited to, sending the first output to the first motive source optionally in real time.

The following provides a description of illustrative computer program products 1200, 1300, and/or 1400 based on one or more of the operational flows 600, 700, and/or 800 and variations thereof as described above. These computer program products may also be executed in a variety of other contexts and environments, and or in modified versions of those described herein. In addition, although some of the computer program products are presented in sequence, the various instructions may be performed in various repetitions, concurrently, and/or in other orders than those that are illustrated. Although instructions for several computer program products are described separately herein, these instructions may be performed in sequence, in various repetitions, concurrently, and in a variety of orders not specifically illustrated herein. In addition, one or more of the instructions described for one or more computer program products may be added to another computer program product and/or used to replace one or more instructions in the computer program products, with or without deletion of one or more instructions of the computer program products.

Figure 15:
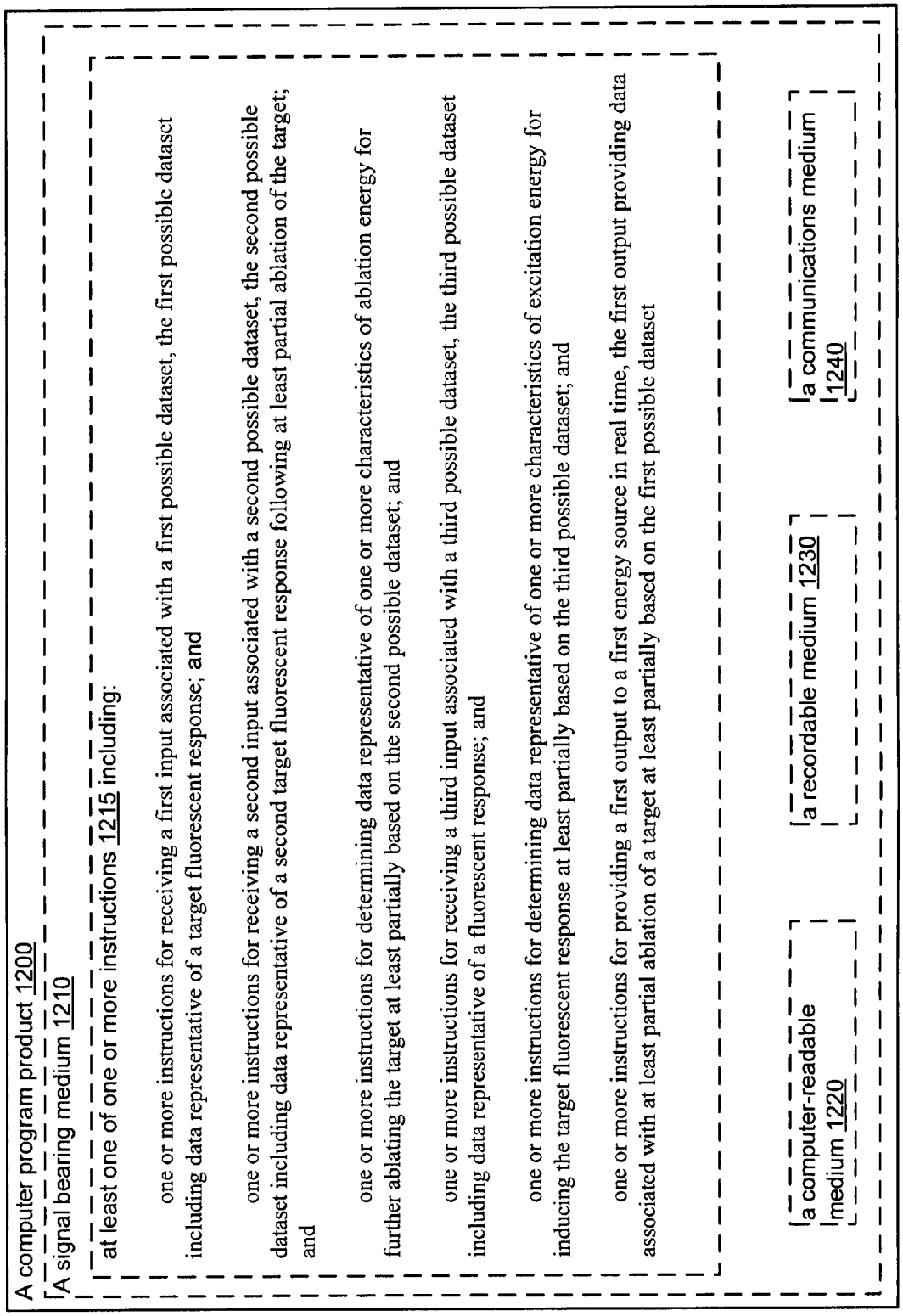

FIG. 14 and FIG. 15 show a schematic of a partial view of an illustrative computer program product 1200 that includes a computer program for executing a computer process on a computing device. An illustrative embodiment of the illustrative computer program product is provided using a signal bearing medium 1210, and may include at least one of one or more instructions 1215 including: one or more instructions for receiving a first input associated with a first possible dataset, the first possible dataset including data representative of a target fluorescent response; one or more instructions for accessing the first possible dataset in response to the first input; one or more instructions for generating the first possible dataset in response to the first input; one or more instructions for determining a graphical illustration of the first possible dataset; one or more instructions for sending the first output associated with the first possible dataset; one or more instructions for determining data representative of one or more characteristics of excitation energy for inducing the target fluorescent response; one or more instructions for determining data representative of one or more characteristics of ablation energy for at least partially ablating a target; one or more instructions for receiving a second input associated with a second possible dataset, the second possible dataset including data representative of a second target fluorescent response following at least partial ablation of a target; one or more instructions for determining data representative of one or more characteristics of ablation energy for further ablating a target at least partially based on the second possible dataset; one or more instructions for receiving a third input associated with a third possible dataset, the third possible dataset including data representative of a fluorescent response; one or more instructions for determining data representative of one or more characteristics of excitation energy for inducing the target fluorescent response at least partially based on the third possible dataset; one or more instructions for providing a first output to a first energy source in real time, the first output providing data associated with at least partial ablation of a target at least partially based on the first possible dataset. The one or more instructions may be, for example, computer executable and/or logic implemented instructions. In some embodiments, the signal bearing medium 1210 of the one or more computer program products 1200 include a computer-readable medium 1220, a recordable medium 1230, and/or a communications medium 1240.

Figure 16:
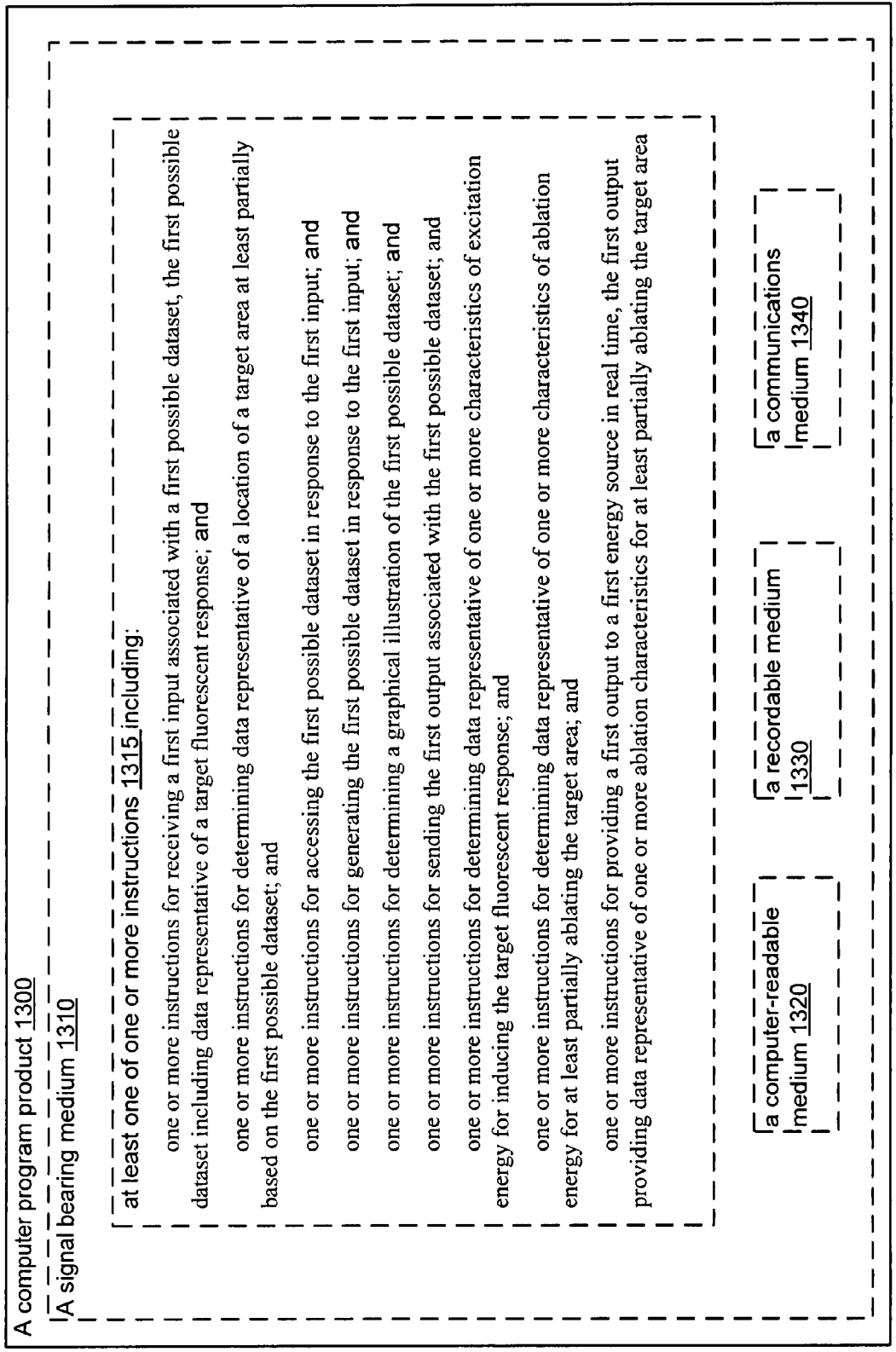
Figure 17:
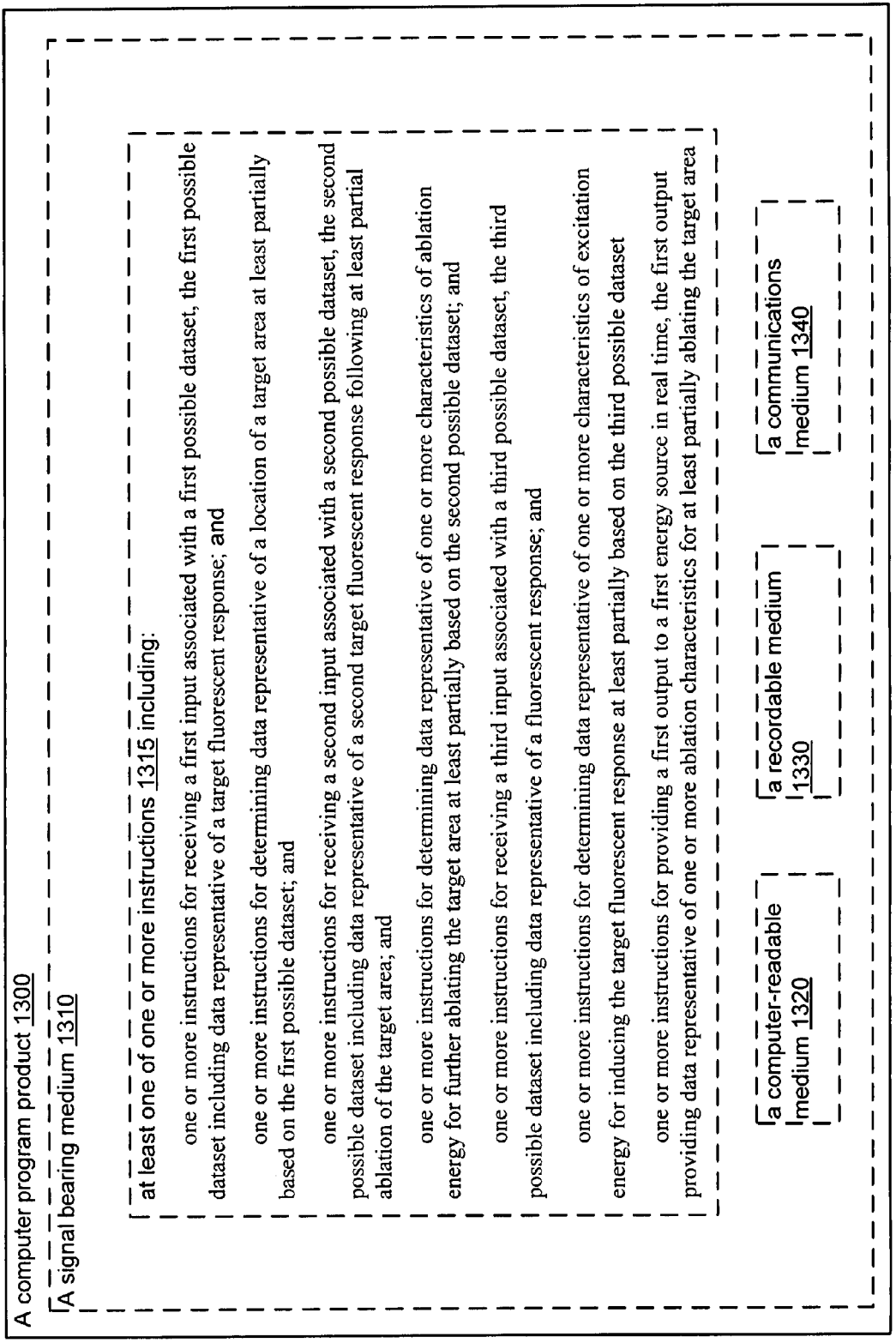

FIG. 16 and FIG. 17 show a schematic of a partial view of an illustrative computer program product 1300 that includes a computer program for executing a computer process on a computing device. An illustrative embodiment of the illustrative computer program product is provided using a signal bearing medium 1310, and may include at least one of one or more instructions 1315 including: one or more instructions for receiving a first input associated with a first possible dataset, the first possible dataset including data representative of a target fluorescent response; one or more instructions for accessing the first possible dataset in response to the first input; one or more instructions for generating the first possible dataset in response to the first input; one or more instructions for determining a graphical illustration of the first possible dataset; one or more instructions for determining data representative of a location of a target area at least partially based on the first possible dataset; one or more instructions for sending the first output associated with the first possible dataset; one or more instructions for determining data representative of one or more characteristics of excitation energy for inducing the target fluorescent response; one or more instructions for determining data representative of one or more characteristics of ablation energy for at least partially ablating a target; one or more instructions for receiving a second input associated with a second possible dataset, the second possible dataset including data representative of a second target fluorescent response following at least partial ablation of a target; one or more instructions for determining data representative of one or more characteristics of ablation energy for further ablating a target at least partially based on the second possible dataset; one or more instructions for receiving a third input associated with a third possible dataset, the third possible dataset including data representative of a fluorescent response; one or more instructions for determining data representative of one or more characteristics of excitation energy for inducing the target fluorescent response at least partially based on the third possible dataset; one or more instructions for providing a first output to a first energy source in real time, the first output providing data representative of one or more ablation characteristics for at least partially ablating the target area. The one or more instructions may be, for example, computer executable and/or logic implemented instructions. In some embodiments, the signal bearing medium 1310 of the one or more computer program products 1300 include a computer-readable medium 1320, a recordable medium 1330, and/or a communications medium 1340.

Figure 18:
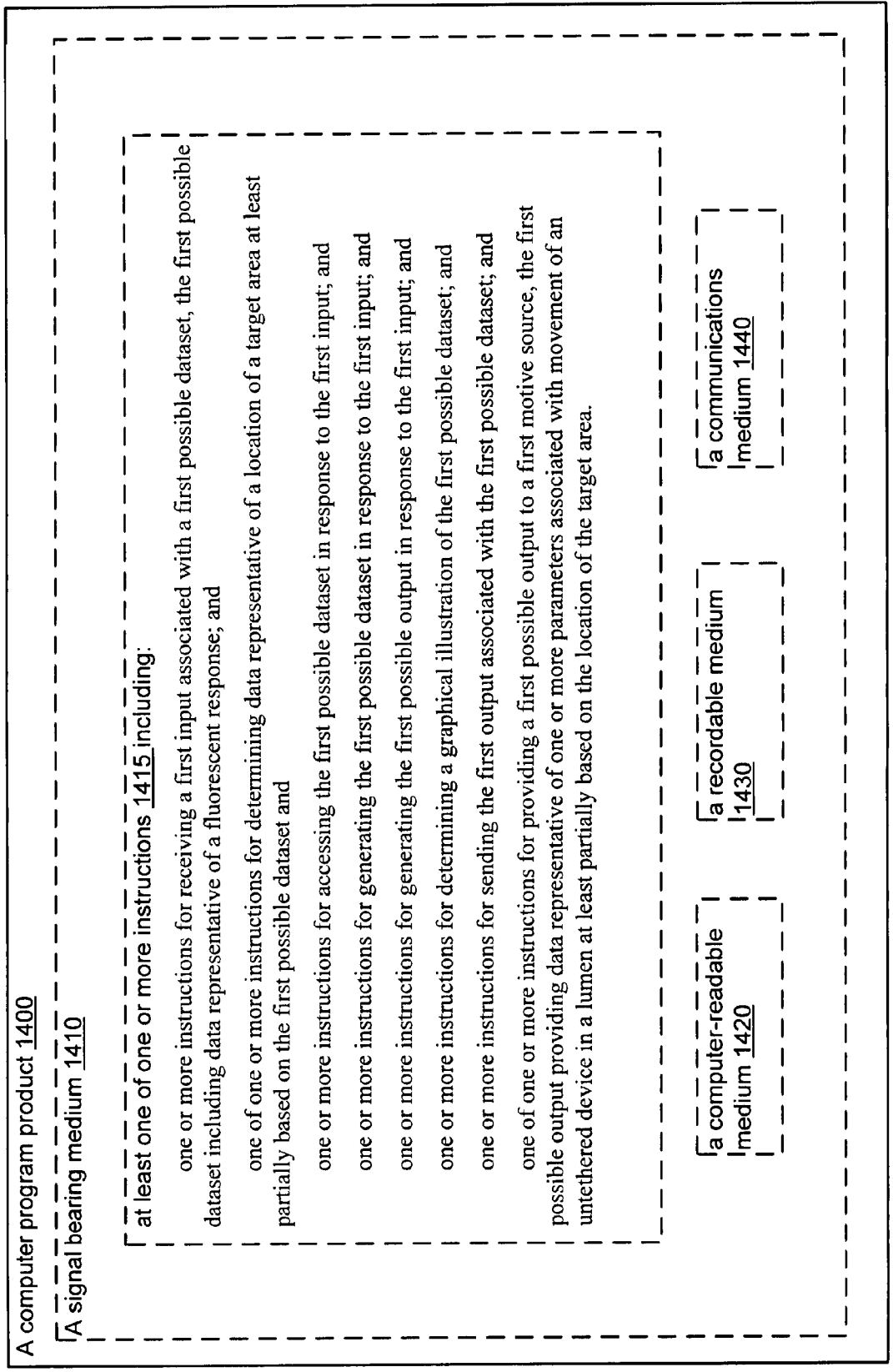
Figure 19:
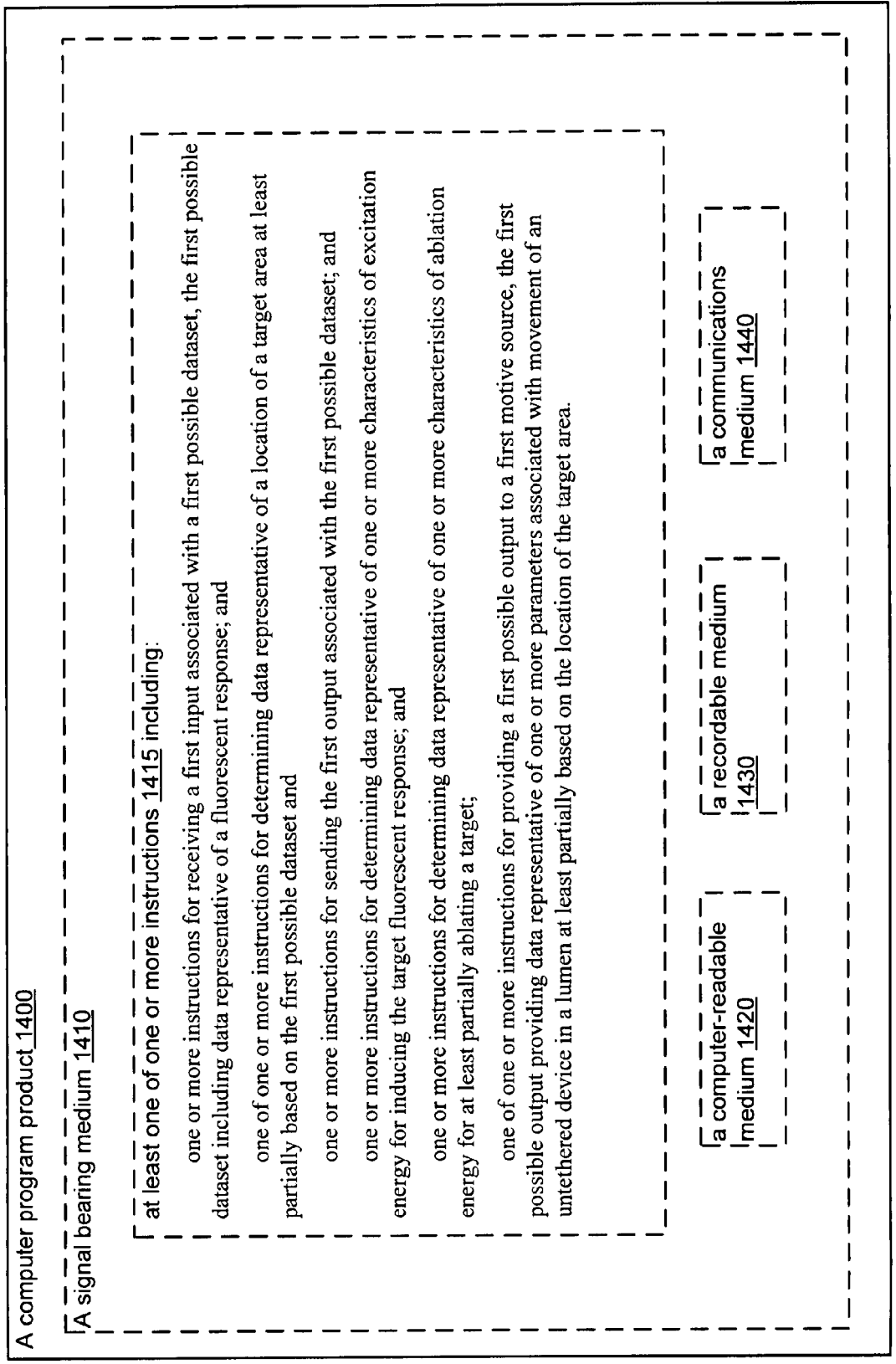

FIG. 18 and FIG. 19 show a schematic of a partial view of an illustrative computer program product 1400 that includes a computer program for executing a computer process on a computing device. An illustrative embodiment of the illustrative computer program product is provided using a signal bearing medium 1410, and may include at least one of one or more instructions 1415 including: one or more instructions for receiving a first input associated with a first possible dataset, the first possible dataset including data representative of a fluorescent response; one or more instructions for accessing the first possible dataset in response to the first input; one or more instructions for generating the first possible dataset in response to the first input; one or more instructions for determining a graphical illustration of the first possible dataset; one or more instructions for determining data representative of a location of a target area at least partially based on the first possible dataset; one or more instructions for generating the first possible output in response to the first input; one or more instructions for sending the first output associated with the first possible dataset; one or more instructions for determining data representative of one or more characteristics of excitation energy for inducing the target fluorescent response; one or more instructions for determining data representative of one or more characteristics of ablation energy for at least partially ablating a target; one or more instructions for providing a first possible output to a first motive source, the first possible output providing data representative of one or more parameters associated with movement of an untethered device in a lumen at least partially based on the location of the target area. The one or more instructions may be, for example, computer executable and/or logic implemented instructions. In some embodiments, the signal bearing medium 1410 of the one or more computer program products 1400 include a computer-readable medium 1420, a recordable medium 1430, and/or a communications medium 1440.

The following provides a description of illustrative systems based on one or more of the operational flows 600, 700, and/or 800 and/or computer program products 1200, 1300, and/or 1400 and/or variations thereof as described above. These systems may also be executed in a variety of other contexts and environments, and or in modified versions of those described herein.

Figure 20:
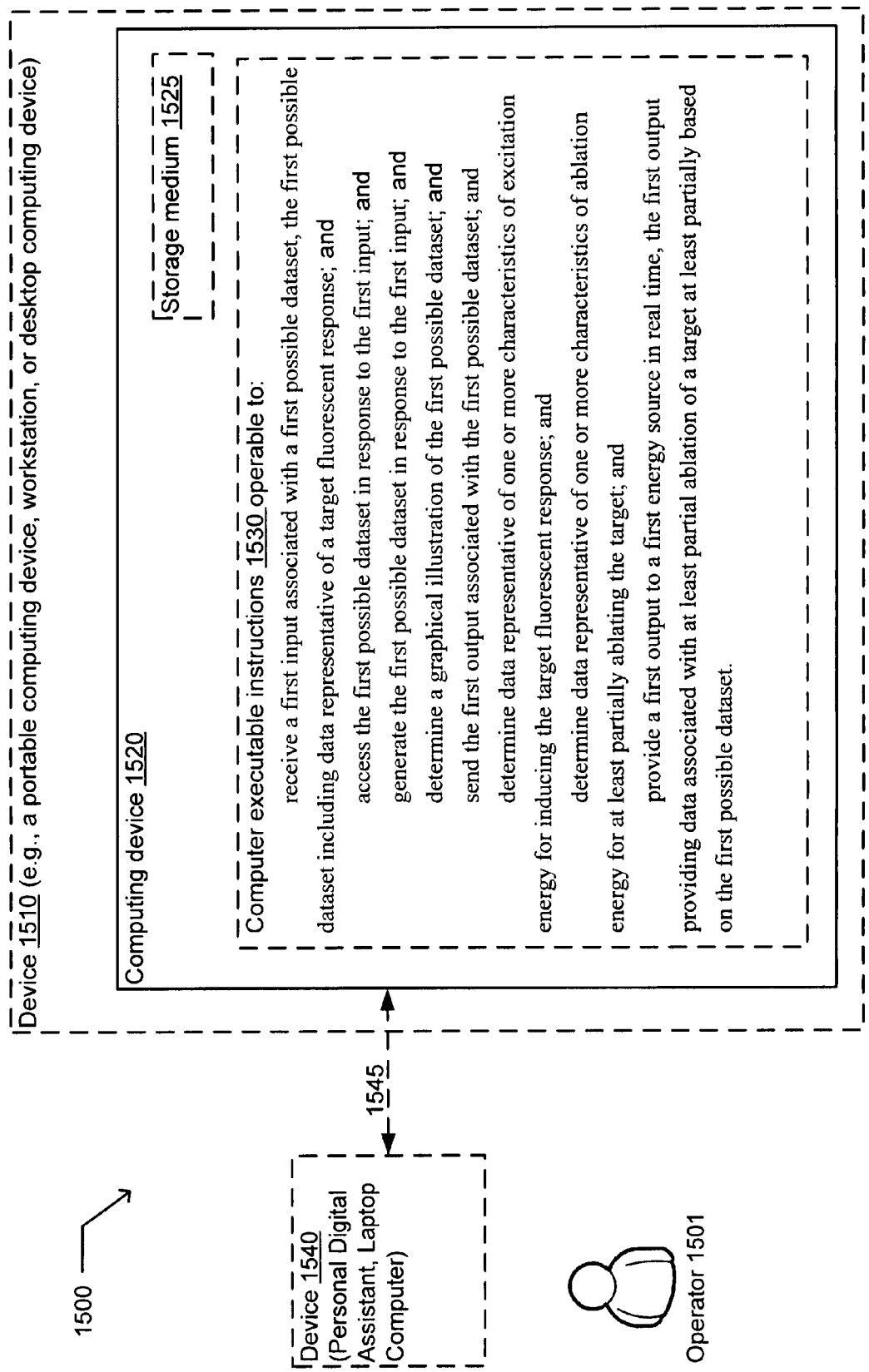
FIGS. 20-25 show an illustrative embodiment of a system in which embodiments may be implemented.
Figure 21:
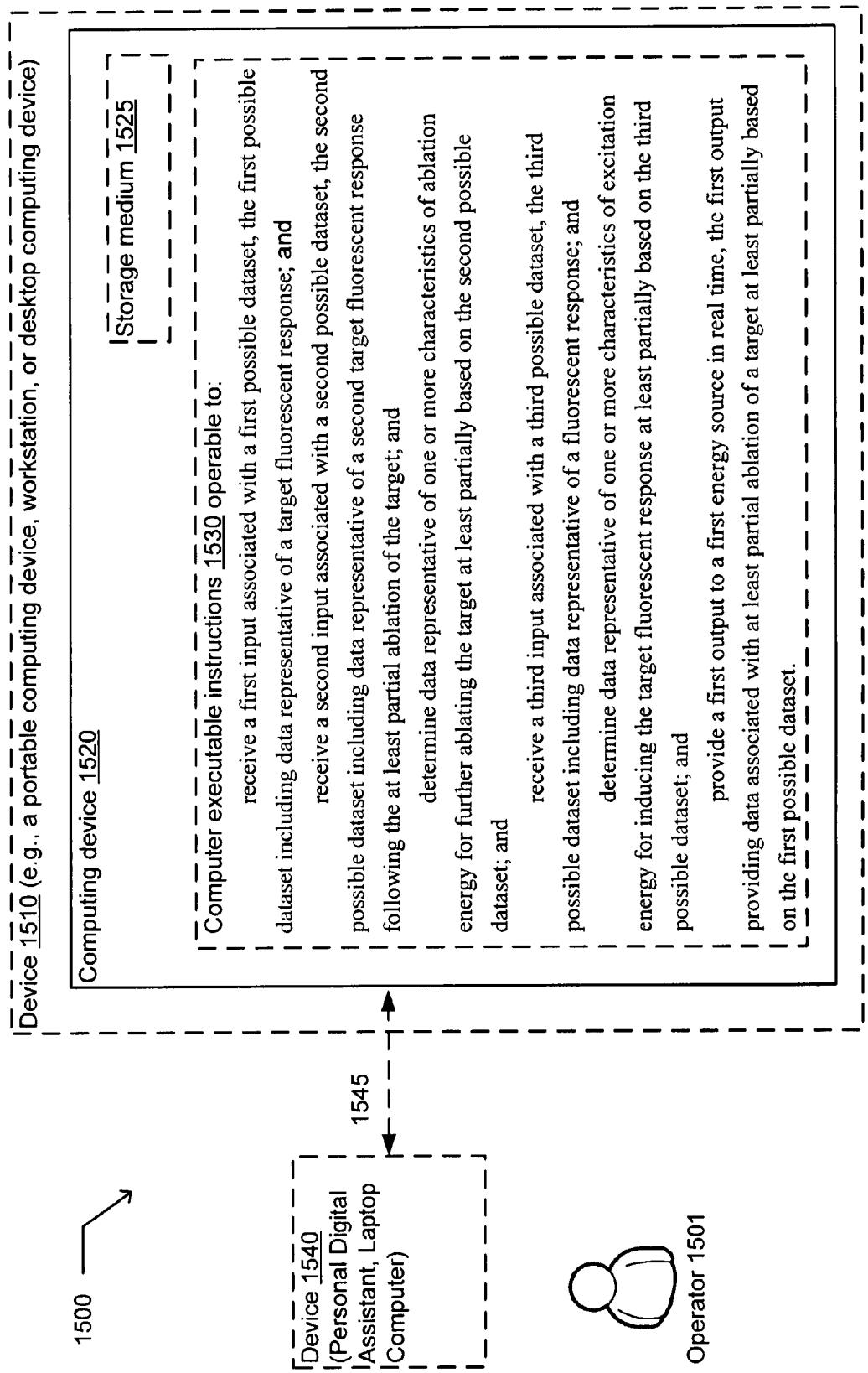

FIG. 20 and FIG. 21 show a schematic of an illustrative system 1500 in which embodiments may be implemented. In some embodiments, system 1500 may be the same as system 1600 and/or system 1700. In some embodiments, system 1500 may be different from system 1600 and/or system 1700. System 1500 may include a computing system environment 1510. System 1500 also illustrates an operator 1501 (e.g. a medical or veterinary professional, optionally a surgeon, a veterinarian, a nurse, a technician, etc.) using a device 1540 that is optionally shown as being in communication with a computing device 1520 by way of an optional coupling 1545. The optional coupling may represent a local, wide area, or peer-to-peer network, or may represent a bus that is internal to a computing device (e.g. in illustrative embodiments the computing device 1520 is contained in whole or in part within the device 1510, 1540, 200, 300, and/or 400 or within one or more apparatus 100 and/or 500, or one or more control circuitry 130). An optional storage medium 1525 may be any computer storage medium.

The computing device 1520 includes one or more computer executable instructions 1530 that when executed on the computing device 1520 cause the computing device 1520 receive a first input associated with a first possible dataset, the first possible dataset including data representative of a target fluorescent response; access the first possible dataset in response to the first input; generate the first possible dataset in response to the first input; determine a graphical illustration of the first possible dataset; send the first output associated with the first possible dataset; determine data representative of one or more characteristics of excitation energy for inducing the target fluorescent response; determine data representative of one or more characteristics of ablation energy for at least partially ablating a target; receive a second input associated with a second possible dataset, the second possible dataset including data representative of a second target fluorescent response following at least partial ablation of a target; determine data representative of one or more characteristics of ablation energy for further ablating a target at least partially based on the second possible dataset; receive a third input associated with a third possible dataset, the third possible dataset including data representative of a fluorescent response; determine data representative of one or more characteristics of excitation energy for inducing the target fluorescent response at least partially based on the third possible dataset; provide a first output to a first energy source in real time, the first output providing data associated with at least partial ablation of a target at least partially based on the first possible dataset. In some illustrative embodiments, the computing device 1520 may optionally be contained in whole or in part within one or more parts of an apparatus 100 and/or 500 and/or one or more devices 200, 300, and/or 400 (e.g. control circuitry 130 of one or more tethered and/or untethered, internal and/or external, movable and/or fixed apparatus and/or device), or may optionally be contained in whole or in part within the operator device 1540.

The system 1500 includes at least one computing device 1510, 1520, 1540 and/or control circuitry 130 on which the computer-executable instructions 1530 may be executed. For example, one or more of the computing devices 1510, 1520, 1540 and/or control circuitry 130 may execute the one or more computer executable instructions 1530 and output a result and/or receive information from the operator 1501, from other external sources, and/or from one or more sensor 120, on the same or a different computing device 1510, 1520, 1540, 1610, 1620, 1640, 1710, 1720, and/or 1740 and/or output a result and/or receive information from one or more apparatus 100 and/or 500 and/or one or more device 200, 300 and/or 400 in order to perform and/or implement one or more of the techniques, processes, or methods described herein, and/or other techniques.

The computing device 1510, 1520, and/or 1540 may include one or more of a desktop computer, a workstation computer, a computing system comprised a cluster of processors, a networked computer, a tablet personal computer, a laptop computer, or a personal digital assistant, or any other suitable computing unit. In some embodiments, any one of the one or more computing devices 1510, 1520, and/or 1540 and/or control circuitry 130 may be operable to communicate with a database to access the first possible dataset and/or subsequent datasets. In some embodiments, the computing device 1510, 1520, and/or 1540 is operable to communicate with the one or more apparatus 100 and/or 500 and/or device 200, 300, and/or 400 (e.g. control circuitry 130).

Figure 22:
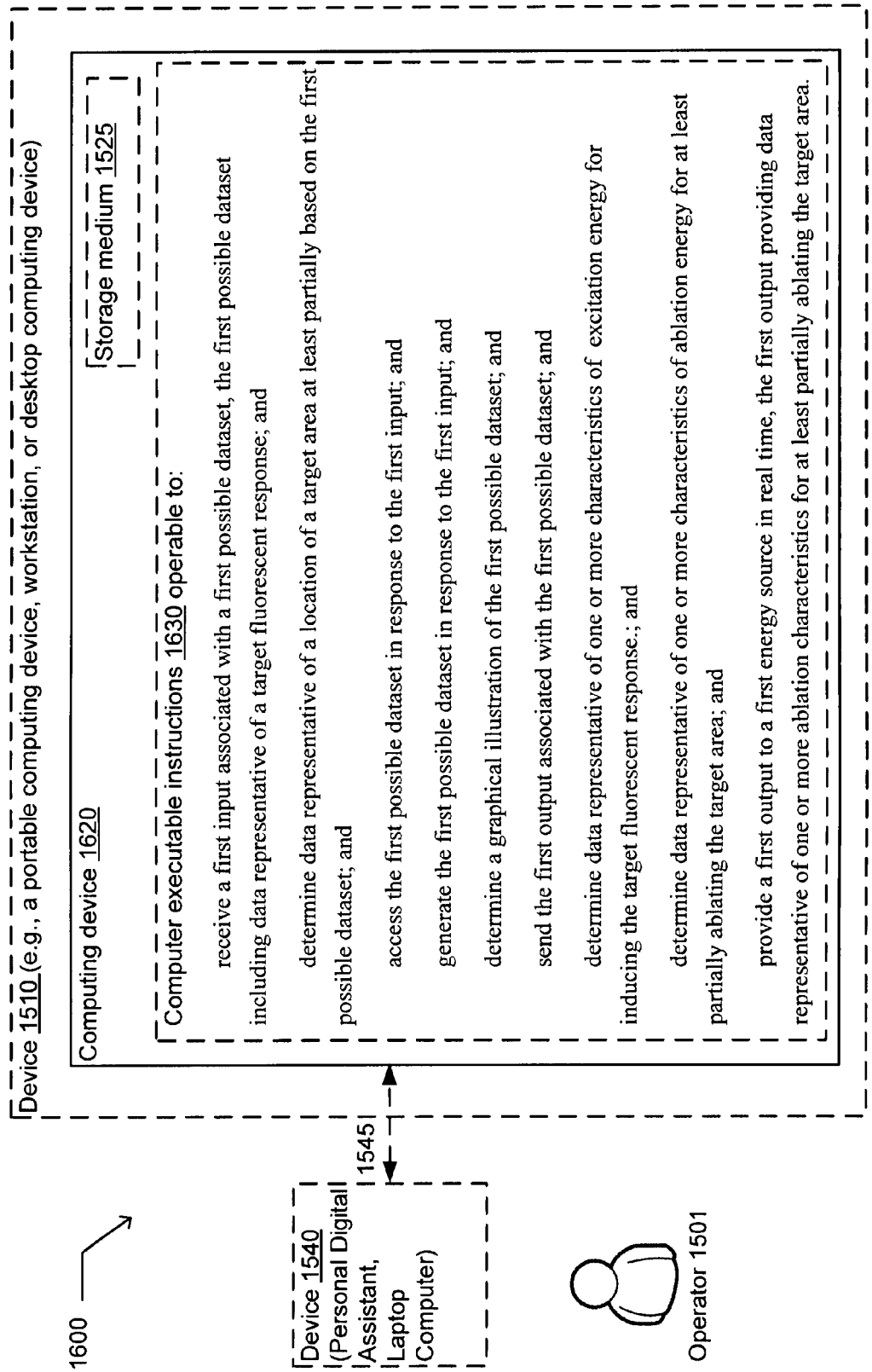
Figure 23:
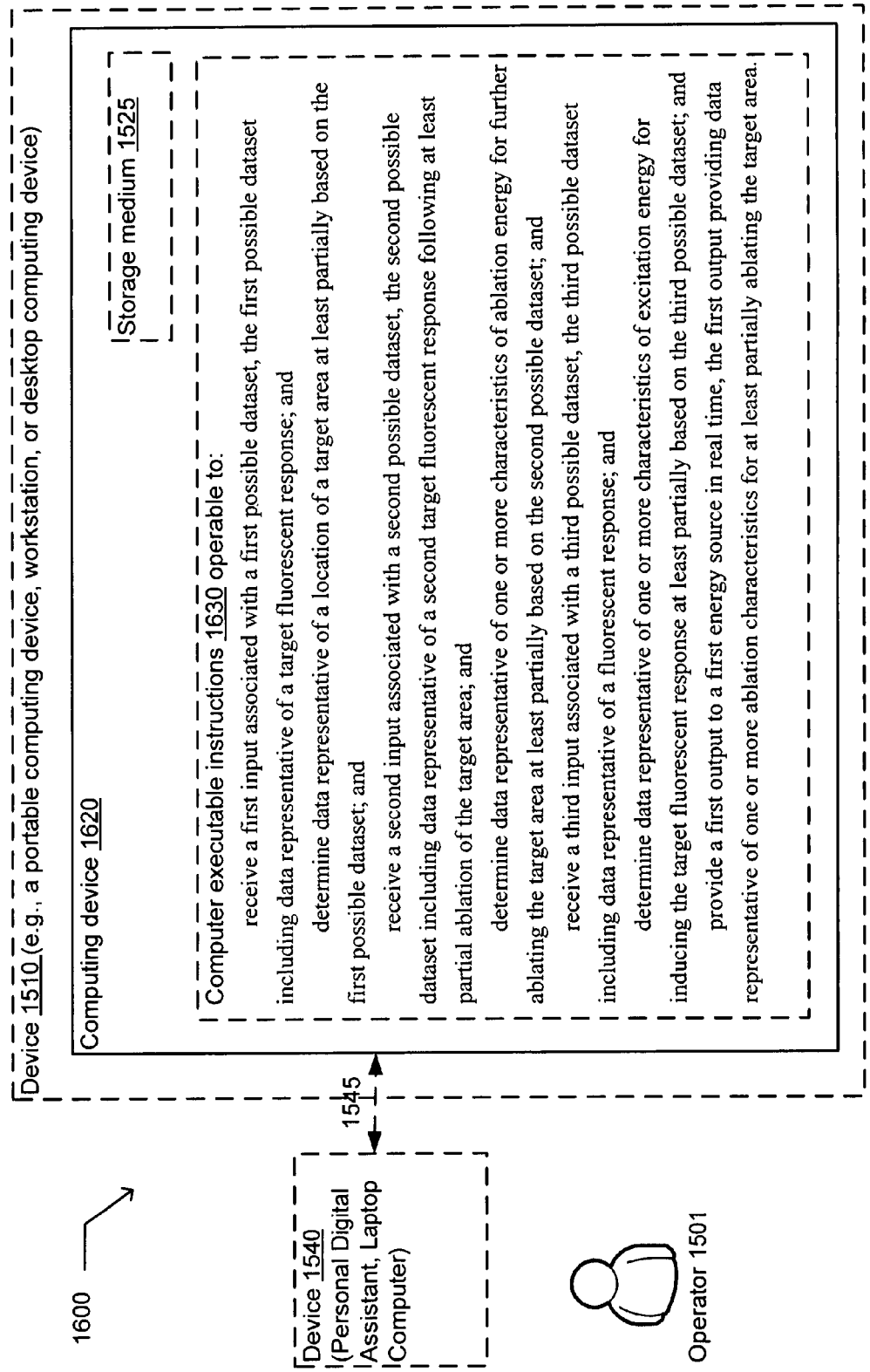

FIG. 22 and FIG. 23 show a schematic of an illustrative system 1600 in which embodiments may be implemented. In some embodiments, system 1600 may be the same as system 1500 and/or system 1700. In some embodiments, system 1600 may be different from system 1500 and/or system 1700. System 1600 may include a computing system environment 1510. System 1600 also illustrates an operator 1501 (e.g. a medical or veterinary professional, optionally a surgeon, a veterinarian, a nurse, a technician, etc.) using a device 1540 that is optionally shown as being in communication with a computing device 1620 by way of an optional coupling 1545. An optional storage medium 1525 may be any computer storage medium.

The computing device 1620 includes one or more computer executable instructions 1630 that when executed on the computing device 1620 cause the computing device 1620 to receive a first input associated with a first possible dataset, the first possible dataset including data representative of a target fluorescent response; access the first possible dataset in response to the first input; generate the first possible dataset in response to the first input; determine a graphical illustration of the first possible dataset; determine data representative of a location of a target area at least partially based on the first possible dataset; send the first output associated with the first possible dataset; determine data representative of one or more characteristics of excitation energy for inducing the target fluorescent response; determine data representative of one or more characteristics of ablation energy for at least partially ablating a target; receive a second input associated with a second possible dataset, the second possible dataset including data representative of a second target fluorescent response following at least partial ablation of a target; determine data representative of one or more characteristics of ablation energy for further ablating a target at least partially based on the second possible dataset; receive a third input associated with a third possible dataset, the third possible dataset including data representative of a fluorescent response; determine data representative of one or more characteristics of excitation energy for inducing the target fluorescent response at least partially based on the third possible dataset; provide a first output to a first energy source in real time, the first output providing data representative of one or more ablation characteristics for at least partially ablating the target area.

In some illustrative embodiments, the computing device 1620 may optionally be contained in whole or in part within one or more parts of an apparatus 100 and/or 500 and/or one or more devices 200, 300, and/or 400 (e.g. control circuitry 130 of one or more tethered and/or untethered, internal and/or external, movable and/or fixed apparatus and/or device), or may optionally be contained in whole or in part within the operator device 1540.

The system 1600 includes at least one computing device 1510, 1620, 1540 and/or control circuitry 130 on which the computer-executable instructions 1630 may be executed. For example, one or more of the computing devices 1510, 1620, 1540 and/or control circuitry 130 may execute the one or more computer executable instructions 1630 and output a result and/or receive information from the operator 1501, from other external sources, and/or from one or more sensor 120, on the same or a different computing device 1510, 1520, 1540, 1620, and/or 1720 and/or output a result and/or receive information from one or more apparatus 100 and/or 500 and/or one or more device 200, 300 and/or 400 in order to perform and/or implement one or more of the techniques, processes, or methods described herein, and/or other techniques.

The computing device 1510, 1620, 1540 may include one or more of a desktop computer, a workstation computer, a computing system comprised a cluster of processors, a networked computer, a tablet personal computer, a laptop computer, or a personal digital assistant, or any other suitable computing unit. In some embodiments, any one of the one or more computing devices 1510, 1620, and/or 1540 and/or control circuitry 130 may be operable to communicate with a database to access the first possible dataset and/or subsequent datasets. In some embodiments, the computing device 1510, 1620, and/or 1540 is operable to communicate with the one or more apparatus 100 and/or 500 and/or device 200, 300, and/or 400 (e.g. control circuitry 130).

Figure 24:
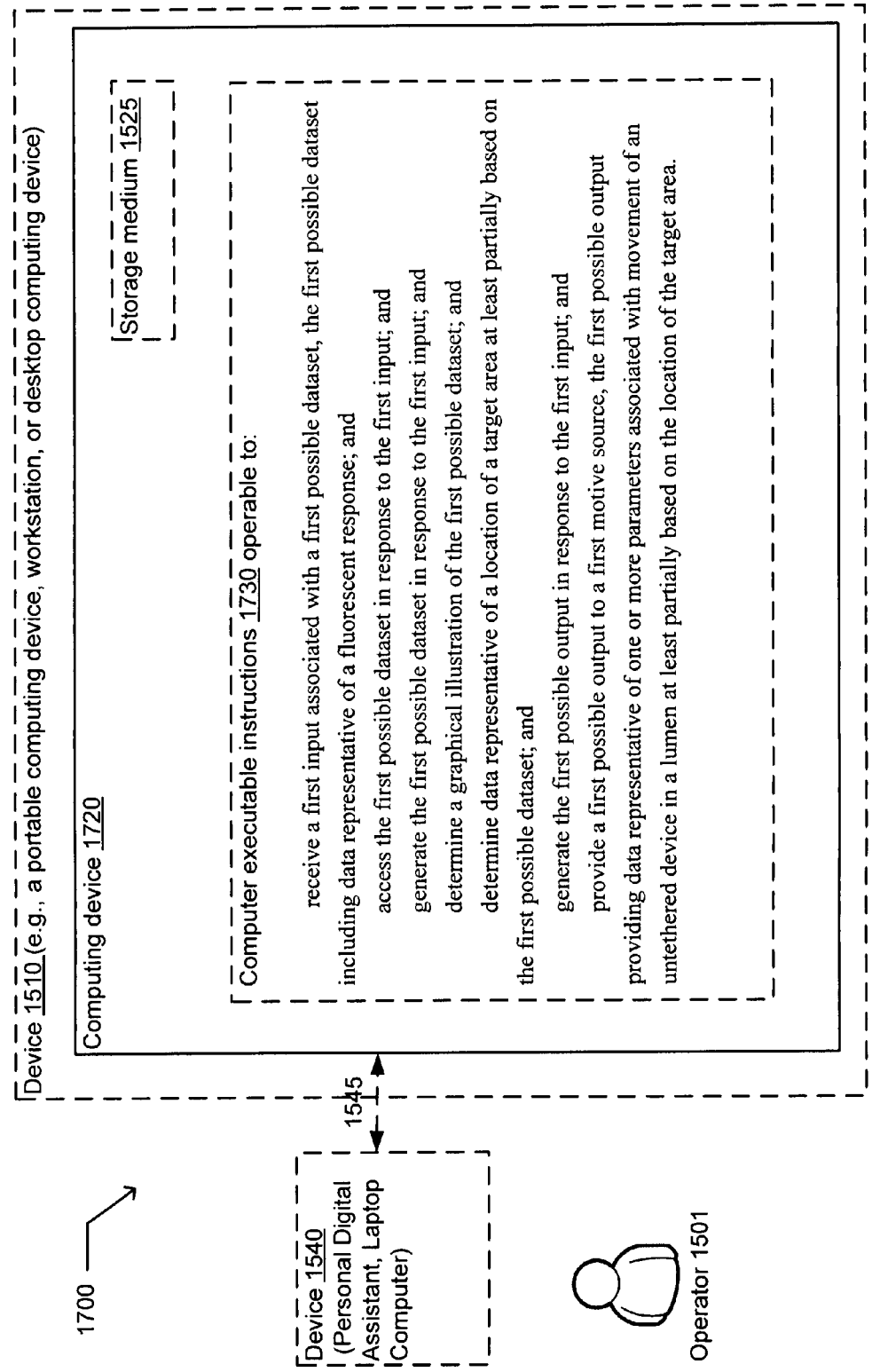
Figure 25:
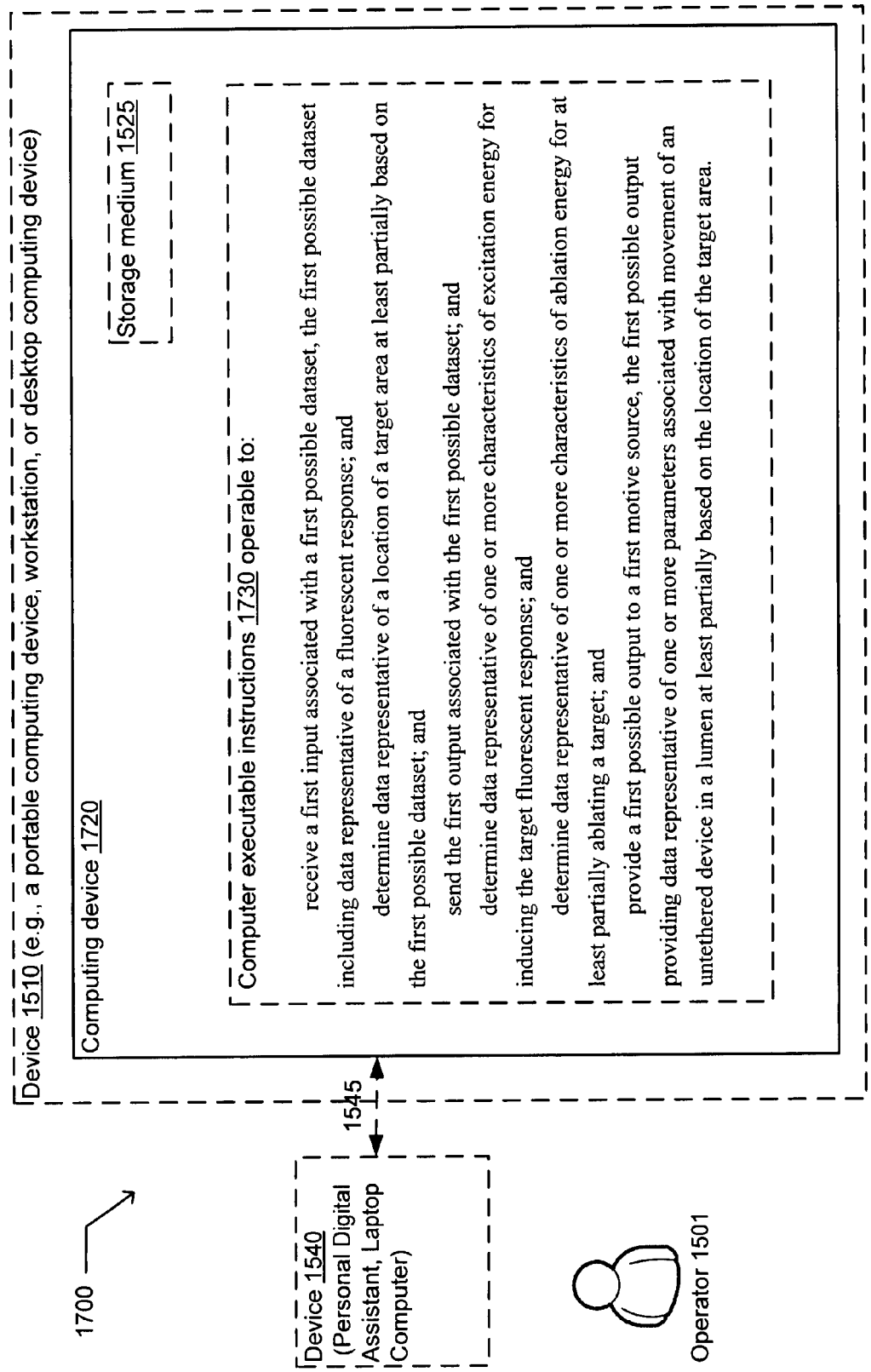

FIG. 24 and FIG. 25 show a schematic of an illustrative system 1700 in which embodiments may be implemented. In some embodiments, system 1700 may be the same as system 1500 and/or system 1600. In some embodiments, system 1700 may be different from system 1500 and/or system 1600. System 1700 may include a computing system environment 1510. System 1700 also illustrates an operator 1501 (e.g. a medical or veterinary professional, optionally a surgeon, a veterinarian, a nurse, a technician, etc.) using a device 1540 that is optionally shown as being in communication with a computing device 1720 by way of an optional coupling 1545. An optional storage medium 1525 may be any computer storage medium.

The computing device 1720 includes one or more computer executable instructions 1730 that when executed on the computing device 1720 cause the computing device 1720 receive a first input associated with a first possible dataset, the first possible dataset including data representative of a fluorescent response; access the first possible dataset in response to the first input; generate the first possible dataset in response to the first input; determine a graphical illustration of the first possible dataset; determine data representative of a location of a target area at least partially based on the first possible dataset; generate the first possible output in response to the first input; send the first output associated with the first possible dataset; determine data representative of one or more characteristics of excitation energy for inducing the target fluorescent response; determine data representative of one or more characteristics of ablation energy for at least partially ablating a target; provide a first possible output to a first motive source, the first possible output providing data representative of one or more parameters associated with movement of an untethered device in a lumen at least partially based on the location of the target area.

In some illustrative embodiments, the computing device 1720 may optionally be contained in whole or in part within one or more parts of an apparatus 100 and/or 500 and/or one or more devices 200, 300, and/or 400 (e.g. control circuitry 130 of one or more tethered and/or untethered, internal and/or external, movable and/or fixed apparatus and/or device), or may optionally be contained in whole or in part within the operator device 1540.

The system 1700 includes at least one computing device 1510, 1720, 1540 and/or control circuitry 130 on which the computer-executable instructions 1730 may be executed. For example, one or more of the computing devices 1510, 1720, 1540 and/or control circuitry 130 may execute the one or more computer executable instructions 1730 and output a result and/or receive information from the operator 1501, from other external sources, and/or from one or more sensor 120, on the same or a different computing device 1510, 1520, 1540, 1620, and/or 1720 and/or output a result and/or receive information from one or more apparatus 100 and/or 500 and/or one or more device 200, 300 and/or 400 in order to perform and/or implement one or more of the techniques, processes, or methods described herein, and/or other techniques.

The computing device 1510, 1720, 1540 may include one or more of a desktop computer, a workstation computer, a computing system comprised a cluster of processors, a networked computer, a tablet personal computer, a laptop computer, or a personal digital assistant, or any other suitable computing unit. In some embodiments, any one of the one or more computing devices 1510, 1720, and/or 1540 and/or control circuitry 130 may be operable to communicate with a database to access the first possible dataset and/or subsequent datasets. In some embodiments, the computing device 1510, 1720, and/or 1540 is operable to communicate with the one or more apparatus 100 and/or 500 and/or device 200, 300, and/or 400 (e.g. control circuitry 130).

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

For ease of reading, all values described herein, and all numerical ranges described herein are approximate and should be read as including the word "about" or "approximately" prior to each numeral, unless context indicates otherwise. For example, the range "0.0001 to 0.01" is meant to read as "about 0.0001 to about 0.01."

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for treating or ameliorating a pathogenic condition associated with at least one of *Enterococcus faecalis, Bacteroides vulgatis, Serratia marcescens, Propinibacterium acnes, Bifidobacterium, Actinomyces, Candida albicans, Escherichia coli, Salmonella, Vibrio cholera, Campylobacter, Listeria monocytogenes, shigella, Helicobacter pylori*, rotovirus, Calicivirus, *Giardia lamblia, Entamoeba histolytica, Cryptosporidium*, neoplastic cells, or cancerous cells, the method comprising:
   providing to the digestive tract of the subject an untethered ingestible mass having a core;
   passing cells through the core of the untethered ingestible mass;
   emitting electromagnetic energy from a first optical energy source in the untethered ingestible mass in a manner selected to induce fluorescence in some of the cells;
   identifying target cells by analyzing the fluorescence with control circuitry located in the untethered ingestible mass, wherein the target cells are associated with the pathogenic condition;
   aligning a second optical energy source with the first optical energy source; and
   emitting variable directional electromagnetic energy at the target cells from the second optical energy source in the untethered ingestible mass in a manner selected to induce photodynamic cell death in some of the target cells.

2. The method of claim 1, wherein the untethered ingestible mass comprises:
   a motor coupled to a movable mass.

3. The method of claim 2, further comprising:
   inducing variable moments of inertia by moving the movable mass.

4. The method of claim 2, further comprising:
   inducing the movable mass to undergo unbalanced rotation.

5. The method of claim 2, further comprising:
   inducing the movable mass to undergo linear oscillatory movement.

6. The method of claim 2, further comprising:
   inducing the movable mass to undergo eccentric movement.

7. The method of claim 2, wherein the untethered ingestible mass includes a power source.

8. The method of claim 1, further comprising:
   monitoring the untethered ingestible mass from one or more external sources.

9. The method of claim 1, further comprising:
   providing one or more outputs from the untethered ingestible mass to one or more external sources.

10. The method of claim 1, further comprising:
    detecting one or more environmental parameters.

11. The method of claim 1, wherein emitting variable directional electromagnetic energy from the untethered ingestible mass in a manner selected to induce photodynamic cell death in some of the target cells comprises:
    emitting the variable directional electromagnetic energy from the untethered ingestible mass in a spatially variable manner.

12. The method of claim 1, wherein emitting variable directional electromagnetic energy from the untethered ingestible mass in a manner selected to induce photodynamic cell death in some of the target cells comprises:
    emitting the variable directional electromagnetic energy from the untethered ingestible mass at one or more intervals at least partially based on pH.

13. The method of claim 1, wherein emitting variable directional electromagnetic energy from the untethered ingestible mass in a manner selected to induce photodynamic cell death in some of the target cells comprises:
    emitting the variable directional electromagnetic energy from the second optical energy source of the untethered ingestible mass at one or more intervals at least partially based on orientation of the second optical energy source aligned with the first optical energy source.

14. The method of claim 1, further comprising:
controlling the emission of the variable directional electromagnetic energy from the untethered ingestible mass using the control circuitry located in the untethered ingestible mass.

15. The method of claim 14, further comprising:
detecting one or more environmental parameters using a sensor coupled to the control circuitry located in the untethered ingestible mass.

16. The method of claim 15, further comprising:
emitting the variable directional electromagnetic energy from the untethered ingestible mass at least partially based on the one or more environmental parameters.

17. The method of claim 1, wherein inducing fluorescence of some of the target cells includes inducing autofluorescence of some of the target cells.

18. The method of claim 1, wherein inducing fluorescence of some of the target cells includes inducing fluorescence from one or more fluorescence tags.

19. The method of claim 14, comprising:
detecting fluorescence in some of the target cells using a sensor coupled to the control circuitry located in the untethered ingestible mass.

20. The method of claim 1, wherein identifying a target area by analyzing the fluorescence with control circuitry located in the untethered ingestible mass includes determining one or more of a direction from the first optical energy source, a distance the first optical energy source, a tissue depth at the target area, or coordinates from which the fluorescence originated.

21. The method of claim 1, further comprising aligning a second optical energy source with the first optical energy source by analyzing the alignment with the control circuitry located in the untethered ingestible mass.

22. The method of claim 1, further comprising emitting variable directional electromagnetic energy at the target area from the second optical energy source by analyzing the energy emission with the control circuitry located in the untethered ingestible mass in a manner selected to induce photodynamic cell death in some of the abnormal cells.

23. A method for ablating cells, the method comprising:
providing to a digestive tract of a subject an untethered ingestible mass having a core;
passing cells through the core of the untethered ingestible mass;
emitting electromagnetic energy from a first optical energy source in the untethered ingestible mass in a manner selected to induce fluorescence in at least some of the cells;
identifying target cells by analyzing the fluorescence with control circuitry located in the untethered ingestible mass;
aligning a second optical energy source with the first optical energy source; and
emitting variable directional electromagnetic energy at the target cells from the second optical energy source in the untethered ingestible mass in a manner selected to induce photodynamic cell death in at least some of the target cells.

* * * * *